(12) United States Patent
Bernardelli et al.

(10) Patent No.: US 7,851,493 B2
(45) Date of Patent: Dec. 14, 2010

(54) PHENYL-1,2,4-OXADIAZOLONE DERIVATIVES WITH PHENYL GROUP, PROCESSES FOR THEIR PREPARATION AND THEIR USE AS PHARMACEUTICALS

(75) Inventors: Patrick Bernardelli, Villepreux (FR); Stefanie Keil, Hofheim (DE); Matthias Urmann, Eschborn (DE); Hans Matter, Langenselbold (DE); Wolfgang Wendler, Selters (DE); Maike Glien, Wiesbaden (DE); Karen Chandross, Somerset, NJ (US); Lan Lee, Pluckemin, NJ (US); Corinne Terrier, Livry Gargan (FR); Herve Minoux, Thiais (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/474,838

(22) Filed: May 29, 2009

(65) Prior Publication Data

US 2009/0281084 A1 Nov. 12, 2009

Related U.S. Application Data

(63) Continuation of application No. 12/055,793, filed on Mar. 26, 2008, now abandoned, which is a continuation of application No. PCT/EP2006/009298, filed on Sep. 26, 2006.

(30) Foreign Application Priority Data

Sep. 29, 2005 (EP) .................................. 05021235

(51) Int. Cl.
*A61K 31/4245* (2006.01)
*C07D 271/113* (2006.01)

(52) U.S. Cl. ...................................... 514/364; 548/144
(58) Field of Classification Search ................. 514/364; 548/144
See application file for complete search history.

(56) References Cited

U.S. PATENT DOCUMENTS 5,641,796 A  6/1997  Dominianni et al.
6,710,063 B1  3/2004  Chao et al.

FOREIGN PATENT DOCUMENTS

| DE | 10112768 | 9/2002 |
|---|---|---|
| EP | 1424330 | 6/2004 |
| EP | 1586573 | 10/2005 |
| WO | WO 96/13264 | 5/1996 |
| WO | WO 96/34851 | 11/1996 |
| WO | WO 97/40017 | 10/1997 |
| WO | WO 00/78313 | 12/2000 |
| WO | WO 01/00603 | 1/2001 |
| WO | WO 02/092590 | 11/2002 |
| WO | WO 2004/080943 | 9/2004 |
| WO | WO 2005/054213 | 6/2005 |
| WO | WO 2005/097762 | 10/2005 |
| WO | WO 2005/097786 | 10/2005 |

OTHER PUBLICATIONS

Kulkarni, S.S., et. al., Three-Dimensional Quantitative Structure Activity Relationships (3-D-QSAR) of Antihyperglycemic Agents, Bioorganic & Medicinal Chemistry vol. 7, (1999) pp. 1475-1485.

*Primary Examiner*—Taofiq A Solola
(74) *Attorney, Agent, or Firm*—Jiang Lin

(57) ABSTRACT

The invention relates to phenyl-1,2,4-oxadiazolone derivatives with phenyl group and to their physiologically acceptable salts and physiologically functional derivatives showing PPARdelta agonist activity.

What are described are compounds of the formula I,

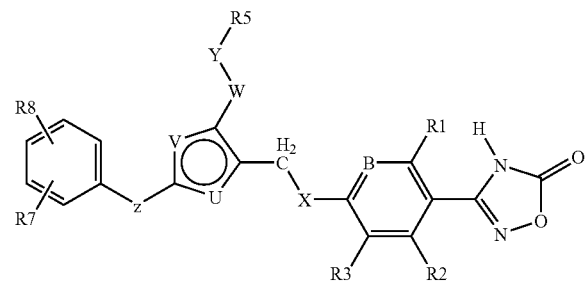

in which the radicals are as defined, and their physiologically acceptable salts and processes for their preparations. The compounds are suitable for the treatment and/or prevention of disorders of fatty acid metabolism and glucose utilization disorders as well as of disorders in which insulin resistance is involved and demyelinating and other neurodegenerative disorders of the central and peripheral nervous system.

21 Claims, No Drawings

PHENYL-1,2,4-OXADIAZOLONE DERIVATIVES WITH PHENYL GROUP, PROCESSES FOR THEIR PREPARATION AND THEIR USE AS PHARMACEUTICALS

This application is a Continuation of U.S. application Ser. No. 12/055,793, filed Mar. 26, 2008, which is a Continuation of International Application No. PCT/EP2006/009298, filed Sep. 26, 2006, all of which are incorporated herein by reference in their entireties.

FIELD OF THE INVENTION

The invention relates to phenyl-1,2,4-oxadiazolone derivatives with phenyl group and to their physiologically acceptable salts and physiologically functional derivatives showing PPARdelta agonist activity.

BACKGROUND OF THE INVENTION

PPARdelta agonists have been described in the prior art (e.g. WO 01/00603, WO 02/092590, WO2004/080943, WO2005/054213 and WO2005/097786). Compounds comprising an oxadiazolone feature as inhibitors of factor Xa were disclosed in DE 101 12 768 A1, oral hypoglycemic agents in WO 96/13264. From WO 97/40017 compounds having a phenyl group linked to heterocycles are known as modulators of molecules with phosphotyrosine recognition units. Benzene derivatives as inhibitors of squalene synthase and protein farnesyltransferase are described in WO96/34851.

The invention is based on the object of providing compounds, which permit therapeutically utilizable modulation of lipid and/or carbohydrate metabolism and are thus suitable for the prevention and/or treatment of diseases such as type 2 diabetes and atherosclerosis and the diverse sequelae thereof. Another purpose of the invention is to treat demyelinating and other neurodegenerative disorders of the central and peripheral nervous systems.

A series of compounds which modulate the activity of PPA receptors has been found. The compounds are suitable in particular for activating PPARdelta or PPARdelta and PPARalpha, however it being possible for the extent of the relative activation to vary depending on the compounds.

SUMMARY OF THE INVENTION

Compounds of the present invention are described by formula I:

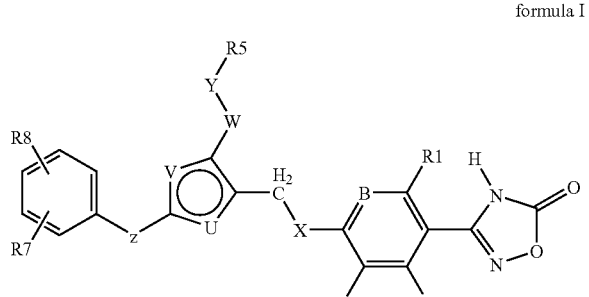

formula I wherein
B is C(R4) or N;
R1 is H, halogen, (C1-C8)alkyl, (C0-C4)alkylene-O—(C0-C4)alkylene-H, (C0-C2)alkylene-O—(C0-C2)alkylene-(C3-C6)cycloalkyl, SCH3, CN, wherein alkyl and alkylene are unsubstituted or mono, di- or trisubstituted by F;
R2, R3, R4 are independently
 H, halogen, (C1-C8)alkyl, (C0-C4)alkylene-O—(C0-C4) alkylene-H, SCH3, CN, wherein alkyl and alkylene are unsubstituted or mono, di- or trisubstituted by F;
X is O, S, S(O), S(O)2, O—CH2, S—CH2, CH2-O, CH2-S;
one of U and V is N the other is S or O;
W is a bond, (C1-C8)alkylene, (C2-C8)alkenylene, (C0-C6)alkylene-(C3-C6) cycloalkylene, (C3-C6)cycloalkylene-(C1-C6)alkylene, wherein alkylene and alkenylene and cycloalkylene are unsubstituted or mono-, di- or trisubstituted by OH and F;
Y is a bond, O, S, S(O), S(O)2, N(R6) and
R5 is H, (C1-C8)alkyl, (C0-C4)alkylene-(C3-C13)cycloalkyl, (C0-C4)alkylene-(C6-C14)aryl, (C2-C8)alkenyl, (C0-C4)alkylene-(C3-C15)heterocycloalkyl, (C0-C4)alkylene-(C3-C15)heterocycloalkenyl, (C0-C4)alkylene-(C5-C15) heteroaryl, (C0-C4)alkylene-CO—(C1-C4)alkyl, (C0-C4)alkylene-CO—(C0-C4) alkylene-(C3-C13) cycloalkyl, (C0-C4)alkylene-CO—(C0-C4)alkylene-(C6-C10)aryl, (C0-C4)alkylene-CO—(C0-C4)alkylene-(C3-C15) heterocycloalkyl, (C0-C4)alkylene-CO—(C0-C4) alkylene-(C3-C15) heterocycloalkenyl, (C0-C4)alkylene-CO—(C0-C4)alkylene-(C5-C15) heteroaryl, SO2-(C1-C4)alkyl, SO2-(C0-C4)alkylene-(C3-C13)cycloalkyl, SO2-(C0-C4)alkylene-(C6-C10)aryl, SO2-(C0-C4)alkylene-(C3-C15) heterocycloalkyl, SO2-(C0-C4)alkylene-(C3-C15) heterocycloalkenyl, SO2-(C0-C4)alkylene-(C5-C15)heteroaryl, CO—O—(C0-C4)alkylene-(C6-C10) aryl, CO—O—(C1-C4)alkyl, CO—O—(C0-C4)alkylene-(C3-C13)-cycloalkyl, CO—O—(C0-C4)alkylene-(C3-C15)heterocycloalkyl, CO—O—(C0-C4)alkylene-(C3-C15)heterocycloalkenyl, CO—O—(C0-C4)alkylene-(C5-C15)heteroaryl, CO—N((C0-C4)alkylene-H)—(C0-C4)alkylene-(C6-C10)aryl, CO—N((C0-C4) alkylene-H)—(C0-C4)alkylene-H, CO—N((C0-C4)alkylene-H)—(C0-C4) alkylene-(C3-C13)cycloalkyl, CO—N((C0-C4) alkylene-H)—(C0-C4)alkylene-(C3-C15) heterocycloalkyl, CO—N((C0-C4)alkylene-H)—(C0-C4) alkylene-(C3-C15)heterocycloalkenyl, CO—N((C0-C4) alkylene-H)—(C0-C4)alkylene-(C5-C15)heteroaryl, SO2-N((C0-C4)alkylene-H)—(C0-C4)alkylene-(C6-C10)aryl, SO2-N((C0-C4)alkylene-H)—(C0-C4)alkylene-H, SO2-N((C0-C4) alkylene-H)—(C0-C4)alkylene-(C3-C13)cycloalkyl, SO2-N((C0-C4)alkylene-H)—(C0-C4)alkylene-(C3-C15)heterocycloalkyl, SO2-N((C0-C4) alkylene-H)—(C0-C4)alkylene-(C3-C15) heterocycloalkenyl, SO2-N((C0-C4)alkylene-H)—(C0-C4)alkylene-(C5-C15)heteroaryl wherein alkyl and alkylene are unsubstituted or mono-, di- or trisubstituted by F, S—(C1-C4)alkyl, SO—(C1-C4)alkyl, SO2-(C1-C4) alkyl, CO—N((C0-C4)alkylene-H)—(C0-C4)alkylene-H, N((C0-C4)alkylene-H)—(C0-C4)alkylene-H, CO—O (C1-C4)alkyl, (C1-C4) alkyl and O—(C0-C4)alkylene-H and wherein cycloalkyl, aryl, heterocycloalkyl, heterocycloalkenyl and heteroaryl are unsubstituted or mono-, di- or trisubstituted by F, Cl, Br, CF3, (C1-C4)alkyl and (C0-C4)-alkylen-O—(C0-C4)alkylene-H,
with the proviso that,
if Y is S, S(O) or S(O)2 then
R5 is unequal SO2-(C1-C4)alkyl, SO2-(C0-C4)alkylene-(C3-C13)cycloalkyl, SO2-(C0-C4)alkylene-(C6C10)aryl, SO2-(C0-C4)alkylene-(C3-C15)heterocycloalkyl, SO2-(C0-C4)alkylene-(C3-C15)heterocycloalkenyl, SO2-(C0-C4)alkylene-(C5-C15)heteroaryl, SO2-N((C0-C4)alkylene-H)—(C0-C4)alkylene-(C6-C10)aryl, SO2-N((C0-C4)alkylene-H)—(C0-C4)alkylene-H, SO2-N((C0-C4)alkylene-H)—(C0-C4)alkylene-(C3-C13)cycloalkyl, SO2-N((C0-C4)alkylene-H)—(C0-C4)alkylene-(C3-C15)heterocycloalkyl, SO2-N((C0-C4)alkylene-H)—(C0-C4)alkylene-(C3-C15)heterocycloalkenyl, SO2-N((C0-C4)alkylene-H)—(C0-C4)alkylene-(C5-C15) heteroaryl;

with the proviso that,
if Y is a bond or O then
Z is unequal a bond;

or
Y is a bond,
with the proviso that
R5 is CN, (C1-C8)alkyl mono-, di- or trisubstituted by F, CO—(C1-C4)alkyl, CO—N((C0-C4)alkylene-H)—(C0-C4)alkylene-H, SO2-N((C0-C4)alkylene-H)—(C0-C4)alkylene-H, N((C0-C4)alkylene-H)—CO—(C0-C4)alkylene-H, (C1-C6)alkylene-(C3-C13)cycloalkyl, (C3-C15) heterocycloalkyl, (C3-C15) heterocycloalkenyl, (C5-C15)heteroaryl;

or
Y is O,
with the proviso that
R5 is (C1-C8)alkyl mono-, di- or trisubstituted by F, CO—(C1-C4) alkyl, CO—O—(C0-C4)alkylene-(C6-C10) aryl, CO—O—(C0-C4) alkylene-(C3-C13)cycloalkyl, CO—O—(C0-C4)alkylene-(C3-C15)heterocycloalkyl, CO—O—(C0-C4)alkylene-(C3-C15)heterocycloalkenyl, CO—O—(C0-C4)alkylene-(C5-C15)heteroaryl, CO—N((C0-C4)alkylene-H)—(C0-C4)alkylene-H, CO—N((C0-C4)alkylene-H)—(C0-C4)alkylene-(C6-C10)aryl, CO—N((C0-C4)alkylene-H)—(C0-C4)alkylene-(C3-C13)cycloalkyl, CO—N((C0-C4)alkylene-H)—(C0-C4)alkylene-(C3-C15)heterocycloalkyl, CO—N((C0-C4)alkylene-H)—(C0-C4)alkylene-(C3-C15)heterocycloalkenyl, CO—N((C0-C4)alkylene-H)—(C0-C4)alkylene-(C3-C13)cycloalkyl, CO—N((C0-C4)alkylene-H)—(C0-C4)alkylene-(C5-C15)heteroaryl, (C0-C4) alkylene-(C3-C13) cycloalkyl, (C0-C4)alkylene-(C3-C15) heterocycloalkyl, (C0-C4) alkylene-(C3-C15) heterocycloalkenyl, (C0-C4) alkylene-(C5-C15)heteroaryl, (C0-C4)alkylene-N((C0-C4) alkylene-H)—(C0-C4)alkylene-H, (C0-C4) alkylene-N((C0-C4) alkylene-H)—(C0-C4)alkylene-(C3-C13)cycloalkyl, (C0-C4) alkylene-N((C0-C4) alkylene-H)—(C0-C4)alkylene-(C6-C10)aryl, (C0-C4) alkylene-N((C0-C4)alkylene-H)—(C0-C4)alkylene-(C3-C15)heterocycloalkyl, (C0-C4)alkylene-N((C0-C4)alkylene-H)—(C0-C4)alkylene-(C3-C15) heterocycloalkenyl, (C0-C4)alkylene-N((C0-C4) alkylene-H)—(C0-C4)alkylene-(C5-C15)heteroaryl;

R6 is H, (C1-C8)alkyl, (C2-C8)alkenyl, (C0-C4)alkylene-(C3-C6)cycloalkyl, wherein alkyl and alkenyl are unsubstituted or mono-, di- or trisubstituted by F and O—(C0-C4)-alkylene-H;

R5 and R6 together with the nitrogen atom to which they are bonded (Y=N(R6)) form a (C3-C15)-heterocycloalkyl, a (C3-C15)-heterocycloalkenyl or a (C5-C15)-heteroaryl which can contain additionally 1 to 3 heteroatoms N, O, S in which further the heteroatoms can be oxidized and which is unsubstituted or mono-, di- or trisubstituted by halogen, CN, CF3, (C1-C4)alkyl, (C0-C4) alkylene-(C3-C6)cycloalkyl, (C0-C4)alkylene-O—(C0-C4)alkylene-H, (C0-C4) alkylene-O—(C0-C4)alkylene-(C3-C6)cycloalkyl, (C0-C4)alkylene-O—(C0-C4)alkylene-(C6-C10)aryl, (C0-C4)alkylene-O—(C0-C4)alkylene-(C3-C15)heterocycloalkyl, (C0-C4)alkylene-O—(C0-C4)alkylene-(C3-C15) heterocycloalkenyl, (C0-C4)alkylene-O—(C0-C4)alkylene-(C5-C15) heteroaryl, (C0-C4)alkylene-S—(C1-C4)alkyl, (C0-C4)alkylene-SO—(C1-C4) alkyl, (C0-C4)alkylene-SO2-(C1-C4)alkyl, (C0-C4)alkylene-CO—(C1-C4) alkyl, (C0-C4)alkylene-CO—(C6-C10)aryl, (C0-C4)alkylene-CO—(C3-C15)heterocycloalkyl, (C0-C4)alkylene-CO—(C3-C15)heterocycloalkenyl, (C0-C4)alkylene-CO—(C5-C15)heteroaryl, (C0-C4)alkylene-CO—N((C0-C4) alkylene-H)—(C0-C4)alkylene-H, (C0-C4)alkylene-CO—N((C0-C4)alkylene-H)—(C0-C4)alkylene-(C3-C6)cycloalkyl, (C0-C4)alkylene-CO—N((C0-C4)alkylene-H)—(C0-C4)alkylene-(C6-C10)aryl, (C0-C4)alkylene-CO—N((C0-C4)alkylene-H)—(C0-C4)alkylene-(C3-C15)heterocycloalkyl, (C0-C4)alkylene-CO—N((C0-C4)alkylene-H)—(C0-C4)alkylene-(C3-C15)heterocycloalkenyl, (C0-C4)alkylene-CO—N((C0-C4)alkylene-H)—(C0-C4)alkylene-(C5-C15)heteroaryl, (C0-C4)alkylene-N((C0-C4)alkylene-H)—CO—(C1-C4)alkyl, (C0-C4) alkylene-N((C0-C4)alkylene-H)—CO—(C0-C4)alkylene-(C3-C6)cycloalkyl, (C0-C4)alkylene-N((C0-C4)alkylene-H)—CO—(C0-C4)alkylene-(C6-C10)aryl, (C0-C4)alkylene-N((C0-C4)alkylene-H)—CO—(C0-C4)alkylene-(C3-C15)heterocycloalkyl, (C0-C4)alkylene-N((C0-C4)alkylene-H)—CO—(C0-C4)alkylene-(C3-C15) heterocycloalkenyl, (C0-C4)alkylene-N((C0-C4) alkylene-H)—CO—(C0-C4)alkylene-(C5-C15)heteroaryl, (C0-C4)alkylene-(C6-C14)aryl and (C0-C4)alkylene-(C3-C15)heterocycloalkyl, (C0-C4) alkylene-(C3-C15)heterocycloalkenyl, (C0-C4)alkylene-(C5-C15) heteroaryl whereby heteroaryl, heterocycloalkyl and heterocycloalkenyl can mono- or disubstituted by oxo residue and where alkyl can be unsubstituted or mono-, di- or trisubstituted by F;

Z is a bond, (C1-C8)alkylene, (C2-C8)alkenylene, (C2-C8) alkylidene, (C1-C6)alkylene-O—(C1-C6)alkylene;

R7, R8 are independently selected from the group consisting of H, halogen, (C1-C8) alkyl, (C0-C4)alkylene-O—(C0-C4)alkylene-H, SCF3, SF5, S(O)2CF3, (C0-C4) alkylene-O—(C6-C12)aryl, (C0-C4)alkylene (C6-C12)aryl, NO2, wherein alkyl and alkylene are unsubstituted or mono-, di- or trisubstituted by F and aryl is unsubstituted or mono-, di- or trisubstituted by halogen, (C1-C4)alkyl or O—(C1-C4) alkyl;

in all its stereoisomeric forms, enantiomeric forms and mixtures in any ratio, and its physiologically acceptable salts and tautomeric forms.

DETAILED DESCRIPTION OF THE INVENTION

Another embodiment according to the invention are compounds of the formula I, wherein
R2,R3 are independently
H, halogen, (C1-C8)alkyl, (C0-C4)alkylene-O—(C0-C4) alkylene-H, SCH3, CN, wherein alkyl and alkylene are unsubstituted or mono, di- or trisubstituted by F;
R4 is H, (C1-C8)alkyl, (C0-C4)alkylene-O—(C0-C4)alkylene-H wherein alkyl and alkylene are unsubstituted or mono, di- or trisubstituted by F.

Another embodiment according to the invention are compounds of the formula I, wherein
B is C(R4) and
R4 is H.

Another embodiment according to the invention are compounds of the formula I, wherein
B is C(R4) and
R4 is H;
R1 is H, halogen, (C1-C8)alkyl, (C0-C4)alkylene-O—(C0-C4)alkylene-H, SCH3,
CN, wherein alkyl and alkylene are unsubstituted or mono, bi- or trisubstituted by F;
R2, R3, R4 are independently
H, halogen, (C1-C8)alkyl, (C0-C4)alkylene-O—(C0-C4)alkylene-H, SCH3, CN, wherein alkyl and alkylene are unsubstituted or mono, bi- or trisubstituted by F;
X is O, S, S(O), S(O)2, O—CH2, S—CH2, CH2-O, CH2-S;
one of U and V is N the other is S or O;
W is a bond, (C1-C8)alkylene, (C2-C8)alkenylene, (C0-C6)alkylene-(C3-C6) cycloalkylene, (C3-C6)cycloalkylen-(C1-C6)alkylene, wherein alkylene and alkenylene and cycloalkylene are unsubstituted or mono-, di- or trisubstituted by OH and F;
Y is N(R6);
R5 is H, (C1-C8)alkyl, (C0-C4)alkylene-(C3-C13)cycloalkyl, (C0-C4)alkylene-(C6-C14)aryl, (C2-C8)alkenyl, (C0-C4)alkylene-(C3-C15)heterocycloalkyl, (C0-C4)alkylene-(C3-C15)heterocycloalkenyl, (C0-C4)alkylene-(C5-C15) heteroaryl, (C0-C4)alkylene-CO—(C1-C4)alkyl, (C0-C4)alkylene-CO—(C0-C4) alkylene-(C3-C13) cycloalkyl, (C0-C4)alkylene-CO—(C0-C4)alkylene-(C6-C10)aryl, (C0-C4)alkylene-CO—(C0-C4)alkylene-(C3-C15) heterocycloalkyl, (C0-C4)alkylene-CO—(C0-C4) alkylene-(C3-C15) heterocycloalkenyl, (C0-C4)alkylene-CO—(C0-C4)alkylene-(C5-C15) heteroaryl, SO2-(C1-C4)alkyl, SO2-(C0-C4)alkylene-(C3-C13)cycloalkyl, SO2-(C0-C4)alkylene-(C6-C10) aryl, SO2-(C0-C4)alkylene-(C3-C15) heterocycloalkyl, SO2-(C0-C4)alkylene-(C3-C15)heterocycloalkenyl, SO2-(C0-C4)alkylene-(C5-C15) heteroaryl, CO—O—(C0-C4)alkylene-(C6-C10) aryl, CO—O—(C1-C4)alkyl, CO—O—(C0-C4)alkylene-(C3-C13)cycloalkyl, CO—O—(C0-C4)alkylene-(C3-C15)heterocycloalkyl, CO—O—(C0-C4)alkylene-(C3-C15)heterocycloalkenyl, CO—O—(C0-C4)alkylene-(C5-C15)heteroaryl, CO—N((C0-C4)alkylene-H)—(C0-C4)alkylene-(C6-C10) aryl, CO—N((C0-C4) alkylene-H)—(C0-C4)alkylene-H, CO—N((C0-C4)alkylene-H)—(C0-C4) alkylene-(C3-C13)cycloalkyl, CO—N((C0-C4)alkylene-H)—(C0-C4)alkylene-(C3-C15)heterocycloalkyl, CO—N((C0-C4)alkylene-H)—(C0-C4)alkylene-(C3-C15) heterocycloalkenyl, CO—N((C0-C4)alkylene-H)—(C0-C4)alkylene-(C5-C15) heteroaryl, SO2-N((C0-C4)alkylene-H)—(C0-C4)alkylene-(C6-C10)aryl, SO2-N((C0-C4)alkylene-H)—(C0-C4)alkylene-H, SO2-N((C0-C4) alkylene-H)—(C0-C4)alkylene-(C3-C13)cycloalkyl, SO2-N((C0-C4)alkylene-H)—(C0-C4)alkylene-(C3-C15)heterocycloalkyl, SO2-N((C0-C4)alkylene-H)—(C0-C4)alkylene-(C3-C15) heterocycloalkenyl, SO2-N((C0-C4)alkylene-H)—(C0-C4)alkylene-(C5-C15)heteroaryl wherein alkyl and alkylene are unsubstituted or mono-, di- or trisubstituted by F, S—(C1-C4)alkyl, SO—(C1-C4)alkyl, SO2-(C1-C4)alkyl, CO—N((C0-C4)alkylene-H)—(C0-C4)alkylene-H, N((C0-C4)alkylene-H)—(C0-C4)alkylene-H, CO—O (C1-C4)alkyl, (C1-C4) alkyl and O—(C0-C4)alkylene-H and wherein cycloalkyl, aryl and heterocycloalkyl, heterocycloalkenyl and heteroaryl are unsubstituted or mono-, di- or trisubstituted by F, Cl, Br, CF3, (C1-C4)alkyl and (C0-C4)-alkylen-O—(C0-C4)alkylene-H;
R6 is H, (C1-C8)alkyl, (C2-C8)alkenyl, (C0-C4)alkylene-(C3-C6)cycloalkyl, wherein alkyl and alkenyl are unsubstituted or mono-, di- or trisubstituted by F and O—(C0-C4)-alkylene-H;
R5 and R6 together with the nitrogen atom to which they are bonded (Y=N(R6)) can form a (C3-C15)-heterocycloalkyl, a (C3-C15)-heterocycloalkenyl or a (C5-C15)-heteroaryl which can contain additionally 1 to 3 heteroatoms N, O, S and which is unsubstituted or mono-, di- or trisubstituted by halogen, CN, CF3, (C1-C4)alkyl, (C0-C4)alkylene-(C3-C6)cycloalkyl, (C0-C4)alkylene-O—(C0-C4)alkylene-H, (C0-C4)alkylene-O—(C0-C4)alkylene-(C3-C6) cycloalkyl, (C0-C4)alkylene-O—(C0-C4)alkylene-(C6-C10)aryl, (C0-C4)alkylene-O—(C0-C4)alkylene-(C3-C15) heterocycloalkyl, (C0-C4)alkylene-O—(C0-C4)alkylene-(C3-C15) heterocycloalkenyl, (C0-C4)alkylene-O—(C0-C4)alkylene-(C5-C15) heteroaryl, (C0-C4)alkylene-S—(C1-C4)alkyl, (C0-C4) alkylene-SO—(C1-C4)alkyl, (C0-C4)alkylene-SO2-(C1-C4)alkyl, (C0-C4) alkylene-CO—(C1-C4)alkyl, (C0-C4)alkylene-CO—(C6-C10)aryl, (C0-C4) alkylene-CO—(C3-C15) heterocycloalkyl, (C0-C4)alkylene-CO—(C3-C15)heterocycloalkenyl, (C0-C4)alkylene-CO—(C5-C15) heteroaryl, (C0-C4) alkylene-CO—N((C0-C4)alkylene-H)—(C0-C4)alkylene-H, (C0-C4)alkylene-CO—N((C0-C4)alkylene-H)—(C0-C4)alkylene-(C3-C6)cycloalkyl, (C0-C4)alkylene-CO—N((C0-C4)alkylene-H)—(C0-C4)alkylene-(C6-C10)aryl, (C0-C4)alkylene-CO—N((C0-C4)alkylene-H)—(C0-C4)alkylene-(C3-C15)heterocycloalkyl, (C0-C4)alkylene-CO—N((C0-C4)alkylene-H)—(C0-C4)alkylene-(C3-C15)heterocycloalkenyl, (C0-C4)alkylene-CO—N((C0-C4)alkylene-H)—(C0-C4)alkylene-(C5-C15)heteroaryl, (C0-C4)alkylene-N((C0-C4)alkylene-H)—CO—(C1-C4)alkyl, (C0-C4)alkylene-N((C0-C4) alkylene-H)—CO—(C0-C4)alkylene-(C3-C6)cycloalkyl, (C0-C4)alkylene-N((C0-C4)alkylene-H)—CO—(C0-C4)alkylene-(C6-C10)aryl, (C0-C4)alkylene-N((C0-C4)alkylene-H)—CO—(C0-C4)alkylene-(C3-C15)heterocycloalkyl, (C0-C4)alkylene-N((C0-C4)alkylene-H)—CO—(C0-C4)alkylene-(C3-C15) heterocycloalkenyl, (C0-C4)alkylene-N((C0-C4)alkylene-H)—CO—(C0-C4)alkylene-(C5-C15) heteroaryl, (C0-C4)alkylene-(C6-C14)aryl and (C0-C4)alkylene-(C3-C15) heterocycloalkyl, (C0-C4)alkylene-(C3-C15) heterocycloalkenyl, (C0-C4)alkylene-(C5-C15) heteroaryl whereby heteroaryl, heterocycloalkyl and heterocycloalkenyl can mono- or disubstituted by oxo residue and where alkyl can be unsubstituted or mono-, di- or trisubstituted by F;
Z is a bond, (C1-C8)alkylene, (C2-C8)alkenylene, (C2-C8)alkylidene, (C1-C6)alkylene-O—(C1-C6)alkylene;
R7, R8 are independently selected from the group consisting of H, halogen, (C1-C8) alkyl, (C0-C4)alkylene-O—(C0-C4)alkylene-H, SCF3, SF5, S(O)2CF3, (C0-C4) alkylene-O—(C6-C12)aryl, (C0-C4)alkylene (C6-C12)aryl, NO2, wherein alkyl and alkylene are unsubstituted or mono-, di- or trisubstituted by F and aryl is unsubstituted or mono-, di- or trisubstituted by halogen, (C1-C4)alkyl or O—(C1-C4)alkyl.

Another embodiment according to the invention are compounds of the formula I, wherein
B is C(R4) and
R4 is H.

R1 is H, halogen, (C1-C8)alkyl, (C0-C4)alkylene-O—(C0-C4)alkylene-H, SCH3, CN, wherein alkyl and alkylene are unsubstituted or mono, bi- or trisubstituted by F;

R2, R3, R4 are independently
H, halogen, (C1-C8)alkyl, (C0-C4)alkylene-O—(C0-C4)alkylene-H, SCH3, CN, wherein alkyl and alkylene are unsubstituted or mono, bi- or trisubstituted by F;

X is O, S, S(O), S(O)2, O—CH2, S—CH2, CH2-O, CH2-S;

one of U and V is N the other is S or O;

W is a bond, (C1-C8)alkylene, (C2-C8)alkenylene, (C0-C6)alkylene-(C3-C6) cycloalkylene, (C3-C6)cycloalkylen-(C1-C6)alkylene, wherein alkylene and alkenylene and cycloalkylene are unsubstituted or mono-, di- or trisubstituted by OH and F;

Y is a bond, O, S, S(O), S(O)2 and

R5 is H, (C1-C8)alkyl, (C0-C4)alkylene-(C3-C13)cycloalkyl, (C0-C4)alkylene-(C6-C14) aryl, (C2-C8)alkenyl, (C0-C4)alkylene-(C3-C15) heterocycloalkyl, (C0-C4)alkylene-(C3-C15) heterocycloalkenyl, (C0-C4)alkylene-(C5-C15) heteroaryl, (C0-C4)alkylene-CO—(C1-C4)alkyl, (C0-C4)alkylene-CO—(C0-C4) alkylene-(C3-C13)cycloalkyl, (C0-C4)alkylene-CO—(C0-C4)alkylene-(C6-C10)aryl, (C0-C4)alkylene-CO—(C0-C4)alkylene-(C3-C15) heterocycloalkyl, (C0-C4)alkylene-CO—(C0-C4)alkylene-(C3-C15) heterocycloalkenyl, (C0-C4)alkylene-CO—(C0-C4)alkylene-(C5-C15) heteroaryl, SO2-(C1-C4)alkyl, SO2-(C0-C4)alkylene-(C3-C13)cycloalkyl, SO2-(C0-C4)alkylene-(C6-C10) aryl, SO2-(C0-C4)alkylene-(C3-C15) heterocycloalkyl, SO2-(C0-C4)alkylene-(C3-C15)heterocycloalkenyl, SO2-(C0-C4)alkylene-(C5-C15)heteroaryl, CO—O—(C0-C4)alkylene-(C6-C10) aryl, CO—O—(C1-C4)alkyl, CO—O—(C0-C4)alkylene-(C3-C13)cycloalkyl, CO—O—(C0-C4)alkylene-(C3-C15)heterocycloalkyl, CO—O—(C0-C4)alkylene-(C3-C15)heterocycloalkenyl, CO—O—(C0-C4)alkylene-(C5-C15)heteroaryl, CO—N((C0-C4)alkylene-H)—(C0-C4)alkylene-(C6-C10) aryl, CO—N((C0-C4)alkylene-H)—(C0-C4)alkylene-H, CO—N((C0-C4)alkylene-H)—(C0-C4) alkylene-(C3-C13)cycloalkyl, CO—N((C0-C4)alkylene-H)—(C0-C4)alkylene-(C3-C15)heterocycloalkyl, CO—N((C0-C4)alkylene-H)—(C0-C4)alkylene-(C3-C15)heterocycloalkenyl, CO—N((C0-C4)alkylene-H)—(C0-C4)alkylene-(C5-C15)heteroaryl, SO2-N((C0-C4)alkylene-H)—(C0-C4)alkylene-(C6-C10)aryl, SO2-N((C0-C4)alkylene-H)—(C0-C4)alkylene-H, SO2-N((C0-C4) alkylene-H)—(C0-C4)alkylene-(C3-C13)cycloalkyl, SO2-N((C0-C4)alkylene-H)—(C0-C4)alkylene-(C3-C15)heterocycloalkyl, SO2-N((C0-C4)alkylene-H)—(C0-C4)alkylene-(C3-C15)heterocycloalkenyl, SO2-N((C0-C4)alkylene-H)—(C0-C4)alkylene-(C5-C15)heteroaryl wherein alkyl and alkylene are unsubstituted or mono-, di- or trisubstituted by F, S—(C1-C4)alkyl, SO—(C1-C4)alkyl, SO2-(C1-C4)alkyl, CO—N((C0-C4)alkylene-H)—(C0-C4)alkylene-H, N((C0-C4)alkylene-H)—(C0-C4)alkylene-H, CO—O (C1-C4)alkyl, (C1-C4) alkyl and O—(C0-C4)alkylene-H and wherein cycloalkyl, aryl and heterocycloalkyl, heterocycloalkenyl and heteroaryl are unsubstituted or mono-, di- or trisubstituted by F, Cl, Br, CF3, (C1-C4)alkyl and (C0-C4)-alkylen-O—(C0-C4)alkylene-H;

with the proviso that, if Y is S, S(O) or S(O)2 then

R5 is unequal SO2-(C1-C4)alkyl, SO2-(C0-C4)alkylene-(C3-C13)cycloalkyl, SO2-(C0-C4)alkylene-(C6C10) aryl, SO2-(C0-C4)alkylene-(C3-C15)heterocycloalkyl, SO2-(C0-C4)alkylene-(C3-C15)heterocycloalkenyl, SO2-(C0-C4)alkylene-(C5-C15)heteroaryl, SO2-N((C0-C4)alkylene-H)—(C0-C4)alkylene-(C6-C10) aryl, SO2-N((C0-C4)alkylene-H)—(C0-C4)alkylene-H, SO2-N((C0-C4)alkylene-H)—(C0-C4)alkylene-(C3-C13)cycloalkyl, SO2-N((C0-C4)alkylene-H)—(C0-C4)alkylene-(C3-C15)heterocycloalkyl, SO2-N((C0-C4)alkylene-H)—(C0-C4)alkylene-(C3-C15)heterocycloalkenyl, SO2-N((C0-C4)alkylene-H)—(C0-C4)alkylene-(C5-C15)heteroaryl;

with the proviso that, if Y is a bond or O then

Z is unequal a bond;

or

Y is a bond, with the proviso that

R5 is CN, (C1-C8)alkyl mono-, di- or trisubstituted by F, CO—(C1-C4)alkyl, CO—N((C0-C4)alkylene-H)—(C0-C4)alkylene-H, SO2-N((C0-C4)alkylene-H)—(C0-C4)alkylene-H, N((C0-C4)alkylene-H)—CO—(C0-C4)alkylene-H, (C1-C6)alkylene-(C3-C13)cycloalkyl, (C3-C15) heterocycloalkyl, (C3-C15) heterocycloalkenyl, (C5-C15) heteroaryl;

or

Y is O, with the proviso that

R5 is (C1-C8)alkyl mono-, di- or trisubstituted by F, CO—(C1-C4) alkyl, CO—O—(C0-C4)alkylene-(C6-C10) aryl, CO—O—(C0-C4) alkylene-(C3-C13)cycloalkyl, CO—O—(C0-C4)alkylene-(C3-C15)heterocycloalkyl, CO—O—(C0-C4)alkylene-(C3-C15)heterocycloalkenyl, CO—O—(C0-C4)alkylene-(C5-C15)heteroaryl, CO—N((C0-C4)alkylene-H)—(C0-C4)alkylene-H, CO—N((C0-C4)alkylene-H)—(C0-C4)alkylene-(C6-C10) aryl, CO—N((C0-C4)alkylene-H)—(C0-C4)alkylene-(C3-C13)cycloalkyl, CO—N((C0-C4)alkylene-H)—(C0-C4)alkylene-(C3-C15)heterocycloalkyl, CO—N((C0-C4)alkylene-H)—(C0-C4) alkylene-(C3-C13)cycloalkyl, CO—N((C0-C4)alkylene-H)—(C0-C4)alkylene-(C3-C15)heterocycloalkenyl, CO—N((C0-C4)alkylene-H)—(C0-C4)alkylene-(C3-C13) cycloalkyl, CO—N((C0-C4)alkylene-H)—(C0-C4)alkylene-(C5-C15)heteroaryl, (C0-C4) alkylene-(C3-C13) cycloalkyl, (C0-C4)alkylene-(C3-C15) heterocycloalkyl, (C0-C4)alkylene-(C3-C15) heterocycloalkenyl, (C0-C4)alkylene-(C5-C15) heteroaryl, (C0-C4)alkylene-N((C0-C4) alkylene-H)—(C0-C4)alkylene-H, (C0-C4)alkylene-N((C0-C4) alkylene-H)—(C0-C4)alkylene-(C3-C13)cycloalkyl, (C0-C4)alkylene-N((C0-C4)alkylene-H)—(C0-C4)alkylene-(C6-C10)aryl, (C0-C4)alkylene-N((C0-C4)alkylene-H)—(C0-C4)alkylene-(C3-C15)heterocycloalkyl, (C0-C4)alkylene-N((C0-C4)alkylene-H)—(C0-C4)alkylene-(C3-C15)heterocycloalkenyl, (C0-C4)alkylene-N((C0-C4)alkylene-H)—(C0-C4)alkylene-(C5-C15)heteroaryl;

Z is a bond, (C1-C8)alkylene, (C2-C8)alkenylene, (C2-C8)alkylidene, (C1-C6)alkylene-O—(C1-C6)alkylene;

R7, R8 are independently selected from the group consisting of H, halogen, (C1-C8) alkyl, (C0-C4)alkylene-O—(C0-C4)alkylene-H, SCF3, SF5, S(O)2CF3, (C0-C4) alkylene-O—(C6-C12)aryl, (C0-C4)alkylene (C6-C12)aryl, NO2, wherein alkyl and alkylene are unsubstituted or mono-, di- or trisubstituted by F and aryl is unsubstituted or mono-, di- or trisubstituted by halogen, (C1-C4)alkyl or O—(C1-C4) alkyl.

Another embodiment according to the invention are compounds of the formula I wherein R1 is halogen, (C1-C4)alkyl, (C0-C4)alkylene-O—(C0-C2) alkylene-H, O—(C0-C2) alkylene-(C3-C6)cycloalkyl, wherein alkyl and alkylene are unsubstituted or mono, di- or trisubstituted by F.

Another embodiment according to the invention are compounds of the formula I wherein W is (C1-C3)alkylene;

Y is N(R6) and

R5 and R6 together with the nitrogen atom to which they are bonded (Y=N(R6)) form a (C3-C7)-heterocycloalkyl, a (C4-C7)-heterocycloalkenyl or a (C5-C8)-heteroaryl which can contain additionally 1 to 2 heteroatoms N, O, S and which is unsubstituted or mono- or disubstituted by F, CF3, (C1-C3)alkyl, (C0-C3)alkylene-O—(C0-C3)alkylene-H, SO2-(C1-C3)alkyl, CO—(C1-C3) alkyl, CO—NH2, NH—CO—(C1-C3)alkyl, phenyl, (C5-C6) heteroaryl, (C3-C7) heterocycloalkyl and (C4-C7)heterocycloalkenyl, whereby heterocycloalkyl, heterocycloalkenyl and heteroaryl can be mono- or disubstituted by oxo residue Another embodiment according to the invention are compounds of the formula I wherein W is (C1-C3) alkylene;

Y is N(R6) and

R5 is H, (C1-C4)alkyl, (C0-C3)alkylene-(C3-C7)cycloalkyl, (C0-C3) alkylene-phenyl, (C0-C3)alkylene-(C3-C7) heterocycloalkyl, (C0-C4)alkylene-(C4-C7) heterocycloalkenyl, (C0-C3)alkylene-(C5-C6) heteroaryl, CO—(C0-C3)alkyl, CO—O-phenyl, wherein alkyl and alkylene can be mono-, di- or trisubstituted by F, S—(C1-C3)alkyl, SO—(C1-C3)alkyl, SO2-(C1-C3)alkyl, N((C0-C3)alkylene-H)—(C0-C3) alkylene-H, CO—O(C1-C3)alkyl and O—(C0-C3) alkylene-H and wherein cycloalkyl, phenyl, heterocycloalkyl, heterocycloalkenyl and heteroaryl are mono-, di- or trisubstituted by F and (C0-C4)-alkylen-O—(C0-C4)alkylene-H;

R6 is H, (C1-C3)alkyl or (C0-C3)alkylene-(C3-C6)cycloalkyl, wherein alkyl is unsubstituted or mono-, di- or trisubstituted by O—(C0-C4)-alkylene-H; or Y is S, S(O), S(O)2 and R5 is (C1-C3)alkyl or (C0-C3)alkylene-(C3-C6)cycloalkyl, wherein alkyl is unsubstituted or mono-, di- or trisubstituted by F; or Y is O and R5 is (C1-C4)alkyl mono-, di- or trisubstituted by F, CO—(C1-C3)alkyl, (C0-C3) alkylene-(C3-C6)cycloalkyl, (C0-C3)alkylene-(C3-C7)heterocycloalkyl, (C0-C3)alkylene-(C5-C8)heteroaryl; or Z is —CH2-, —CH2-CH2-, —CH2-O—CH2-, —CH=CH—.

Another embodiment according to the invention are compounds of the formula I wherein R1 is F, Cl, (C1-C4)alkyl, O—(C1-C4)alkyl, wherein alkyl and alkylene are unsubstituted or mono-, bi- or trisubstituted by F;

Another embodiment according to the invention are compounds of the formula I wherein R1 is F, Cl, CH3 or OCH3.

Another embodiment according to the invention are compounds of the formula I wherein V is N and U is O; or V is N and U is S.

Another embodiment according to the invention are compounds of the formula I wherein X is O or O—CH2.

Another embodiment according to the invention are compounds of the formula I wherein X is O.

Another embodiment according to the invention are compounds of the formula I wherein X is OCH2.

Another embodiment according to the invention are compounds of the formula I wherein W is a bond or —CH2-.

Another embodiment according to the invention are compounds of the formula I wherein R7 is in para-position.

Another embodiment according to the invention are compounds of the formula I wherein R8 is H.

Another embodiment according to the invention are compounds of the formula I wherein R1 is F or OCH3.

Another embodiment according to the invention are compounds of the formula I wherein R1 is Cl or CH3.

Another embodiment according to the invention are compounds of the formula I wherein R1 is Cl.

Another embodiment according to the invention are compounds of the formula I wherein R1 is halogen, (C1-C4)alkyl, (C0-C4)alkylene-O—(C0-C2) alkylene-H, O—(C0-C2) alkylene-(C3-C6)cycloalkyl, wherein alkyl and alkylene are unsubstituted or mono, di- or trisubstituted by F;

W is (C1-C3)alkylene;

Y is N(R6) and

R5 and R6 together with the nitrogen atom to which they are bonded (Y=N(R6)) form a (C3-C7)-heterocycloalkyl, a (C4-C7)-heterocycloalkenyl or a (C5-C8)-heteroaryl which can contain additionally 1 to 2 heteroatoms N, O, S and which is unsubstituted or mono- or disubstituted by F, CF3, (C1-C3)alkyl, (C0-C3)alkylene-O—(C0-C3)alkylene-H, SO2-(C1-C3)alkyl, CO—(C1-C3) alkyl, CO—NH2, NH—CO—(C1-C3)alkyl, phenyl, (C5-C6) heteroaryl, (C3-C7) heterocycloalkyl and (C4-C7)heterocycloalkenyl, whereby heterocycloalkyl, heterocycloalkenyl and heteroaryl can be mono- or disubstituted by oxo residue;

Another embodiment according to the invention are compounds of the formula I wherein R1 is halogen, (C1-C4)alkyl, (C0-C4)alkylene-O—(C0-C2) alkylene-H, O—(C0-C2) alkylene-(C3-C6)cycloalkyl, wherein alkyl and alkylene are unsubstituted or mono, di- or trisubstituted by F;

W is (C1-C3)alkylene;

Y is N(R6) and

R5 is H, (C1-C4)alkyl, (C0-C3)alkylene-(C3-C7)cycloalkyl, (C0-C3) alkylene-phenyl, (C0-C3)alkylene-(C3-C7) heterocycloalkyl, (C0-C4)alkylene-(C4-C7) heterocycloalkenyl, (C0-C3)alkylene-(C5-C6) heteroaryl, CO—(C0-C3)alkyl, CO—O-phenyl, wherein alkyl and alkylene can be mono-, di- or trisubstituted by F, S—(C1-C3)alkyl, SO—(C1-C3)alkyl, SO2-(C1-C3)alkyl, N((C0-C3)alkylene-H)—(C0-C3) alkylene-H, CO—O((C1-C3)alkyl and O—(C0-C3) alkylene-H and wherein cycloalkyl, phenyl, heterocycloalkyl, heterocycloalkenyl and heteroaryl are mono-, di- or trisubstituted by F and (C0-C4)-alkylen-O—(C0-C4)alkylene-H;

R6 is H, (C1-C3)alkyl or (C0-C3)alkylene-(C3-C6)cycloalkyl, wherein alkyl is unsubstituted or mono-, di- or trisubstituted by O—(C0-C4)-alkylene-H;

Y is S, S(O), S(O)2 and
R5 is (C1-C3)alkyl or (C0-C3)alkylene-(C3-C6)cycloalkyl, wherein alkyl is unsubstituted or mono-, di- or trisubstituted by F;

Y is O and
R5 is (C1-C4)alkyl mono-, di- or trisubstituted by F, CO—(C1-C3)alkyl, (C0-C3) alkylene-(C3-C6)cycloalkyl, (C0-C3)alkylene-(C3-C7)heterocycloalkyl, (C0-C3)alkylene-(C5-C8)heteroaryl; or Z is —CH2-, —CH2-CH2-, —CH2-O—CH2-, —CH═CH—.

Another embodiment according to the invention are compounds of the formula I wherein R1 is halogen, (C1-C4)alkyl, (C0-C4)alkylene-O—(C0-C2)alkylene-H, O—(C0-C2) alkylene-(C3-C6)cycloalkyl, wherein alkyl and alkylene are unsubstituted or mono, di- or trisubstituted by F;

W is (C1-C3)alkylene;
Y is N(R6) and
R5 and R6 together with the nitrogen atom to which they are bonded (Y=N(R6)) form a (C3-C7)-heterocycloalkyl, a (C4-C7)-heterocycloalkenyl or a (C5-C8)-heteroaryl which can contain additionally 1 to 2 heteroatoms N, O, S and which is unsubstituted or mono- or disubstituted by F, CF3, (C1-C3)alkyl, (C0-C3)alkylene-O—(C0-C3)alkylene-H, SO2-(C1-C3)alkyl, CO—(C1-C3) alkyl, CO—NH2, NH—CO—(C1-C3)alkyl, phenyl, (C5-C6) heteroaryl, (C3-C7) heterocycloalkyl and (C4-C7)heterocycloalkenyl, whereby heterocycloalkyl, heterocycloalkenyl and heteroaryl can be mono- or disubstituted by oxo residue;

W is (C1-C3)alkylene;
Y is N(R6) and
R5 is H, (C1-C4)alkyl, (C0-C3)alkylene-(C3-C7)cycloalkyl, (C0-C3) alkylene-phenyl, (C0-C3)alkylene-(C3-C7) heterocycloalkyl, (C0-C4)alkylene-(C4-C7) heterocycloalkenyl, (C0-C3)alkylene-(C5-C6) heteroaryl, CO—(C0-C3)alkyl, CO—O-phenyl, wherein alkyl and alkylene can be mono-, di- or trisubstituted by F, S—(C1-C3)alkyl, SO—(C1-C3)alkyl, SO2-(C1-C3)alkyl, N((C0-C3)alkylene-H)—(C0-C3) alkylene-H, CO—O(C1-C3)alkyl and O—(C0-C3)alkylene-H and wherein cycloalkyl, phenyl, heterocycloalkyl, heterocycloalkenyl and heteroaryl are mono-, di- or trisubstituted by F and (C0-C4)-alkylen-O—(C0-C4)alkylene-H;

R6 is H, (C1-C3)alkyl or (C0-C3)alkylene-(C3-C6)cycloalkyl, wherein alkyl is unsubstituted or mono-, di- or trisubstituted by O—(C0-C4)-alkylene-H;

Y is S, S(O), S(O)2 and
R5 is (C1-C3)alkyl or (C0-C3)alkylene-(C3-C6)cycloalkyl, wherein alkyl is unsubstituted or mono-, di- or trisubstituted by F;

Y is O and
R5 is (C1-C4)alkyl mono-, di- or trisubstituted by F, CO—(C1-C3)alkyl, (C0-C3) alkylene-(C3-C6)cycloalkyl, (C0-C3)alkylene-(C3-C7)heterocycloalkyl, (C0-C3)alkylene-(C5-C8)heteroaryl; or Z is —CH2-, —CH2-CH2-, —CH2-O—CH2-, —CH═CH—.

Another embodiment according to the invention are compounds of the formula I where one or more substituents have the following meaning:

B is C(R4) and
R4 is H.
R1 is halogen, (C1-C8)alkyl, (C0-C4)alkylene-O—(C1-C4) alkylene-H, (C0-C2) alkylene-O—(C0-C2)alkylene-(C3-C6)cycloalkyl, wherein alkyl and alkylene are unsubstituted or mono, bi- or trisubstituted by F;
R2 is H;
R3 is H, F, Br;
R4 is H;
X is O, O—CH2;
U is S, O and
V is N
Or
U is N and
V is O;
W is a bond, (C1-C4)alkylene;
Y is N(R6) and
R5 is selected from the group consisting of (C1-C8)alkyl, (C0-C4) alkylene-(C3-C13)cycloalkyl, (C0-C4)alkylene-(C6-C12)aryl, (C0-C4)alkylene-(C3-C15) heterocycloalkyl, (C0-C4)alkylene-(C3-C15)heterocycloalkenyl, (C0-C4)alkylene-(C5-C15) heteroaryl, CO—(C0-C4)alkyl, CO—O—(C6-C10) aryl, wherein alkyl and alkylene can be mono-, di- or trisubstituted by F, S—(C1-C4) alkyl, SO—(C1-C4)alkyl, N((C0-C4)alkylene-H)—(C0-C4) alkylene-H, CO—O(C1-C4)alkyl and O—(C0-C4)alkylene-H and wherein cycloalkyl, aryl, heterocycloalkyl, heterocycloalkenyl and heteroaryl are mono-, di- or trisubstituted by F and (C0-C4)-alkylene-O—(C0-C4)alkylene-H;

Y is a bond and
R5 is (C1-C6)alkyl mono-, di- or trisubstituted by F;
Y is O and
R5 is (C1-C8)alkyl mono-, di- or trisubstituted by F, CO—(C1-C4) alkyl, (C0-C4)alkylene-(C3-C6)cycloalkyl, (C0-C4)alkylene-(C3-C15) heterocycloalkyl, (C0-C4)alkylene-(C3-C15) heterocycloalkenyl, (C0-C4)alkylene-(C5-C15)heteroaryl; or Z is —CH2-, —CH2-CH2-, —CH2-O—CH2-, —CH═CH—.

R6 is H, (C1-C8)alkyl or (C0-C4)alkylene-(C3-C6)cycloalkyl, wherein alkyl is unsubstituted or mono-, di- or trisubstituted by O—(C0-C4)-alkylene-H;

R5 and R6 together with the nitrogen atom to which they are bonded (Y=N(R6)) can form a (C3-C8)-heterocycloalkyl, a (C3-C10)-heterocycloalkenyl or a (C5-C8)-heteroaryl which can contain additionally 1 to 3 heteroatoms N, O, S and which is unsubstituted or mono-, di- or trisubstituted by F, CF3, (C1-C4) alkyl, (C0-C4)alkylene-O—(C0-C4) alkylene-H, SO2-(C1-C4)alkyl, CO—(C1-C4)alkyl, CO—NH2, NH—CO—(C1-C4)alkyl, phenyl, (C5-C6) heteroaryl, (C3-C7)heterocycloalkyl and (C3-C7)heterocycloalkenyl, whereby heterocycloalkyl, heterocycloalkenyl and heteroaryl can mono- or disubstituted by oxo residue;

Z is a bond, (C1-C2)alkylene, (C2) alkenylene, (C1-C2)alkylene-O—(C1-C2) alkylene;
R7 is H, O—(C1-C4)alkyl, CF3;
R8 is H.

Another embodiment according to the invention are compounds of the formula I where one or more substituents have the following meaning:
B is C(R4) and
R4 is H.

R1 is F, Cl, (C1-C4)alkyl, (C0-C4)alkylene-O—(C1-C4)alkylene-H, (C0-C2) alkylene-O—(C0-C2)alkylene-(C3-C6)cycloalkyl, wherein alkyl and alkylene are unsubstituted or mono, bi- or trisubstituted by F;
R2 is H;
R3 is H, F, Br;
R4 is H;
X is O, O—CH2;
U is S, O and
V is N Or U is N and
V is O;
W is a bond, (C1-C4)alkylene;
Y is N(R6) and
  R5 is selected from the group consisting of (C1-C8)alkyl, (C0-C4) alkylene-(C3-C13) cycloalkyl, (C0-C4)alkylene-(C6-C12) aryl, (C0-C4)alkylene-(C3-C15) heterocycloalkyl, CO—(C0-C4)alkyl, CO—O—(C6-C10) aryl, wherein alkyl and alkylene can be mono-, di- or trisubstituted by S—(C1-C4)alkyl, SO—(C1-C4)alkyl, N((C0-C4)alkylene-H)—(C0-C4)alkylene-H and O—(C0-C4)alkylene-H and wherein aryl and heterocycloalkyl are mono-, di- or trisubstituted by F and (C0-C4)-alkylene-O—(C0-C4)alkylene-H;
Y is O and
  R5 is (C1-C8)alkyl mono-, di- or trisubstituted by F, CO—(C1-C4) alkyl, (C0-C4)alkylene-(C3-C6)cycloalkyl; or
  Z is —CH2-, —CH2-CH2-, —CH2-O—CH2-, —CH=CH—.
Y is S, S(O), S(O)2 and
  R5 is (C1-C3)alkyl;
R6 is H, (C1-C8)alkyl or (C0-C4)alkylene-(C3-C6)cycloalkyl, wherein alkyl is unsubstituted or mono-, di- or trisubstituted by O—(C0-C4)-alkylene-H;
R5 and R6 together with the nitrogen atom to which they are bonded (Y=N(R6)) can form a (C3-C8)-heterocycloalkyl or a (C3-C10)-heterocycloalkenyl which can contain additionally 1 to 3 heteroatoms N, O, S and which is unsubstituted or mono-, di- or trisubstituted by F, CF3, (C1-C4) alkyl, (C0-C4)alkylene-O—(C0-C4)alkylene-H, SO2-(C1-C4)alkyl, CO—(C1-C4)alkyl, whereby heterocycloalkyl can mono- or disubstituted by oxo residue;
Z is a bond, (C1-C2)alkylene, (C2) alkenylene, (C1-C2)alkylene-O—(C1-C2) alkylene;
R7 is H, O—(C1-C4)alkyl, CF3;
R8 is H.

Another embodiment according to the invention are compounds of the formula I where one or more substituents have the following meaning:
R1 is halogen, (C1-C4)alkyl, OH, O—(C1-C3)alkyl, wherein alkyl is unsubstituted or mono, di- or trisubstituted by F;
R2 is H;
R3 is H, F;
B is C(R4) or N, and
R4 is H;
X is O;
one of U and V is N the other is S or O;
W is (C1-C3)alkylene;
Y is N(R6) and
R5 and R6 together with the nitrogen atom to which they are bonded (Y=N(R6)) form a (C3-C7)-heterocycloalkyl, a (C4-C7)-heterocycloalkenyl or a (C5-C8)-heteroaryl which can contain additionally 1 to 2 heteroatoms N, O, S and which is unsubstituted or mono- or disubstituted by F, CF3, (C1-C3)alkyl, (C0-C3)alkylene-O—(C0-C3)alkylene-H, SO2-(C1-C3)alkyl, CO—(C1-C3) alkyl, CO—NH2, NH—CO—(C1-C3)alkyl, phenyl, (C5-C6) heteroaryl, (C3-C7) heterocycloalkyl and (C4-C7)heterocycloalkenyl, whereby heterocycloalkyl, heterocycloalkenyl and heteroaryl can be mono- or disubstituted by oxo residue;
Y is N(R6) and
  R5 is H, (C1-C4)alkyl, (C0-C3)alkylene-(C3-C7)cycloalkyl, (C0-C3) alkylene-phenyl, (C0-C3)alkylene-(C3-C7) heterocycloalkyl, (C0-C4)alkylene-(C4-C7) heterocycloalkenyl, (C0-C3)alkylene-(C5-C6) heteroaryl, CO—(C0-C3)alkyl, CO—O-phenyl, wherein alkyl and alkylene can be mono-, di- or trisubstituted by F, S—(C1-C3)alkyl, SO—(C1-C3)alkyl, SO2-(C1-C3)alkyl, N((C0-C3)alkylene-H)—(C0-C3)alkylene-H, CO—O(C1-C3)alkyl and O—(C0-C3)alkylene-H and wherein cycloalkyl, phenyl, heterocycloalkyl, heterocycloalkenyl and heteroaryl are mono-, di- or trisubstituted by F and (C0-C4)-alkylen-O—(C0-C4)alkylene-H;
R6 is H, (C1-C3)alkyl or (C0-C3)alkylene-(C3-C6)cycloalkyl, wherein alkyl is unsubstituted or mono-, di- or trisubstituted by O—(C0-C4)-alkylene-H;
Y is S, S(O), S(O)2 and
  R5 is (C1-C3)alkyl or (C0-C3)alkylene-(C3-C6)cycloalkyl, wherein alkyl is unsubstituted or mono-, di- or trisubstituted by F;
Y is O and
  R5 is (C1-C4)alkyl mono-, di- or trisubstituted by F, CO—(C1-C3) alkyl, (C0-C3) alkylene-(C3-C6)cycloalkyl, (C0-C3)alkylene-(C3-C7)heterocycloalkyl, (C0-C3)alkylene-(C5-C8)heteroaryl; or
  Z is —CH2-, —CH2-CH2-, —CH2-O—CH2-, —CH=CH—.
Z is a bond, (C1-C2)alkylene, (C2) alkenylene, (C1-C2)alkylene-O—(C1-C2) alkylene;
R7 is H, halogen, (C1-C3)alkyl, O—(C1-C3)alkyl, wherein alkyl is unsubstituted or mono-, di- or trisubstituted by F;
R8 is H.

Another embodiment according to the invention are compounds of the formula I where one or more substituents have the following meaning:
R1 is F, OH, OCH3, OCHF2, OCH2CF3;
R2 is H;
R3 is H, F;
B is C(R4) or N, and
R4 is H;
X is O;
one of U and V is N the other is S or O;
W is CH2, CH2CH2CH2;
Y is N(R6) and
R5 and R6 together with the nitrogen atom to which they are bonded (Y=N(R6)) form a piperidine, pyrrolidine, azetidine, azepine, morpholine, thiomorpholine, thiomorpholine-5-oxide, thiomorpholine-5-dioxide, piperazine, piperazinone, iso-indoline, which is unsubstituted or mono- or disubstituted by F, CF3, (C1-C3)alkyl, O—(C1-C3)alkyl, OH, CH2OH, SO2CH3, COCH3, phenyl;
Y is S, S(O), S(O)2 and
  R5 is CH3;
Z is a bond;
R7 is CF3;
R8 is H.

Another embodiment according to the invention are compounds of the formula I where one or more substituents have the following meaning:

R1 is H, F, Cl;
R2 is H;
R3 is H;
B is C(R4) or N, and
R4 is H;
X is O;
U is S, O and
V is N;
W is CH2;
Y is a bond or O;
X is a bond;
R5 is (C1-C6)alkyl mono-, di- or trisubstituted by F;
R7 is in para-position and (C1-C4)alkyl, (C0-C4)alkylen-O—(C0-C4)alkylen-H, SF5, (C0-C4)alkylen-O-phenyl, wherein alkyl, alkylen and phenyl are mono-, di- or trisubstituted by F;
R8 is H.

Most preferred compounds are:

3-{2-Methoxy-4-[2-(4-trifluoromethyl-phenyl)-4-(4-trifluoromethyl-piperidin-1-ylmethyl)-thiazol-5-ylmethoxy]-phenyl}-4H-[1,2,4]oxadiazol-5-one
3-{2-Chloro-4-[4-morpholin-4-ylmethyl-2-(4-trifluoromethyl-phenyl)-thiazol-5-ylmethoxy]-phenyl}-4H-[1,2,4]oxadiazol-5-one
3-{2-Methoxy-4-[4-morpholin-4-ylmethyl-2-(4-trifluoromethyl-phenyl)-thiazol-5-ylmethoxy]-phenyl}-4H-[1,2,4]oxadiazol-5-one
3-{4-[4-(4,4-Difluoro-piperidin-1-ylmethyl)-2-(4-trifluoromethyl-phenyl)-thiazol-5-ylmethoxy]-2-methoxy-phenyl}-4H-[1,2,4]oxadiazol-5-one
3-{2-Methoxy-4-[4-(4-methyl-piperazin-1-ylmethyl)-2-(4-trifluoromethyl-phenyl)-thiazol-5-ylmethoxy]-phenyl}-4H-[1,2,4]oxadiazol-5-one
3-{2-Methoxy-4-[4-pyrrolidin-1-ylmethyl-2-(4-trifluoromethyl-phenyl)-thiazol-5-ylmethoxy]-phenyl}-4H-[1,2,4]oxadiazol-5-one
3-{4-[4-(4-Fluoro-piperidin-1-ylmethyl)-2-(4-trifluoromethyl-phenyl)-thiazol-5-ylmethoxy]-2-methoxy-phenyl}-4H-[1,2,4]oxadiazol-5-one
3-{4-[4-Diethylaminomethyl-2-(4-trifluoromethyl-phenyl)-thiazol-5-ylmethoxy]-2-methoxy-phenyl}-4H-[1,2,4]oxadiazol-5-one
3-{2-Methoxy-4-[2-(4-trifluoromethyl-phenyl)-4-(3-trifluoromethyl-pyrrolidin-1-ylmethyl)-thiazol-5-ylmethoxy]-phenyl}-4H-[1,2,4]oxadiazol-5-one
3-{4-[4-{[Ethyl-(2-methoxy-ethyl)-amino]-methyl}-2-(4-trifluoromethyl-phenyl)-thiazol-5-ylmethoxy]-2-methoxy-phenyl}-4H-[1,2,4]oxadiazol-5-one
3-{4-[4-[([1,4]Dioxan-2-ylmethyl-methyl-amino)-methyl]-2-(4-trifluoromethyl-phenyl)-thiazol-5-ylmethoxy]-2-methoxy-phenyl}-4H-[1,2,4]oxadiazol-5-one
3-{2-Methoxy-4-[4-(4-methoxy-piperidin-1-ylmethyl)-2-(4-trifluoromethyl-phenyl)-thiazol-5-ylmethoxy]-phenyl}-4H-[1,2,4]oxadiazol-5-one
3-{4-[4-(4-Ethyl-piperazin-1-ylmethyl)-2-(4-trifluoromethyl-phenyl)-thiazol-5-ylmethoxy]-2-methoxy-phenyl}-4H-[1,2,4]oxadiazol-5-one
Cyclopropyl-[5-[3-methoxy-4-(5-oxo-4,5-dihydro-[1,2,4]oxadiazol-3-yl)-phenoxymethyl]-2-(4-trifluoromethyl-phenyl)-thiazol-4-ylmethyl]-carbamic acid phenyl ester
3-{4-[4-Cyclopropylaminomethyl-2-(4-trifluoromethyl-phenyl)-thiazol-5-ylmethoxy]-2-methoxy-phenyl}-4H-[1,2,4]oxadiazol-5-one
3-{4-[4-(3-Azetidin-1-yl-propyl)-2-(4-trifluoromethyl-phenyl)-thiazol-5-ylmethoxy]-2-methoxy-phenyl}-4H-[1,2,4]oxadiazol-5-one
3-{2-Fluoro-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one
3-{4-[4-(4,4-Difluoro-piperidin-1-ylmethyl)-2-(4-trifluoromethyl-phenyl)-thiazol-5-ylmethoxy]-2-fluoro-phenyl}-4H-[1,2,4]oxadiazol-5-one
3-{2-Fluoro-4-[4-{[(2-hydroxy-ethyl)-methyl-amino]-methyl}-2-(4-trifluoromethyl-phenyl)-thiazol-5-ylmethoxy]-phenyl}-4H-[1,2,4]oxadiazol-5-one
3-{2-Fluoro-4-[4-(4-methyl-piperazin-1-ylmethyl)-2-(4-trifluoromethyl-phenyl)-thiazol-5-ylmethoxy]-phenyl}-4H-[1,2,4]oxadiazol-5-one
3-{2-Fluoro-4-[4-morpholin-4-ylmethyl-2-(4-trifluoromethyl-phenyl)-thiazol-5-ylmethoxy]-phenyl}-4H-[1,2,4]oxadiazol-5-one
3-{4-[4-(1,3-Dihydro-isoindol-2-ylmethyl)-2-(4-trifluoromethyl-phenyl)-thiazol-5-ylmethoxy]-2-fluoro-phenyl}-4H-[1,2,4]oxadiazol-5-one
3-{2-Fluoro-4-[4-[(4-fluoro-benzylamino)-methyl]-2-(4-trifluoromethyl-phenyl)-thiazol-5-ylmethoxy]-phenyl}-4H-[1,2,4]oxadiazol-5-one
3-{2-Fluoro-4-[4-(2-hydroxymethyl-pyrrolidin-1-ylmethyl)-2-(4-trifluoromethyl-phenyl)-thiazol-5-ylmethoxy]-phenyl}-4H-[1,2,4]oxadiazol-5-one
3-{2-Fluoro-4-[4-{[(furan-2-ylmethyl)-amino]-methyl}-2-(4-trifluoromethyl-phenyl)-thiazol-5-ylmethoxy]-phenyl}-4H-[1,2,4]oxadiazol-5-one
3-{2-Fluoro-4-[4-[(3-methylsulfanyl-propylamino)-methyl]-2-(4-trifluoromethyl-phenyl)-thiazol-5-ylmethoxy]-phenyl}-4H-[1,2,4]oxadiazol-5-one
4-[5-[3-Fluoro-4-(5-oxo-4,5-dihydro-[1,2,4]oxadiazol-3-yl)-phenoxymethyl]-2-(4-trifluoromethyl-phenyl)-thiazol-4-ylmethyl]-piperazin-2-one
3-{2-Fluoro-4-[4-[(4-methoxy-benzylamino)-methyl]-2-(4-trifluoromethyl-phenyl)-thiazol-5-ylmethoxy]-phenyl}-4H-[1,2,4]oxadiazol-5-one
3-{4-[4-[(1R,4R)-1-(2,5-Diaza-bicyclo[2.2.1]hept-2-yl)methyl]-2-(4-trifluoromethyl-phenyl)-thiazol-5-ylmethoxy]-2-fluoro-phenyl}-4H-[1,2,4]oxadiazol-5-one
3-{2-Fluoro-4-[4-(3-hydroxymethyl-piperidin-1-ylmethyl)-2-(4-trifluoromethyl-phenyl)-thiazol-5-ylmethoxy]-phenyl}-4H-[1,2,4]oxadiazol-5-one
3-{5-Bromo-2-methoxy-4-[4-piperidin-1-ylmethyl-2-(4-trifluoromethyl-phenyl)-thiazol-5-ylmethoxy]-phenyl}-4H-[1,2,4]oxadiazol-5-one
3-{5-Fluoro-2-methoxy-4-[2-(4-trifluoromethyl-phenyl)-4-(4-trifluoromethyl-piperidin-1-ylmethyl)-thiazol-5-ylmethoxy]-phenyl}-4H-[1,2,4]oxadiazol-5-one
Acetic acid 5-[3-fluoro-4-(5-oxo-4,5-dihydro-[1,2,4]oxadiazol-3-yl)-phenoxymethyl]-2-(4-trifluoromethyl-phenyl)-thiazol-4-ylmethyl ester
Acetic acid 5-[3-methoxy-4-(5-oxo-4,5-dihydro-[1,2,4]oxadiazol-3-yl)-phenoxymethyl]-2-(4-trifluoromethyl-phenyl)-thiazol-4-ylmethyl ester
3-{2-Fluoro-4-[4-pyrrolidin-1-ylmethyl-2-(4-trifluoromethyl-phenyl)-thiazol-5-ylmethoxy]-phenyl}-4H-[1,2,4]oxadiazol-5-one
3-(2-Methoxy-4-{2-(4-trifluoromethyl-phenyl)-4-[(3,3,3-trifluoro-propylamino)-methyl]-thiazol-5-ylmethoxy}-phenyl)-4H-[1,2,4]oxadiazol-5-one
3-{4-[4-((1R,2R,4S)-Bicyclo[2.2.1]hept-2-ylaminomethyl)-2-(4-trifluoromethyl-phenyl)-thiazol-5-ylmethoxy]-2-methoxy-phenyl}-4H-[1,2,4]oxadiazol-5-one
3-{2-Methoxy-4-[4-({[(S)-1-(tetrahydro-furan-2-yl)methyl]-amino}-methyl)-2-(4-trifluoromethyl-phenyl)-thiazol-5-ylmethoxy]-phenyl}-4H-[1,2,4]oxadiazol-5-one 3-{2-Methoxy-4-[4-({[(R)-1-(tetrahydro-furan-2-yl)methyl]-amino}-methyl)-2-(4-trifluoromethyl-phenyl)-thiazol-5-ylmethoxy]-phenyl}-4H-[1,2,4]oxadiazol-5-one 3-{4-[4-[(Cyclopropylmethyl-amino)-methyl]-2-(4-trifluoromethyl-phenyl)-thiazol-5-ylmethoxy]-2-methoxy-phenyl}-4H-[1,2,4]oxadiazol-5-one 3-{4-[4-Cyclobutylaminomethyl-2-(4-trifluoromethyl-phenyl)-thiazol-5-ylmethoxy]-2-methoxy-phenyl}-4H-[1,2,4]oxadiazol-5-one 3-{4-[4-(4-Methanesulfonyl-piperazin-1-ylmethyl)-2-(4-trifluoromethyl-phenyl)-thiazol-5-ylmethoxy]-2-methoxy-phenyl}-4H-[1,2,4]oxadiazol-5-one 3-{4-[4-{[Bis-(2-hydroxy-ethyl)-amino]-methyl}-2-(4-trifluoromethyl-phenyl)-thiazol-5-ylmethoxy]-2-methoxy-phenyl}-4H-[1,2,4]oxadiazol-5-one 3-{4-[4-[(2-Methanesulfinyl-ethylamino)-methyl]-2-(4-trifluoromethyl-phenyl)-thiazol-5-ylmethoxy]-2-methoxy-phenyl}-4H-[1,2,4]oxadiazol-5-one 3-{2-Methoxy-4-[4-thiomorpholin-4-ylmethyl-2-(4-trifluoromethyl-phenyl)-thiazol-5-ylmethoxy]-phenyl}-4H-[1,2,4]oxadiazol-5-one 3-{4-[4-(1,1-Dioxo-1$\lambda^6$-thiomorpholin-4-ylmethyl)-2-(4-trifluoromethyl-phenyl)-thiazol-5-ylmethoxy]-2-methoxy-phenyl}-4H-[1,2,4]oxadiazol-5-one 3-{2-Methyl-4-[4-propylaminomethyl-2-(4-trifluoromethyl-phenyl)-thiazol-5-ylmethoxy]-phenyl}-4H-[1,2,4]oxadiazol-5-one 3-{4-[4-[(2-Methoxy-ethylamino)-methyl]-2-(4-trifluoromethyl-phenyl)-thiazol-5-ylmethoxy]-2-methyl-phenyl}-4H-[1,2,4]oxadiazol-5-one 3-{2-Methyl-4-[4-{[2-(1-methyl-pyrrolidin-2-yl)-ethylamino]-methyl}-2-(4-trifluoromethyl-phenyl)-thiazol-5-ylmethoxy]-phenyl}-4H-[1,2,4]oxadiazol-5-one 3-{2-Methyl-4-[4-[(2-pyrrolidin-1-yl-ethylamino)-methyl]-2-(4-trifluoromethyl-phenyl)-thiazol-5-ylmethoxy]-phenyl}-4H-[1,2,4]oxadiazol-5-one 3-{2-Methyl-4-[4-[(2-morpholin-4-yl-ethylamino)-methyl]-2-(4-trifluoromethyl-phenyl)-thiazol-5-ylmethoxy]-phenyl}-4H-[1,2,4]oxadiazol-5-one 3-{2-Methyl-4-[4-[(2-piperidin-1-yl-ethylamino)-methyl]-2-(4-trifluoromethyl-phenyl)-thiazol-5-ylmethoxy]-phenyl}-4H-[1,2,4]oxadiazol-5-one 3-{4-[4-[(2-Dimethylamino-ethylamino)-methyl]-2-(4-trifluoromethyl-phenyl)-thiazol-5-ylmethoxy]-2-methyl-phenyl}-4H-[1,2,4]oxadiazol-5-one 3-(2-Chloro-4-{4-methyl-2-[2-(4-trifluoromethyl-phenyl)-ethyl]-oxazol-5-ylmethoxy}-phenyl)-4H-[1,2,4]oxadiazol-5-one 3-(2-Chloro-4-{4-methoxymethyl-2-[2-(4-methoxy-phenyl)-vinyl]-oxazol-5-ylmethoxy}-phenyl)-4H-[1,2,4]oxadiazol-5-one 3-[4-(2-Benzyloxymethyl-4-methyl-oxazol-5-ylmethoxy)-2-chloro-phenyl]-4H-[1,2,4]oxadiazol-5-one 3-{2-Chloro-4-[2-(4-methoxy-benzyl)-4-methyl-oxazol-5-ylmethoxy]-phenyl}-4H-[1,2,4]oxadiazol-5-one 3-(2-Chloro-4-{4-methoxymethyl-2-[2-(4-trifluoromethyl-phenyl)-vinyl]-thiazol-5-ylmethoxy}-phenyl)-4H-[1,2,4]oxadiazol-5-one 3-{2-Chloro-4-[4-(2,2,2-trifluoro-ethoxymethyl)-2-(4-trifluoromethyl-phenyl)-oxazol-5-ylmethoxy]-phenyl}-4H-[1,2,4]oxadiazol-5-one 3-{4-[4-{[Ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one 3-{4-[4-Diethylaminomethyl-2-(4-methoxy-phenyl)-oxazol-5-ylmethoxy]-2-methyl-phenyl}-4H-[1,2,4]oxadiazol-5-one 3-{4-[2-(4-Methoxy-phenyl)-4-pyrrolidin-1-ylmethyl-oxazol-5-ylmethoxy]-2-methyl-phenyl}-4H-[1,2,4]oxadiazol-5-one 3-{4-[2-(4-Methoxy-phenyl)-4-morpholin-4-ylmethyl-oxazol-5-ylmethoxy]-2-methyl-phenyl}-4H-[1,2,4]oxadiazol-5-one 3-{4-[4-{[Bis-(2-methoxy-ethyl)-amino]-methyl}-2-(4-methoxy-phenyl)-oxazol-5-ylmethoxy]-2-methyl-phenyl}-4H-[1,2,4]oxadiazol-5-one 3-{4-[2-(4-Methoxy-phenyl)-4-piperidin-1-ylmethyl-oxazol-5-ylmethoxy]-2-methyl-phenyl}-4H-[1,2,4]oxadiazol-5-one 3-{4-[2-(4-Methoxy-phenyl)-5-piperidin-1-ylmethyl-oxazol-4-ylmethoxy]-2-methyl-phenyl}-4H-[1,2,4]oxadiazol-5-one 3-{4-[2-(4-Methoxy-phenyl)-5-pyrrolidin-1-ylmethyl-oxazol-4-ylmethoxy]-2-methyl-phenyl}-4H-[1,2,4]oxadiazol-5-one 3-{4-[2-(4-Methoxy-phenyl)-5-morpholin-4-ylmethyl-oxazol-4-ylmethoxy]-2-methyl-phenyl}-4H-[1,2,4]oxadiazol-5-one 3-{4-[5-{[Bis-(2-methoxy-ethyl)-amino]-methyl}-2-(4-methoxy-phenyl)-oxazol-4-ylmethoxy]-2-methyl-phenyl}-4H-[1,2,4]oxadiazol-5-one 3-{2-Chloro-4-[2-(4-methoxy-phenyl)-4-morpholin-4-ylmethyl-oxazol-5-ylmethoxy]-phenyl}-4H-[1,2,4]oxadiazol-5-one 3-{2-Chloro-4-[4-{[ethyl-(2-methoxy-ethyl)-amino]-methyl}-2-(4-methoxy-phenyl)-oxazol-5-ylmethoxy]-phenyl}-4H-[1,2,4]oxadiazol-5-one 3-{4-[4-{[Bis-(2-methoxy-ethyl)-amino]-methyl}-2-(4-methoxy-phenyl)-oxazol-5-ylmethoxy]-2-chloro-phenyl}-4H-[1,2,4]oxadiazol-5-one 3-{2-Chloro-4-[4-piperidin-1-ylmethyl-2-(4-trifluoromethyl-phenyl)-thiazol-5-ylmethoxy]-phenyl}-4H-[1,2,4]oxadiazol-5-one 3-{4-[4-(4-Acetyl-piperazin-1-ylmethyl)-2-(4-trifluoromethyl-phenyl)-thiazol-5-ylmethoxy]-2-chloro-phenyl}-4H-[1,2,4]oxadiazol-5-one 3-{2-Chloro-4-[4-(4-methyl-piperazin-1-ylmethyl)-2-(4-trifluoromethyl-phenyl)-thiazol-5-ylmethoxy]-phenyl}-4H-[1,2,4]oxadiazol-5-one 3-{2-Chloro-4-[4-{[ethyl-(2-methoxy-ethyl)-amino]-methyl}-2-(4-trifluoromethyl-phenyl)-thiazol-5-ylmethoxy]-phenyl}-4H-[1,2,4]oxadiazol-5-one 3-{4-[4-{[Bis-(2-methoxy-ethyl)-amino]-methyl}-2-(4-trifluoromethyl-phenyl)-thiazol-5-ylmethoxy]-2-chloro-phenyl}-4H-[1,2,4]oxadiazol-5-one 3-{2-Chloro-4-[4-pyrrolidin-1-ylmethyl-2-(4-trifluoromethyl-phenyl)-thiazol-5-ylmethoxy]-phenyl}-4H-[1,2,4]oxadiazol-5-one 3-{2-Chloro-4-[4-diethylaminomethyl-2-(4-trifluoromethyl-phenyl)-thiazol-5-ylmethoxy]-phenyl}-4H-[1,2,4]oxadiazol-5-one 3-{2-Chloro-4-[4-(4,4-difluoro-piperidin-1-ylmethyl)-2-(4-trifluoromethyl-phenyl)-thiazol-5-ylmethoxy]-phenyl}-4H-[1,2,4]oxadiazol-5-one 3-{2-Chloro-4-[4-(4-phenyl-piperazin-1-ylmethyl)-2-(4-trifluoromethyl-phenyl)-thiazol-5-ylmethoxy]-phenyl}-4H-[1,2,4]oxadiazol-5-one 3-{2-Chloro-4-[4-(2-morpholin-4-yl-ethoxymethyl)-2-(4-trifluoromethyl-phenyl)-thiazol-5-ylmethoxy]-phenyl}-4H-[1,2,4]oxadiazol-5-one 3-{2-Chloro-4-[4-(2-cyclohexyl-ethoxymethyl)-2-(4-trifluoromethyl-phenyl)-thiazol-5-ylmethoxy]-phenyl}-4H-[1,2,4]oxadiazol-5-one 3-{2-Chloro-4-[4-difluoromethyl-2-(4-methoxy-phenyl)-thiazol-5-ylmethoxy]-phenyl}-4H-[1,2,4]oxadiazol-5-one 3-{4-[4-(4-Hydroxy-piperidin-1-ylmethyl)-2-(4-trifluoromethyl-phenyl)-thiazol-5-ylmethoxy]-2-methoxy-phenyl}-4H-1,2,4-oxadiazol-5-one 3-{4-[4-(1,4-Dioxa-8-aza-spiro[4.5]dec-8-ylmethyl)-2-(4-trifluoromethyl-phenyl)-thiazol-5-ylmethoxy]-2-methoxy-phenyl}-4H-1,2,4-oxadiazol-5-one 3-{4-[4-(4,4-Dihydroxy-piperidin-1-ylmethyl)-2-(4-trifluoromethyl-phenyl)-thiazol-5-ylmethoxy]-2-methoxy-phenyl}-4H-1,2,4-oxadiazol-5-one 3-{2-Methoxy-4-[4-(1-oxo-1$\lambda^4$-thiomorpholin-4-ylmethyl)-2-(4-trifluoromethyl-phenyl)-thiazol-5-ylmethoxy]-phenyl}-4H-1,2,4-oxadiazol-5-one 3-{2-Methoxy-4-[4-methylsulfanylmethyl-2-(4-trifluoromethyl-phenyl)-thiazol-5-ylmethoxy]-phenyl}-4H-1,2,4-oxadiazol-5-one 3-{4-[4-Methanesulfinylmethyl-2-(4-trifluoromethyl-phenyl)-thiazol-5-ylmethoxy]-2-methoxy-phenyl}-4H-1,2,4-oxadiazol-5-one 3-{4-[4-Methanesulfonylmethyl-2-(4-trifluoromethyl-phenyl)-thiazol-5-ylmethoxy]-2-methoxy-phenyl}-4H-1,2,4-oxadiazol-5-one 3-{4-[4-Aminomethyl-2-(4-trifluoromethyl-phenyl)-thiazol-5-ylmethoxy]-2-fluoro-phenyl}-4H-1,2,4-oxadiazol-5-one N-[5-[3-Fluoro-4-(5-oxo-4,5-dihydro-1,2,4-oxadiazol-3-yl)-phenoxymethyl]-2-(4-trifluoromethyl-phenyl)-thiazol-4-ylmethyl]-acetamide 3-{2-Difluoromethoxy-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one 3-{2-Difluoromethoxy-5-fluoro-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one 3-{2-Isopropoxy-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one 3-{2-Cyclopropylmethoxy-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one 3-{2-(2,2,2-Trifluoro-ethoxy)-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one 3-{5-Fluoro-2-(2,2,2-trifluoro-ethoxy)-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one 3-{6-[4-Butyl-2-(4-trifluoromethyl-phenyl)-thiazol-5-ylmethoxy]-2-methyl-pyridin-3-yl}-4H-[1,2,4]oxadiazol-5-one 3-{2-Methoxy-4-[4-(3-methylsulfanyl-propyl)-2-(4-trifluoromethyl-phenyl)-thiazol-5-ylmethoxy]-phenyl}-4H-1,2,4-oxadiazol-5-one 3-{4-[4-(3-Methanesulfonyl-propyl)-2-(4-trifluoromethyl-phenyl)-thiazol-5-ylmethoxy]-2-methoxy-phenyl}-4H-1,2,4-oxadiazol-5-one 3-{2-Methoxy-4-[4-(3-thiomorpholin-4-yl-propyl)-2-(4-trifluoromethyl-phenyl)-thiazol-5-ylmethoxy]-phenyl}-4H-1,2,4-oxadiazol-5-one 3-{2-Methoxy-4-[4-(3-perhydro-azepin-1-yl-propyl)-2-(4-trifluoromethyl-phenyl)-thiazol-5-ylmethoxy]-phenyl}-4H-1,2,4-oxadiazol-5-one 3-{2-Methoxy-4-[4-(3-morpholin-4-yl-propyl)-2-(4-trifluoromethyl-phenyl)-thiazol-5-ylmethoxy]-phenyl}-4H-1,2,4-oxadiazol-5-one 3-{2-Methoxy-4-[4-[3-(4-methyl-piperazin-1-yl)-propyl]-2-(4-trifluoromethyl-phenyl)-thiazol-5-ylmethoxy]-phenyl}-4H-1,2,4-oxadiazol-5-one 3-{2-Methoxy-4-[4-(3-piperidin-1-yl-propyl)-2-(4-trifluoromethyl-phenyl)-thiazol-5-ylmethoxy]-phenyl}-4H-1,2,4-oxadiazol-5-one 3-{2-Methoxy-4-[4-(3-pyrrolidin-1-yl-propyl)-2-(4-trifluoromethyl-phenyl)-thiazol-5-ylmethoxy]-phenyl}-4H-1,2,4-oxadiazol-5-one 3-{2-Fluoro-4-[4-(3-morpholin-4-yl-propyl)-2-(4-trifluoromethyl-phenyl)-thiazol-5-ylmethoxy]-phenyl}-4H-1,2,4-oxadiazol-5-one 3-{2-Fluoro-4-[4-(3-pyrrolidin-1-yl-propyl)-2-(4-trifluoromethyl-phenyl)-thiazol-5-ylmethoxy]-phenyl}-4H-1,2,4-oxadiazol-5-one 3-{4-[4-[3-(Benzyl-methyl-amino)-propyl]-2-(4-trifluoromethyl-phenyl)-thiazol-5-ylmethoxy]-2-methoxy-phenyl}-4H-[1,2,4]oxadiazol-5-one 3-(2-Methoxy-4-{2-(4-trifluoromethyl-phenyl)-4-[3-(4-trifluoromethyl-piperidin-1-yl)-propyl]-thiazol-5-ylmethoxy}-phenyl)-4H-[1,2,4]oxadiazol-5-one.

This invention also encompasses all combinations of preferred aspects of the invention described herein.

As used herein, the term alkyl is to be understood in the broadest sense to mean saturated hydrocarbon residues which can be linear, i.e. straight-chain, or branched. If not otherwise defined alkyl has 1 to 8 carbon atoms. Examples of "—(C1-C8)-alkyl" are alkyl residues containing 1, 2, 3, 4, 5, 6, 7 or 8 carbon atoms are methyl, ethyl, propyl, butyl, pentyl, hexyl, heptyl or octyl, the n-isomers of all these residues, isopropyl, isobutyl, 1-methylbutyl, isopentyl, neopentyl, 2,2-dimethyl-butyl, 2-methylpentyl, 3-methylpentyl, isohexyl, sec-butyl, tert-butyl or tert-pentyl. The term "—(C0-C8)-alkyl" is a hydrocarbon residue containing 1, 2, 3, 4, 5, 6, 7 or 8 carbon atoms, in which the term "—C0-alkyl" is a covalent bond. All these statements apply also to the term alkylene.

As used herein, the term alkenyl is to be understood in the broadest sense to mean hydrocarbon residues which has 1 to 4 double bonds and can be linear, i.e. straight-chain, or branched. If not otherwise defined alkenyl has 2 to 8 carbon atoms.

Examples of "—(C2-C8)-alkenyl" are alkenyl residues containing 2, 3, 4, 5, 6, 7 or 8 carbon atoms are, for example vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl. All these statements apply also to the term alkenylene.

As used herein, the term alkinyl is to be understood in the broadest sense to mean hydrocarbon residues, which has 1 to 4 triple bonds and can be linear, i.e. straight-chain, or branched. If not otherwise defined alkinyl has 2 to 8 carbon atoms. Examples of "—(C2-C8)-alkinyl" are alkinyl residues containing 2, 3, 4, 5, 6, 7 or 8 carbon atoms are, for example ethynyl, 1-propynyl, 2-propynyl (=propargyl) or 2-butynyl. All these statements apply also to the term alkylidene.

All these statements also apply if an alkyl group occurs as a substituent on another residue, for example in an alkyloxy residue, an alkyloxycarbonyl residue or an arylalkyl residue.

If not otherwise defined, alkyl, alkylene, alkenyl, alkenylene, alkinyl and alkinylene are unsubstituted or mono, di- or trisubstituted independently of one another by suitable groups such as, for example: F, Cl, Br, I, CF3, NO2, CN, COOH, CO—O—(C0-C4) alkylene-(C6-C10) aryl, CO—O—(C1-C4)alkyl, CO—O—(C0-C4)alkylene-(C3-C13)cycloalkyl, CO—O—(C0-C4)alkylene-(C3-C15)heterocycle, CO—N((C0-C4)alkylene-H)—(C0-C4)alkylene-(C6-C10)aryl, CO—N((C0-C4)alkylene-H)—(C0-C4)

alkylene-H, CO—N((C0-C4)alkylene-H)—(C0-C4)alkylene-(C3-C13)cycloalkyl, CO—N((C0-C4) alkylene-H)—(C0-C4)alkylene-(C3-C15)heterocycle, (C0-C4)alkylene-(C3-C6)cycloalkyl, (C0-C4)alkylene-(C6-C10) aryl, (C0-C4)alkylene-(C3-C15)heterocycle, (C2-C6)-alkenyl, (C2-C6)-alkinyl, O—(C0-C6)-alkyl, O—(C0-C4)alkylene-(C6-C10)aryl, O—(C0-C4)alkylene-(C3-C12)cycloalkyl, O—(C0-C4)alkylene-(C3-C15)heterocycle, O—CO—O—(C0-C4)alkylene-(C6-C10) aryl, O—CO—O—(C1-C4)alkyl, O—CO—O—(C0-C4) alkylene-(C3-C13)cycloalkyl, O—CO—O—(C0-C4)alkylene-(C3-C15)heterocycle, S—(C1-C4)alkyl, S—(C0-C4)alkylene-(C3-C13)cycloalkyl, S—(C0-C4)alkylene-(C6-C10) aryl, S—(C0-C4)alkylene-(C3-C15)heterocycle, SO—(C1-C4)alkyl, SO—(C0-C4)alkylene-(C3-C13)cycloalkyl, SO—(C0-C4)alkylene-(C6-C10) aryl, SO—(C0-C4)alkylene-(C3-C15) heterocycle, SO2-(C1-C4)alkyl, SO2-(C0-C4)alkylene-(C3-C13)cycloalkyl, SO2-(C0-C4)alkylene-(C6-C10) aryl, SO2-(C0-C4)alkylene-(C3-C15) heterocycle, SO2-N((C0-C4)alkylene-H)—(C0-C4)alkylene-(C6-C10) aryl, SO2-N((C0-C4)alkylene-H)—(C0-C4)alkylene-H, SO2-N((C0-C4)alkylene-H)—(C0-C4)alkylene-(C3-C13)cycloalkyl, SO2-N((C0-C4)alkylene-H)—(C0-C4)alkylene-(C3-C15)heterocycle where the aryl ring or heterocyclic ring is unsubstituted or mono- or disubstituted by F, Cl, Br, OH, CF3, NO2, CN, OCF3, O—(C1-C6)-alkyl, (C1-C6)-alkyl, N((C0-C4)-alkylene-H)—(C0-C4)-alkylene-H; N((C0-C4)-alkylene-H)—(C0-C4)-alkylene-H, N((C0-C4)alkylene-H)—(C0-C4)alkylene-H)—(C1-C6)cycloalkyl, N((C0-C4)alkylene-H)—(C0-C4)alkylene-(C6-C12)-aryl, N((C0-C4)alkylene-H)—(C0-C4)alkylene-(C3-C15)heterocycle, N((C0-C4)alkylene-H)—CO—(C0-C4)alkylene-(C6-C12)-aryl, N((C0-C4)alkylene-H)—CO—(C0-C4)alkyl, N((C0-C4)alkylene-H)—CO—(C0-C4)alkylene-(C3-C13)cycloalkyl, N((C0-C4)alkylene-H)—CO—(C0-C4)alkylene-(C3-C15)heterocycle, N((C0-C4)alkylene-H)—CO—O—(C0-C4)alkylene-(C6-C12)-aryl, N((C0-C4)alkylene-H)—CO—O—(C0-C4)alkyl, N((C0-C4)alkylene-H)—CO—O—(C0-C4)alkylene-(C3-C13)cycloalkyl, N((C0-C4)alkylene-H)—CO—O—(C0-C4)alkylene-(C3-C15)heterocycle, N((C0-C4)alkylene-H)—CO—N((C0-C4)-alkylene-H)—(C0-C4)alkylene-(C6-C12)-aryl, N((C0-C4)alkylene-H)—CO—N((C0-C4)-alkylene-H)—(C0-C4)alkyl, N((C0-C4)alkylene-H)—CO—N((C0-C4)-alkylene-H)—(C0-C4)alkylene-(C3-C13)cycloalkyl, N((C0-C4)alkylene-H)—CO—N((C0-C4)-alkylene-H)—(C0-C4)alkylene-(C3-C15)heterocycle, where the aryl ring or heterocyclic ring is unsubstituted or mono- or disubstituted by F, Cl, Br, I, OH, CF3, NO2, CN, OCF3, O—(C1-C6)-alkyl, (C1-C6)-alkyl, N((C0-C4)-alkylene-H)—(C0-C4)-alkylene-H, SO2-CH3, COOH, COO—(C1-C6)-alkyl, SF5, CONH2.

The term cycloalkyl is to be understood to mean saturated hydrocarbon cycle containing from 3 to 13 carbon atoms in a mono- or bicyclic, fused, bridged or spirocyclic ring. Examples of (C3-C13)-cycloalkyl cyclic alkyl residues are cycloalkyl residues containing 3, 4, 5, 6, 7, 8, 9, 10, 11, 12 or 13 ring carbon atoms like cyclopropyl, cyclobutyl, cyclopentyl, cyclohexyl, cycloheptyl, cyclooctyl, cyclononyl, cyclodecyl, cycloundecyl or cyclododecyl. The term cycloalkyl also includes bicyclic groups in which any of the above cycloalkyl ring is fused to a benzene ring, for example indane and 1,2,3,4-tetrahydronaphthalene.

The term cycloalkenyl is to be understood to mean unsaturated hydrocarbon cycle containing from 3 to 8 carbon atoms in a mono- or bicyclic, fused or bridged ring, wherein the one, two or three double bonds are not located within a cyclic alkyl group in such a manner that an aromatic system results. Examples of unsaturated cycloalkenyl groups are cyclopentenyl or cyclohexenyl, which can be bonded via any carbon atom. The term cycloalkenyl also includes bicyclic groups in which any of the above cycloalkenyl ring is fused to a benzene ring, for example 1,2-dihydronaphthalene, 1,4-dihydronaphthalene and 1H-indene.

If not otherwise defined cycloalkyl or cycloalkenyl are unsubstituted or mono, di- or trisubstituted independently of one another by suitable groups such as, for example: F, Cl, Br, I, CF3, NO2, CN, COOH, CO—O—(C0-C4)alkylene-(C6-C10) aryl, CO—O—(C1-C4) alkyl, CO—O—(C0-C4)alkylene-(C3-C13)cycloalkyl, CO—O—(C0-C4)alkylene-(C3-C15)heterocycle, CO—N((C0-C4)alkylene-H)—(C1-C6)alkylene-H, CO—N((C0-C4) alkylene-H)—(C1-C6)cycloalkyl, CON((C0-C4)alkylene-H)—(C0-C4)alkylene-(C6-C12)aryl, (C0-C4)alkylene-(C3-C6)cycloalkyl, (C3-C6)alkyl, (C2-C6)-alkenyl, (C2-C6)alkinyl, (C0-C4)alkylene-(C6-C10)aryl, (C0-C4)alkylene-(C3-C15)heterocycle, O—(C0-C6)-alkyl, (C0-C4)alkylene-O—(C0-C4)alkyl, (C0-C4)alkylene-O—(C0-C4)alkylene-(C3-C13)cycloalkyl, (C0-C4)alkylene-O—(C0-C4)alkylene-(C6-C10)aryl, (C0-C4) alkylene-O—(C0-C4)alkylene-(C3-C15)heterocycle, O—CO—O—(C0-C4)alkylene-(C6-C10)aryl, O—CO—O—(C1-C4)alkyl, O—CO—O—(C0-C4)alkylene-(C3-C13)cycloalkyl, O—CO—O—(C0-C4)alkylene-(C3-C15)heterocycle, O—CO—N((C0-C4)alkylene-H)—(C0-C4) alkylene-(C6-C10) aryl, O—CO—N((C0-C4)alkylene-H)—(C0-C4)alkylene-H, O—CO—N((C0-C4)alkylene-H)—(C0-C4)alkylene-(C3-C13)cycloalkyl, O—CO—N((C0-C4) alkylene-H)—(C0-C4)alkylene-(C3-C15) heterocycle, S—(C1-C4)alkyl, S—(C0-C4) alkylene-(C3-C13)cycloalkyl, S—(C0-C4)alkylene-(C6-C10)aryl, S—(C0-C4)alkylene-(C3-C15)heterocycle, SO—(C1-C4)alkyl, SO—(C0-C4)alkylene-(C3-C13)cycloalkyl, SO—(C0-C4)alkylene-(C6-C10)aryl, SO—(C0-C4)alkylene-(C3-C15)heterocycle, SO2-(C1-C4)alkyl, SO2-(C0-C4)alkylene-(C3-C13)cycloalkyl, SO2-(C0-C4)alkylene-(C6-C10) aryl, SO2-(C0-C4)alkylene-(C3-C15) heterocycle, SO2-N((C0-C4)alkylene-H)—(C0-C4)alkylene-(C6-C10)aryl, SO2-N((C0-C4)alkylene-H)—(C0-C4)alkylene-H, SO2-N((C0-C4) alkylene-H)—(C0-C4)alkylene-(C3-C13)cycloalkyl, SO2-N((C0-C4)alkylene-H)—(C0-C4)alkylene-(C3-C15) heterocycle, where the aryl ring or heterocyclic ring is unsubstituted or mono- or disubstituted by F, Cl, Br, OH, CF3, NO2, CN, OCF3, O—(C1-C6)-alkyl, (C1-C6)-alkyl, N((C0-C4)-alkylene-H)—(C0-C4)-alkylene-H; N((C0-C4)-alkylene-H)—(C0-C4)-alkylene-H, N((C0-C4)alkylene-H)—(C0-C4)alkylene-H)—(C1-C6)cycloalkyl, N((C0-C4)alkylene-H)—(C0-C4)alkylene-(C6-C12)-aryl, N((C0-C4)alkylene-H)—(C0-C4)alkylene-(C3-C15)heterocycle, N((C0-C4)alkylene-H)—CO—(C0-C4)alkylene-(C6-C12)-aryl, N((C0-C4)alkylene-H)—CO—(C0-C4)alkyl, N((C0-C4)alkylene-H)—CO—(C0-C4)alkylene-(C3-C13)cycloalkyl, N((C0-C4)alkylene-H)—CO—(C0-C4)alkylene-(C3-C15)heterocycle, N((C0-C4)alkylene-H)—CO—O—(C0-C4)alkylene-(C6-C12)-aryl, N((C0-C4)alkylene-H)—CO—O—(C0-C4)alkyl, N((C0-C4)alkylene-H)—CO—O—(C0-C4)alkylene-(C3-C13)cycloalkyl, N((C0-C4)alkylene-H)—CO—O—(C0-C4)alkylene-(C3-C15)heterocycle, N((C0-C4)alkylene-H)—CO—N((C0-C4)-alkylene-H)—(C0-C4)alkylene-(C6-C12)-aryl, N((C0-C4)alkylene-H)—CO—N((C0-C4)-alkylene-H)—(C0-C4)alkyl, N((C0-C4)alkylene-H)—CO—N((C0-C4)-alkylene-H)—(C0-C4)alkylene-(C3-C13)cycloalkyl, N((C0-C4)alkylene-H)—CO—N((C0-C4)-alkylene-H)—(C0-C4)alkylene-(C3-C15)heterocycle, where the aryl or heterocyclic ring is unsubstituted or monoor disubstituted by F, Cl, Br, I, OH, CF3, NO2, CN, OCF3, O—(C1-C6)-alkyl, (C1-C6)-alkyl, N((C0-C4)-alkylene-H)—(C0-C4)-alkylene-H, SO2-CH3, COOH, COO—(C1-C6)-alkyl, SF5, CONH2.

The term "aryl" is understood to mean aromatic hydrocarbon ring containing from 6 to 14 carbon atoms in a mono- or bicyclic ring. Examples of (C6-C14)-aryl rings are phenyl, naphthyl, for example 1-naphthyl and 2-naphthyl, biphenylyl, for example 2-biphenylyl, 3-biphenylyl and 4-biphenylyl, anthryl or fluorenyl. Biphenylyl rings, naphthyl ring and, in particular, phenyl ring are further embodiments of aryl ring.

The terms heterocycle is understood to mean saturated (heterocycloalkyl), partly unsaturated (heterocycloalkenyl) or unsaturated (heteroaryl)hydrocarbon rings containing from 3 to 15 carbon atoms in a mono- or bicyclic, fused, bridged or spirocyclic ring in which 1 to 5 carbon atoms of the 3 to 15 ring carbon atoms are replaced by heteroatoms such as nitrogen, oxygen or sulfur in which further the heteroatoms can be oxidized, for example N=O, S=O, SO2. Examples of heterocycles are acridinyl, azaindole (1H-pyrrolopyridinyl), azabenzimidazolyl, azaspirodecanyl, azepinyl, azetidinyl, aziridinyl, benzimidazolyl, benzofuranyl, dihydrobenzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

The heterocyclic rings are unsubstituted or mono-, di- or trisubstituted by suitable groups such as, for example: F, Cl, Br, I, CF3, NO2, CN, COOH, CO—O—(C0-C4) alkylene-(C6-C10) aryl, CO—O—(C1-C4)alkyl, CO—O—(C0-C4) alkylene-(C3-C13) cycloalkyl, CO—O—(C0-C4)alkylene-(C3-C15)heterocycle, CO—N((C0-C4)alkylene-H)—(C1-C6)alkylene-H, CO—N((C0-C4)alkylene-H)—(C1-C6) cycloalkyl, CON((C0-C4) alkylene-H)—(C0-C4)alkylene-(C6-C12)-aryl, (C0-C4)alkylene-(C3-C6)cycloalkyl, (C3-C6)alkyl, (C2-C6)-alkenyl, (C2-C6)-alkinyl, (C0-C4) alkylene-(C6-C10) aryl, (C0-C4) alkylene-(C3-C15) heterocycle, O—(C0-C6)-alkyl, (C0-C4)alkylene-O—(C0-C4)alkyl, (C0-C4)alkylene-O—(C0-C4)alkylene-(C3-C13) cycloalkyl, (C0-C4)alkylene-O—(C0-C4) alkylene-(C6-C10)aryl, (C0-C4)alkylene-O—(C0-C4)alkylene-(C3-C15) heterocycle, O—CO—O—(C0-C4)alkylene-(C6-C10)aryl, O—CO—O—(C1-C4)alkyl, O—CO—O—(C0-C4) alkylene-(C3-C13)cycloalkyl, O—CO—O—(C0-C4)alkylene-(C3-C15)heterocycle, O—CO—N((C0-C4)alkylene-H)—(C0-C4)alkylene-(C6-C10) aryl, O—CO—N((C0-C4) alkylene-H)—(C0-C4)alkylene-H, O—CO—N((C0-C4) alkylene-H)—(C0-C4)alkylene-(C3-C13)cycloalkyl, O—CO—N((C0-C4)alkylene-H)—(C0-C4)alkylene-(C3-C15) heterocycle, S—(C1-C4)alkyl, S—(C0-C4)alkylene-(C3-C13)cycloalkyl, S—(C0-C4) alkylene-(C6-C10)aryl, S—(C0-C4)alkylene-(C3-C15) heterocycle, SO—(C1-C4) alkyl, SO—(C0-C4)alkylene-(C3-C13)cycloalkyl, SO—(C0-C4)alkylene-(C6-C10) aryl, SO—(C0-C4)alkylene-(C3-C15) heterocycle, SO2-(C1-C4)alkyl, SO2-(C0-C4) alkylene-(C3-C13)cycloalkyl, SO2-(C0-C4)alkylene-(C6-C10) aryl, SO2-(C0-C4)alkylene-(C3-C15) heterocycle, SO2-N((C0-C4)alkylene-H)—(C0-C4)alkylene-(C6-C10) aryl, SO2-N((C0-C4)alkylene-H)—(C0-C4)alkylene-H, SO2-N((C0-C4)alkylene-H)—(C0-C4)alkylene-(C3-C13) cycloalkyl, SO2-N((C0-C4)alkylene-H)—(C0-C4)alkylene-(C3-C15)heterocycle, where the aryl ring or heterocyclic ring is unsubstituted or mono- or disubstituted by F, Cl, Br, OH, CF3, NO2, CN, OCF3, O—(C1-C6)-alkyl, (C1-C6)-alkyl, N((C0-C4)-alkylene-H)—(C0-C4)-alkylene-H; N((C0-C4)-alkylene-H)—(C0-C4)-alkylene-H, N((C0-C4)alkylene-H)—(C0-C4)alkylene-H)—(C1-C6)cycloalkyl, N((C0-C4) alkylene-H)—(C0-C4)alkylene-(C6-C12)-aryl, N((C0-C4) alkylene-H)—(C0-C4)alkylene-(C3-C15)heterocycle, N((C0-C4)alkylene-H)—CO—(C0-C4)alkylene-(C6-C12)-aryl, N((C0-C4)alkylene-H)—CO—(C0-C4)alkyl, N((C0-C4)alkylene-H)—CO—(C0-C4)alkylene-(C3-C13)cycloalkyl, N((C0-C4)alkylene-H)—CO—(C0-C4)alkylene-(C3-C15)heterocycle, N((C0-C4)alkylene-H)—CO—O—(C0-C4)alkylene-(C6-C12)-aryl, N((C0-C4)alkylene-H)—CO—O—(C0-C4)alkyl, N((C0-C4)alkylene-H)—CO—O—(C0-C4)alkylene-(C3-C13)cycloalkyl, N((C0-C4) alkylene-H)—CO—O—(C0-C4)alkylene-(C3-C15) heterocycle, N((C0-C4)alkylene-H)—CO—N((C0-C4)-alkylene-H)—(C0-C4)alkylene-(C6-C12)-aryl, N((C0-C4) alkylene-H)—CO—N((C0-C4)-alkylene-H)—(C0-C4) alkyl, N((C0-C4)alkylene-H)—CO—N((C0-C4)-alkylene-H)—(C0-C4)alkylene-(C3-C13)cycloalkyl, N((C0-C4) alkylene-H)—CO—N((C0-C4)-alkylene-H)—(C0-C4) alkylene-(C3-C15)heterocycle, where the aryl or heterocyclic ring is unsubstituted or mono- or disubstituted by F, Cl, Br, I, OH, CF3, NO2, CN, OCF3, O—(C1-C6)-alkyl, (C1-C6)-alkyl, N((C0-C4)-alkylene-H)—(C0-C4)-alkylene-H, SO2-CH3, COOH, COO—(C1-C6)-alkyl, SF5, CONH2.

The term "R5 and R6 together with the nitrogen atom to which they are bonded (Y=N(R6)) can form a (C3-C9)-heterocycle which for example can contain additionally 1 to 3 heteroatoms" refer to structures of heterocycles which can be derived from compounds such as for example pyrrolidine, morpholine, thiomorpholine, piperidine, piperazine, azetidine, 2,3-dihydro-1H-isoindole, piperazin-2-one, azetidine, isoindoline, 2,5-diazabicyclo[2.2.1]heptane, thiomorpholine 1-oxide, thiomorpholine 1,1-dioxide, piperidin-4-one, piperidin-3-one, homopiperidine, homopiperazine, homomorpholine, 2,3,6,7-tetrahydro-(1H)-1,4-diazepin-5(4H)-one, 4-oxazolidine, azetidin-3-one, thiazolidine, thiazolidine 1-oxide, thiazolidine 1,1-dioxide, 4-imidazolidinone, 5,6,7,8-tetrahydro-[1,2,4]triazolo[4,3-a]pyrazine, 1,4-diazabicyclo[4.3.0]nonane, 2-aza-5-oxabicyclo[2.2.1]heptane, 2-oxa-5-azabicyclo[2.2.1]heptane, diazabicyclo[4.4.0]decane, 4,5,6,7-tetrahydrothieno[3,2-c]pyridine, 4,5,6,7-tetrahydro-1H-imidazol[4,5-c]-pyridine, 4,5,6,7-tetrahydro-1H-pyrazolo[4,3-c]pyridine, 3,8-diaza-bicyclo[3.2.1]octane, octahydropyrrolo[3,4-c]pyrrole, 2,5-diazabicyclo[2.2.2]octane, 4-spiro-[3-(N-methyl-2-pyrrolidinone)]-piperidine, 2,8-diaza-spiro[5.5]undecane, 2,7-diaza-spiro[4.4]nonane, 3,9-diaza-spiro[5.5]undecane, 2,8-diaza-spiro[4.5]decane, 2,7-diaza-spiro[3.5]nonane, 2,9-diaza-spiro[5.5]undecane, 2,7-diaza-spiro[4.5]decane, 1-oxa-4,9-diaza-spiro[5.5]undecane, 1-oxa-4,8-diaza-spiro[5.5]undecane.

The term "oxo-residue" or "=O" refers to residues such as carbonyl (—CO—), nitroso (—N=O), sulfinyl (—SO—) or sulfonyl (—SO2-).

Halogen is fluorine, chlorine, bromine or iodine.

Optically active carbon atoms present in the compounds of the formula I can independently of each other have R configuration or S configuration. The compounds of the formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula I and it comprises all ratios of the stereoisomers in the mixtures. In case the compounds of the formula I can be present as E isomers or Z isomers (or cis isomers or trans isomers) the invention relates both to pure E isomers and pure Z isomers and to E/Z mixtures in all ratios. The invention also comprises all tautomeric forms of the compounds of the formula I.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula I can also be obtained by employing stereochemically uniform starting materials or by using stereoselective reactions.

The compounds of the formula I may exist in the form of their racemates, racemic mixtures, pure enantiomers, diastereomers and mixtures of diastereomers as well in their tautomeric forms. The present invention encompasses all these isomeric and tautomeric forms of the compounds of the formula I. These isomeric forms can be obtained by known methods even if not specifically described in some cases.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives also include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

Use

This invention relates further to the use of compounds of the formula I and their pharmaceutical compositions as PPAR ligands. The PPAR ligands of the invention are suitable as modulators of PPAR activity.

Peroxisome proliferator-activated receptors (PPAR) are transcription factors which can be activated by ligands and belong to the class of nuclear hormone receptors. There are three PPAR isoforms, PPARalpha, PPARgamma and PPARdelta (identical to PPARbeta), which are encoded by different genes (Peroxisome proliferator-activated receptor (PPAR): structure, mechanisms of activation and diverse functions: Motojima K., Cell Struct Funct., 1993, 18(5), 267-77).

In humans, PPARgamma exists in three variants, PPAR-gamma$_1$, gamma$_2$, and gamma$_3$, which are the result of alternative use of promoters and differential mRNA splicing. Different PPARs have different tissue distribution and modulate different physiological functions. The PPARs play a key role in various aspects of the regulation of a large number of genes, the products of which genes are directly or indirectly crucially involved in lipid and carbohydrate metabolism. Thus, for example, the PPARalpha receptor plays an important part in the regulation of fatty acid catabolism or lipoprotein metabolism in the liver, while PPARgamma is crucially involved for example in regulating adipose cell differentiation. In addition, however, PPARs are also involved in the regulation of many other physiological processes, including those which are not directly connected with carbohydrate or lipid metabolism. The activity of different PPARs can be modulated by various fatty acids, fatty acid derivatives and synthetic compounds to varying extents. For relevant reviews about functions, physiological effects and pathophysiology, see: Berger, J. et al., Annu. Rev. Med., 2002, 53, 409-435; Wilson, T. et al., J. Med. Chem., 2000, 43 (4), 527-550; Kliewer, S. et al., Recent Prog Horm Res., 2001, 56, 239-63;

Moller, D. E. and Berger, J. P., Int J Obes Relat Metab Disord., 2003, 27 Suppl 3, 17-21; Ram, V. J., Drugs Today, 2003, 39(8), 609-32).

Among the three PPAR-isoforms the physiological functions of PPARdelta have long remained an enigma. The first proposed pharmacological role for PPARdelta has been the regulation of cholesterol homeostasis. It was shown that the somewhat selective PPARdelta ligand L-165041 raises plasma cholesterol in a diabetic animal model (Berger J. et al., J. Biol. Chem., 1999, 274, 6718-6725; Leibowitz M. D. et al., FEBS Lett., 2000, 473(3), 333-336). In obese, insulin resistant rhesus monkeys, the potent and selective PPARdelta ligand GW501516 raises HDL-cholesterol, decreases plasma LDL-cholesterol, triglycerides and insulin levels (Oliver, W. et al., Proc. Natl. Acad. Sci., 2001, 98, 5306-5361). The dual PPARdelta/PPARalpha agonist YM-16638 significantly lowers plasma lipids in rhesus and cynomolgus monkeys (Goto, S. et al., Br. J. Pharm., 1996, 118, 174-178) and acts in a similar manner in two weeks clinical trials in healthy volunteers (Shimokawa, T. et al., Drug Dev. Res., 1996, 38, 86-92).

More recent publications underline that PPARdelta is an important target for the treatment of dyslipidemia, insulin resistance, type 2 diabetes, atherosclerosis and syndrome X (Wang, Y-X. et al., Cell, 2003, 113, 159-170; Luquet, S. et al., FASEB J., 2003, 17, 209-226; Tanaka, T. et al., PNAS, 2003, 100, 15924-15929; Hoist, D. et al., BioChem. Biophys. Acta, 2003, 1633, 43-50; Dressel, U. et al., Mol. Endocrin., 2003, 17, 2477-2493; Lee, C. H. et al., Science, 2003, 302, 453-457).

Besides its actions as a regulator of the lipid-, glucose- and cholesterol-metabolism PPARdelta is known to play a role in embryonic development, implantation and bone formation (Lim, H. and Dey, S. K., Trends Endocrinol Metab., 2000, 11(4), 137-42; Ding, N. Z. et al., Mol Reprod Dev., 2003, 66(3), 218-24; Mano, H. et al., J Biol Chem., 2000, 275(11), 8126-32).

Numerous publications demonstrate that PPARdelta is triggering proliferation and differentiation of keratinocytes which points to its role in skin disorders and wound healing (Di-Poi, N. et al., J Steroid Biochem Mol Biol., 2003, 85(2-5), 257-65; Tan, N. S. et al., Am J Clin Dermatol., 2003, 4(8), 523-30; Wahli, W., Swiss Med Wkly., 2002, 132(7-8), 83-91).

PPARdelta appears to be significantly expressed in the CNS; however much of its function there still remains undiscovered. Of singular interest however, is the discovery that PPARdelta was expressed in rodent oligodendrocytes, the major lipid producing cells of the CNS (J. Granneman, et al., J. Neurosci. Res., 1998, 51, 563-573). Moreover, it was also found that a PPARdelta selective agonist was found to significantly increase oligodendroglial myelin gene expression and myelin sheath diameter in mouse cultures (I. Saluja et al., Glia, 2001, 33, 194-204). Thus, PPARdelta activators may be of use for the treatment of demyelinating and dysmyelinating diseases. The use of peroxisome proliferator activated receptor delta agonists for the treatment of MS and other demyelinating diseases can be shown as described in WO2005/097098.

Demyelinating conditions are manifested in loss of myelin—the multiple dense layers of lipids and protein which cover many nerve fibers. These layers are provided by oligodendroglia in the central nervous system (CNS), and Schwann cells in the peripheral nervous system (PNS). In patients with demyelinating conditions, demyelination may be irreversible; it is usually accompanied or followed by axonal degeneration, and often by cellular degeneration. Demyelination can occur as a result of neuronal damage or damage to the myelin itself—whether due to aberrant immune responses, local injury, ischemia, metabolic disorders, toxic agents, or viral infections (Prineas and McDonald, Demyelinating Diseases. In Greenfield's Neuropathology, 6.sup.th ed. (Edward Arnold: New York, 1997) 813-811, Beers and Berkow, eds., The Merck Manual of Diagnosis and Therapy, 17.sup.th ed. (Whitehouse Station, N.J.: Merck Research Laboratories, 1999) 1299, 1437, 1473-76, 1483).

Central demyelination (demyelination of the CNS) occurs in several conditions, often of uncertain etiology, that have come to be known as the primary demyelinating diseases. Of these, multiple sclerosis (MS) is the most prevalent. Other primary demyelinating diseases include adrenoleukodystrophy (ALD), adrenomyeloneuropathy, AIDS-vacuolar myelopathy, HTLV-associated myelopathy, Leber's hereditary optic atrophy, progressive multifocal leukoencephalopathy (PML), subacute sclerosing panencephalitis, Guillian-Barre syndrome and tropical spastic paraparesis. In addition, there are acute conditions in which demyelination can occur in the CNS, e.g., acute disseminated encephalomyelitis (ADEM) and acute viral encephalitis. Furthermore, acute transverse myelitis, a syndrome in which an acute spinal cord transfection of unknown cause affects both gray and white matter in one or more adjacent thoracic segments, can also result in demyelination. Also, disorders in which myelin forming glial cells are damaged including spinal cord injuries, neuropathies and nerve injury.

The present invention relates to compounds of the formula I suitable for modulating the activity of PPARs, especially the activity of PPARdelta and PPARalpha. Depending on the modulation profile, the compounds of the formula I are suitable for the treatment, control and prophylaxis of the indications described hereinafter, and for a number of other pharmaceutical applications connected thereto (see, for example, Berger, J., et al., Annu. Rev. Med., 2002, 53, 409-435; Wilson, T. et al., J. Med. Chem., 2000, 43(4), 527-550; Kliewer, S. et al., Recent Prog Horm Res., 2001, 56, 239-63; Fruchart, J. C. et al., 2001, Pharmacological Research, 44(5), 345-52; Kersten, S. et al., Nature, 2000, 405, 421-424; Torra, I. P. et al., Curr Opin Lipidol, 2001, 12, 245-254).

Compounds of this type are particularly suitable for the treatment and/or prevention of:

1. Disorders of fatty acid metabolism and glucose utilization disorders.
   Disorders in which insulin resistance is involved
2. Diabetes mellitus, especially type 2 diabetes, including the prevention of the sequelae associated therewith.
   Particular aspects in this connection are
   hyperglycemia,
   improvement in insulin resistance,
   improvement in glucose tolerance,
   protection of the pancreatic β cells
   prevention of macro- and microvascular disorders
3. Dyslipidemias and their sequelae such as, for example, atherosclerosis, coronary heart disease, cerebrovascular disorders etc, especially those (but not restricted thereto) which are characterized by one or more of the following factors:
   high plasma triglyceride concentrations, high postprandial plasma triglyceride concentrations,
   low HDL cholesterol concentrations
   low ApoA lipoprotein concentrations
   high LDL cholesterol concentrations
   small dense LDL cholesterol particles
   high ApoB lipoprotein concentrations
4. Various other conditions which may be associated with the metabolic syndrome, such as:
   obesity (excess weight), including central obesity thromboses, hypercoagulable and prothrombotic states (arterial and venous)
high blood pressure
heart failure such as, for example (but not restricted thereto), following myocardial infarction, hypertensive heart disease or cardiomyopathy 5. Disorders or conditions in which inflammatory reactions are involved:
atherosclerosis such as, for example (but not restricted thereto), coronary sclerosis including angina pectoris or myocardial infarction, stroke
vascular restenosis or reocclusion
chronic inflammatory bowel diseases such as, for example, Crohn's disease and ulcerative colitis
asthma
lupus erythematosus (LE) or inflammatory rheumatic disorders such as, for example, rheumatoid arthritis
other inflammatory states 6. Disorders of cell cycle or cell differentiation processes:
adipose cell tumors
lipomatous carcinomas such as, for example, liposarcomas
solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc
acute and chronic myeloproliferative disorders and lymphomas
angiogenesis 7. Demyelinating and other neurodegenerative disorders of the central and peripheral nervous systems including:
Alzheimer's disease
multiple sclerosis
Parkinson's disease
adrenoleukodystrophy (ALD)
adrenomyeloneuropathy
AIDS-vacuolar myelopathy
HTLV-associated myelopathy
Leber's hereditary optic atrophy
progressive multifocal leukoencephalopathy (PML)
subacute sclerosing panencephalitis
Guillian-Barre syndrome
tropical spastic paraparesis
acute disseminated encephalomyelitis (ADEM)
acute viral encephalitis
acute transverse myelitis
spinal cord and brain trauma
Charcot-Marie-Tooth disease 8. Skin disorders and/or disorders of wound healing processes:
erythemato-squamous dermatoses such as, for example, psoriasis
acne vulgaris
other skin disorders and dermatological conditions which are modulated by PPAR
eczemas and neurodermitis
dermatitis such as, for example, seborrheic dermatitis or photodermatitis
keratitis and keratoses such as, for example, seborrheic keratoses, senile keratoses, actinic keratosis, photo-induced keratoses or keratosis follicularis
keloids and keloid prophylaxis
warts, including condylomata or condylomata acuminata
human papilloma viral (HPV) infections such as, for example, venereal papillomata, viral warts such as, for example, molluscum contagiosum, leukoplakia
papular dermatoses such as, for example, Lichen planus
skin cancer such as, for example, basal-cell carcinomas, melanomas or cutaneous T-cell lymphomas
localized benign epidermal tumors such as, for example, keratoderma, epidermal naevi
chilblains
wound healing 9. Other disorders
high blood pressure
pancreatitis
syndrome X
polycystic ovary syndrome (PCOS)
asthma
osteoarthritis
lupus erythematosus (LE) or inflammatory rheumatic disorders such as, for example, rheumatoid arthritis
vasculitis
wasting (cachexia)
gout
ischemia/reperfusion syndrome
acute respiratory distress syndrome (ARDS)

Formulations

The amount of a compound of formula I necessary to achieve the desired biological effect depends on a number of factors, for example the specific compound chosen, the intended use, the mode of administration and the clinical condition of the patient. The daily dose is generally in the range from 0.001 mg to 100 mg (typically from 0.01 mg to 50 mg) per day and per kilogram of bodyweight, for example 0.1-10 mg/kg/day. An intravenous dose may be, for example, in the range from 0.001 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampules for injections may contain, for example, from 1 mg to 100 mg, and single-dose formulations which can be administered orally, such as, for example, capsules or tablets, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contain a defined amount of the compound of formula I; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 368 (1986).

The compounds of the formula I are distinguished by favorable effects on metabolic disorders. They beneficially influence lipid and sugar metabolism, in particular they lower the triglyceride level and are suitable for the prevention and treatment of type II diabetes and atherosclerosis and the diverse sequalae thereof.

Combinations with Other Medicaments

The compounds of the invention can be administered alone or in combination with one or more further pharmacologically active substances. In particular, the compounds of the invention can be administered in combination with active ingredients having a similar pharmacological action. For example, they can be administered in combination with active ingredients which have favorable effects on metabolic disturbances or disorders frequently associated therewith. Examples of such medicaments are 1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and
10. active ingredients for the treatment and/or prevention of complications caused by diabetes or associated with diabetes.
11. active ingredients for the treatment of neurodegenerative diseases
12. active ingredients for the treatment of disorders of the central nervous system
13. active ingredients for the treatment of drug, nicotine and alcohol addiction
14. analgesics They can be combined with the compounds of the invention of the formula I in particular for a synergistic enhancement of activity. Administration of the active ingredient combination can take place either by separate administration of the active ingredients to the patient or in the form of combination products in which a plurality of active ingredients are present in one pharmaceutical preparation.

Particularly suitable further active ingredients for the combination preparations are:

All antidiabetics mentioned in the Rote Liste 2006, Chapter 12; all slimming agents/appetite suppressants mentioned in the Rote Liste 2006, Chapter 1; all lipid-lowering agents mentioned in the Rote Liste 2006, Chapter 58. They can be combined with the compound of the formula I according to the invention in particular for a synergistic enhancement of activity. The active compound combination can be administered either by separate administration of the active compounds to the patient or in the form of combination preparations in which a plurality of active compounds are present in a pharmaceutical preparation. Most of the active compounds listed below are disclosed in USP Dictionary of USAN and International Drug Names, US Pharmacopeia, Rockville 2001.

Antidiabetics include insulin and insulin derivatives, such as, for example, Lantus® (see www.lantus.com) or HMR 1964 or those described in WO2005005477 (Novo Nordisk), fast-acting insulins (see U.S. Pat. No. 6,221,633), inhalable insulins, such as, for example, Exubera® or oral insulins, such as, for example, IN-105 (Nobex) or Oral-lyn™ (Generex Biotechnology), GLP-1 derivatives, such as, for example, Exenatide, Liraglutide or those disclosed in WO 98/08871 or WO2005027978 by Novo Nordisk A/S, in WO 01/04156 by Zealand or in WO 00/34331 by Beaufour-Ipsen, pramlintide acetate (Symlin; Amylin Pharmaceuticals), and also orally effective hypoglycemic active ingredients.

The active compounds preferably include
sulfonylureas,
biguanidines,
meglitinides,
oxadiazolidinediones,
thiazolidinediones,
glucosidase inhibitors,
inhibitors of glycogen phosphorylase,
glucagon antagonists,
glucokinase activators,
inhibitors of fructose-1,6-bisphosphatase,
modulators of the glucose transporter 4 (GLUT4),
inhibitors of glutamine:fructose-6-phosphate amidotransferase (GFAT),
GLP-1 agonists,
potassium channel openers, such as, for example, those disclosed in WO 97/26265 and WO 99/03861 by Novo Nordisk A/S,
inhibitors of dipeptidylpeptidase IV (DPP-IV),
insulin sensitizers,
inhibitors of liver enzymes involved in the stimulation of gluconeogenesis and/or
glycogenolysis,
modulators of glucose uptake, glucose transport and glucose backresorption,
inhibitors of 11β-HSD1,
inhibitors of protein tyrosine phosphatase 1B (PTP1B),
modulators of the sodium/glucose cotransporter 1 or 2 (SGLT1, SGLT2),
compounds which alter lipid metabolism, such as antihyperlipidemic active ingredients and antilipidemic active ingredients,
compounds which reduce food intake or food absorption,
compounds which increase thermogenesis,
PPAR and RXR modulators and
active ingredients which act on the ATP-dependent potassium channel of the beta cells.

In one embodiment of the invention, the compound of the formula I is administered in combination with a HMGCoA reductase inhibitor, such as simvastatin, fluvastatin, pravastatin, lovastatin, atorvastatin, cerivastatin, rosuvastatin or L-659699.

In one embodiment of the invention, the compound of the formula I is administered in combination with a cholesterol resorption inhibitor, such as, for example, ezetimibe, tiqueside, pamaqueside, FM-VP4 (sitostanol/campesterol ascorbyl phosphate; Forbes Medi-Tech, WO2005042692), MD-0727 (Microbia Inc., WO2005021497) or with compounds as described in WO2002066464 (Kotobuki Pharmaceutical Co. Ltd.), WO2005062824 (Merck & Co.) or WO2005061451 and WO2005061452 (AstraZeneca AB).

In one embodiment of the invention, the compound of the formula I is administered in combination with a PPAR gamma agonist, such as, for example, rosiglitazone, pioglitazone, JTT-501, GI 262570, R-483 or CS-011 (rivoglitazone).

In one embodiment of the invention, the compound of the formula I is administered in combination with a PPAR alpha agonist, such as, for example, GW9578, GW-590735, K-111, LY-674, KRP-101 or DRF-10945.

In one embodiment of the invention, the compound of the formula I is administered in combination with a mixed PPAR alpha/gamma agonist, such as, for example, muraglitazar, tesaglitazar, naveglitazar, LY-510929, ONO-5129, E-3030 or as described in WO00/64888, WO00/64876, WO03/020269, WO2004075891, WO2004076402, WO2004075815, WO2004076447, WO2004076428, WO2004076401, WO2004076426, WO2004076427, WO2006018118, WO2006018115, and WO2006018116 or in J. P. Berger et al., TRENDS in Pharmacological Sciences 28(5), 244-251, 2005.

In one embodiment of the invention, the compound of the formula I is administered in combination with a PPAR delta agonist, such as, for example, GW-501516 or as described in WO2005097762, WO2005097786, WO2005097763, and WO2006029699.

In one embodiment of the invention, the compound of the formula I is administered in combination with metaglidasen or with MBX-2044 or other partial PPAR gamma agonists/antagonists.

In one embodiment of the invention, the compound of the formula I is administered in combination with a fibrate, such as, for example, fenofibrate, clofibrate or bezafibrate.

In one embodiment of the invention, the compound of the formula I is administered in combination with an MTP inhibitor, such as, for example, implitapide, BMS-201038, R-103757 or those described in WO2005085226.

In one embodiment of the invention, the compound of the formula I is administered in combination with a CETP inhibitor, such as, for example, torcetrapib or JTT-705.

In one embodiment of the invention, the compound of the formula I is administered in combination with a bile acid resorption inhibitor (see, for example, U.S. Pat. Nos. 6,245, 744, 6,221,897 or WO00/61568), such as, for example, HMR 1741 or those described in DE 10 2005 033099.1 and DE 10 2005 033100.9.

In one embodiment of the invention, the compound of the formula I is administered in combination with a polymeric bile acid adsorber, such as, for example, cholestyramine or colesevelam.

In one embodiment of the invention, the compound of the formula I is administered in combination with an LDL receptor inducer (see U.S. Pat. No. 6,342,512), such as, for example, HMR1171, HMR1586 or those described in WO2005097738.

In one embodiment, the compound of the formula I is administered in combination with Omacor® (omega-3 fatty acids; highly concentrated ethyl esters of eicosapentaenoic acid and docosahexaenoic acid).

In one embodiment of the invention, the compound of the formula I is administered in combination with an ACAT inhibitor, such as, for example, avasimibe.

In one embodiment of the invention, the compound of the formula I is administered in combination with an antioxidant, such as, for example, OPC-14117, probucol, tocopherol, ascorbic acid, β-carotene or selenium.

In one embodiment of the invention, the compound of the formula I is administered in combination with a vitamin, such as, for example, vitamin B6 or vitamin B12.

In one embodiment of the invention, the compound of the formula I is administered in combination with a lipoprotein lipase modulator, such as, for example, ibrolipim (NO-1886).

In one embodiment of the invention, the compound of the formula I is administered in combination with an ATP-citrate lyase inhibitor, such as, for example, SB-204990.

In one embodiment of the invention, the compound of the formula I is administered in combination with a squalene synthetase inhibitor, such as, for example, BMS-188494 or as described in WO2005077907.

In one embodiment of the invention, the compound of the formula I is administered in combination with a lipoprotein (a) antagonist, such as, for example, gemcabene (CI-1027).

In one embodiment of the invention, the compound of the formula I is administered in combination with an HM74A receptor agonists, such as, for example, nicotinic acid.

In one embodiment of the invention, the compound of the formula I is administered in combination with a lipase inhibitor, such as, for example, orlistat or cetilistat (ATL-962).

In one embodiment of the invention, the compound of the formula I is administered in combination with insulin.

In one embodiment of the invention, the compound of the formula I is administered in combination with a sulfonylurea, such as, for example, tolbutamide, glibenclamide, glipizide or glimepiride.

In one embodiment of the invention, the compound of the formula I is administered in combination with a biguanide, such as, for example, metformin.

In another embodiment of the invention, the compound of the formula I is administered in combination with a meglitinide, such as, for example, repaglinide or nateglinide.

In one embodiment of the invention, the compound of the formula I is administered in combination with a thiazolidinedione, such as, for example, troglitazone, ciglitazone, pioglitazone, rosiglitazone or the compounds disclosed in WO 97/41097 by Dr. Reddy's Research Foundation, in particular 5-[[4-[(3,4-dihydro-3-methyl-4-oxo-2-quinazolinyl-methoxy]phenyl]methyl]-2,4-thiazolidinedione.

In one embodiment of the invention, the compound of the formula I is administered in combination with an α-glucosidase inhibitor, such as, for example, miglitol or acarbose.

In one embodiment of the invention, the compound of the formula I is administered in combination with an active ingredient which acts on the ATP-dependent potassium channel of the beta cells, such as, for example, tolbutamide, glibenclamide, glipizide, glimepiride or repaglinide.

In one embodiment of the invention, the compound of the formula I is administered in combination with more than one of the compounds mentioned above, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment of the invention, the compound of the formula I is administered in combination with an inhibitor of glycogen phosphorylase, such as, for example, PSN-357 or FR-258900 or those described in WO2003084922, WO2004007455, WO2005073229-31 or WO2005067932.

In one embodiment of the invention, the compound of the formula I is administered in combination with glucagon receptor antagonists, such as, for example, A-770077, NNC-25-2504 or such as in WO2004100875 or WO2005065680.

In one embodiment of the invention, the compound of the formula I is administered in combination with activators of glucokinase, such as, for example, RO-4389620, LY-2121260 (WO2004063179), PSN-105, PSN-110, GKA-50 or those described, for example, by Prosidion in WO2004072031, WO2004072066, WO 05103021 or WO 06016178, by Roche in WO 00058293, WO 00183465, WO 00183478, WO 00185706, WO 00185707, WO 01044216, GB 02385328, WO 02008209, WO 02014312, WO 0246173, WO 0248106, DE 10259786, WO 03095438, U.S. Pat. No. 4,067,939 or WO 04052869, by Novo Nordisk in EP 1532980, WO 03055482, WO 04002481, WO 05049019, WO 05066145 or WO 05123132, by Merck/Banyu in WO 03080585, WO03097824, WO 04081001, WO 05063738 or WO 05090332, by Eli Lilly in WO 04063194, or by Astra Zeneca in WO 01020327, WO 03000262, WO 03000267, WO 03015774, WO 04045614, WO 04046139, WO 05044801, WO 05054200, WO 05054233, WO 05056530, WO 05080359, WO 05080360 or WO 05121110.

In one embodiment of the invention, the compound of the formula I is administered in combination with an inhibitor of gluconeogenesis, such as, for example, FR-225654.

In one embodiment of the invention, the compound of the formula I is administered in combination with inhibitors of fructose-1,6-bisphosphatase (FBPase), such as, for example, CS-917.

In one embodiment of the invention, the compound of the formula I is administered in combination with modulators of the glucose transporter 4 (GLUT4), such as, for example, KST-48 (D.-O. Lee et al.: Arzneim.-Forsch. Drug Res. 54 (12), 835 (2004)).

In one embodiment of the invention, the compound of the formula I is administered in combination with inhibitors of glutamine:fructose-6-phosphate amidotransferase (GFAT), as described, for example, in WO2004101528.

In one embodiment of the invention, the compound of the formula I is administered in combination with inhibitors of dipeptidylpeptidase IV (DPP-IV), such as, for example, vildagliptin (LAF-237), sitagliptin (MK-0431), saxagliptin ((BMS-477118), GSK-823093, PSN-9301, SYR-322, SYR-619, TA-6666, TS-021, GRC-8200, GW-825964x or as described in WO2003074500, WO2003106456, WO200450658, WO2005058901, WO2005012312, WO2005/012308, PCT/EP2005/007821, PCT/EP2005/008005, PCT/EP2005/008002, PCT/EP2005/008004, PCT/EP2005/008283, DE 10 2005 012874.2 or DE 10 2005 012873.4.

In one embodiment of the invention, the compound of the formula I is administered in combination with inhibitors of 11-beta-hydroxysteroid dehydrogenase-1 (11β-HSD1), such as, for example, BVT-2733 or those described, for example, in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004065351, WO2004089367, WO2004089380, WO2004089470-71, WO2004089896, WO2005016877 or WO2005097759.

In one embodiment of the invention, the compound of the formula I is administered in combination with inhibitors of protein tyrosine phosphatase 1B (PTP1B), as described, for example, in WO200119830-31, WO200117516, WO2004506446, WO2005012295, PCT/EP2005/005311, PCT/EP2005/005321, PCT/EP2005/007151, PCT/EP2005/ or DE 10 2004 060542.4.

In one embodiment of the invention, the compound of the formula I is administered in combination with modulators of the sodium/glucose cotransporter 1 or 2 (SGLT1, SGLT2), such as, for example, KGA-2727, T-1095 and SGL-0010 or as described, for example, in WO2004007517, WO200452903, WO200452902, WO2005121161, WO2005085237, JP2004359630 or by A. L. Handlon in Expert Opin. Ther. Patents (2005) 15(11), 1531-1540.

In one embodiment of the invention, the compound of the formula I is administered in combination with inhibitors of hormone-sensitive lipase (HSL), such as those described, for example, in WO01/17981, WO01/66531, WO2004035550, WO2005073199 or WO03/051842.

In one embodiment of the invention, the compound of the formula I is administered in combination with inhibitors of acetyl-CoA carboxylase (ACC) such as those described, for example, in WO199946262, WO200372197, WO2003072197 or WO2005044814.

In one embodiment of the invention, the compound of the formula I is administered in combination with an inhibitor of phosphoenolpyruvate carboxykinase (PEPCK), such as those described, for example, in WO2004074288.

In one embodiment of the invention, the compound of the formula I is administered in combination with an inhibitor of glycogen synthase kinase-3 beta (GSK-3 beta), such as those described, for example, in US2005222220, WO2004046117, WO2005085230, WO2005111018, WO2003078403, WO2004022544, WO2003106410, WO2005058908, US2005038023, WO2005009997, US2005026984, WO2005000836, WO2004106343, EP1460075, WO2004014910, WO2003076442, WO2005087727 or WO2004046117.

In one embodiment of the invention, the compound of the formula I is administered in combination with an inhibitor of protein kinase C beta (PKC beta), such as, for example, ruboxistaurin.

In one embodiment of the invention, the compound of the formula I is administered in combination with an endothelin-A receptor antagonist, such as, for example, avosentan (SPP-301).

In one embodiment of the invention, the compound of the formula I is administered in combination with inhibitors of "I-kappaB kinase" (IKK inhibitors), such as those described, for example, in WO2001000610, WO2001030774, WO2004022553 or WO2005097129.

In one embodiment of the invention, the compound of the formula I is administered in combination with modulators of the glucocorticoid receptor as described, for example, in WO2005090336.

In a further embodiment of the invention, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558); NPY antagonists such as, for example, {4-[(4-aminoquinazolin-2-ylamino)methyl]-cyclohexylmethyl}naphthalene-1-sulfonamide hydrochloride (CGP 71683A);

peptide YY 3-36 (PYY3-36) or analogous compounds, such as, for example, CJC-1682 (PYY3-36 conjugated with human serum albumin via Cys34), CJC-1643 (derivative of PYY3-36 which conjugates in vivo to serum albumin) or those described in WO2005080424;

cannabinoid receptor 1 antagonists, such as, for example, rimonabant, SR147778 or those described, for example, in EP 0656354, WO 00/15609, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509 or WO2005077897;

MC4 agonists (for example [2-(3a-benzyl-2-methyl-3-oxo-2,3,3a,4,6,7-hexahydro-pyrazolo[4,3-c]pyridin-5-yl)-1-(4-chlorophenyl)-2-oxoethyl]-1-amino-1,2,3,4-tetrahydro-naphthalene-2-carboxamide; (WO 01/91752)) or LB53280, LB53279, LB53278 or THIQ, MB243, RY764, CHIR-785, PT-141 or those described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2005042516, WO2005040109, WO2005030797, US20040224901, WO200501921, WO200509184, WO2005000339, EP1460069, WO2005047253, WO2005047251, EP1538159, WO2004072076, WO2004072077 or WO2006024390;

orexin receptor antagonists (for example 1-(2-methylbenzoxazol-6-yl)-3-[1,5]naphthyridin-4-ylurea hydrochloride (SB-334867-A) or those described, for example, in WO200196302, WO200185693, WO2004085403 or WO2005075458);

histamine H3 receptor agonists (for example 3-cyclohexyl-1-(4,4-dimethyl-1,4,6,7-tetrahydroimidazo[4,5-c]pyridin-5-yl)-propan-1-one oxalic acid salt (WO 00/63208) or those described in WO200064884, WO2005082893);

CRF antagonists (for example [2-methyl-9-(2,4,6-trimethylphenyl)-9H-1,3,9-triazafluoren-4-yl]dipropylamine (WO 00/66585));

CRF BP antagonists (for example urocortin);

urocortin agonists;

β3 agonists (such as, for example, 1-(4-chloro-3-methanesulfonylmethylphenyl)-2-[2-(2,3-dimethyl-1H-indol-6-yloxy)ethylamino]ethanol hydrochloride (WO 01/83451));

MSH (melanocyte-stimulating hormone) agonists;

MCH (melanin-concentrating hormone) receptor antagonists (such as, for example, NBI-845, A-761, A-665798, A-798, ATC-0175, T-226296, T-71, GW-803430 or those compounds described in WO2003/15769, WO2005085200, WO2005019240, WO2004011438, WO2004012648, WO2003015769, WO2004072025, WO2005070898, WO2005070925, WO2006018280, WO2006018279, WO2004039780, WO2003033476, WO2002006245, WO2002002744, WO2003004027 or FR2868780);

CCK-A agonists (such as, for example, {2-[4-(4-chloro-2,5-dimethoxyphenyl)-5-(2-cyclohexylethyl)-thiazol-2-ylcarbamoyl]-5,7-dimethylindol-1-yl}acetic acid trifluoroacetic acid salt (WO 99/15525), SR-146131 (WO 0244150) or SSR-125180);

serotonin reuptake inhibitors (for example dexfenfluramine);

mixed serotonin- and noradrenergic compounds (for example WO 00/71549);

5-HT receptor agonists, for example 1-(3-ethylbenzofuran-7-yl)piperazine oxalic acid salt (WO 01/09111);

5-HT2C receptor agonists (such as, for example, APD-356, BVT-933 or those described in WO200077010, WO20077001-02, WO2005019180, WO2003064423, WO200242304 or WO2005082859);

5-HT6 receptor antagonists, such as described, for example, in WO2005058858; bombesin receptor agonists (BRS-3 agonists);

galanin receptor antagonists;

growth hormone (for example human growth hormone or AOD-9604);

growth hormone releasing compounds (tert-butyl 6-benzyloxy-1-(2-diisopropylamino-ethylcarbamoyl)-3,4-dihydro-1H-isoquinoline-2-carboxylate (WO 01/85695));

growth hormone secretagog receptor antagonists (ghrelin antagonists) such as, for example, A-778193 or those described in WO2005030734;

TRH agonists (see, for example, EP 0 462 884);

uncoupling protein 2 or 3 modulators;

leptin agonists (see for example Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881);

DA agonists (bromocriptine or Doprexin);

lipase/amylase inhibitors (as described, for example, in WO 00/40569);

inhibitors of diacylglycerol O-acyltransferases (DGATs) such as described, for example, in US2004/0224997, WO2004094618, WO200058491, WO2005044250, WO2005072740, JP2005206492 or WO2005013907;

inhibitors of fatty acid synthase (FAS) such as, for example, C75 or those described in WO2004005277;

oxyntomodulin;

oleoyl-estrone or thyroid hormone receptor agonists, such as, for example, KB-2115 or those described in WO20058279, WO200172692, WO200194293, WO2003084915, WO2004018421 or WO2005092316.

In one embodiment of the invention, the further active ingredient is leptin; see for example "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment of the invention, the further active ingredient is dexamphetamine or amphetamine.

In one embodiment of the invention, the further active ingredient is fenfluramine or dexfenfluramine.

In another embodiment of the invention, the further active ingredient is sibutramine.

In one embodiment of the invention, the further active ingredient is mazindol or phentermine.

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main). Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compound of the formula I is administered in combination with PDE (phosphodiesterase) inhibitors, as described, for example, in WO2003/077949 or WO2005012485.

In one embodiment of the invention, the compound of the formula I is administered in combination with NAR-1 (nicotinic acid receptor) agonists as described, for example, in WO2004094429.

In one embodiment of the invention, the compound of the formula I is administered in combination with CB2 (cannabinoid receptor) agonists as described, for example, in US2005/143448.

In one embodiment of the invention, the compound of the formula I is administered in combination with histamine 1 agonists as described, for example, in WO2005101979.

In one embodiment of the invention, the compound of the formula I is administered in combination with bupropion, as described in WO2006017504.

In one embodiment of the invention, the compound of the formula I is administered in combination with opioid antagonists as described, for example, in WO2005107806 or WO2004094429.

In one embodiment of the invention, the compound of the formula I is administered in combination with neutral endopeptidase inhibitors as described, for example, in WO200202513, WO2002/06492, WO 2002040008, WO2002040022 or WO2002047670.

In one embodiment of the invention, the compound of the formula I is administered in combination with NPY inhibitors (neuropeptide Y) as described, for example, in WO2002047670.

In one embodiment of the invention, the compound of the formula I is administered in combination with sodium/hydrogen exchange inhibitors as described, for example, in WO2003092694.

In one embodiment of the invention, the compound of the formula I is administered in combination with modulators of the glucocorticoid receptor as described, for example, in WO2005090336.

In one embodiment of the invention, the compound of the formula I is administered in combination with nicotine receptor agonists as described, for example, in WO2004094429.

In one embodiment of the invention, the compound of the formula I is administered in combination with NRIs (norepinephrine reuptake inhibitors) as described, for example, in WO2002053140.

In one embodiment of the invention, the compound of the formula I is administered in combination with MOA (E-beta-methoxyacrylate), such as, for example, segeline, or as described, for example, in WO2002053140.

In one embodiment of the invention, the compound of the formula I is administered in combination with antithrombotic active ingredients, such as, for example, clopidrogel.

It is to be understood that each suitable combination of the compounds according to the invention with one or more of the compounds mentioned above and optionally one or more further pharmacologically active substances is meant to be included in the scope of the present invention.

The formulae for some of the development codes mentioned above are given below.

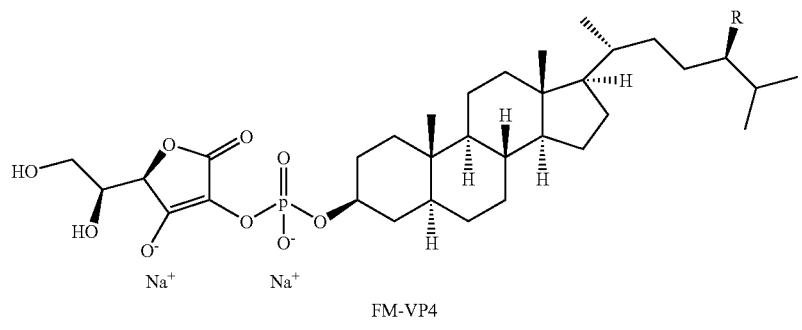
FM-VP4
R = CH₃; CH CH₂—CH₃
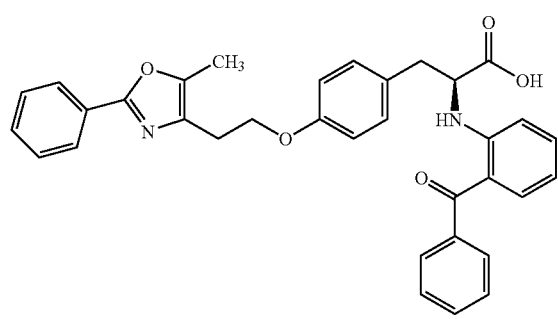
GI 262570
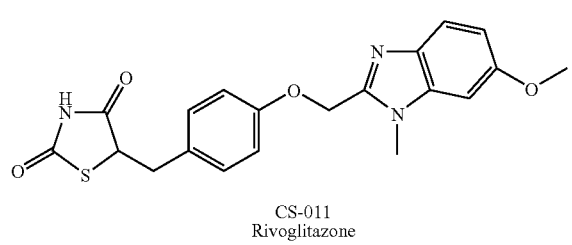
CS-011
Rivoglitazone
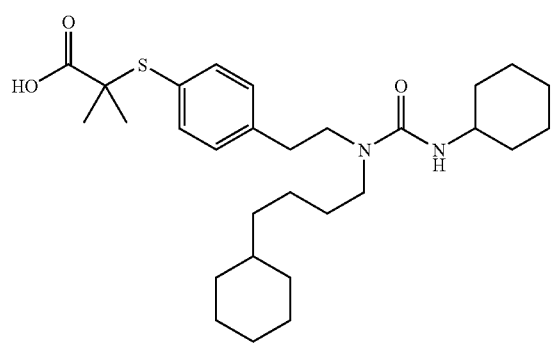
GW-9578
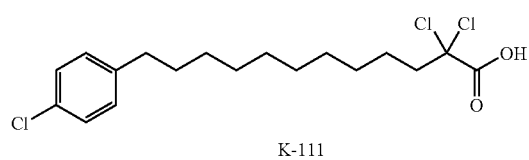
K-111
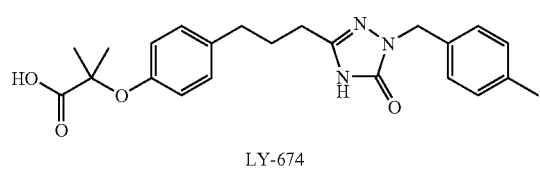
LY-674
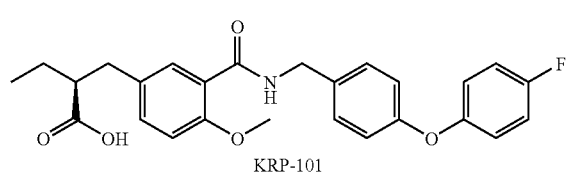
KRP-101
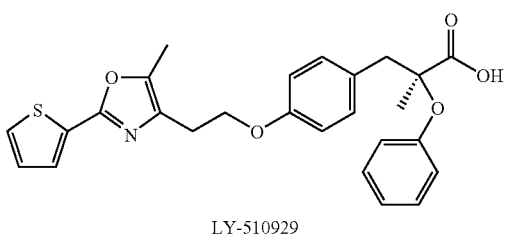
LY-510929

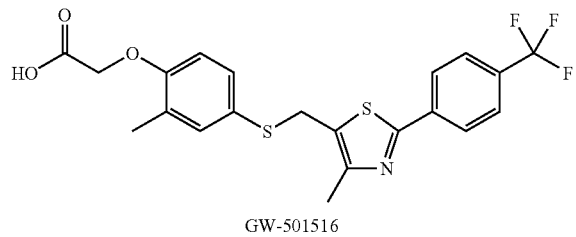
GW-501516
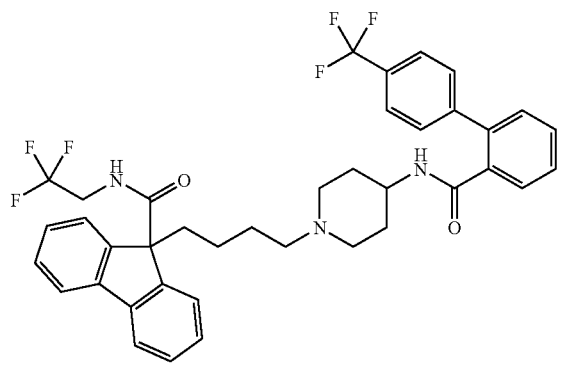
BMS-201038
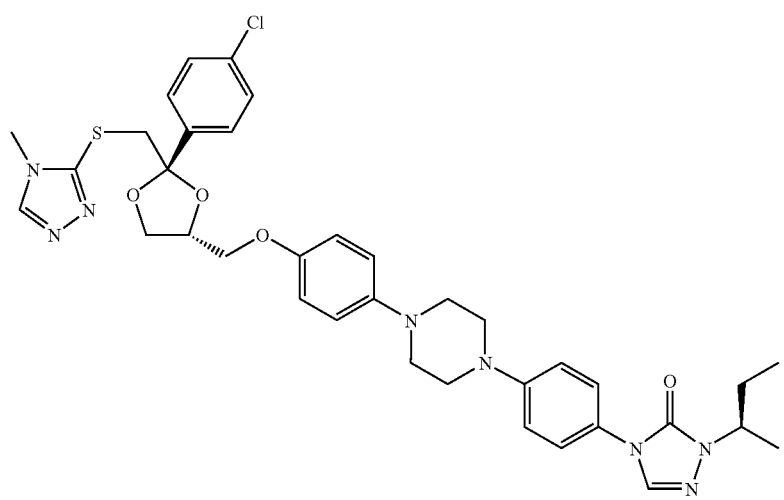
R-103757
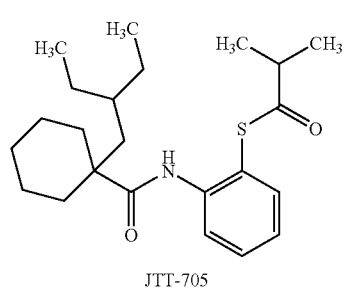
JTT-705
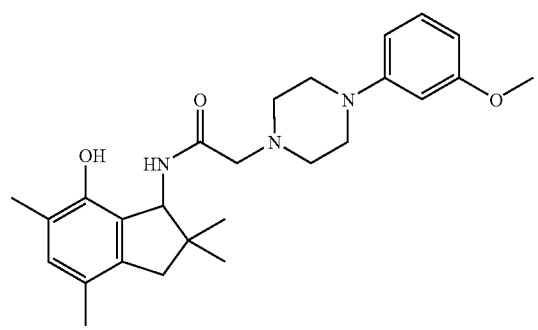
OPC-14117
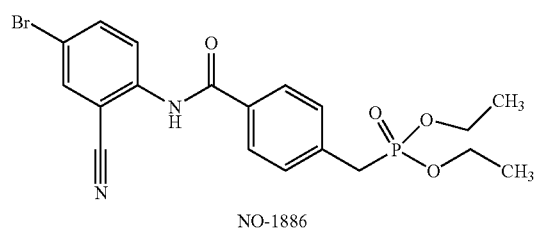
NO-1886
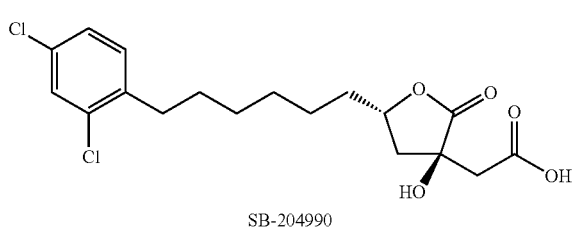
SB-204990

-continued
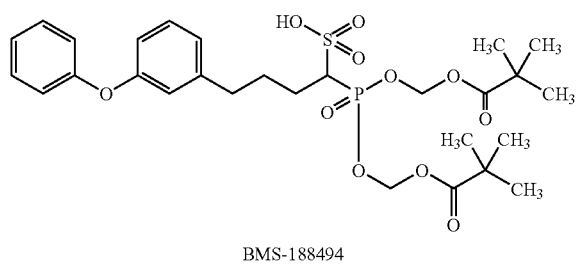
BMS-188494
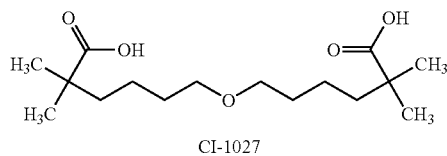
CI-1027
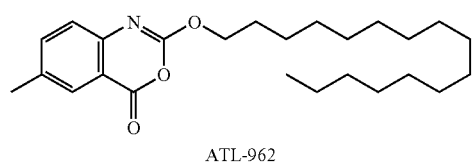
ATL-962
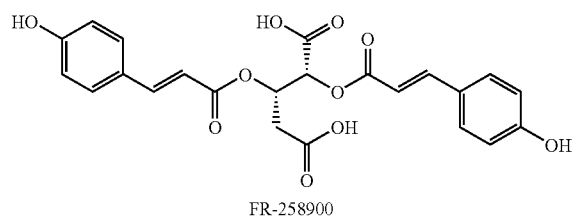
FR-258900
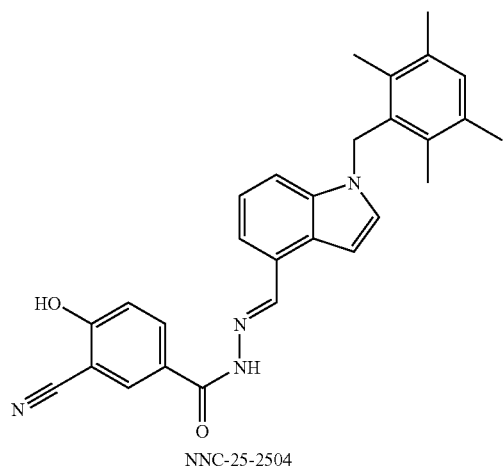
NNC-25-2504
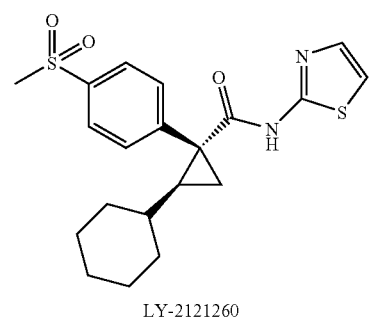
LY-2121260
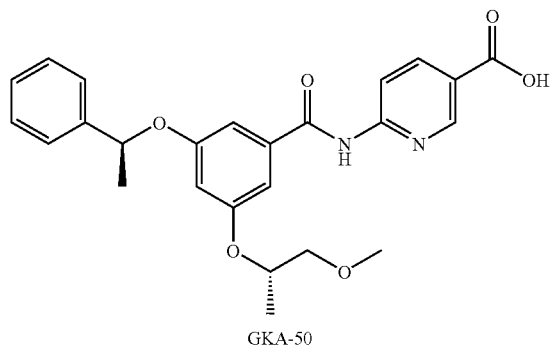
GKA-50
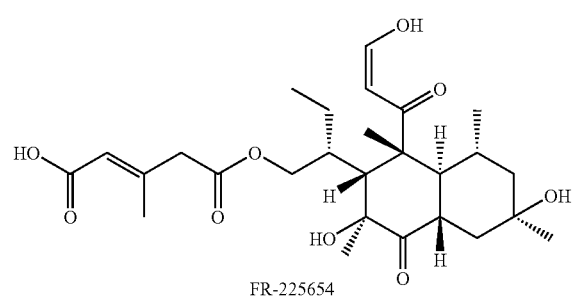
FR-225654
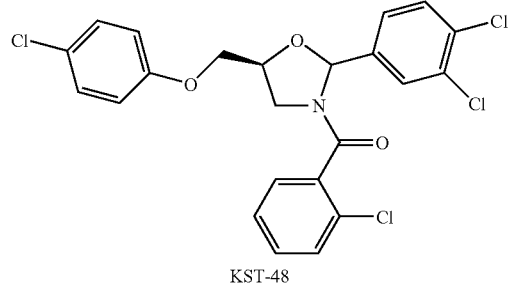
KST-48
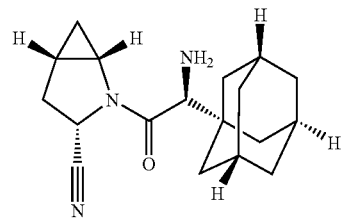
BMS-477118

-continued
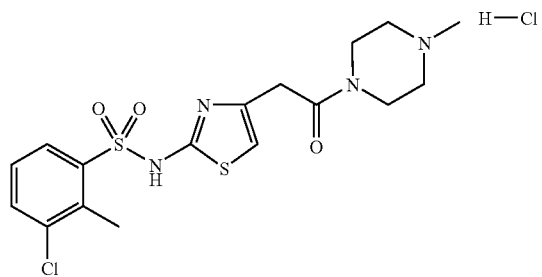
BVT-2733
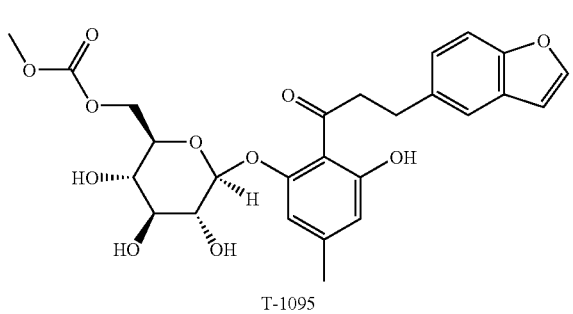
T-1095
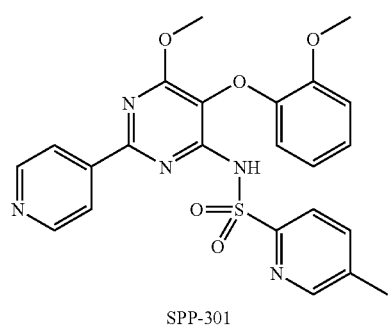
SPP-301
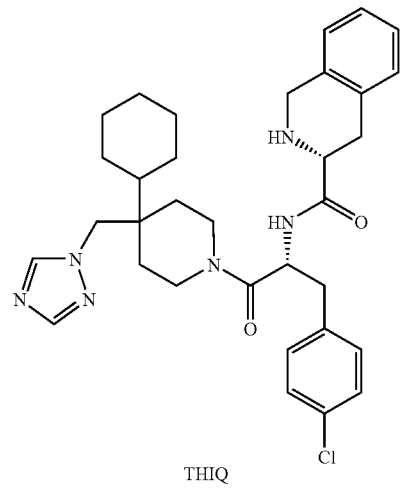
THIQ
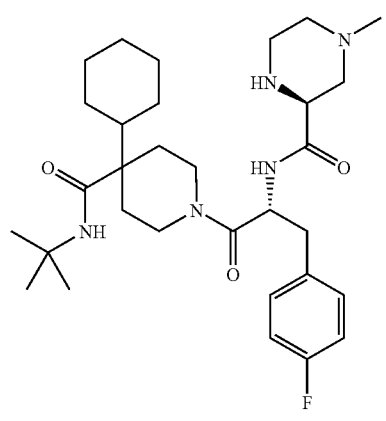
MB243
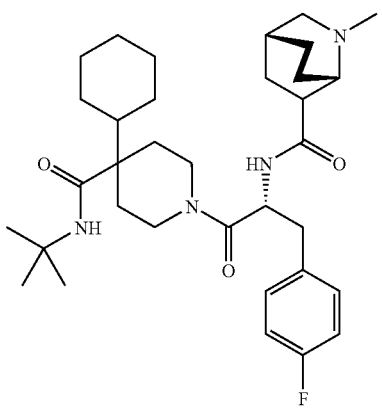
RY764
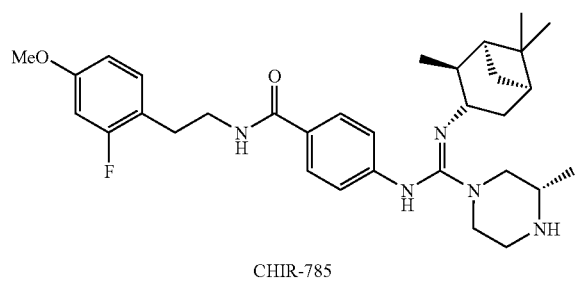
CHIR-785
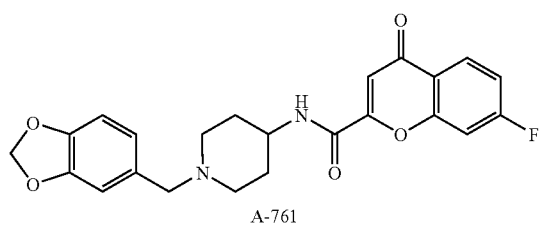
A-761

-continued
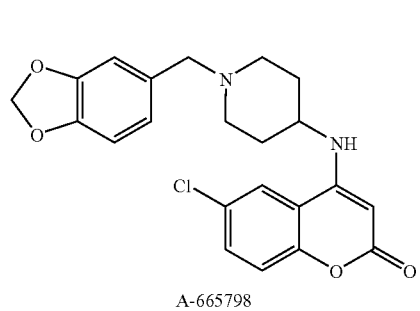
A-665798
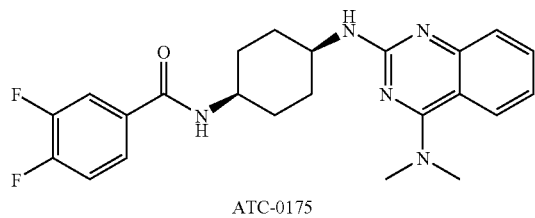
ATC-0175
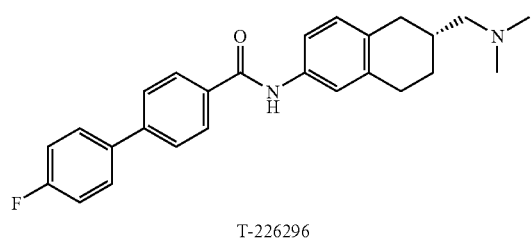
T-226296
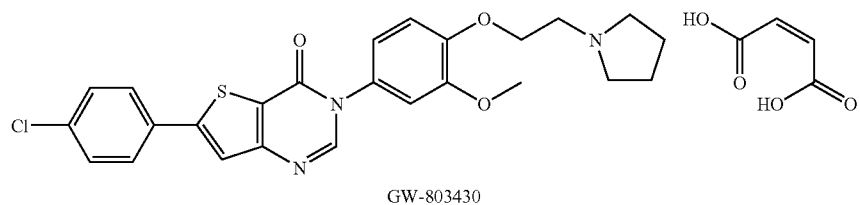
GW-803430
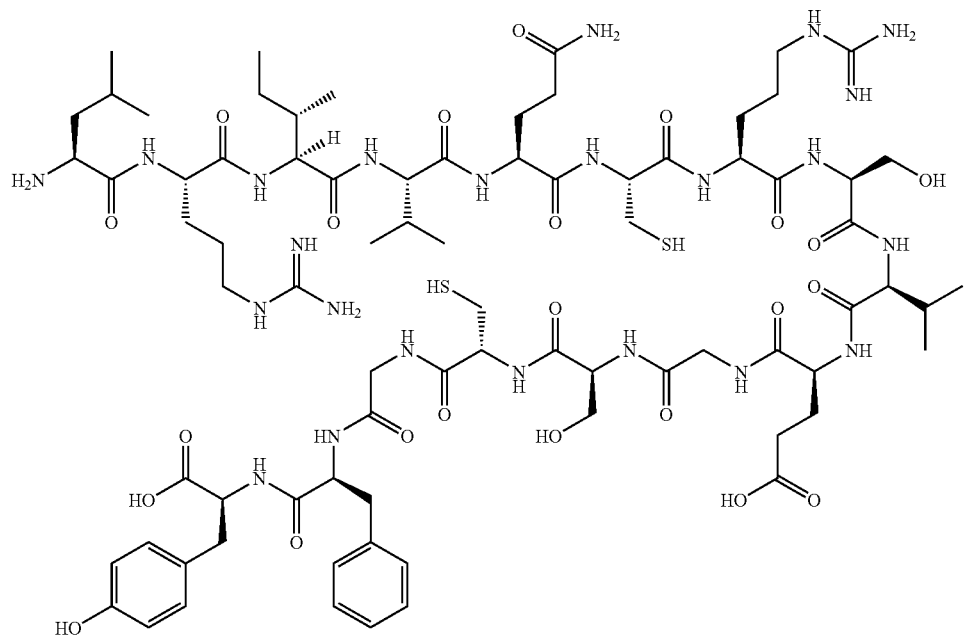
AOD-9604

-continued

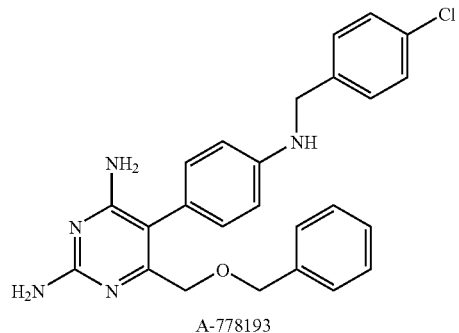
A-778193

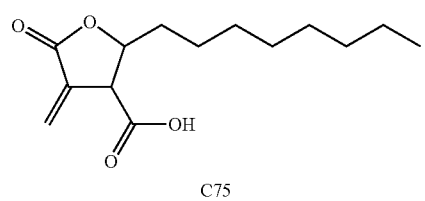
C75

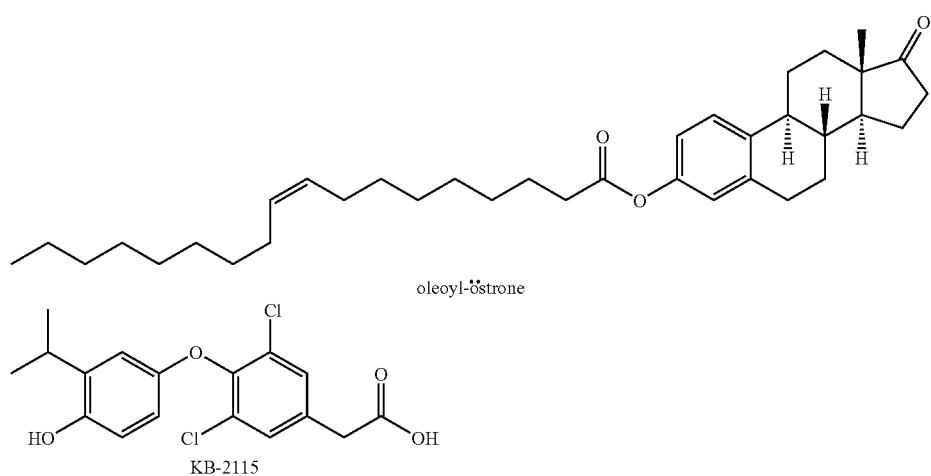
oleoyl-östrone

KB-2115

The activity of the compounds was tested as follows:

Determination of EC50 Values of PPAR Agonists in the Cellular PPARalpha Assay

Principle

The potency of substances which bind to human PPARalpha and activate it in an agonistic manner is analyzed using a stably transfected HEK cell line (HEK=human embryo kidney) which is referred to here as PPARalpha reporter cell line. It contains two genetic elements, a luciferase reporter element (pdeltaM-GAL4-Luc-Zeo) and a PPARalpha fusion protein (GR-GAL4-humanPPARalpha-LBD) which mediates expression of the luciferase reporter element depending on a PPARalpha ligand. The stably and constitutively expressed fusion protein GR-GAL4-humanPPARalpha-LBD binds in the cell nucleus of the PPARalpha reporter cell line via the GAL4 protein portion to the GAL4 DNA binding motifs 5'-upstream of the luciferase reporter element which is stably integrated in the genome of the cell line. There is only weak expression of the luciferase reporter gene in the absence of a PPARalpha ligand if fatty acid-depleted fetal calf serum (cs-FCS) is used in the assay. PPARalpha ligands bind and activate the PPARalpha fusion protein and thereby stimulate the expression of the luciferase reporter gene. The luciferase which is formed can be detected by means of chemiluminescence via an appropriate substrate.

Construction of the PPARalpha Reporter Cell Line

The PPARalpha reporter cell line was prepared in two stages. Firstly, the luciferase reporter element was constructed and stably transfected into HEK cells. For this purpose, five binding sites of the yeast transcription factor GAL4 (Accession #AF264724) were cloned in 5'-upstream of a 68 bp-long minimal MMTV promoter (Accession #V01175). The minimal MMTV promoter section contains a CCMT box and a TATA element in order to enable efficient transcription by RNA polymerase II. The cloning and sequencing of the GAL4-MMTV construct took place in analogy to the description of Sambrook J. et al. (Molecular cloning, Cold Spring Harbor Laboratory Press, 1989). Then the complete Photinus pyralis gene (Accession #15077) was cloned in 3'-downstream of the GAL4-MMTV element. After sequencing, the luciferase reporter element consisting of five GAL4 binding sites, MMTV promoter and luciferase gene was recloned into a plasmid which confers zeocin resistance in order to obtain the plasmid pdeltaM-GAL4-Luc-Zeo. This vector was transfected into HEK cells in accordance with the statements in Ausubel, F. M. et al. (Current protocols in molecular biology, Vol. 1-3, John Wiley & Sons, Inc., 1995). Then zeocin-containing medium (0.5 mg/ml) was used to select a suitable stable cell clone which showed very low basal expression of the luceriferase gene.

In a second step, the PPARalpha fusion protein (GR-GAL4-humanPPARalpha-LBD was introduced into the stable cell clone described. For this purpose, initially the cDNA coding for the N-terminal 76 amino acids of the glucocorticoid receptor (Accession #P04150) was linked to the cDNA section coding for amino acids 1-147 of the yeast transcription factor GAL4 (Accession #P04386). The cDNA of the ligand-binding domain of the human PPARalpha receptor (amino acids S167-Y468; Accession #S74349) was cloned in at the 3'-end of this GR-GAL4 construct. The fusion construct prepared in this way (GR-GAL4-humanPPARalpha-LBD) was recloned into the plasmid pcDNA3 (Invitrogen) in order to enable constitutive expression therein by the cytomegalovirus promoter. This plasmid was linearized with a restriction endonuclease and stably transfected into the previously described cell clone containing the luciferase reporter element. The finished PPARalpha reporter cell line which contains a luciferase reporter element and constitutively expresses the PPARalpha fusion protein (GR-GAL4-human PPARalpha-LBD) was isolated by selection with zeocin (0.5 mg/ml) and G418 (0.5 mg/ml).

Assay Procedure

The activity of PPARalpha agonists is determined in a 3-day assay, which is described below:

Day 1

The PPARalphareporter cell line is cultivated to 80% confluence in DMEM (#41965-039, Invitrogen) which is mixed with the following additions: 10% cs-FCS (fetal calf serum; #SH-30068.03, Hyclone), 0.5 mg/ml zeocin (#R250-01, Invitrogen), 0.5 mg/ml G418 (#10136-027, Invitrogen), 1% penicillin-streptomycin solution (#15140-122, Invitrogen) and 2 mM L-glutamine (#25030-024, Invitrogen). The cultivation takes place in standard cell culture bottles (#353612, Becton Dickinson) in a cell culture incubator at 37° C. in the presence of 5% $CO_2$. The 80%-confluent cells are washed once with 15 ml of PBS (#14190-094, Invitrogen), treated with 3 ml of trypsin solution (#25300-054, Invitrogen) at 37° C. for 2 min, taken up in 5 ml of the DMEM described and counted in a cell counter. After dilution to 500.000 cells/ml, 35,000 cells are seeded in each well of a 96 well microtiter plate with a clear plastic base (#3610, Corning Costar). The plates are incubated in the cell culture incubator at 37° C. and 5% $CO_2$ for 24 h.

Day 2

PPARalpha agonists to be tested are dissolved in DMSO in a concentration of 10 mM. This stock solution is diluted in DMEM (#41965-039, Invitrogen) which is mixed with 5% cs-FCS (#SH-30068.03, Hyclone), 2 mM L-glutamine (#25030-024, Invitrogen) and the previously described antibiotics (zeocin, G418, penicillin and streptomycin).

Test substances are tested in 11 different concentrations in the range from 10 μM to 100 pM. More potent compounds are tested in concentration ranges from 1 μM to 10 pM or between 100 nM and 1 pM.

The medium of the PPARalpha reporter cell line seeded on day 1 is completely removed by aspiration, and the test substances diluted in medium are immediately added to the cells. The dilution and addition of the substances is carried out by a robot (Beckman FX). The final volume of the test substances diluted in medium is 100 μl per well of a 96 well microtiter plate. The DMSO concentration in the assay is less than 0.1% v/v in order to avoid cytotoxic effects of the solvent.

Each plate was charged with a standard PPARalpha agonist, which was likewise diluted in 11 different concentrations, in order to demonstrate the functioning of the assay in each individual plate. The assay plates are incubated in an incubator at 37° C. and 5% $CO_2$ for 24 h.

Day 3

The PPARalpha reporter cells treated with the test substances are removed from the incubator, and the medium is aspirated off. The cells are lyzed by pipetting 50 μl of Bright Glo reagent (from Promega) into each well of a 96 well microtiter plate. After incubation at room temperature in the dark for 10 minutes, the microtiter plates are measured in the luminometer (Trilux from Wallac). The measuring time for each well of a microtiter plate is 1 sec.

Evaluation

The raw data from the luminometer are transferred into a Microsoft Excel file. Dose-effect plots and EC50 values of PPAR agonists are calculated using the XL.Fit program as specified by the manufacturer (IDBS).

The PPARalpha EC50 values for the compounds of Examples 1 to 112 in this assay are in the range from 5 nM to >10 μM. Compounds of the invention of the formula I activate the PPARalpha receptor.

Determination of EC50 Values of PPAR Agonists in the Cellular PPARdelta Assay

Principle

The potency of substances which bind to human PPAR-delta and activate it in an agonistic manner is analyzed using a stably transfected HEK cell line (HEK=human embryo kidney) which is referred to here as PPARdelta reporter cell line. In analogy to the assay described for PPARalpha, the PPARdelta reporter cell line also contains two genetic elements, a luciferase reporter element (pdeltaM-GAL4-Luc-Zeo) and a PPARdelta fusion protein (GR-GAL4-humanP-PARdelta-LBD) which mediates expression of the luciferase reporter element depending on a PPARdelta ligand. The stably and constitutively expressed fusion protein GR-GAL4-humanPPARdelta-LBD binds in the cell nucleus of the PPARdelta reporter cell line via the GAL4 protein portion to the GAL4 DNA binding motifs 5'-upstream of the luciferase reporter element which is stably integrated in the genome of the cell line. There is only little expression of the luciferase reporter gene in the absence of a PPARdelta ligand if fatty acid-depleted fetal calf serum (cs-FCS) is used in the assay. PPARdelta ligands bind and activate the PPARdelta fusion protein and thereby stimulate expression of the luciferase reporter gene. The luciferase which is formed can be detected by means of chemiluminescence via an appropriate substrate.

Construction of the PPARdelta Reporter Cell Line

The production of the stable PPARdelta reporter cell line is based on a stable HEK-cell clone which was stably transfected with a luciferase reporter element. This step was already described above in the section "construction of the PPARalpha reporter cell line". In a second step, the PPARdelta fusion protein (GR-GAL4-humanPPARdelta-LBD was stably introduced into this cell clone. For this purpose, the cDNA coding for the N-terminal 76 amino acids of the glucocorticoid receptor (Accession #P04150) was linked to the cDNA section coding for amino acids 1-147 of the yeast transcription factor GAL4 (Accession #P04386). The cDNA of the ligand-binding domain of the human PPARdelta receptor (amino acids S139-Y441; Accession #L07592) was cloned in at the 3'-end of this GR-GAL4 construct. The fusion construct prepared in this way (GR-GAL4-humanPPAR-delta-LBD) was recloned into the plasmid pcDNA3 (Invitrogen) in order to enable constitutive expression by the cytomegalovirus promoter. This plasmid was linearized with a restriction endonuclease and stably transfected into the previously described cell clone containing the luciferase reporter element. The resulting PPARdelta reporter cell line which contains a luciferase reporter element and constitutively expresses the PPARdelta fusion protein (GR-GAL4-human PPARdelta-LBD) was isolated by selection with zeocin (0.5 mg/ml) and G418 (0.5 mg/ml).

Assay Procedure and Evaluation

The activity of PPARdelta agonists is determined in a 3-day assay in exact analogy to the procedure already described for the PPARalpha reporter cell line except that the PPARdelta reporter cell line and a specific PPARdelta agonist was used as a standard to control test efficacy.

PPARdelta EC50 values in the range from 0.2 nM to >10 μM were measured for the PPAR agonists of Examples 1 to 112 described in this application. Compounds of the invention of the formula I activate the PPARdelta receptor.

The examples given in Table I serve to illustrate the invention, but without limiting it.

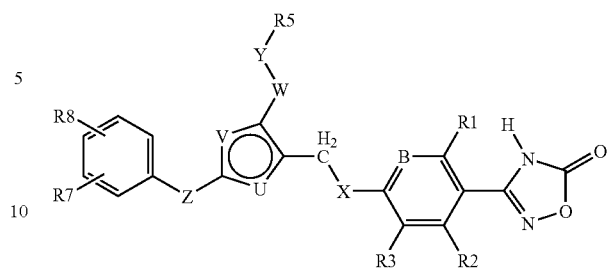

were R2 and R8=H.
A dotted line means the point of attachment.

TABLE I

| Example | Z | X | W | Y | R5 | R6 | U | V | R1 | R3 | R7 | B |
|---|---|---|---|---|---|---|---|---|---|---|---|---|
| 1 | bond | O | —CH2— | | 4-(trifluoromethyl)piperidin-1-yl | | S | N | —OCH3 | H | p-CF3 | CH |
| 2 | bond | O | —CH2— | | morpholin-4-yl | | S | N | Cl | H | p-CF3 | CH |
| 3 | bond | O | —CH2— | | morpholin-4-yl | | S | N | —OCH3 | H | p-CF3 | CH |
| 4 | bond | O | —CH2— | | 4,4-difluoropiperidin-1-yl | | S | N | —OCH3 | H | p-CF3 | CH |
| 5 | bond | O | —CH2— | | 4-methylpiperazin-1-yl | | S | N | —OCH3 | H | p-CF3 | CH |
| 6 | bond | O | —CH2— | | pyrrolidin-1-yl | | S | N | —OCH3 | H | p-CF3 | CH |
| 7 | bond | O | —CH2— | | 4-fluoropiperidin-1-yl | | S | N | —OCH3 | H | p-CF3 | CH |
| 8 | bond | O | —CH2— | N | —CH2CH3 | —CH2CH3 | S | N | —OCH3 | H | p-CF3 | CH |
| 9 | bond | O | —CH2CH2— | | 3-(trifluoromethyl)pyrrolidin-1-yl | | S | N | —OCH3 | H | p-CF3 | CH |
| 10 | bond | O | —CH2— | N | —(CH2)2OCH3 | —CH2CH3 | S | N | —OCH3 | H | p-CF3 | CH |
| 11 | bond | O | —CH2— | N | 1,3-dioxan-2-ylmethyl | —CH3 | S | N | —OCH3 | H | p-CF3 | CH |
| 12 | bond | O | —CH2— | | 4-methoxypiperidin-1-yl | | S | N | —OCH3 | H | p-CF3 | CH |

TABLE I-continued

| Example | Z | X | W | Y | R5 | R6 | U | V | R1 | R3 | R7 | B |
|---|---|---|---|---|---|---|---|---|---|---|---|---|
| 13 | bond | O | —CH2— | | 4-ethylpiperazin-1-yl | | S | N | —OCH3 | H | p-CF3 | CH |
| 14 | bond | O | —CH2— | N | —(CO)OPh | cyclopropyl | S | N | —OCH3 | H | p-CF3 | CH |
| 15 | bond | O | —CH2— | N | cyclopropyl | H | S | N | —OCH3 | H | p-CF3 | CH |
| 16 | bond | O | —(CH2)3— | | azetidin-1-yl | | S | N | —OCH3 | H | p-CF3 | CH |
| 17 | bond | O | —CH2— | | 4-(trifluoromethyl)piperidin-1-yl | | S | N | F | H | p-CF3 | CH |
| 18 | bond | O | —CH2— | | 4,4-difluoropiperidin-1-yl | | S | N | F | H | p-CF3 | CH |
| 19 | bond | O | —CH2— | N | —(CH2)2OH | —CH3 | S | N | F | H | p-CF3 | CH |
| 20 | bond | O | —CH2— | | 4-methylpiperazin-1-yl | | S | N | F | H | p-CF3 | CH |
| 21 | bond | O | —CH2— | | morpholin-4-yl | | S | N | F | H | p-CF3 | CH |
| 22 | bond | O | —CH2— | | isoindolin-2-yl | | S | N | F | H | p-CF3 | CH |
| 23 | bond | O | —CH2— | N | 4-fluorobenzyl | H | S | N | F | H | p-CF3 | CH |
| 24 | bond | O | —CH2— | | (1-methylpyrrolidin-2-yl)methanol | | S | N | F | H | p-CF3 | CH |
| 25 | bond | O | —CH2— | N | furan-2-ylmethyl | H | S | N | F | H | p-CF3 | CH |
| 26 | bond | O | —CH2— | N | —CH2CH2CH2SCH3 | H | S | N | F | H | p-CF3 | CH |
| 27 | bond | O | —CH2— | | 3-oxopiperazin-1-yl | | S | N | F | H | p-CF3 | CH |
| 28 | bond | O | —CH2— | N | 4-methoxybenzyl | H | S | N | F | H | p-CF3 | CH |

TABLE I-continued

| Example | Z | X | W | Y | R5 | R6 | U | V | R1 | R3 | R7 | B |
|---|---|---|---|---|---|---|---|---|---|---|---|---|
| 29 | bond | O | —CH2— | | diazabicyclic structure | | S | N | F | H | p-CF3 | CH |
| 30 | bond | O | —CH2— | | piperidine-CH2OH | | S | N | F | H | p-CF3 | CH |
| 31 | bond | O | —CH2— | | piperidine | | S | N | —OCH3 | Br | p-CF3 | CH |
| 32 | bond | O | —CH2— | | 4-CF3-piperidine | | S | N | —OCH3 | F | p-CF3 | CH |
| 33 | bond | O | —CH2— | O | C(=O)CH3 | | S | N | F | H | p-CF3 | CH |
| 34 | bond | O | —CH2— | O | C(=O)CH3 | | S | N | —OCH3 | H | p-CF3 | CH |
| 35 | bond | O | —CH2— | | pyrrolidine | | S | N | F | H | p-CF3 | CH |
| 36 | bond | O | —CH2— | N | —CH2CH2CF3 | H | S | N | —OCH3 | H | p-CF3 | CH |
| 37 | bond | O | —CH2— | N | bicyclic structure | H | S | N | —OCH3 | H | p-CF3 | CH |
| 38 | bond | O | —CH2— | N | tetrahydrofuranyl-CH2 | H | S | N | —OCH3 | H | p-CF3 | CH |
| 39 | bond | O | —CH2— | N | tetrahydrofuranyl-CH2 | H | S | N | —OCH3 | H | p-CF3 | CH |
| 40 | bond | O | —CH2— | N | cyclopropyl-CH2 | H | S | N | —OCH3 | H | p-CF3 | CH |
| 41 | bond | O | —CH2— | N | cyclobutyl-CH2 | H | S | N | —OCH3 | H | p-CF3 | CH |
| 42 | bond | O | —CH2— | | piperazine-SO2CH3 | | S | N | —OCH3 | H | p-CF3 | CH |
| 43 | bond | O | —CH2— | N | —(CH2)2—OH | —(CH2)2—OH | S | N | —OCH3 | H | p-CF3 | CH |
| 44 | bond | O | —CH2— | N | —CH2CH2S(=O)CH3 | H | S | N | —OCH3 | H | p-CF3 | CH |

TABLE I-continued

| Example | Z | X | W | Y | R5 | R6 | U | V | R1 | R3 | R7 | B |
|---|---|---|---|---|---|---|---|---|---|---|---|---|
| 45 | bond | O | —CH2— | |  | | S | N | —OCH3 | H | p-CF3 | CH |
| 46 | bond | O | —CH2— | | 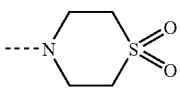 | | S | N | —OCH3 | H | p-CF3 | CH |
| 47 | bond | O | —CH2— | N | —(CH2)2CH3 | H | S | N | —CH3 | H | p-CF3 | CH |
| 48 | bond | O | —CH2— | N | —(CH2)2OCH3 | H | S | N | —CH3 | H | p-CF3 | CH |
| 49 | bond | O | —CH2— | N | 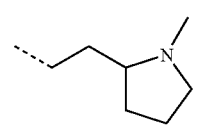 | H | S | N | —CH3 | H | p-CF3 | CH |
| 50 | bond | O | —CH2— | N | 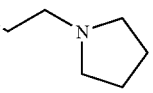 | H | S | N | —CH3 | H | p-CF3 | CH |
| 51 | bond | O | —CH2— | N | 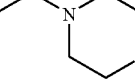 | H | S | N | —CH3 | H | p-CF3 | CH |
| 52 | bond | O | —CH2— | N | 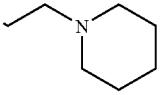 | H | S | N | —CH3 | H | p-CF3 | CH |
| 53 | bond | O | —CH2— | N | —(CH2)2N(CH3)2 | H | S | N | —CH3 | H | p-CF3 | CH |
| 54 | —(CH2)2— | O | —CH2— | bond | H | — | O | N | —Cl | H | p-CF3 | CH |
| 55 | —CH=CH— | O | —CH2— | O | —CH3 | — | O | N | —Cl | H | p-OCH3 | CH |
| 56 | —CH2OCH2— | O | —CH2— | bond | H | — | O | N | —Cl | H | H | CH |
| 57 | —CH2— | O | —CH2— | bond | H | — | O | N | —Cl | H | p-OCH3 | CH |
| 58 | —CH=CH— | O | —CH2— | O | —CH3 | — | S | N | —Cl | H | p-CF3 | CH |
| 59 | bond | O | —CH2— | O | —CH2CF3 | — | O | N | —Cl | H | p-CF3 | CH |
| 60 | bond | O | —CH2— | N | —(CH2)2OCH3 | —CH2CH3 | O | N | —CH3 | H | p-OCH3 | CH |
| 61 | bond | O | —CH2— | N | —CH2CH3 | —CH2CH3 | O | N | —CH3 | H | p-OCH3 | CH |
| 62 | bond | O | —CH2— | | 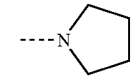 | | O | N | —CH3 | H | p-OCH3 | CH |
| 63 | bond | O | —CH2— | | 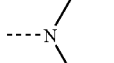 | | O | N | —CH3 | H | p-OCH3 | CH |
| 64 | bond | O | —CH2— | N | —(CH2)2OCH3 | —(CH2)2OCH3 | O | N | —CH3 | H | p-OCH3 | CH |
| 65 | bond | O | —CH2— | | 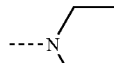 | | O | N | —CH3 | H | p-OCH3 | CH |
| 66 | bond | O | —CH2— | | 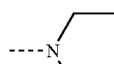 | | N | O | —CH3 | H | p-OCH3 | CH |
| 67 | bond | O | —CH2— | | 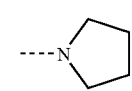 | | N | O | —CH3 | H | p-OCH3 | CH |

TABLE I-continued

| Example | Z | X | W | Y | R5 | R6 | U | V | R1 | R3 | R7 | B |
|---|---|---|---|---|---|---|---|---|---|---|---|---|
| 68 | bond | O | —CH2— | | morpholinyl (N-linked) | | N | O | —CH3 | H | p-OCH3 | CH |
| 69 | bond | O | —CH2— | N | —(CH2)2OCH3 | —(CH2)2OCH3 | N | O | —CH3 | H | p-OCH3 | CH |
| 70 | bond | O | —CH2— | | morpholinyl (N-linked) | | O | N | Cl | H | p-OCH3 | CH |
| 71 | bond | O | —CH2— | N | —(CH2)2OCH3 | —CH2CH3 | O | N | Cl | H | p-OCH3 | CH |
| 72 | bond | O | —CH2— | N | —(CH2)2OCH3 | —(CH2)2OCH3 | O | N | Cl | H | p-OCH3 | CH |
| 73 | bond | O | —CH2— | | piperidinyl (N-linked) | | S | N | Cl | H | p-CF3 | CH |
| 74 | bond | O | —CH2— | | 4-acetylpiperazinyl | | S | N | Cl | H | p-CF3 | CH |
| 75 | bond | O | —CH2— | | 4-methylpiperazinyl | | S | N | Cl | H | p-CF3 | CH |
| 76 | bond | O | —CH2— | N | —(CH2)2OCH3 | —CH2CH3 | S | N | Cl | H | p-CF3 | CH |
| 77 | bond | O | —CH2— | N | —(CH2)2OCH3 | —(CH2)2OCH3 | S | N | Cl | H | p-CF3 | CH |
| 78 | bond | O | —CH2— | | pyrrolidinyl (N-linked) | | S | N | Cl | H | p-CF3 | CH |
| 79 | bond | O | —CH2— | N | —CH2CH3 | —CH2CH3 | S | N | Cl | H | p-CF3 | CH |
| 80 | bond | O | —CH2— | | 4,4-difluoropiperidinyl | | S | N | Cl | H | p-CF3 | CH |
| 81 | bond | O | —CH2— | | 4-phenylpiperazinyl | | S | N | Cl | H | p-CF3 | CH |
| 82 | bond | O | —CH2— | O | 2-morpholinoethyl | — | S | N | Cl | H | p-CF3 | CH |
| 83 | bond | O | —CH2— | O | 2-cyclohexylethyl | — | S | N | Cl | H | p-CF3 | CH |
| 84 | bond | O | bond | bond | CHF2 | — | S | N | Cl | H | p-OCH3 | CH |
| 85 | bond | O | —CH2— | | 4-hydroxypiperidinyl | | S | N | —OCH3 | H | p-CF3 | CH |
| 86 | bond | O | —CH2— | | 1,4-dioxa-8-azaspiro[4.5]decan-8-yl | | S | N | —OCH3 | H | p-CF3 | CH |

TABLE I-continued

| Example | Z | X | W | Y | R5 | R6 | U | V | R1 | R3 | R7 | B |
|---|---|---|---|---|---|---|---|---|---|---|---|---|
| 87 | bond | O | —CH2— | | piperidine-4,4-diol | | S | N | —OCH3 | H | p-CF3 | CH |
| 88 | bond | O | —CH2— | | thiomorpholine S-oxide | | S | N | —OCH3 | H | p-CF3 | CH |
| 89 | bond | O | —CH2— | S | CH3 | — | S | N | —OCH3 | H | p-CF3 | CH |
| 90 | bond | O | —CH2— | S(O) | CH3 | — | S | N | —OCH3 | H | p-CF3 | CH |
| 91 | bond | O | —CH2— | S(O)2 | CH3 | — | S | N | —OCH3 | H | p-CF3 | CH |
| 92 | bond | O | —CH2— | N | H | H | S | N | F | H | p-CF3 | CH |
| 93 | bond | O | —CH2— | N | —C(O)CH3 | H | S | N | F | H | p-CF3 | CH |
| 94 | bond | O | —CH2— | | 4-(trifluoromethyl)piperidine | | S | N | —OCHF2 | H | p-CF3 | CH |
| 95 | bond | O | —CH2— | | 4-(trifluoromethyl)piperidine | | S | N | —OCHF2 | F | p-CF3 | CH |
| 96 | bond | O | —CH2— | | 4-(trifluoromethyl)piperidine | | S | N | —OiPr | H | p-CF3 | CH |
| 97 | bond | O | —CH2— | | 4-(trifluoromethyl)piperidine | | S | N | —OCH2-cyclopropyl | H | p-CF3 | CH |
| 98 | bond | O | —CH2— | | 4-(trifluoromethyl)piperidine | | S | N | —OCH2CF3 | H | p-CF3 | CH |
| 99 | bond | O | —CH2— | | 4-(trifluoromethyl)piperidine | | S | N | —OCH2CF3 | F | p-CF3 | CH |
| 100 | bond | O | —(CH2)3— | bond | —CH3 | — | S | N | —CH3 | H | p-CF3 | N |
| 101 | bond | O | —(CH2)3— | S | CH3 | — | S | N | —OCH3 | H | p-CF3 | CH |
| 102 | bond | O | —(CH2)3— | S(O)2 | CH3 | — | S | N | —OCH3 | H | p-CF3 | CH |
| 103 | bond | O | —(CH2)3— | | thiomorpholine | | S | N | —OCH3 | H | p-CF3 | CH |
| 104 | bond | O | —(CH2)3— | | azepane | | S | N | —OCH3 | H | p-CF3 | CH |
| 105 | bond | O | —(CH2)3— | | morpholine | | S | N | —OCH3 | H | p-CF3 | CH |
| 106 | bond | O | —(CH2)3— | | 4-methylpiperazine | | S | N | —OCH3 | H | p-CF3 | CH |

TABLE I-continued

| Example | Z | X | W | Y | R5 | R6 | U | V | R1 | R3 | R7 | B |
|---|---|---|---|---|---|---|---|---|---|---|---|---|
| 107 | bond | O | —(CH2)3— | | piperidin-1-yl | | S | N | —OCH3 | H | p-CF3 | CH |
| 108 | bond | O | —(CH2)3— | | pyrrolidin-1-yl | | S | N | —OCH3 | H | p-CF3 | CH |
| 109 | bond | O | —(CH2)3— | | morpholin-4-yl | | S | N | —F | H | p-CF3 | CH |
| 110 | bond | O | —(CH2)3— | | pyrrolidin-1-yl | | S | N | —F | H | p-CF3 | CH |
| 111 | bond | O | —(CH2)3— | | N-methyl-N-benzylamino | | S | N | —OCH3 | H | p-CF3 | CH |
| 112 | bond | O | —(CH2)3— | | 4-(trifluoromethyl)piperidin-1-yl | | S | N | —OCH3 | H | p-CF3 | CH |

The potency of some of the described examples in the human GAL4 assays are indicated in the following table:

| Example | PPARdelta EC50 (µM) | PPARalpha EC50 (µM) |
|---|---|---|
| 1 | 0.056 | 0.830 |
| 9 | 0.056 | 0.729 |
| 15 | 0.153 | >10 |
| 19 | 0.171 | 1.19 |
| 33 | 0.299 | 1.41 |
| 51 | 0.228 | 1.21 |
| 55 | 0.003 | 0.319 |
| 56 | 0.358 | 2.19 |
| 68 | 0.661 | 1.20 |
| 77 | 0.003 | 0.530 |
| 83 | 0.012 | 0.398 |
| 89 | 0.153 | 2.62 |
| 94 | 0.018 | 0.664 |
| 100 | 0.008 | 0.315 |
| 102 | 0.022 | 1.780 |
| 103 | 0.008 | 0.483 |

Processes

The compounds of the general formula I according to the invention can be obtained as outlined to the reaction schemes below:

Process A

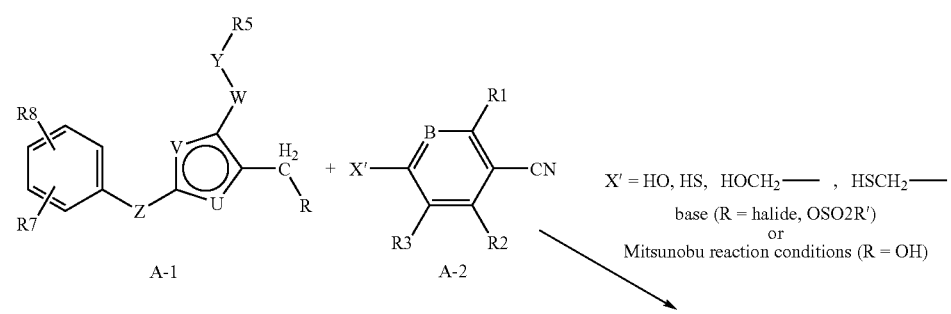

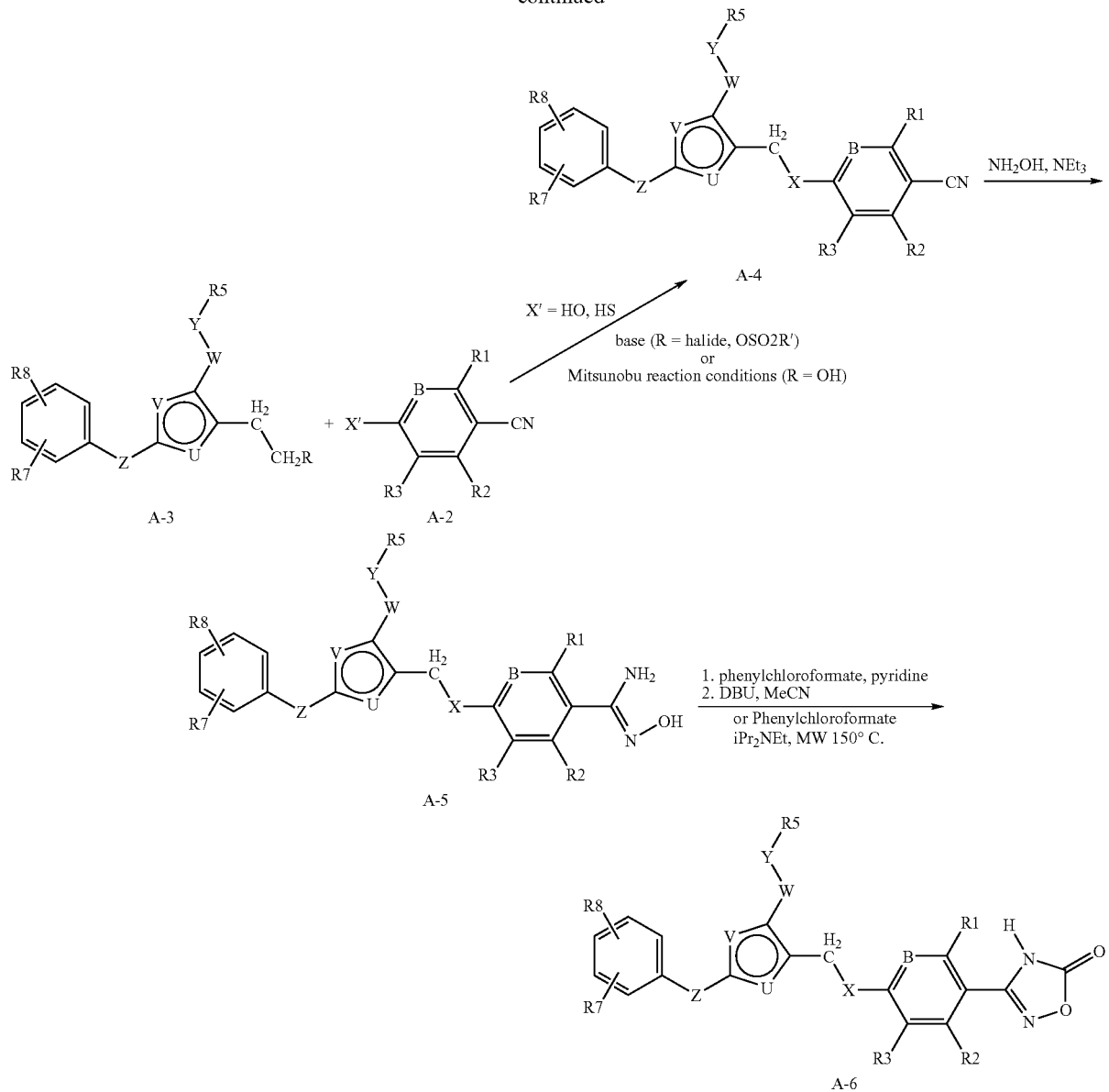

-continued

A compound of general formula A-2 where X' is —OH, —SH, —CH2OH or —CH2SH and R1, R2, R3, B as defined above is either reacted with a compound of general formula A-1 where R is halide (I, Br, Cl) or a sulfonate (OSO₂CH₃, OSO₂C₆H₄CH₃) and R5, R7, R8, U, V, W, Y and Z are as defined above in the presence of a base as cesium carbonate or sodium hydride in a solvent as dimethylformamide or with an alcohol of general formula A-1 where R═OH and R5, R7, R8, U, V, W, Y and Z are as defined above under Mitsunobu reaction conditions (triphenylphosphine, diethylazodicarboxylate for instance) in an apolar solvent as dichloromethane to give a compound of general formula A-4 where X═O, S, —OCH₂— or —SCH₂—. This process can be applied to a compound of general formula A-3 where R is halide (I, Br, Cl) or a sulfonate (OSO₂CH₃, OSO₂PhCH₃) and R5, R7, R8, U, V, W, Y and Z are as defined above or with an alcohol of general formula A-3 where R═OH and R5, R7, R8, U, V, W, Y and Z are as defined above under reaction conditions as previously described to lead to a compound of general formula A-4 where X═—CH₂O— or —CH₂O—.

The compound of general formula A-4 is reacted with hydroxylamine hydrochloride in the presence of a base as triethylamine in a solvent as tetrahydrofuran and methanol to obtain a compound of general formula A-5. This reaction can be facilitated by heating the reaction mixture under microwave irradiation. This compound of general formula A-5 is converted to the product of general formula A-6 by reaction with phenylchloroformate in the presence of a base as pyridine or diisopropylethylamine followed by heating the reaction mixture with microwave irradiation to allow cyclization or alternatively isolating the resulting intermediate and treating it with a base as 1,8-diazabicyclo[5.4.0]undec-7-ene in a solvent as acetonitrile.

When R5 is H in the substrate A-5, the compound of general formula A-6 with R5=C(=O)C₆H₅ is formed which can be hydrolyzed with a hydroxide salt such as potassium hydroxide into a product of general formula A-6 where R5 is H.

Examples 54-59 were obtained according to process A.

Other compounds can be obtained accordingly or by known processes.

Process B mamide to give a compound of general formula B-3. This reaction can be performed by heating the reaction mixture at 60° C. under microwave irradiation. As described in process A, compound B-3 is treated with hydroxylamine hydrochloride in the presence of a base such as triethylamine in a solvent as tetrahydrofuran and methanol to obtain a compound of general formula B-4. This reaction can be facilitated by heating the reaction mixture under microwave irradiation. Compound B-4 is converted to the product of general formula B-5

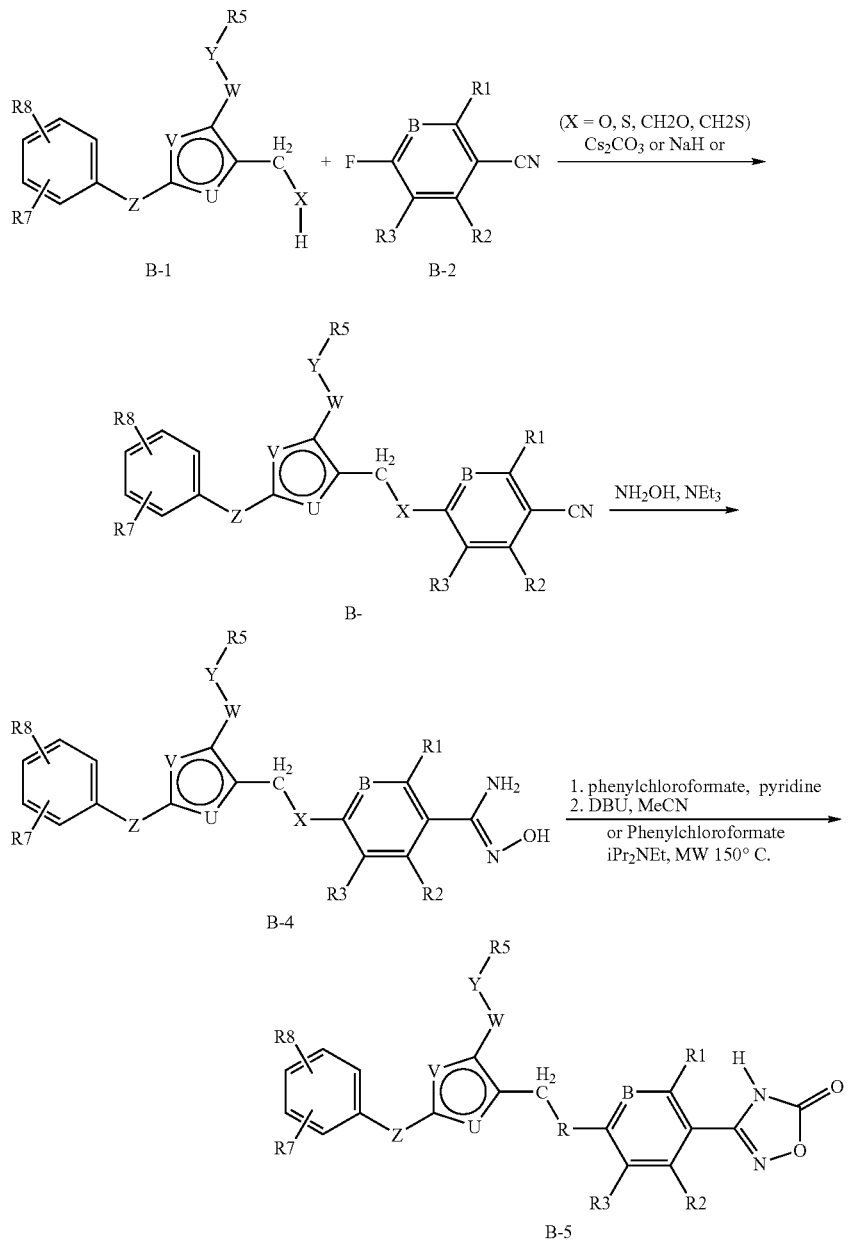

A compound of general formula B-1 where X is O, S, CH₂O or CH₂S and R5, R7, R8, U, V, W, Y and Z are as defined above is reacted with a fluoro-nitrile of general formula B-2 where B, R1, R2 and R3 are as defined above in the presence of a base such as cesium carbonate, sodium hydride or potassium tert-butoxide in a solvent such as dimethylformamide to give a compound of general formula B-3. This reaction can be performed by heating the reaction mixture at by reaction with phenylchloroformate in the presence of a base as pyridine or diisopropylethylamine followed by heating the reaction mixture under microwave irradiation to allow cyclization or alternatively isolating the resulting intermediate and treating it with a base as 1,8-diazabicyclo[5.4.0]undec-7-ene in a solvent as acetonitrile.

Examples 1-15, 94-98 and example 100 were obtained according to process B.

Other compounds can be obtained accordingly or by known processes.

Process C

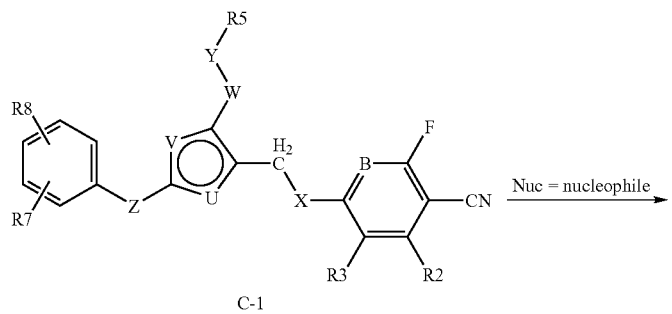

C-1

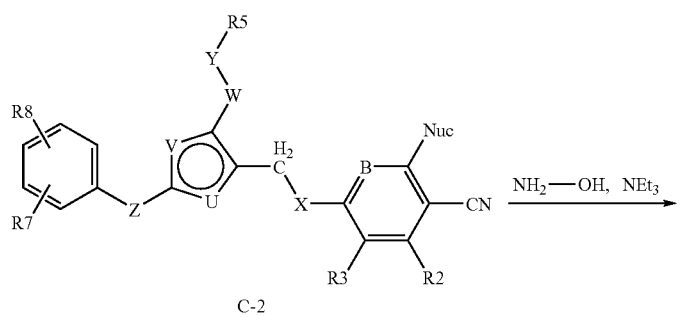

C-2

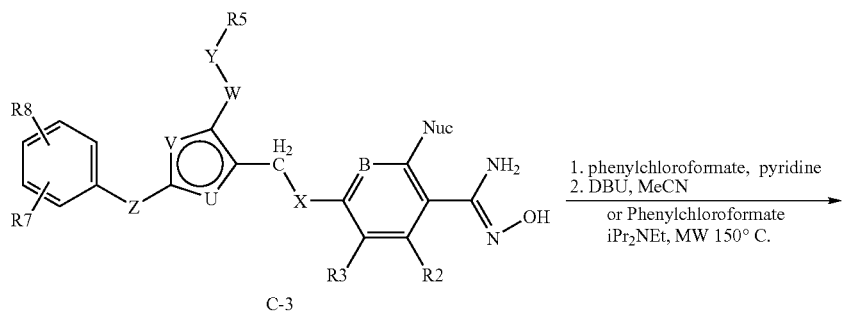

C-3

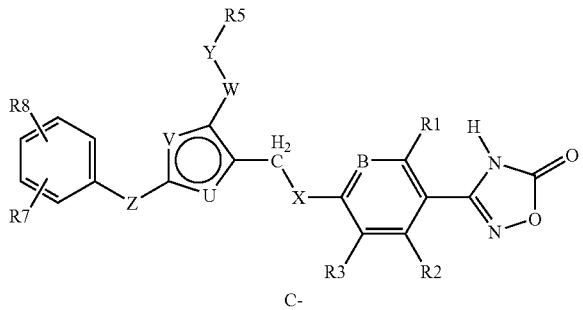

C-

A compound of general formula C-1 where R1=F and B, R2, R3, R5, R7, R8, U, V, W, Y and Z are as defined above is reacted with a nucleophile, e.g. sodium methylate, to obtain a compound of general formula C-2. A compound of general formula C-2 is reacted with hydroxylamine hydrochloride in the presence of a base as triethylamine in a solvent as tetrahydrofuran and methanol to obtain a compound of general formula C-3. This reaction can be facilitated by heating the reaction mixture under microwave irradiation. A compound of general formula C-3 is converted to the product of general formula C-4 by reaction with phenylchloroformate in the presence of a base as pyridine or diisopropylethylamine followed by heating the reaction mixture with microwave irradiation to allow cyclization or alternatively isolating the resulting intermediate and treating it with a base as 1,8-diazabicyclo[5.4.0]undec-7-ene in a solvent as acetonitrile.

Example 99 was obtained according to process C.

Other compounds can be obtained accordingly or by known processes.

Process D:
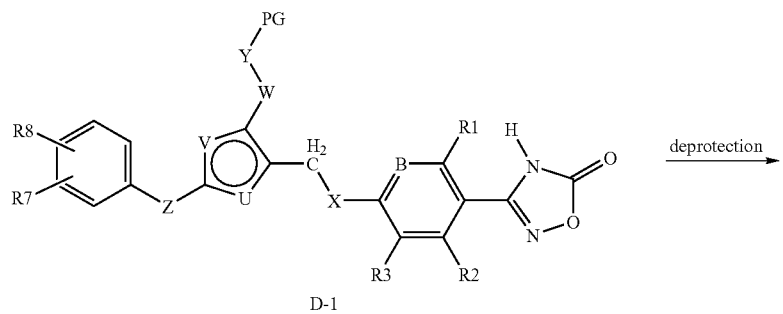
D-1
↓ deprotection
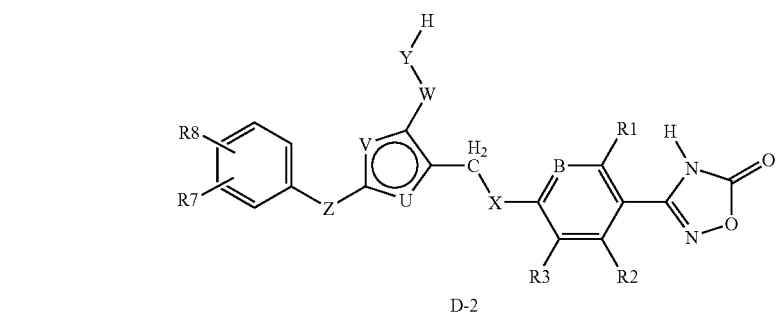
D-2
D-2 (Y = N, S) → electrophile →
D-3
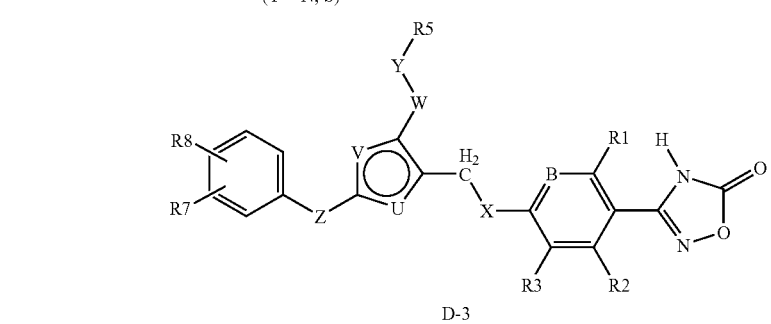
D-2 (Y = O) → MsCl or Ms₂O, base →

-continued

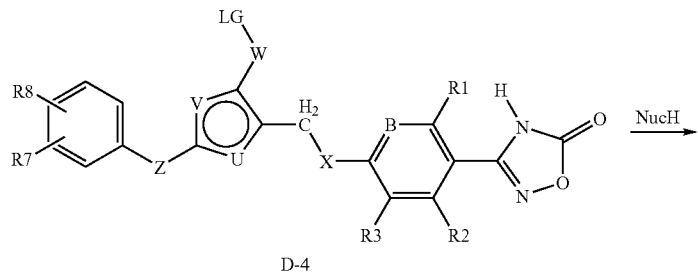

D-4

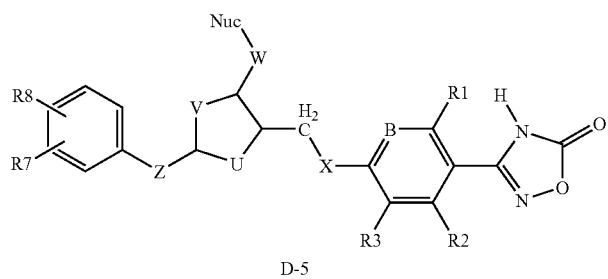

D-5

A compound of general formula D-1 where PG is a protecting group and R1, R2, R3, R7, R8, B, U, V, W, Y and X are as defined above is deprotected under appropriate reaction conditions depending on Y and its protecting group according to methods known by the person skilled of the art to give the compound of general formula D-2. If Y=N, the compound of formula D-2 can be reacted with an electrophile such as an alkyl halide or an acyl halide in the presence of a base such as diisopropyl ethyl amine in a polar solvent such dimethylformamide to obtain the compound of general formula D-3 where Y=N. If Y=S, the compound of formula D-2 can be reacted with an electrophile such as an alkyl halide or an acyl halide in the presence of a stronger base such as sodium methoxide in a polar solvent such dimethylformamide to obtain the compound of general formula D-3 where Y=S.

If Y=O, the alcohol of formula D-2 can be converted to an electrophile of general formula D-4 such as a halide (LG=Br, I, Cl) or as a sulfonate, for example mesylate ($LG=OSO_2CH_3$) by treatment with mesyl chloride or mesyl anhydride in the presence of a base as triethylamine in a polar solvent as dimethylformamide. The compound of general formula D-4 is reacted with a nucleophile, for example a primary or secondary amine or a sodium salt of a thiol or an alcohol, in a polar solvent such a dimethylformamide to obtain the compound of general formula D-5. This reaction can be facilitated by heating the reaction mixture under microwave irradiation.

Example 16, 42-46, 85-91, 101-112 were obtained according to process D.

Other compounds can be obtained accordingly or by known processes.

Process E:

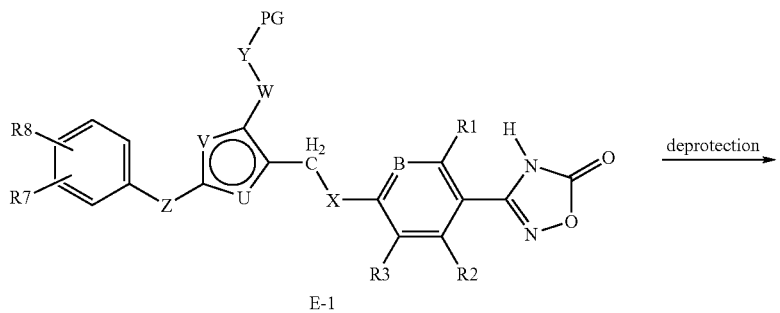

E-1

-continued
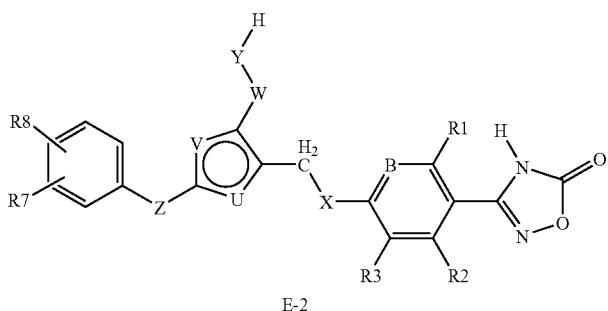
E-2
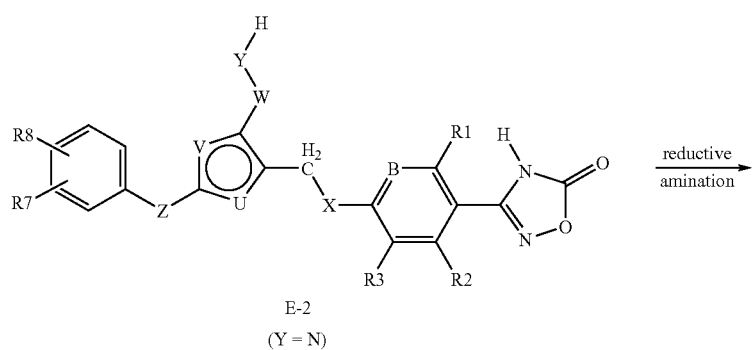
E-2
(Y = N)
reductive amination
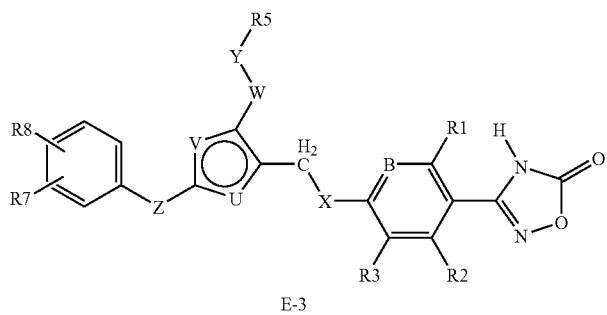
E-3
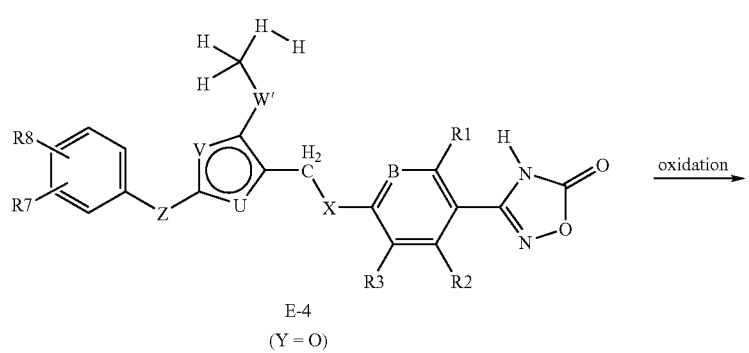
E-4
(Y = O)
oxidation
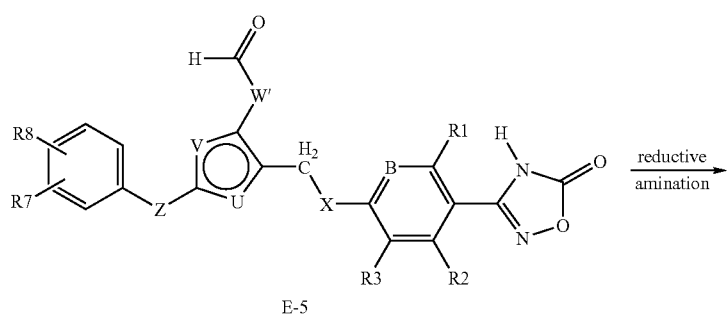
E-5
reductive amination -continued

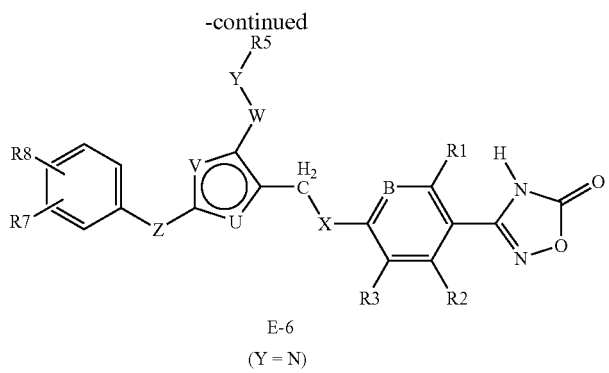

E-6
(Y = N)

A compound of general formula E-1 where PG is a protecting group and R1, R2, R3, R7, R8, B, U, V, W, Y and X are as defined above is deprotected under appropriate reaction conditions depending on Y and its protecting group according to methods known by the person skilled in the art to give the compound of general formula E-2. If Y=N, the amine of formula E-2 can be transformed into an amine of general formula E-3 by reductive amination following either a two-step procedure involving imine formation with an aldehyde and triethylamine in a solvent such as methanol then reduction by adding a reducing agent such as sodium borohydride, or a one-step procedure using an aldehyde and a reducing agent such as sodium triacetoxyborohydride in a solvent as dichloromethane.

If Y=O and W=W'CH2 in E-2 where W' follows the definition of W previously cited, the corresponding primary alcohol of formula E-4 can be oxidized to an aldehyde of general formula E-5 with one of the methods known by the person skilled of the art such as treatment with Dess-Martin periodinane in a solvent as dichloromethane or dimethylformamide. The compound of general formula E-5 is converted into an amine of general formula E-6 by reductive amination following either a two-step procedure involving imine formation with a primary or secondary amine and triethylamine in a solvent such as methanol then reduction by adding a reducing agent such as sodium borohydride, or a one-step procedure using a primary or secondary amine and a reducing agent such as sodium triacetoxyborohydride in a solvent as dichloromethane.

Examples 35-41 and 47-53 were obtained according to process E.

Other compounds can be obtained accordingly or by known processes.

Process F:

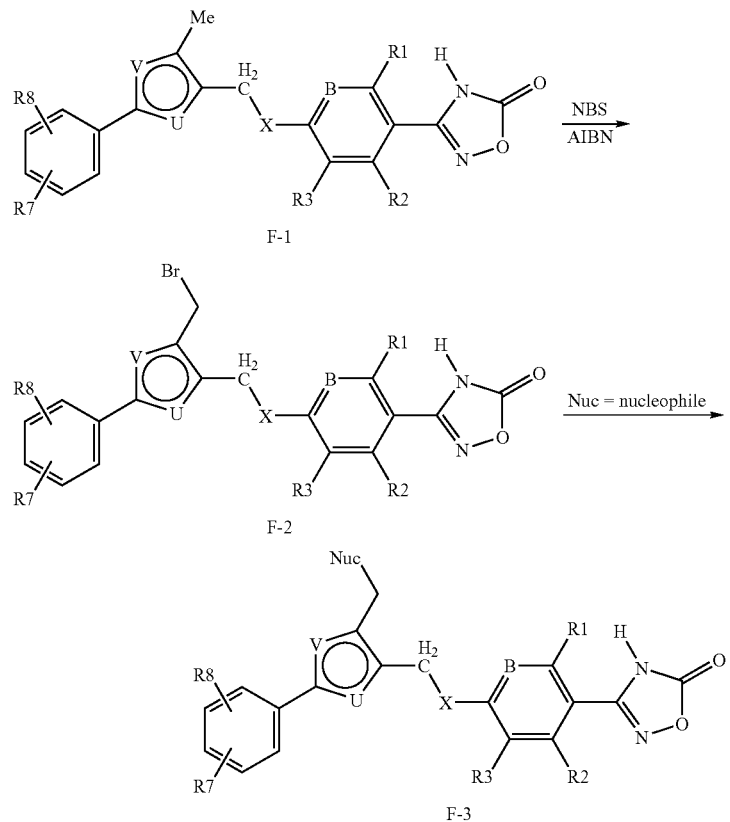

A compound of general formula F-1 where WYR5=CH3 and R1, R2, R3, R7, R8, B, U, V and X are as defined above is reacted with N-bromosuccinimide or bromine in an inert solvent such as carbon tetrachloride (an inert polar co-solvent such as hexafluoroisopropanol may be added to help solubilize the starting material) in the presence of a radical initiator such as AIBN or a peroxide to obtain the compound of general formula F-2. The resulting bromide of general formula F-2 is displaced with a nucleophile, for example a primary or secondary amine, in a polar solvent such a dimethylformamide to give a compound of general formula F-3.

Examples 17-32, 92-93 were obtained according to process F.

Other compounds can be obtained accordingly or by known processes.

Process G:

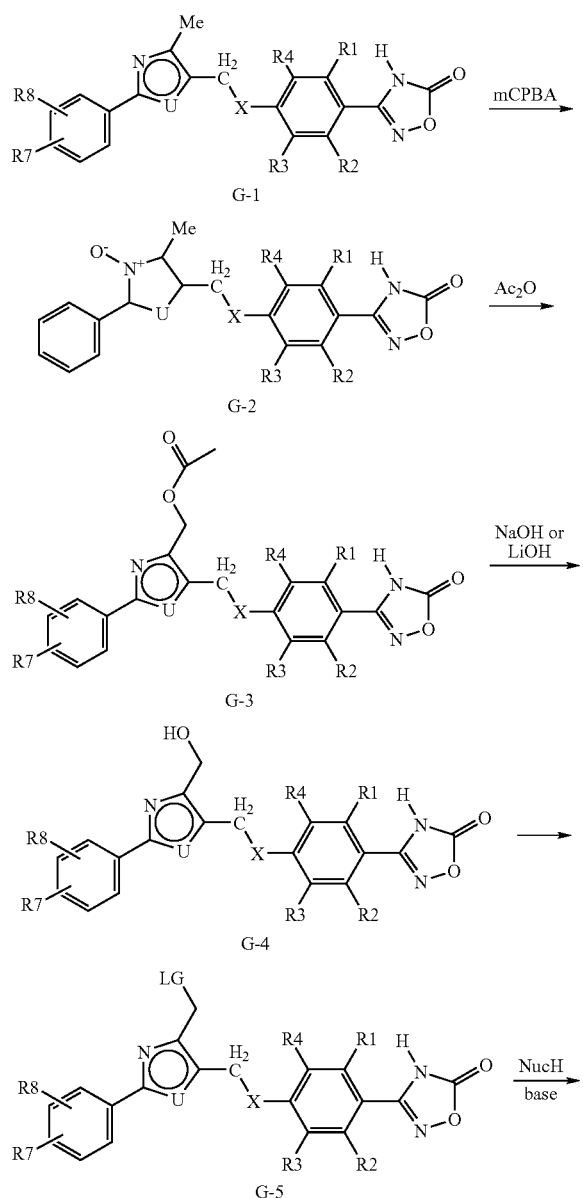

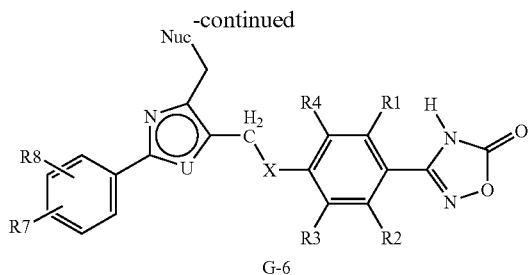

A compound of general formula G-1 where B=C(R4), WYR5=CH3, V=N, X=O or OCH$_2$ and R1, R2, R3, R4, R7, R8 and U are as defined above is reacted with an oxidant such as meta-chloroperbenzoic acid MCPBA in a solvent such as dichloromethane (a polar co-solvent such as hexafluoroisopropanol may be added to help solubilize the starting material) to give the N-oxide of general formula G-2. The compound of general formula G-2 is subjected to a Polonovsky-type rearrangement by heating it with acetic anhydride to lead to an acetate of general formula G-3. This acetate can be hydrolyzed to the corresponding alcohol of general formula G-4 with for instance lithium hydroxide in water and an organic solvent such as methanol or tetrahydrofuran. The alcohol of general formula G-4 can be converted to an electrophile of general formula G-5 such as a halide (LG=Br, I, Cl) or as a sulfonate, for example mesylate (LG=OSO$_2$CH$_3$) by treatment with mesyl chloride or mesyl anhydride in the presence of a base as triethylamine in a polar solvent as dimethylformamide. The compound of general formula G-5 is reacted with a nucleophile, for example a primary or secondary amine, to obtain the compound of general formula G-6.

Alternatively, the alcohol of general formula G-4 can be oxidized to an aldehyde of general formula G-7 with one of the methods known by the person skilled of the art such as treatment with manganese dioxide in a solvent as dichloromethane or dimethylformamide or with Dess-Martin periodinane. The compound of general formula G-7 is converted into an amine of general formula G-8 by reductive amination following either a two-step procedure involving imine formation with a primary or secondary amine and triethylamine in a solvent such as methanol then reduction by adding a reducing agent such as sodium borohydride, or a one-step procedure using a primary or secondary amine and a reducing agent such as sodium triacetoxyborohydride in a solvent as dichloromethane.

Examples 33-34 were obtained according to process G.

Other compounds can be obtained accordingly or by known processes.

Process H:

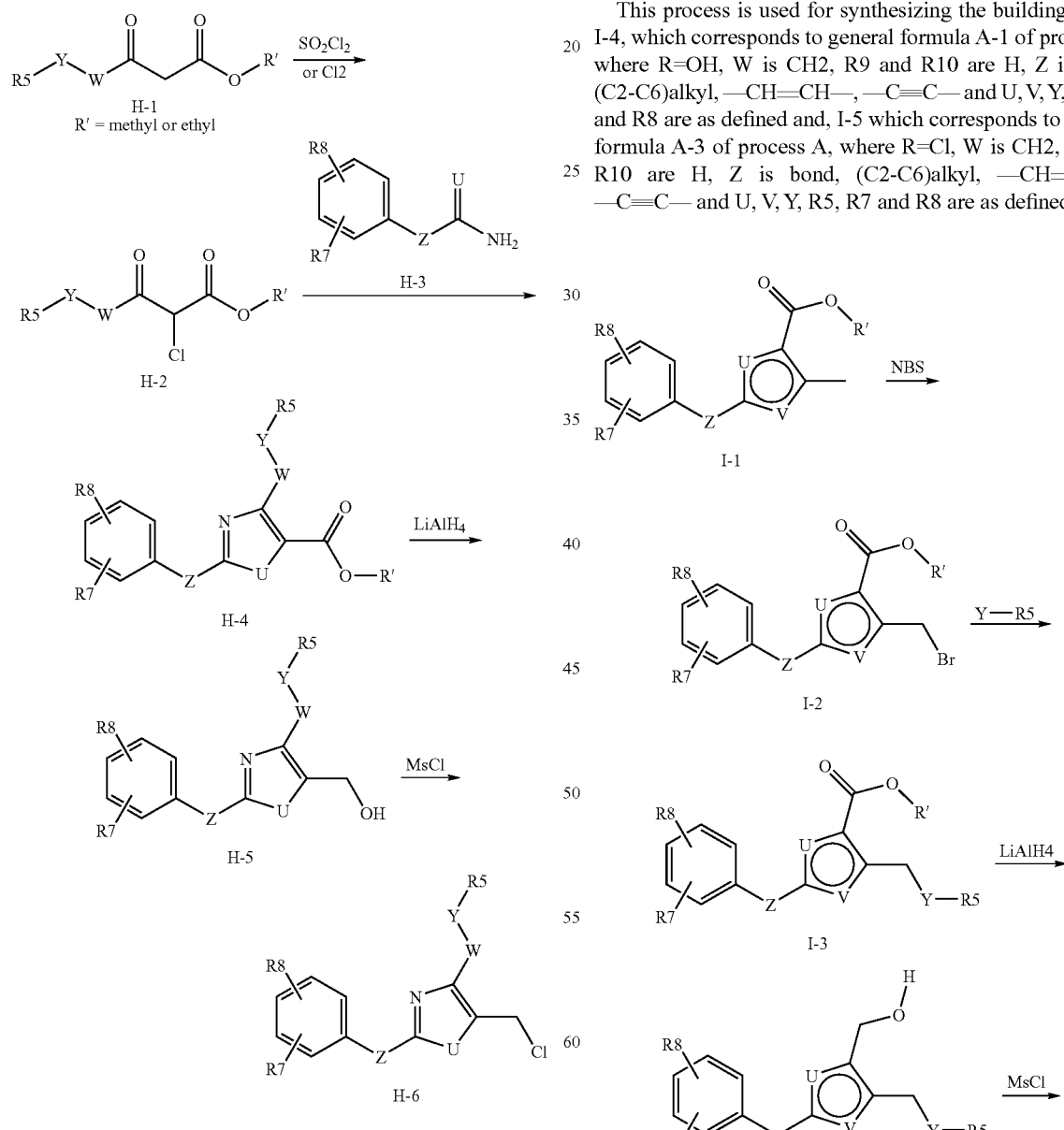

A 3-oxo-carboxylic acid methyl- or ethyl ester of general formula H-1 where R5, Y and W are as defined above is reacted with sulfuryl chloride or chlorine to yield the corresponding chloride of general formula H-2. This compound of general formula H-2 is reacted with a benzamide or thiobenzamide of general formula H-3, where U is S or O and R7, R8 and Z are as defined above to obtain a phenylthiazole or phenyloxazole ester of general formula H-4. The ester of general formula H-4 is reduced with a reducing agent, for example lithium aluminium hydride, to the alcohol of general formula H-5. The alcohol of general formula H-5 is reacted with methanesulfonyl chloride in the presence of a base as triethylamine in a solvent as dichloromethane to obtain the building block of general formula H-6, where R5, R7, R8, U, W, Y and Z are as defined above.

Other compounds can be obtained accordingly or by known processes.

Process I:

This process is used for synthesizing the building blocks I-4, which corresponds to general formula A-1 of process A, where R=OH, W is CH2, R9 and R10 are H, Z is bond, (C2-C6)alkyl, —CH═CH—, —C≡C— and U, V, Y, R5, R7 and R8 are as defined and, I-5 which corresponds to general formula A-3 of process A, where R=Cl, W is CH2, R9 and R10 are H, Z is bond, (C2-C6)alkyl, —CH═CH—, —C≡C— and U, V, Y, R5, R7 and R8 are as defined.

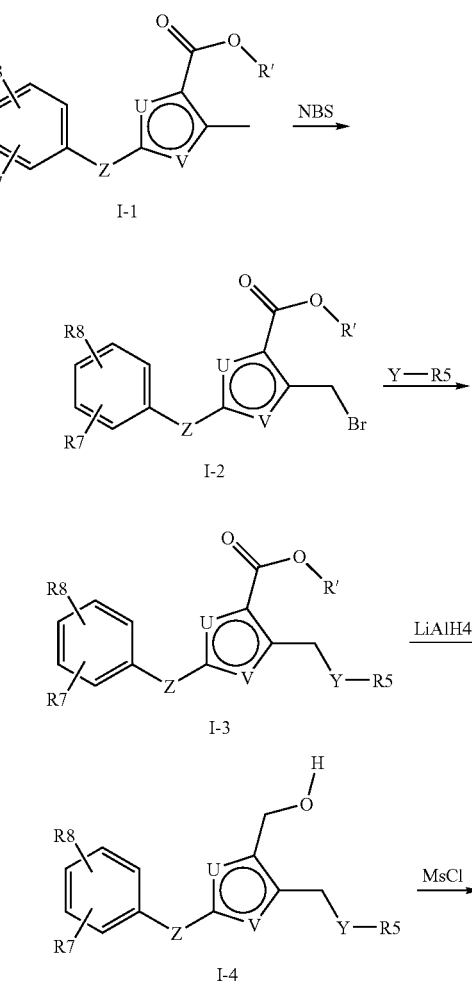

-continued

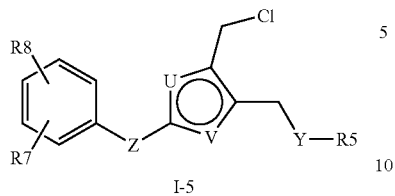
I-5

The oxazole or thiazole ester of general formula I-1 where Z is a bond, (C2-C6)alkyl, —CH═CH— or —C≡C—, W is CH2, Y is a bond, R5 is H and U, V, R7 and R8 are as defined, is brominated by the treatment with N-bromosuccinimide in refluxing tetrachloromethane in the presence of a radical initiator like AIBN to yield the brominated product of general formula I-2. In case Z is (C2-C6)alkyl, the carbon atom directly attached to the oxazole or thiazole ring is brominated as well. The brominated product of general formula I-2 is reacted with a nucleophile Y—R5 where Y is OH or Y is NH(R6) and R5 is as defined in a polar solvent like tetrahydrofuran in the presence of a base like DBU to obtain a compound of general formula I-3. In case the carbon atom directly attached to the oxazole or thiazole ring of the compound of general formula I-2 was brominated as well, this will eliminate under the reaction conditions to yield a double bond. In case Z is —CH2-CH2- the elimination takes place under the bromination conditions. The double bond can be hydrogenated with hydrogen in the presence of a palladium catalyst in a polar solvent as ethanol or methanol.

The ester of general formula I-3 is reduced with a reducing agent, e.g. lithium aluminium hydride, to the alcohol of general formula I-4. The alcohol of general formula I-4 is reacted with methanesulfonyl chloride in the presence of a base as triethylamine in a solvent as dichloromethane to obtain the building block of general formula I-5.

Other compounds can be obtained accordingly or by known processes.

Process J:

This process is used for synthesizing the building blocks J-5 and J-6, which corresponds to general formula A-1 of process A, where R5=PG (PG=protecting group), Y=O, Z is a bond, W=—CH2, R9 and R10 are H, R=—OH or —Cl and U, V, R7 and R8 are as defined above.

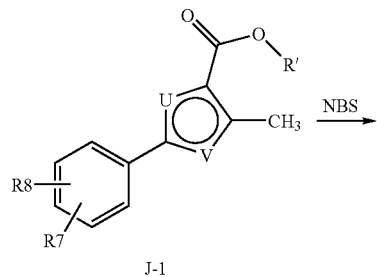
J-1

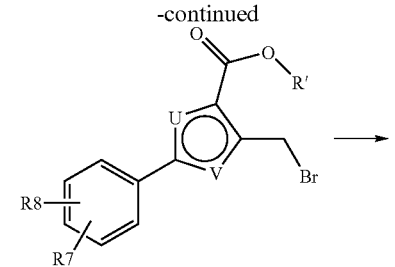
J-2

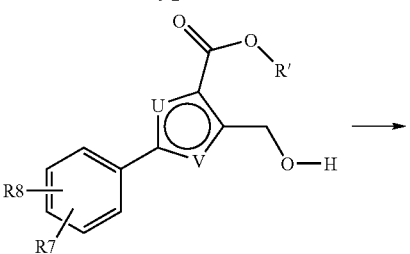
J-3

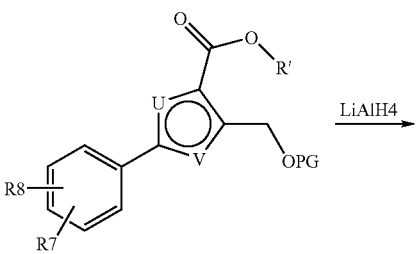
J-4

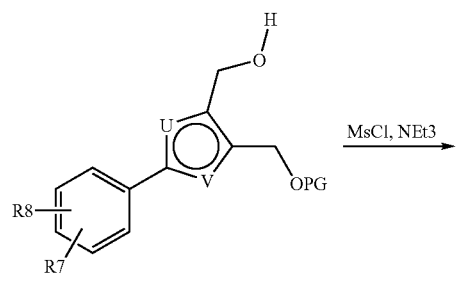
J-5

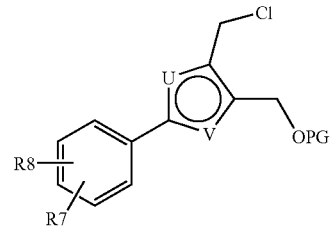
J-6

A compound of the general formula J-1 where R' is alkyl as methyl or ethyl, and U, V, R8 and R7 are as defined above is brominated upon treatment with N-bromosuccinimide in an apolar solvent as tetrachloromethane to obtain a compound of general formula J-2. The bromide of general formula J-2 is converted into the alcohol of general formula J-3 upon treatment with silver trifluoroacetate in a solvent as dimethylformamide and subsequent heating of the resulting trifluoroacetate in a solvent as ethanol. The hydroxyl group of the compound of general formula J-2 is protected for example as a tetrahydropyranylether by treatment with 3,4-dihydro-2H-pyran in a solvent as dichloromethane in the presence of an acid as pyridinium para-toluenesulfonate to obtain a compound of general formula J-4. The ester of the compound of general formula J-4 is reduced with an agent as lithium aluminium hydride in a solvent as tetrahydrofuran to obtain the compound of general formula J-5, where R is OH. The hydroxyl group can be converted into a chlorine by treatment with methanesulfonylchloride in the presence of a base as triethylamine in a solvent as dichloromethane to obtain a compound of general formula J-6, where R is Cl.

Other compounds can be obtained accordingly or by known processes.

Process K:

This process is used for synthesizing the building blocks K7 and K-8, which corresponds to general formula A-1 of process A, where R5=PG (PG=protecting group), Y=O, W=—CH2-, V is O and U is N, R=—OH or —OMs, R9=H, R10=H, Z is a bond R8 and R7 are as defined above.

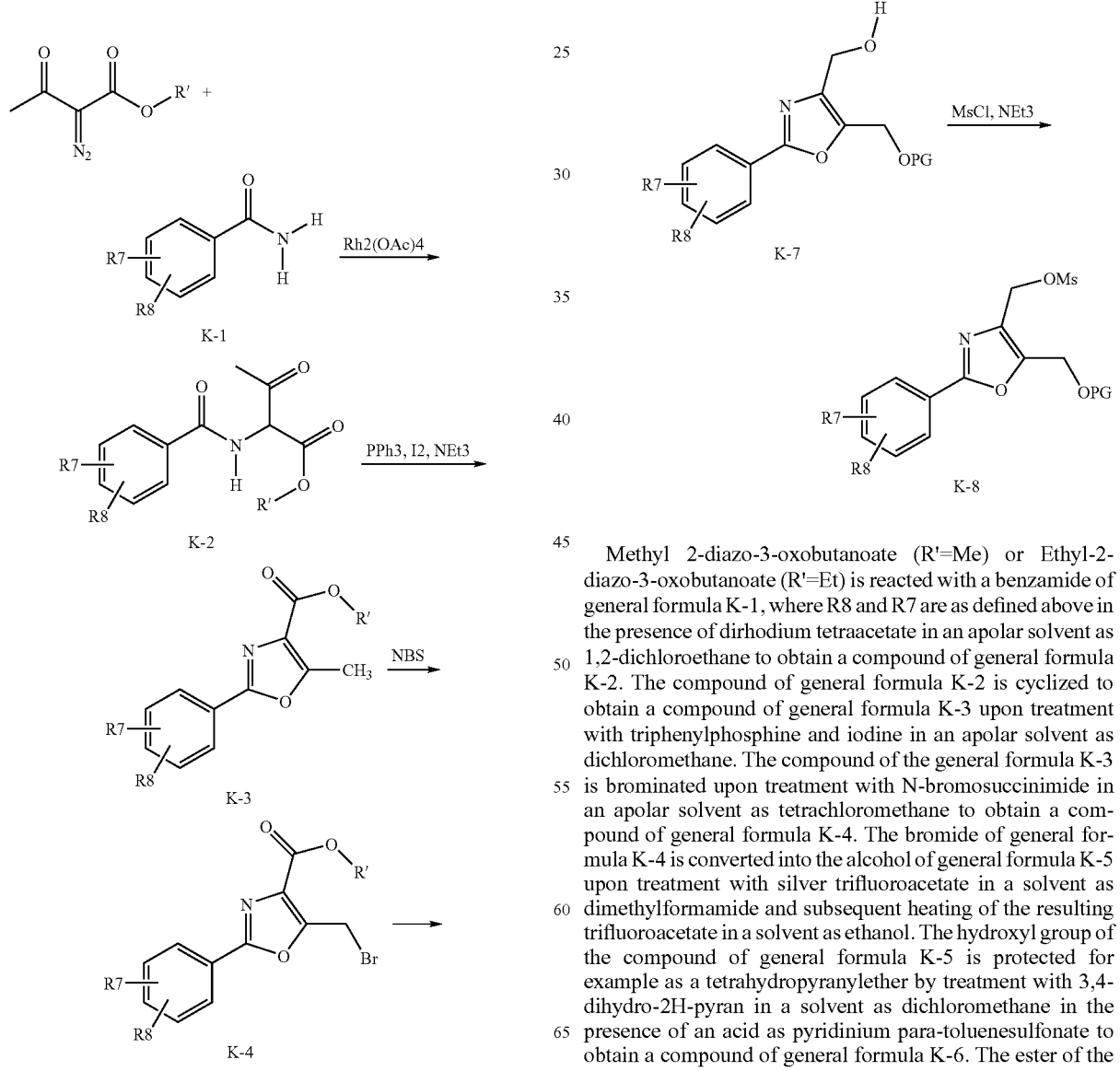

Methyl 2-diazo-3-oxobutanoate (R'=Me) or Ethyl-2-diazo-3-oxobutanoate (R'=Et) is reacted with a benzamide of general formula K-1, where R8 and R7 are as defined above in the presence of dirhodium tetraacetate in an apolar solvent as 1,2-dichloroethane to obtain a compound of general formula K-2. The compound of general formula K-2 is cyclized to obtain a compound of general formula K-3 upon treatment with triphenylphosphine and iodine in an apolar solvent as dichloromethane. The compound of the general formula K-3 is brominated upon treatment with N-bromosuccinimide in an apolar solvent as tetrachloromethane to obtain a compound of general formula K-4. The bromide of general formula K-4 is converted into the alcohol of general formula K-5 upon treatment with silver trifluoroacetate in a solvent as dimethylformamide and subsequent heating of the resulting trifluoroacetate in a solvent as ethanol. The hydroxyl group of the compound of general formula K-5 is protected for example as a tetrahydropyranylether by treatment with 3,4-dihydro-2H-pyran in a solvent as dichloromethane in the presence of an acid as pyridinium para-toluenesulfonate to obtain a compound of general formula K-6. The ester of the compound of general formula K-6 is reduced with a reducing agent as lithium aluminium hydride in a solvent as tetrahydrofuran to obtain the compound of general formula K-7. The hydroxyl group can be converted into a mesylate by treatment with methanesulfonylchloride in the presence of a base as triethylamine in a solvent as dichloromethane to obtain a compound of general formula K-8.

Process L

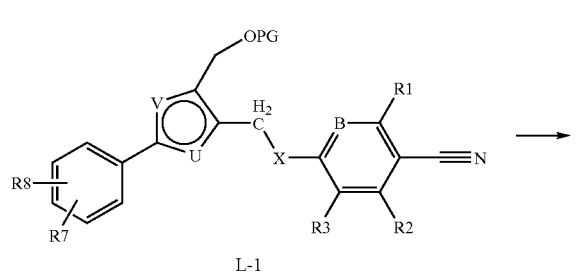

L-1

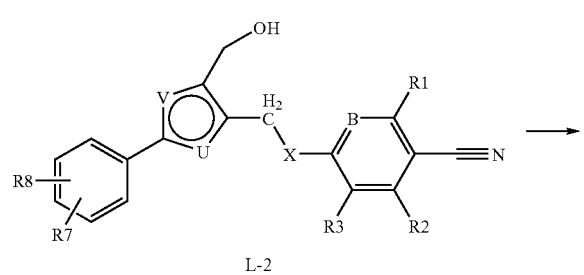

L-2

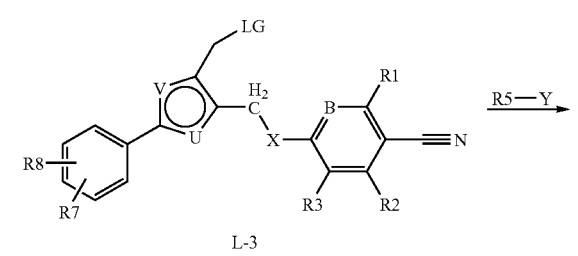

L-3

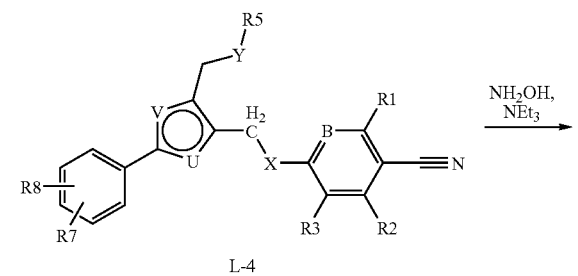

L-4

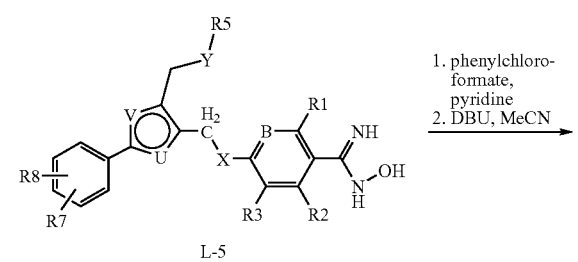

L-5

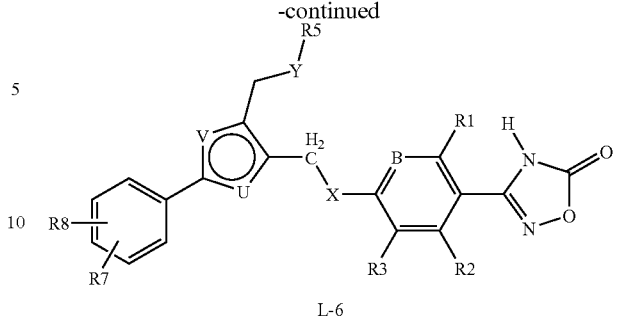

L-6

A compound of the general formula L-1 (which can be synthesized according to process A, where the substituent W—Y—R5 of building blocks A-1 is —CH2-OPG; synthesis of this building block is described in process J and K) where B, U, V, X, R1, R2, R3, R4, R7 and R8 are as defined and PG means a protecting group as for example a tetrahydropyranylether. The protecting group of the compound of the general formula L-1 is removed, in case PG is a tetrahydropyranylether for example by treatment with an acid in polar solvent as methanol to obtain a compound of general formula I-2. The hydroxyl group of the compound of general formula L-2 is converted into a leaving group (LG) for example a mesylate or chloride by treatment with methanesulfonylchloride in the presence of a base as triethylamine in a solvent as dichloromethane to obtain a compound of general formula L-3. The compound of general formula L-3 is reacted with an nucleophile Y—R5 where Y is OH or Y is NH(R6) and R5 is as defined in a polar solvent like tetrahydrofuran in the presence of a base like DBU to obtain a compound of general formula L-4. The compound of the general formula L-4 is reacted with hydroxylamine hydrochloride in the presence of a base as triethylamine in a solvent as tetrahydrofuran and methanol to obtain a compound of the general formula L-5. A compound of the general formula L-5 is converted to the product of general formula L-6 by reaction with phenylchloroformate in the presence of a base as pyridine and treating this intermediate with a base as 1,8-diazabicyclo[5.4.0]undec-7-ene in a solvent as acetonitrile.

Examples 60-83 were obtained according to process L.

Other compounds can be obtained accordingly or by known processes.

Process M:

This process is used for synthesizing the building blocks M-2, which corresponds to general formula B-2 of process B, where B=C(R4), R1=OR, R is (C1-C4)alkyl or (C0-C2)alkylene-(C3-C6)cycloalkyl wherein alkyl and alkylene are unsubstituted or mono, di- or trisubstituted by F, and where R2, R3 and R4 are H.

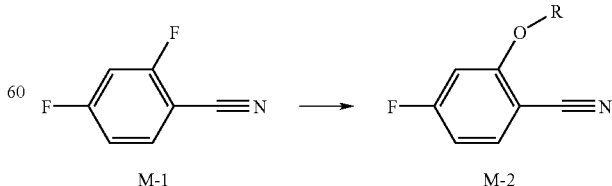

2,4-Difluoro-benzonitrile of formula M-1 is treated with an alcohol ROH in a solvent such as tetrahydrofuran in presence of a base such as potassium tert-butoxide at 0-5° C. to give the ether of general formula M-2 where R is (C1-C4)alkyl or (C0-C2)alkylene-(C3-C6)cycloalkyl wherein alkyl and alkylene are unsubstituted or mono, di- or trisubstituted by F.

Other compounds can be obtained accordingly or by known processes.

Process N:

This process is used for synthesizing the building blocks N-3, which corresponds to general formula B-2 of process B, where B=C(R4), R1=OR, R is (C1-C4)alkyl or (C0-C2)alkylene-(C3-C6)cycloalkyl wherein alkyl and alkylene are unsubstituted or mono, di- or trisubstituted by F, and where R2, R3 and R4 are as defined above.

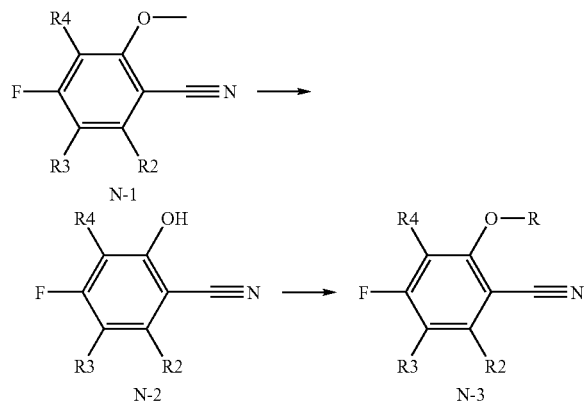

The aryl methyl ether of general formula N-1 where R2, R3 and R4 are as defined above, is demethylated by the treatment with aluminium trichloride in refluxing dichloroethane to give the phenol of general formula N-2. The phenol of general formula N-2 is reacted with an electrophile RX where X is a leaving group such as halide or a sulfonate in a polar solvent like dimethylformamide in the presence of a base like potassium carbonate to obtain a compound of general formula N-3. When methyl chlorodifluororacetate is used as electrophile and the reaction mixture is heated to 60-120° C. in a solvent such as dimethylformamide or dimethylacetamide, the compound of general formula N-3 where R is CHF2 is obtained.

Other compounds can be obtained accordingly or by known processes.

LIST OF ABBREVIATION

Ac acetyl
AIBN 2,2'-azobis(2-methylpropionitrile)
Bn benzyl
iBu isobutyl
tBu tert-Butyl
BuLi n-butyllithium
Bz benzoyl
CI Chemical ionization (MS)
Cy cyclohexyl
DBU 1,8-diazabicyclo[5.4.0]undec-7-ene
DEAD diethylazodicarboxylate
DCI Direct chemical ionization (MS)
DCM dichloromethane
DMAP N,N-dimethylaminopyridine
DMF N,N-dimethylformamide
DMSO dimethylsulfoxide
EE ethyl acetate
eq equivalents
EI Electron impact ionization (MS)
ESI electrospray-Ionization (MS)
FG Functional group
F-TEDA 1-chloromethyl-4-fluoro-1,4-diazoniabicyclo[2.2.2]octane bis(tetrafluoroborate)
Hal halogen
HPLC High performance liquid chromatography
LC-MS liquid chromatography coupled with mass-spectroscopy
LG Leaving Group
Me methyl
MCPBA Meta-chloroperbenzoic acid
MS mass-spectroscopy
MsCl Methanesulfonylchloride
MW microwave
NBS N-bromosuccinimide
NMR Nuclear magnetic resonance
p para
Pd/C palladium on carbon
PG Protecting Group
iPr isopropyl
nPr n-propyl
pTsOH p-toluenesulfonic acid
Rf retention factor (TLC)
tert Tertiary
TLC Thin layer chromatography
TMS trimethylsilyl Further compounds of the formula I can be prepared correspondingly or by known processes.

The experimental procedures for preparing the examples mentioned above are described below:

EXAMPLES

Building Block Synthesis According to Process I 2-(4-Trifluoromethyl-phenyl)-4-(4-trifluoromethyl-piperidin-1-ylmethyl)-thiazol-5-yl]-methanol

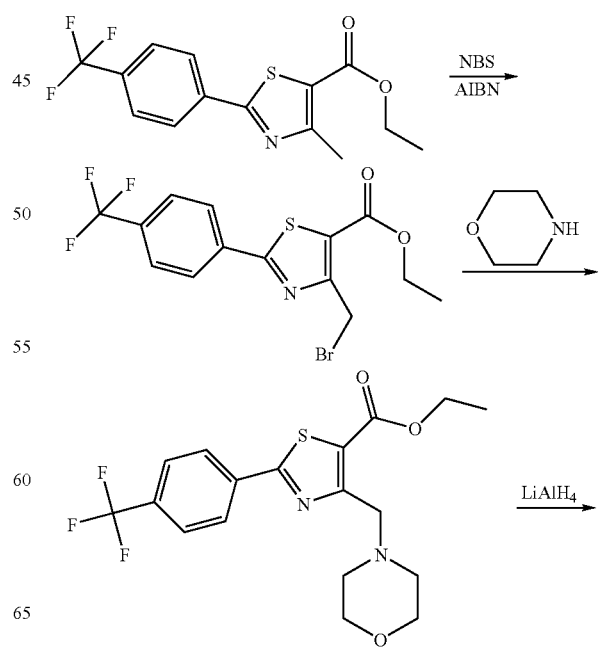

-continued

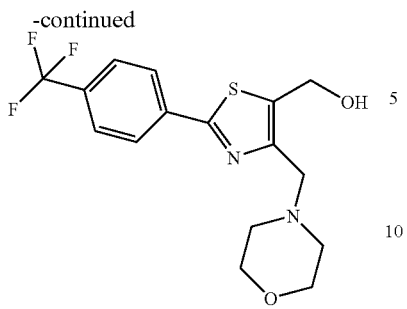

4-Bromomethyl-2-(4-trifluoromethyl-phenyl)-thiazole-5-carboxylic acid ethyl ester[1]

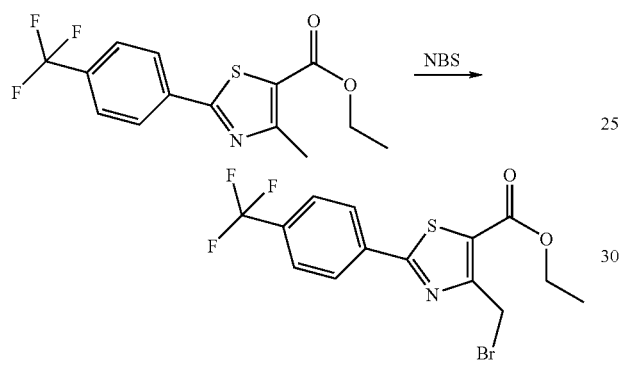

To a solution of 1 g of 4-methyl-2-(4-trifluoromethyl-phenyl)-thiazole-5-carboxylic acid ethyl ester in 8 mL of carbon tetrachloride was added portionwise 0.1 g of benzoyl peroxide and 0.56 g of NBS. The resulting mixture was heated to 80° C. for 1.5 h. 0.1 g of NBS was added and the reaction mixture was heated to 80° C. overnight. An additional 0.1 g of NBS was added and the reaction mixture was heated to 80° C. for 2 h. It was then poured into water and extracted with dichloromethane. The organic extracts were dried over magnesium sulfate, filtered, and concentrated under reduced pressure. The crude product was purified by column chromatography on silica gel (heptane 1/toluene 1 followed by pure toluene) to give 1.02 g of 4-bromomethyl-2-(4-trifluoromethyl-phenyl)-thiazole-5-carboxylic acid ethyl ester.

[1] WO02067912

C14H11BrF3NO2S (394.21), MS (EI): 394 (M+H$^+$).

4-Morpholin-4-ylmethyl-2-(4-trifluoromethyl-phenyl)-thiazole-5-carboxylic acid ethyl ester

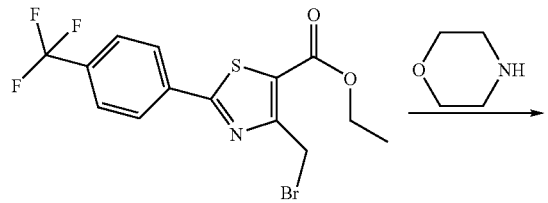

-continued

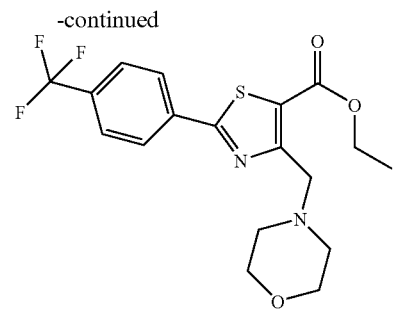

To a solution of 500 mg of 4-bromomethyl-2-(4-trifluoromethyl-phenyl)-thiazole-5-carboxylic acid ethyl ester in 5 mL of acetonitrile was added 190 mg of potassium carbonate and 110.5 mg of morpholine. The resulting mixture was stirred at room temperature overnight. Water was added and the mixture was extracted with dichloromethane. The organic extracts were dried over magnesium sulfate, filtered, and concentrated under reduced pressure. The crude product was purified by column chromatography on silica gel (gradient of dichloromethane/methanol from 100/0 to 50/50) followed by washing of the collected solid with diisopropyl ether to give 355 mg of 4-morpholin-4-ylmethyl-2-(4-trifluoromethyl-phenyl)-thiazole-5-carboxylic acid ethyl ester.

C18H19F3N2O3S (400.42), MS (EI): 400 (M$^+$).

[4-Morpholin-4-ylmethyl-2-(4-trifluoromethyl-phenyl)-thiazol-5-yl]-methanol

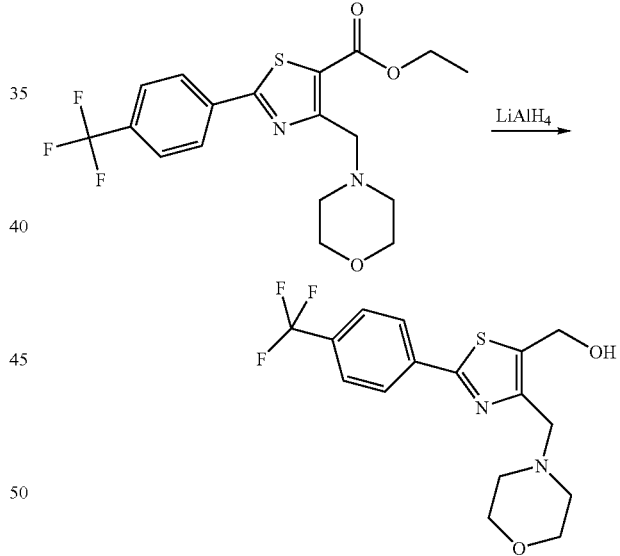

To a solution of 355 mg of 4-morpholin-4-ylmethyl-2-(4-trifluoromethyl-phenyl)-thiazole-5-carboxylic acid ethyl ester in 1 mL of tetrahydrofuran was added 0.88 mL of a 1M solution of lithium aluminium hydride in tetrahydrofuran. The resulting mixture was stirred at room temperature for 1 h. Water was slowly added and the mixture was extracted with dichloromethane. The organic extracts were dried over magnesium sulfate, filtered, and concentrated under reduced pressure. The crude product was purified by column chromatography on silica gel (gradient of dichloromethane/methanol from 100/0 to 90/10) to give 276 mg of [4-morpholin-4-ylmethyl-2-(4-trifluoromethyl-phenyl)-thiazol-5-yl]-methanol.

C16H17F3N2O2S (358.39), MS (EI): 358 (M$^+$).

[2-(4-Trifluoromethyl-phenyl)-4-(4-trifluoromethyl-piperidin-1-ylmethyl)-thiazol-5-yl]-methanol

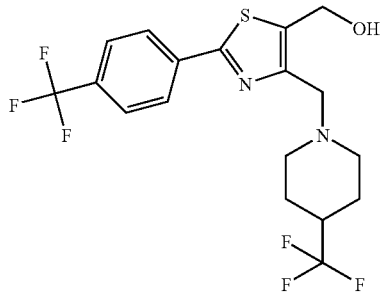

According to the method described for [4-morpholin-4-ylmethyl-2-(4-trifluoromethyl-phenyl)-thiazol-5-yl]-methanol, [2-(4-trifluoromethyl-phenyl)-4-(4-trifluoromethyl-piperidin-1-ylmethyl)-thiazol-5-yl]-methanol was obtained from 4-bromomethyl-2-(4-trifluoromethyl-phenyl)-thiazole-5-carboxylic acid ethyl ester and 4-trifluoromethyl-piperidine.

C18H18F6N2OS (424.41), MS (ESI): 425 (M+H$^+$).

[4-(4,4-Difluoro-piperidin-1-ylmethyl)-2-(4-trifluoromethyl-phenyl)-thiazol-5-yl]-methanol

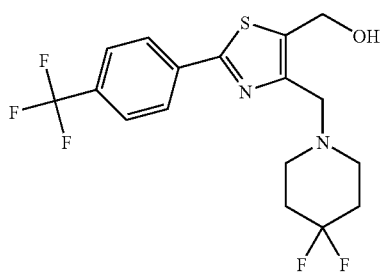

According to the method described for [4-morpholin-4-ylmethyl-2-(4-trifluoromethyl-phenyl)-thiazol-5-yl]-methanol, 4-(4,4-difluoro-piperidin-1-ylmethyl)-2-(4-trifluoromethyl-phenyl)-thiazol-5-yl]-methanol was obtained from 4-bromomethyl-2-(4-trifluoromethyl-phenyl)-thiazole-5-carboxylic acid ethyl ester and 4,4-difluoro-piperidine.

C17H17F5N2OS (392.39), MS (EI): 392 (M$^+$).

[4-(4-Methyl-piperazin-1-ylmethyl)-2-(4-trifluoromethyl-phenyl)-thiazol-5-yl]-methanol

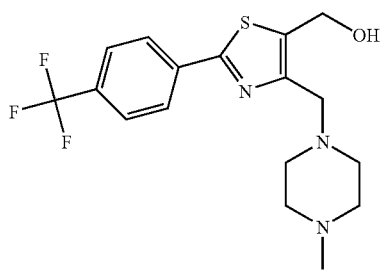

According to the method described for [4-morpholin-4-ylmethyl-2-(4-trifluoromethyl-phenyl)-thiazol-5-yl]-methanol, [4-(4-methyl-piperazin-1-ylmethyl)-2-(4-trifluoromethyl-phenyl)-thiazol-5-yl]-methanol was obtained from 4-bromomethyl-2-(4-trifluoromethyl-phenyl)-thiazole-5-carboxylic acid ethyl ester and 1-methyl-piperazine.

C17H20F3N3OS (371.43), MS (EI): 371 (M$^+$).

[4-Pyrrolidin-1-ylmethyl-2-(4-trifluoromethyl-phenyl)-thiazol-5-yl]-methanol

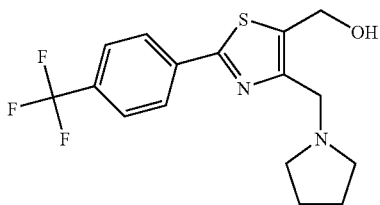

According to the method described for [4-morpholin-4-ylmethyl-2-(4-trifluoromethyl-phenyl)-thiazol-5-yl]-methanol, [4-pyrrolidin-1-ylmethyl-2-(4-trifluoromethyl-phenyl)-thiazol-5-yl]-methanol was obtained from 4-bromomethyl-2-(4-trifluoromethyl-phenyl)-thiazole-5-carboxylic acid ethyl ester and pyrrolidine.

C16H17F3N2OS (342.38), MS (ESI): 343 (M+H$^+$).

[4-(4-Fluoro-piperidin-1-ylmethyl)-2-(4-trifluoromethyl-phenyl)-thiazol-5-yl]-methanol

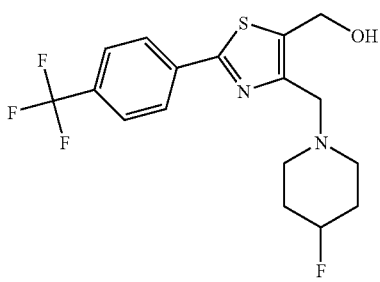

According to the method described for [4-morpholin-4-ylmethyl-2-(4-trifluoromethyl-phenyl)-thiazol-5-yl]-methanol, [4-(4-fluoro-piperidin-1-ylmethyl)-2-(4-trifluoromethyl-phenyl)-thiazol-5-yl]-methanol was obtained from 4-bromomethyl-2-(4-trifluoromethyl-phenyl)-thiazole-5-carboxylic acid ethyl ester and 4-fluoro-piperidine.

C17H18F4N2OS (374.40), MS (ESI): 375 (M+H$^+$).

[4-Diethylaminomethyl-2-(4-trifluoromethyl-phenyl)-thiazol-5-yl]-methanol

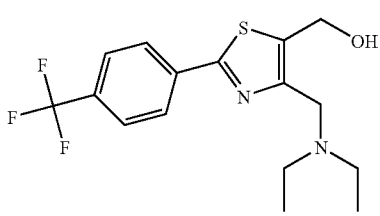

According to the method described for [4-morpholin-4-ylmethyl-2-(4-trifluoromethyl-phenyl)-thiazol-5-yl]-methanol, [4-diethylaminomethyl-2-(4-trifluoromethyl-phenyl)-thiazol-5-yl]-methanol was obtained from 4-bromomethyl-2-(4-trifluoromethyl-phenyl)-thiazole-5-carboxylic acid ethyl ester and diethylamine.

C16H19F3N2OS (344.40), MS (ESI): 345 (M+H$^+$).

[2-(4-Trifluoromethyl-phenyl)-4-(3-trifluoromethyl-pyrrolidin-1-ylmethyl)-thiazol-5-yl]-methanol

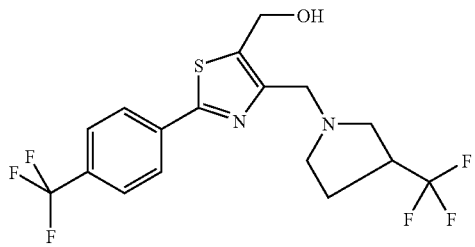

According to the method described for [4-morpholin-4-ylmethyl-2-(4-trifluoromethyl-phenyl)-thiazol-5-yl]-methanol, racemic [2-(4-trifluoromethyl-phenyl)-4-(3-trifluoromethyl-pyrrolidin-1-ylmethyl)-thiazol-5-yl]-methanol was obtained from 4-bromomethyl-2-(4-trifluoromethyl-phenyl)-thiazole-5-carboxylic acid ethyl ester and racemic 4-trifluoromethyl-pyrrolidine.

C17H16F6N2OS (410.38), MS (ESI): 411 (M+H$^+$).

[4-{[Ethyl-(2-methoxy-ethyl)-amino]-methyl}-2-(4-trifluoromethyl-phenyl)-thiazol-5-yl]-methanol

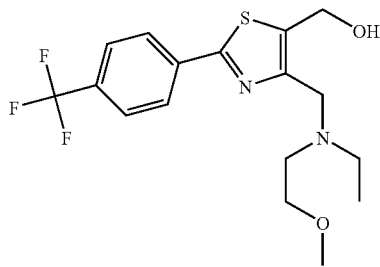

According to the method described for [4-morpholin-4-ylmethyl-2-(4-trifluoromethyl-phenyl)-thiazol-5-yl]-methanol, [4-{[ethyl-(2-methoxy-ethyl)-amino]-methyl}-2-(4-trifluoromethyl-phenyl)-thiazol-5-yl]-methanol was obtained from 4-bromomethyl-2-(4-trifluoromethyl-phenyl)-thiazole-5-carboxylic acid ethyl ester and ethyl-(2-methoxy-ethyl)-amine.

C17H21F3N2O2S (374.42), MS (ESI): 375 (M+H$^+$).

[4-[([1,4]Dioxan-2-ylmethyl-methyl-amino)-methyl]-2-(4-trifluoromethyl-phenyl)-thiazol-5-yl]-methanol

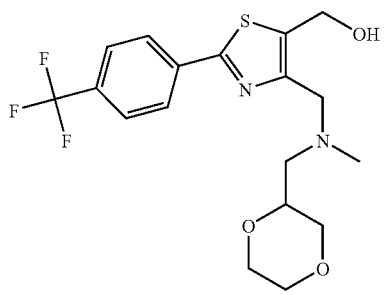

According to the method described for [4-morpholin-4-ylmethyl-2-(4-trifluoromethyl-phenyl)-thiazol-5-yl]-methanol, racemic [4-[([1,4]dioxan-2-ylmethyl-methyl-amino)-methyl]-2-(4-trifluoromethyl-phenyl)-thiazol-5-yl]-methanol was obtained from 4-bromomethyl-2-(4-trifluoromethyl-phenyl)-thiazole-5-carboxylic acid ethyl ester and racemic [1,4]dioxan-2-ylmethyl-methyl-amine.

C18H21F3N2O3S (402.43), MS (ESI): 403 (M+H$^+$).

[4-(4-Methoxy-piperidin-1-ylmethyl)-2-(4-trifluoromethyl-phenyl)-thiazol-5-yl]-methanol

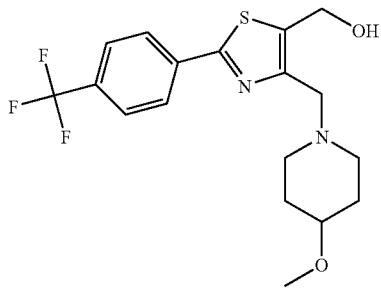

According to the method described for [4-Morpholin-4-ylmethyl-2-(4-trifluoromethyl-phenyl)-thiazol-5-yl]-methanol, [4-(4-methoxy-piperidin-1-ylmethyl)-2-(4-trifluoromethyl-phenyl)-thiazol-5-yl]-methanol was obtained from 4-bromomethyl-2-(4-trifluoromethyl-phenyl)-thiazole-5-carboxylic acid ethyl ester and 4-methoxy-piperidine.

C18H21F3N2O2S (386.44), MS (ESI): 387 (M+H$^+$).

[4-(4-Ethyl-piperazin-1-ylmethyl)-2-(4-trifluoromethyl-phenyl)-thiazol-5-yl]-methanol

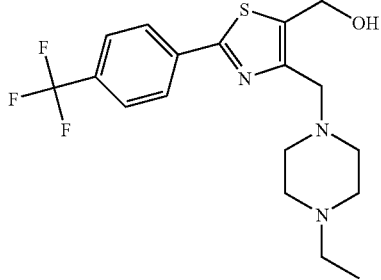

According to the method described for [4-morpholin-4-ylmethyl-2-(4-trifluoromethyl-phenyl)-thiazol-5-yl]-methanol, [4-(4-ethyl-piperazin-1-ylmethyl)-2-(4-trifluoromethyl-phenyl)-thiazol-5-yl]-methanol was obtained from 4-bromomethyl-2-(4-trifluoromethyl-phenyl)-thiazole-5-carboxylic acid ethyl ester and 1-piperazin-1-yl-ethanone. The amide function in the piperazine group is reduced to the corresponding amine in the reduction step. This building block could also be prepared starting from 4-ethyl-piperazine.

C18H22F3N3OS (385.45), MS (ESI): 386 (M+H$^+$).

[4-Cyclopropylaminomethyl-2-(4-trifluoromethyl-phenyl)-thiazol-5-yl]-methanol

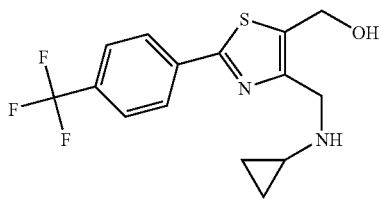

101

According to the method described for [4-morpholin-4-ylmethyl-2-(4-trifluoromethyl-phenyl)-thiazol-5-yl]-methanol, [4-cyclopropylaminomethyl-2-(4-trifluoromethyl-phenyl)-thiazol-5-yl]-methanol was obtained from 4-bromomethyl-2-(4-trifluoromethyl-phenyl)-thiazole-5-carboxylic acid ethyl ester and cyclopropylamine.

C15H15F3N2OS (328.36), MS (ESI): 329 (M+H$^+$).

5-Chloromethyl-4-methoxymethyl-2-[2-(4-methoxy-phenyl)-vinyl]-oxazole

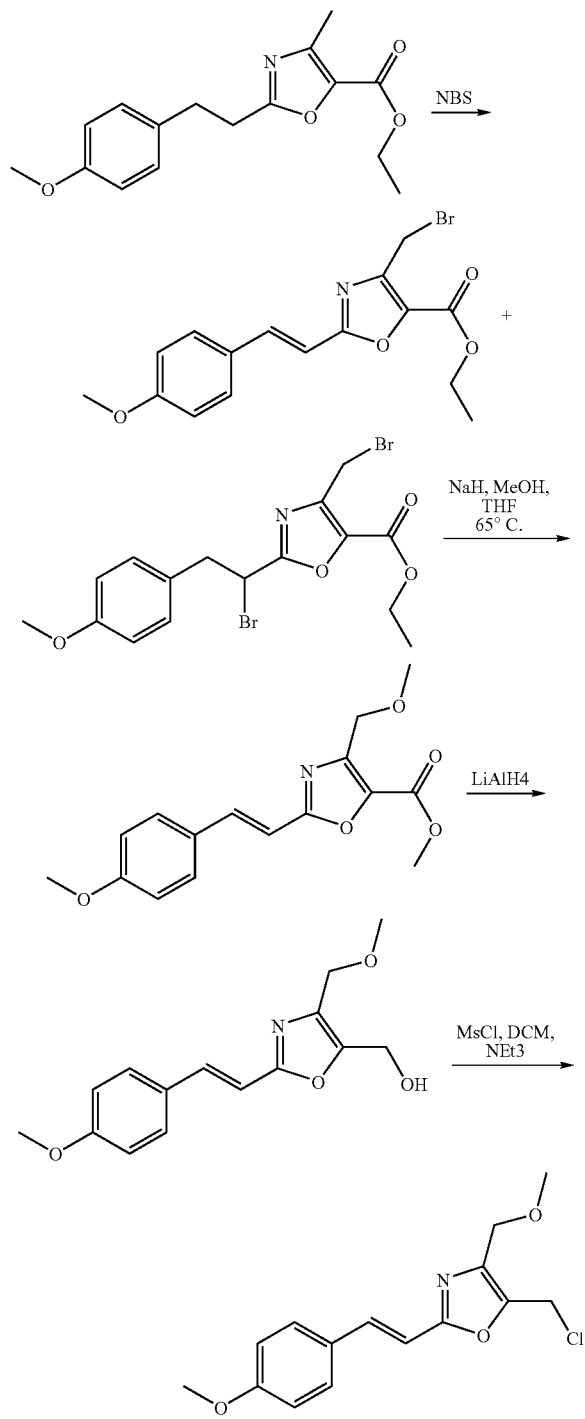

102

4-Methoxymethyl-2-[2-(4-methoxy-phenyl)-vinyl]-oxazole-5-carboxylic acid methyl ester

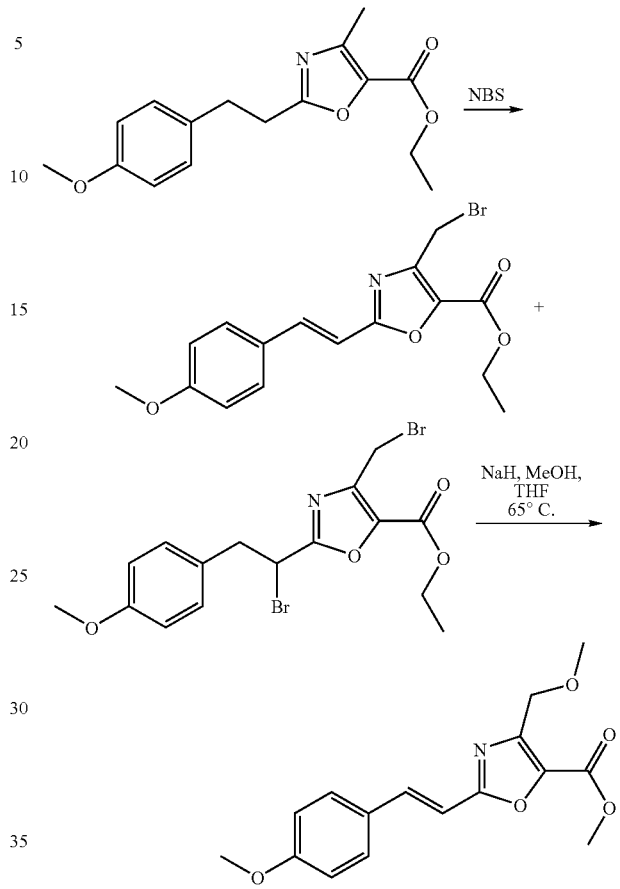

To a refluxing mixture of 6.40 g 2-[2-(4-methoxy-phenyl)-ethyl]-4-methyl-oxazole-5-carboxylic acid ethyl ester (synthesized according to the method described for 5-chloromethyl-4-methyl-2-[2-(4-trifluoromethyl-phenyl)-ethyl]-oxazole from 3-(4-methoxyphenyl)propionamide and 2-chloroacetoacetate) in 90 ml tetrachloromethane were added portionwise a mixture of 9.82 g N-bromosuccinimide and 3.63 g 2,2'-azobis(2-methylpropionitrile). The reaction mixture was heated under reflux for three hours. The cooled reaction mixture was filtered over a celite pad, the filtrate was evaporated in vacuo and the resulting residue was purified by chromatography on silica gel with the eluent n-heptane:ethyl acetate=15:1=>5:1 to provide 11.0 g of a mixture of 4-bromomethyl-2-[2-(4-methoxy-phenyl)-vinyl]-oxazole-5-carboxylic acid ethyl ester and 2-[1-bromo-2-(4-methoxy-phenyl)-ethyl]-4-bromomethyl-oxazole-5-carboxylic acid ethyl ester.

This mixture was dissolved in a mixture of 50 ml methanol and 10 ml tetrahydrofuran. 1.87 g sodium hydride was added and the reaction mixture stirred at 65° C. for one hour. The cooled reaction mixture was neutralized by the addition of acetic acid (pH ~6). The solvents were removed in vacuo, the residue was dissolved in 100 ml ethyl acetate and washed with 50 ml brine. The organic phase was dried over MgSO4. The solvent was removed in vacuo. The residue was purified by RP-HPLC to obtain 1.1 g 4-methoxymethyl-2-[2-(4-methoxy-phenyl)-vinyl]-oxazole-5-carboxylic acid methyl ester as an oil.

C16H17NO5 (303.32), MS (ESI): 304.2 (M+H$^+$).

{4-Methoxymethyl-2-[2-(4-methoxy-phenyl)-vinyl]-oxazol-5-yl}-methanol

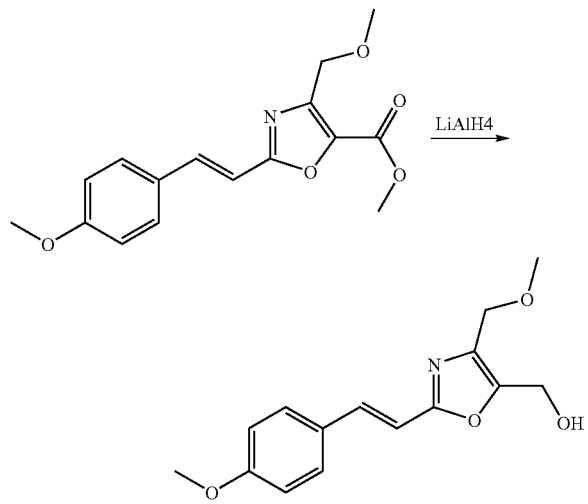

1.10 g 4-Methoxymethyl-2-[2-(4-methoxy-phenyl)-vinyl]-oxazole-5-carboxylic acid methyl ester were dissolved in 15 ml tetrahydrofuran and added to a ice cooled solution of 137 mg lithium aluminium hydride in 7 ml tetrahydrofuran. The reaction mixture was stirred at 0° C. for one hour. Then 50 ml ethyl acetate and 20 ml saturated NH4Cl solution were added. The precipitate was filtered off through a celite pad and washed with ethyl acetate. The organic layer of the filtrate was separated. The aqueous layer of the filtrate was extracted two times with portions of 100 ml ethyl acetate. The combined organic layers were dried over MgSO4. The solvent was removed in vacuo and the residue purified by RP-HPLC to obtain to 420 mg {4-methoxymethyl-2-[2-(4-methoxy-phenyl)-vinyl]-oxazol-5-yl}-methanol as an oil.

C15H17NO4 (275.31), MS (ESI): 276.2.

5-Chloromethyl-4-methoxymethyl-2-[2-(4-methoxy-phenyl)-vinyl]-oxazole

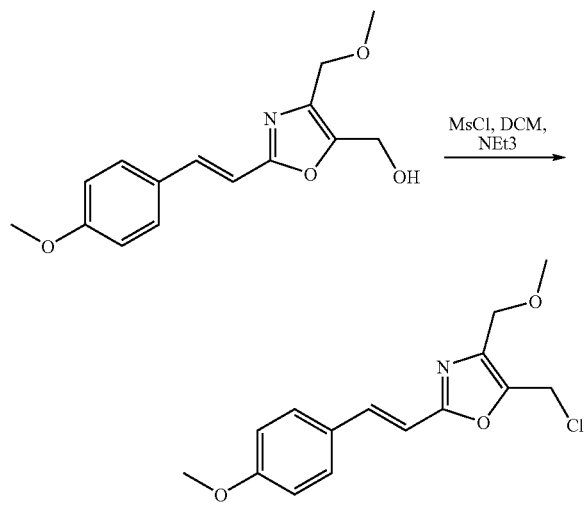

420 mg {4-Methoxymethyl-2-[2-(4-methoxy-phenyl)-vinyl]-oxazol-5-yl}-methanol were dissolved in 5 ml dichloromethane and cooled in an ice bath. 0.32 ml triethylamine were added, followed by the addition of 141 µl methanesulfonylchloride. The ice bath was removed and the resulting mixture stirred at room temperature over night. 50 ml dichloromethane were added and the reaction mixture was then washed with water and brine, dried over MgSO4 and the solvent removed in vacuo to obtain 491 mg 5-chloromethyl-4-methoxymethyl-2-[2-(4-methoxy-phenyl)-vinyl]-oxazole as an oil which was used without further purification.

C15H16ClNO3 (293.75), Rf (ethyl acetate:n-heptane=1:1)=0.44.

5-Chloromethyl-4-(2,2,2-trifluoro-ethoxymethyl)-2-(4-trifluoromethyl-phenyl)-oxazole

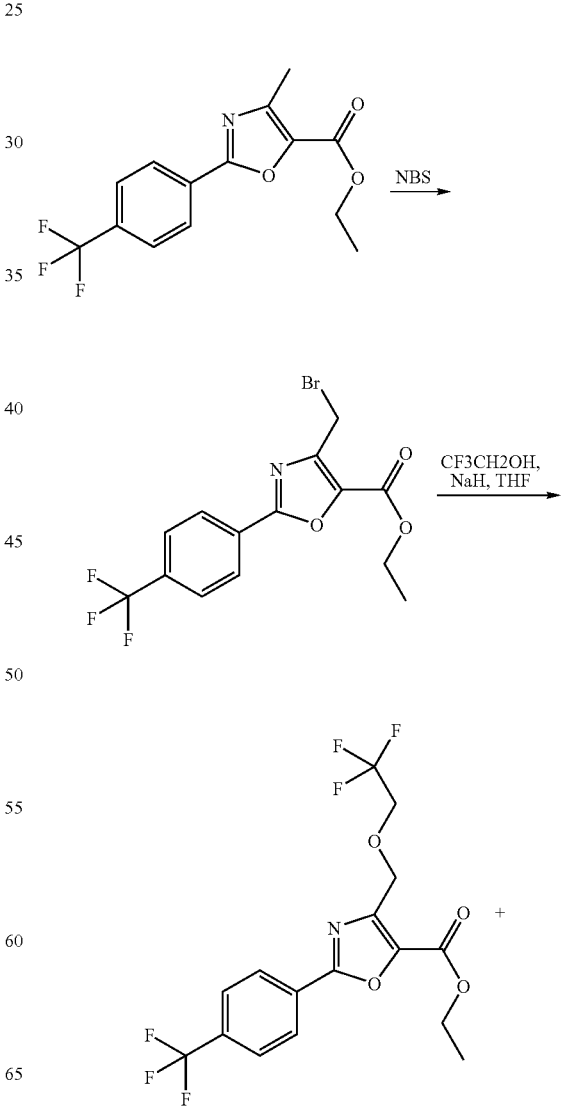

-continued

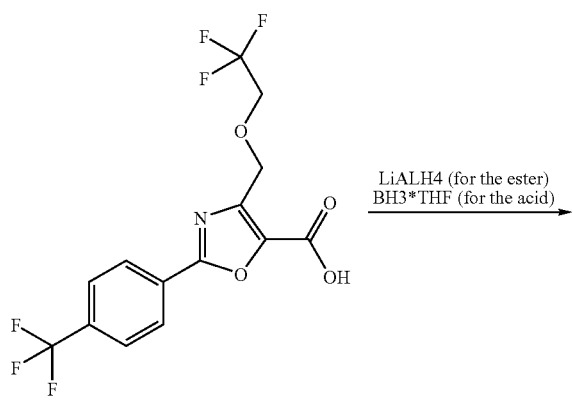

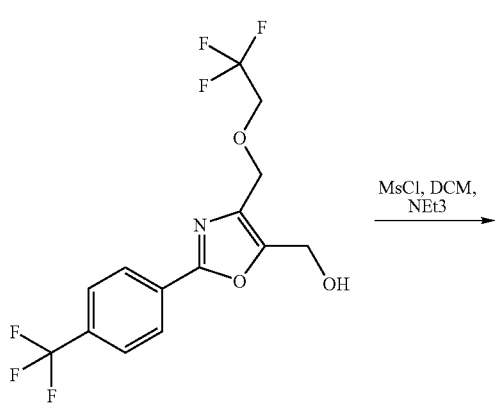

4-Bromomethyl-2-(4-trifluoromethyl-phenyl)-oxazole-5-carboxylic acid ethyl ester

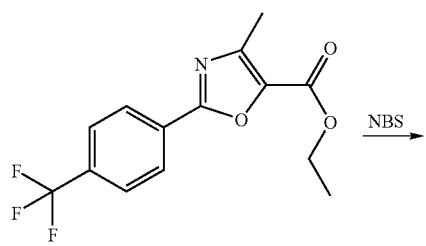

-continued

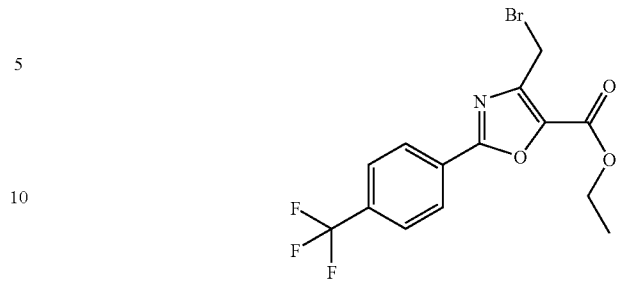

To a refluxing mixture of 21.5 g 4-methyl-2-(4-trifluoromethyl-phenyl)-oxazole-5-carboxylic acid ethyl ester (synthesized according to the method described for 5-chloromethyl-4-methyl-2-[2-(4-trifluoromethyl-phenyl)-ethyl]-oxazole from 4-trifluoromethyl-benzamide and 2-chloroacetoacetate) in 180 ml tetrachloro-methane were added portionwise a mixture of 15.4 g N-bromosuccinimide and 4.73 g 2,2'-azobis(2-methylpropionitrile). The reaction mixture was heated under reflux for five hours. The cooled reaction mixture was filtered over a celite pad, the filtrate was evaporated in vacuo and the resulting residue was purified by chromatography on silica gel with the eluent petroleum benzene:dichloromethane=7:3 to provide 18.5 g 4-bromomethyl-2-(4-trifluoromethyl-phenyl)-oxazole-5-carboxylic acid ethyl ester.

C14H11BrF3NO3 (378.15), MS (ESI): 378.3, 380.3 (M+H$^+$).

4-(2,2,2-Trifluoro-ethoxymethyl)-2-(4-trifluoromethyl-phenyl)-oxazole-5-carboxylic acid ethyl ester and 4-(2,2,2-Trifluoro-ethoxymethyl)-2-(4-trifluoromethyl-phenyl)-oxazole-5-carboxylic acid

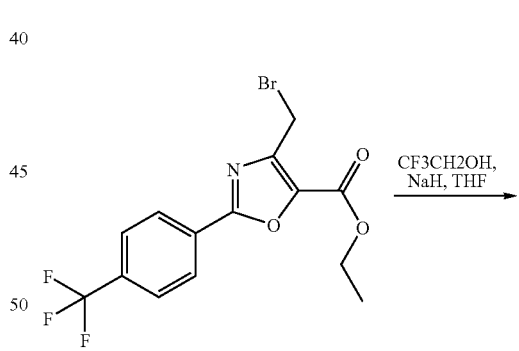

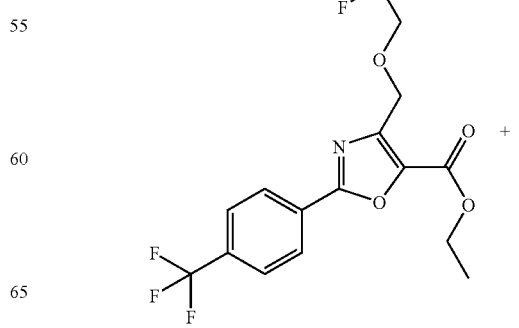

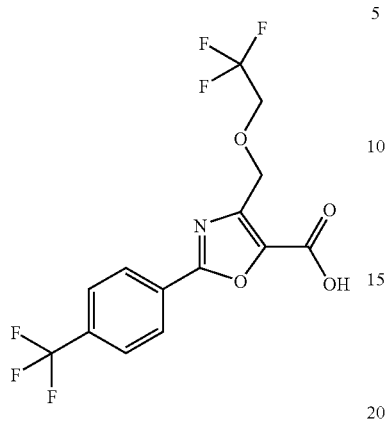

4.0 g 4-Bromomethyl-2-(4-trifluoromethyl-phenyl)-oxazole-5-carboxylic acid ethyl ester is dissolved in a mixture of 20 ml tetrahydrofuran and 50 ml 2,2,2-trifluoroethanol. 635 mg sodium hydride were added and the reaction mixture stirred at 60° C. for three hours. The cooled reaction mixture was neutralized by the addition of acetic acid (pH ~6). The solvents were removed in vacuo, the residue was dissolved in 250 ml ethyl acetate and washed with 100 ml brine. The organic phase was dried over MgSO4. The solvent was removed in vacuo. The residue was purified by RP-HPLC to obtain 1.0 g 4-(2,2,2-trifluoro-ethoxymethyl)-2-(4-trifluoromethyl-phenyl)-oxazole-5-carboxylic acid C14H9F6NO4 (369.22), MS (ESI): 369.9 (M+H+). and 830 mg 4-(2,2,2-trifluoro-ethoxymethyl)-2-(4-trifluoromethyl-phenyl)-oxazole-5-carboxylic acid ethyl ester.

C16H13F6NO4 (397.28), MS (ESI): 398.0 (M+H+).

[4-(2,2,2-Trifluoro-ethoxymethyl)-2-(4-trifluoromethyl-phenyl)-oxazol-5-yl]-methanol

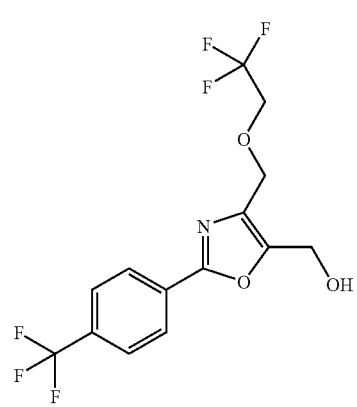

1.0 g 4-(2,2,2-Trifluoro-ethoxymethyl)-2-(4-trifluoromethyl-phenyl)-oxazole-5-carboxylic acid were dissolved in 30 ml tetrahydrofuran. At 0-5° C. 6.6 ml of a one molar solution of borane tetrahydrofuran complex were added. The reaction mixture was stirred at room temperature for three hours and at 60° C. for one hour. The cooled reaction mixture was diluted by addition of 100 ml ethyl acetate and washed with 50 ml water. The organic phase was dried over MgSO4 then the solvent was removed in vacuo. The residue was purified by RP-HPLC to obtain 422 mg [4-(2,2,2-trifluoro-ethoxymethyl)-2-(4-trifluoromethyl-phenyl)-oxazol-5-yl]-methanol.

C14H11F6NO3 (355.24), MS (ESI): 356.0 (M+H+).

5-Chloromethyl-4-(2,2,2-trifluoro-ethoxymethyl)-2-(4-trifluoromethyl-phenyl)-oxazole

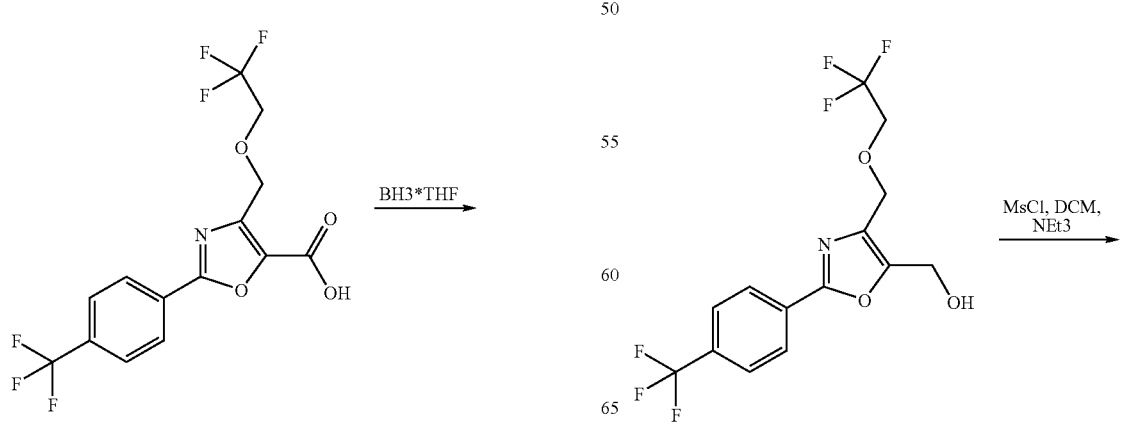

-continued

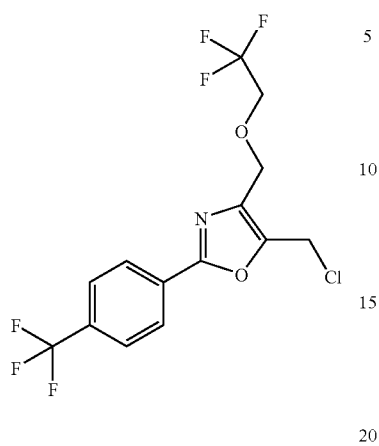

422 mg [4-(2,2,2-Trifluoro-ethoxymethyl)-2-(4-trifluoromethyl-phenyl)-oxazol-5-yl]-methanol were dissolved in 5 ml dichloromethane and cooled in an ice bath. 247 μl triethylamine were added, followed by the addition of 110 μl methanesulfonylchloride. The ice bath was removed and the resulting mixture stirred at room temperature over night. 50 ml dichloromethane were added and the reaction mixture was then washed with water and brine, dried over MgSO4 and the solvent removed in vacuo to obtain 509 mg 5-chloromethyl-4-(2,2,2-trifluoro-ethoxymethyl)-2-(4-trifluoromethyl-phenyl)-oxazole as an oil which was used without further purification.

C14H10ClF6NO2 (373.68), MS (ESI): 373.9 (M+H$^+$).

Building Block Synthesis According to Process H

[4-(3-Benzyloxy-propyl)-2-(4-trifluoromethyl-phenyl)-thiazol-5-yl]-methanol

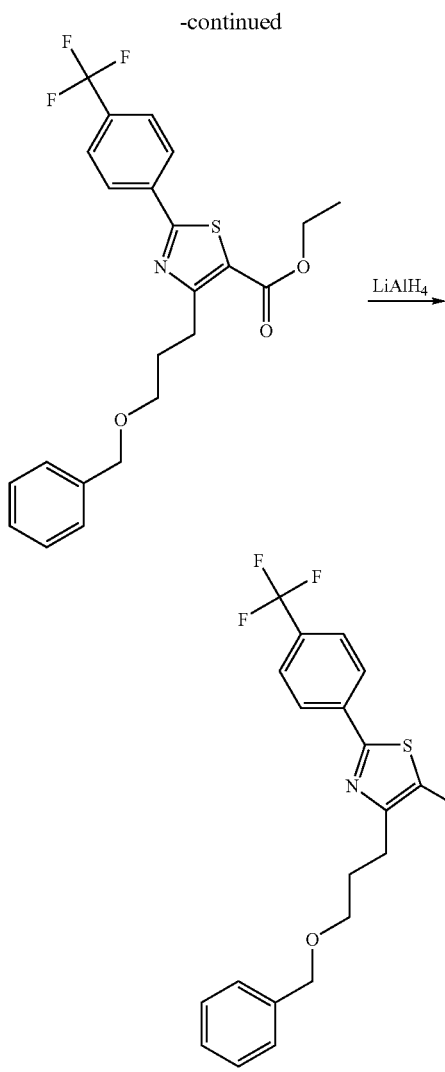

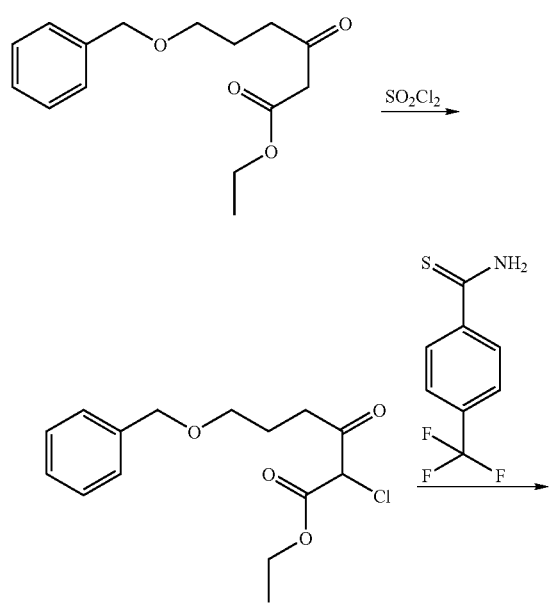

6-Benzyloxy-2-chloro-3-oxo-hexanoic acid ethyl ester

To a solution of 1 g of 6-benzyloxy-3-oxo-hexanoic acid ethyl ester[2] in 10 ml of anhydrous dichloromethane at 0° C.

was dropwise added 0.307 ml of sulfurylchloride. The reaction mixture was stirred at room temperature for 30 minutes at 0° C. and 1 h at room temperature. The reaction mixture was poured onto 20 ml of water and extracted twice with portions of 100 ml of dichloromethane. The combined organic extracts were washed with water, dried over magnesium sulfate, filtered and concentrated under reduced pressure to provide 1.15 g of 6-benzyloxy-2-chloro-3-oxo-hexanoic acid ethyl ester which was used in the next step without further purification.

[2] Paulvannan, K.; Stille, J. R. *J. Org. Chem.*, 1994, 59, 1613-1620.

4-(3-Benzyloxy-propyl)-2-(4-trifluoromethyl-phenyl)-thiazole-5-carboxylic acid ethyl ester

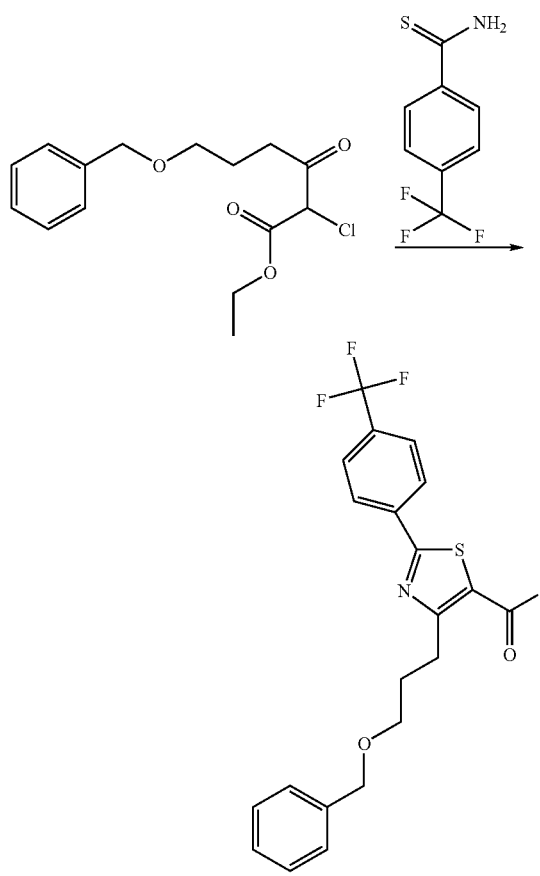

[4-(3-Benzyloxy-propyl)-2-(4-trifluoromethyl-phenyl)-thiazol-5-yl]-methanol

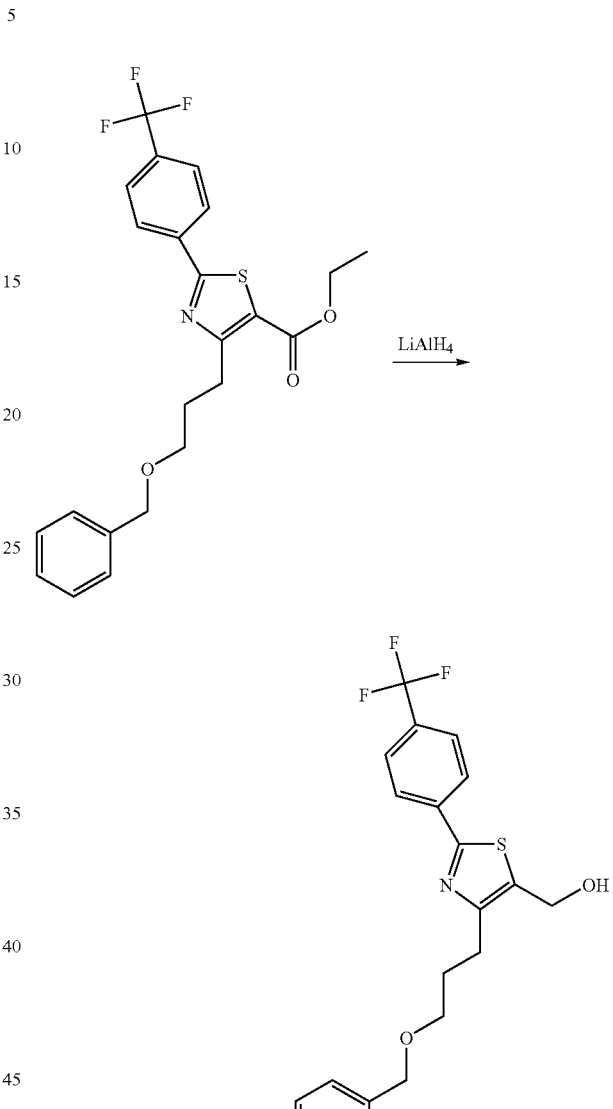

To a solution of 1.15 g of 6-benzyloxy-2-chloro-3-oxo-hexanoic acid ethyl ester in 10 ml of ethanol was added 0.932 g of 4-(trifluoromethyl)thiobenzamide. The reaction mixture was refluxed overnight. The solvent was removed under reduced pressure. The resulting residue was taken into ethyl acetate, washed with water. The aqueous layer was separated and extracted with ethyl acetate. The combined organic extracts were washed with water, dried over magnesium sulfate, filtered and concentrated under reduced pressure. The crude product was purified by column chromatography on silica gel (heptane 90/ethyl acetate 10) to give 1.15 g of 4-(3-benzyloxy-propyl)-2-(4-trifluoromethyl-phenyl)-thiazole-5-carboxylic acid ethyl ester as a colorless liquid.

$C_{23}H_{22}F_3NO_3S$ (449.49), MS (ESI): 450 (M+H$^+$).

To a solution of 2.76 g of 4-(3-benzyloxy-propyl)-2-(4-trifluoromethyl-phenyl)-thiazole-5-carboxylic acid ethyl ester in 50 mL of tetrahydrofuran was added 6.14 mL of a 1M solution of lithium aluminium hydride in tetrahydrofuran. The resulting mixture was stirred at room temperature for 1 h. Ethyl acetate was added followed by a saturated aqueous solution of ammonium chloride. The aqueous layer was separated and extracted three times with ethyl acetate. The combined organic extracts were washed with water, dried over magnesium sulfate, filtered and concentrated under reduced pressure. The crude product was purified by column chromatography on silica gel (heptane 70/ethyl acetate 30) to give 1.69 g of [4-(3-benzyloxy-propyl)-2-(4-trifluoromethyl-phenyl)-thiazol-5-yl]-methanol as a white solid.

$C_{21}H_{20}F_3NO_2S$ (407.45), MS (ESI): 408 (M+H$^+$).

113
4-(3-Benzyloxy-propyl)-5-chloromethyl-2-(4-trifluoromethyl-phenyl)-thiazole

114
5-Chloromethyl-4-methyl-2-[2-(4-trifluoromethyl-phenyl)-ethyl]-oxazole

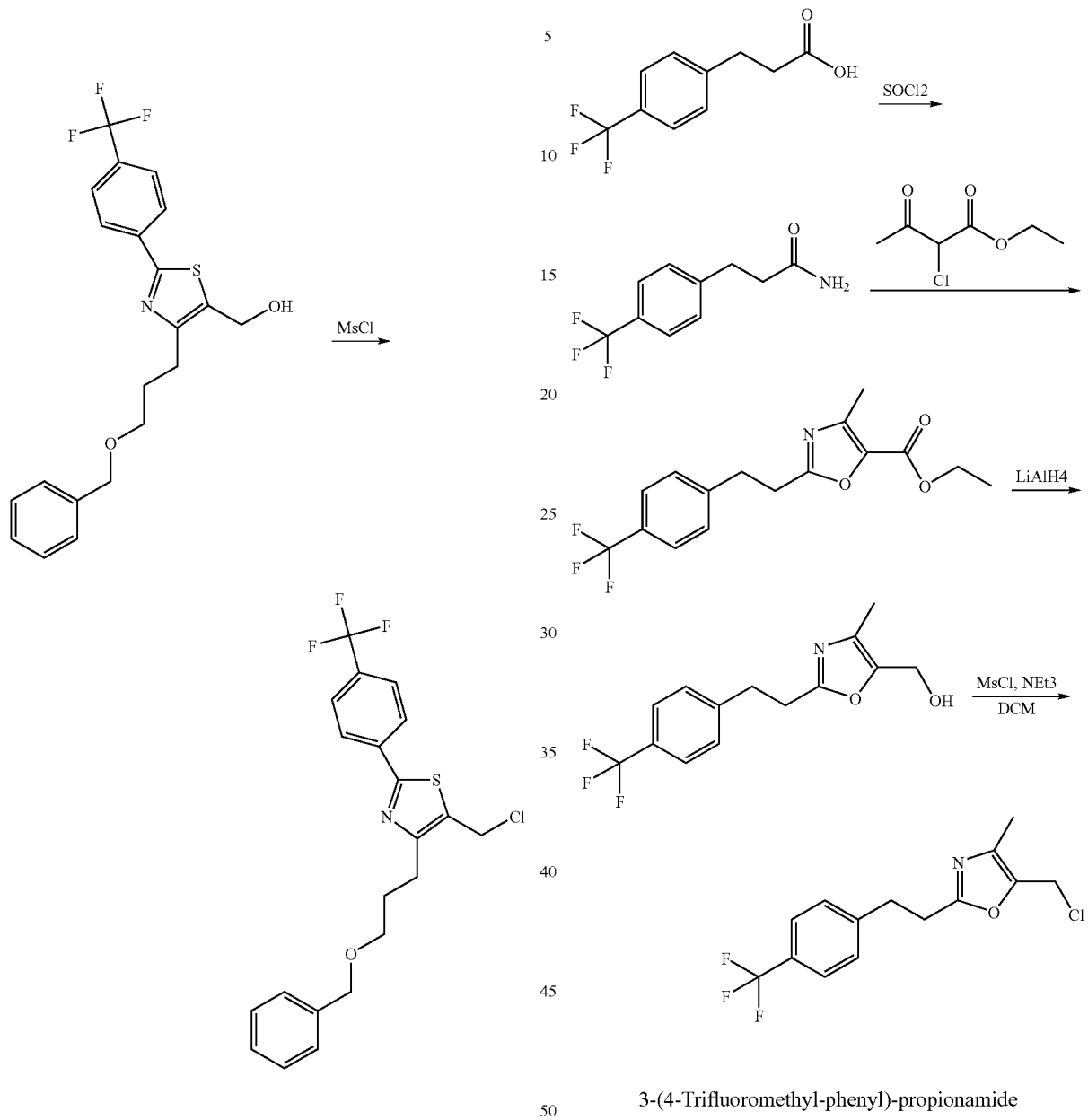

To a solution of 1.5 g of [4-(3-benzyloxy-propyl)-2-(4-trifluoromethyl-phenyl)-thiazol-5-yl]-methanol in 15 mL of dichloromethane was added 1.026 mL of triethylamine and 0.484 mL of methanesulfonyl chloride. The resulting mixture was stirred at room temperature for 2 h. The mixture was then diluted with dichloromethane and water was added. The aqueous layer was separated and extracted three times with dichloromethane. The combined organic extracts were washed with water, dried over magnesium sulfate, filtered and concentrated under reduced pressure. The crude product was purified by column chromatography on silica gel (heptane 90/ethyl acetate 10) to give 0.84 g of 4-(3-benzyloxy-propyl)-5-chloromethyl-2-(4-trifluoromethyl-phenyl)-thiazole as a yellow oil.

C21H19ClF3NOS (425.90), MS (EI): 425 (M+).

3-(4-Trifluoromethyl-phenyl)-propionamide

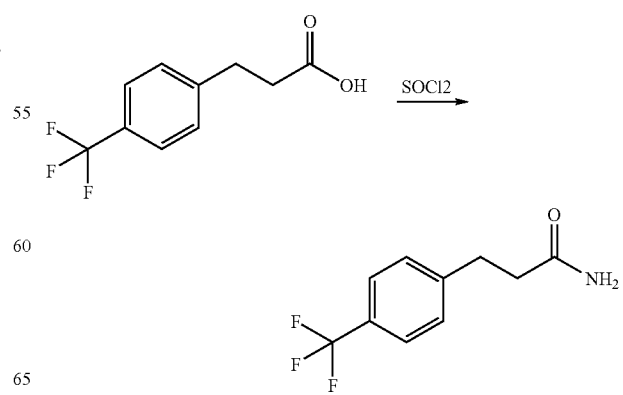

20.0 g 4-(Trifluoromethyl)hydrocinnamic acid were heated under reflux in 150 ml thionyl chloride for three hours. The thionyl chloride was removed in vacuo and the residue dissolved in 150 ml tetrahydrofuran and added dropwise to a stirred solution of concentrated ammonia in water. The reaction mixture was stirred at room temperature. After 15 minutes the organic layer was separated and the aqueous layer was extracted two times with portions of 100 ml ethyl acetate. The combined organic layers were dried over MgSO4. The solvent was removed in vacuo to obtain 18.6 g 3-(4-trifluoromethyl-phenyl)-propionamide as white solid.

C10H10F3NO (217.19), MS (ESI): 218.1.

4-Methyl-2-[2-(4-trifluoromethyl-phenyl)-ethyl]-oxazole-5-carboxylic acid ethyl ester

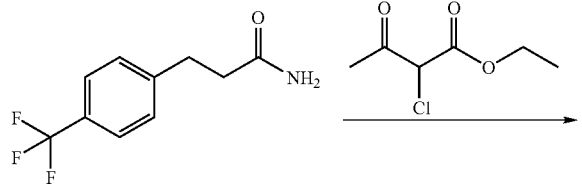

18.6 g 3-(4-Trifluoromethyl-phenyl)-propionamide and 42.8 ml ethyl 2-chloroacetoacetate were mixed and stirred at 150° C. for eight hours. Excess ethyl 2-chloroacetoacetate was removed in vacuo (oil pump) and the residue purified by chromatography on silica gel with the eluent petroleum benzene:ethyl acetate=3:1 to obtain 13.75 g 4-methyl-2-[2-(4-trifluoromethyl-phenyl)-ethyl]-oxazole-5-carboxylic acid ethyl ester as an oil.

C16H16F3NO3 (327.31), MS (ESI): 328.2.

{4-Methyl-2-[2-(4-trifluoromethyl-phenyl)-ethyl]-oxazol-5-yl}-methanol

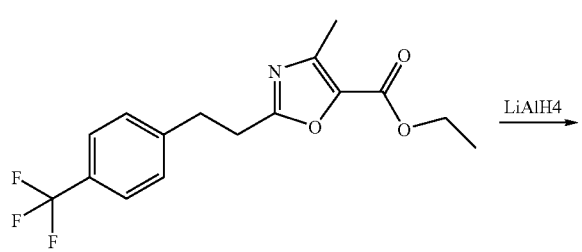

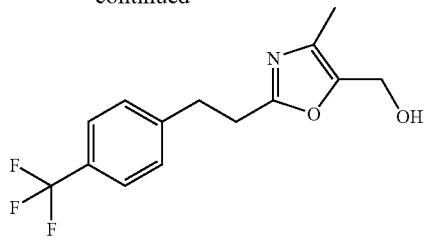

9.70 g 4-Methyl-2-[2-(4-trifluoromethyl-phenyl)-ethyl]-oxazole-5-carboxylic acid ethyl ester were dissolved in 20 ml tetrahydrofuran and added to a ice cooled solution of 1.13 g lithium aluminium hydride in 10 ml tetrahydrofuran. The reaction mixture was stirred at 0° C. for one hour. Then 100 ml ethyl acetate and 50 ml saturated NH4Cl solution were added. The precipitate was filtered off through a celite pad and washed with ethyl acetate. The organic layer of the filtrate was separated. The aqueous layer of the filtrate was extracted two times with portions of 100 ml ethyl acetate. The combined organic layers were dried over MgSO4. The solvent was removed in vacuo and the residue purified by chromatography on silica gel with the eluent petroleum benzene:ethyl acetate=1:1 to obtain to 4.20 g {4-methyl-2-[2-(4-trifluoromethyl-phenyl)-ethyl]-oxazol-5-yl}-methanol a yellow solid.

C14H14F3NO2 (285.27), MS (ESI): 286.2.

5-Chloromethyl-4-methyl-2-[2-(4-trifluoromethyl-phenyl)-ethyl]-oxazole

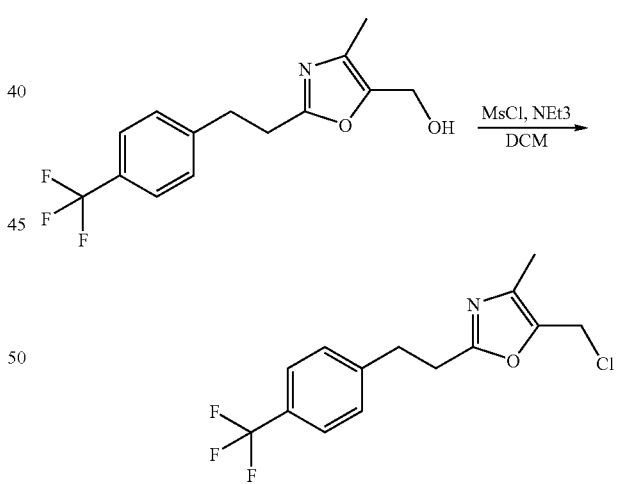

4.20 g {4-Methyl-2-[2-(4-trifluoromethyl-phenyl)-ethyl]-oxazol-5-yl}-methanol were dissolved in 20 ml dichloromethane and cooled in an ice bath. 3.10 ml triethylamine were added, followed by the addition of 1.37 ml methanesulfonylchloride. The ice bath was removed and the resulting mixture stirred at room temperature over night. The reaction mixture was then washed with water and brine, dried over MgSO4 and the solvent removed in vacuo to obtain 4.0 g 5-chloromethyl-4-methyl-2-[2-(4-trifluoromethyl-phenyl)-ethyl]-oxazole as an oil which was used without further purification.

C14H13ClF3NO (303.71), MS (ESI): 304.1 (M+H⁺), Rf (ethyl acetate:n-heptane=1:1)=0.52.

2-Benzyloxymethyl-5-chloromethyl-4-methyl-oxazole

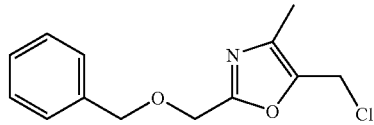

According to the method described for 5-chloromethyl-4-methyl-2-[2-(4-trifluoromethyl-phenyl)-ethyl]-oxazole, 2-benzyloxymethyl-5-chloromethyl-4-methyl-oxazole was obtained from benzyloxyacetic acid and ethyl 2-chloroacetoacetate.

C13H14ClNO2 (251.72), Rf (n-heptane:ethyl acetate=1:1)=0.51.

5-Chloromethyl-2-(4-methoxy-benzyl)-4-methyl-oxazole

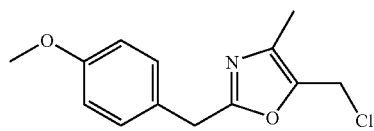

According to the method described for 5-chloromethyl-4-methyl-2-[2-(4-trifluoromethyl-phenyl)-ethyl]-oxazole, 5-chloromethyl-2-(4-methoxy-benzyl)-4-methyl-oxazole was obtained from 4-methoxyphenylacetamide and ethyl 2-chloroacetoacetate.

C13H14ClNO2 (251.72), MS (ESI): 252.1 (M+H⁺), Rf (n-heptane:ethyl acetate=1:1)=0.49.

2-Chloro-4-methoxy-3-oxo-butyric acid methyl ester

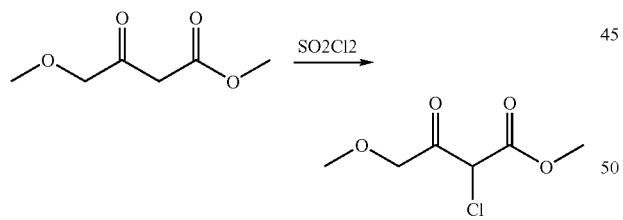

46.0 g Methyl 4-methoxyacetoacetate were dissolved in 500 ml dichloromethane. 28.1 ml Sulfuryl chloride were added in one portion. The reaction mixture was stirred overnight at room temperature. The solvent was removed under reduced pressure, the resulting residue was dissolved in 300 ml ethyl acetate and washed with 100 ml water and 100 ml brine. The organic layer was dried over MgSO4 and the solvent removed under reduced pressure. The resulting residue was purified by chromatography on silica gel with the eluent n-heptane:ethyl acetate=5:1=>2:1 to obtain 45.0 g 2-chloro-4-methoxy-3-oxo-butyric acid methyl ester as a yellow oil.

C6H9ClO4 (180.59), MS (ESI): 181.2 (M+H⁺), Rf (n-heptane:ethyl acetate=2:1)=0.31.

5-Chloromethyl-4-methoxymethyl-2-[2-(4-trifluoromethyl-phenyl)-vinyl]-thiazole

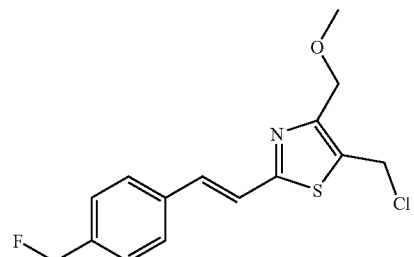

According to the method described for 5-chloromethyl-4-methyl-2-[2-(4-trifluoromethyl-phenyl)-ethyl]-oxazole, 5-chloromethyl-4-methoxymethyl-2-[2-(4-trifluoromethyl-phenyl)-vinyl]-thiazole was obtained from 4-(trifluoromethyl)cinnamide and 2-chloro-4-methoxy-3-oxo-butyric acid methyl ester.

C15H13ClF3NOS (347.79), MS (ESI): 348.0 (M+H⁺).

5-Chloromethyl-4-difluoromethyl-2-(4-methoxy-phenyl)-thiazole

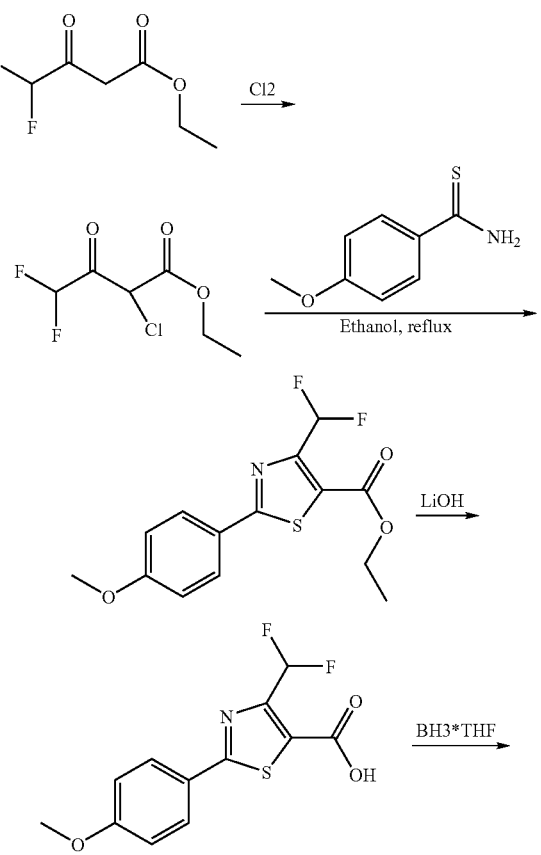

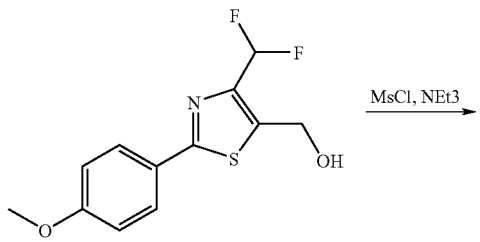

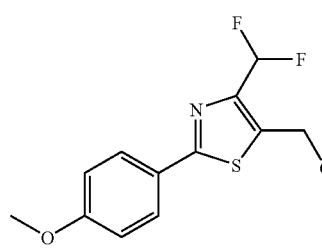

2-Chloro-4,4-difluoro-3-oxo-butyric acid ethyl ester

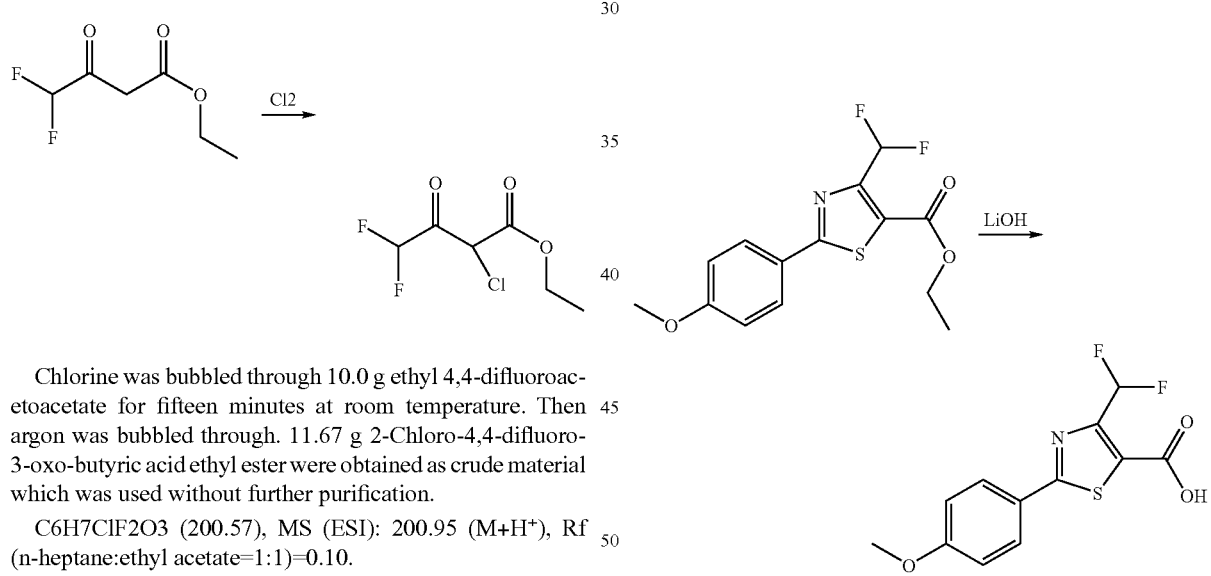

Chlorine was bubbled through 10.0 g ethyl 4,4-difluoroacetoacetate for fifteen minutes at room temperature. Then argon was bubbled through. 11.67 g 2-Chloro-4,4-difluoro-3-oxo-butyric acid ethyl ester were obtained as crude material which was used without further purification.

C6H7ClF2O3 (200.57), MS (ESI): 200.95 (M+H$^+$), Rf (n-heptane:ethyl acetate=1:1)=0.10.

4-Difluoromethyl-2-(4-methoxy-phenyl)-thiazole-5-carboxylic acid ethyl ester

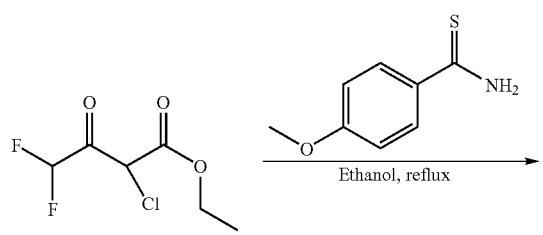

8.84 g 4-Methoxythiobenzamide were dissolved in 100 ml ethanol and warmed to 50° C. Then 10.59 g 2-chloro-4,4-difluoro-3-oxo-butyric acid ethyl ester were added and the reaction mixture stirred under reflux for three hours. The cooled reaction mixture was evaporated in vacuo and the residue purified by chromatograph on silica gel with the eluent ethyl acetate/petroleum benzene=1:4 to obtain 7.04 g 4-difluoromethyl-2-(4-methoxy-phenyl)-thiazole-5-carboxylic acid ethyl ester as pale yellow solid.

C14H13F2NO3S (313.33), MS (ESI): 313.95 (M+H$^+$).

4-Difluoromethyl-2-(4-methoxy-phenyl)-thiazole-5-carboxylic acid

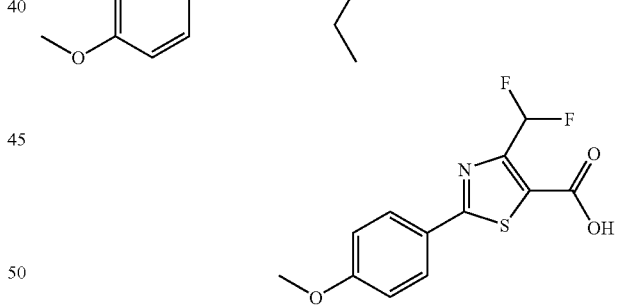

3.0 g 4-Difluoromethyl-2-(4-methoxy-phenyl)-thiazole-5-carboxylic acid ethyl ester were dissolved in 90 ml tetrahydrofuran. A solution of 2.29 g lithium hydroxide dissolved in 30 ml water was added and the reaction mixture stirred at room temperature overnight. Concentrated acetic acid were added until a pH of ~6 was attained, then the tetrahydrofuran was removed in vacuo. The residual aqueous phase was extracted three time with portions of 100 ml ethyl acetate. The combined organic layers were dried over MgSO4. Then the solvent was removed in vacuo to obtain 2.73 g 4-difluoromethyl-2-(4-methoxy-phenyl)-thiazole-5-carboxylic acid as pale yellow solid.

C12H9F2NO3S (285.27), MS (ESI): 285.90 (M+H$^+$).

121

[4-Difluoromethyl-2-(4-methoxy-phenyl)-thiazol-5-yl]-methanol

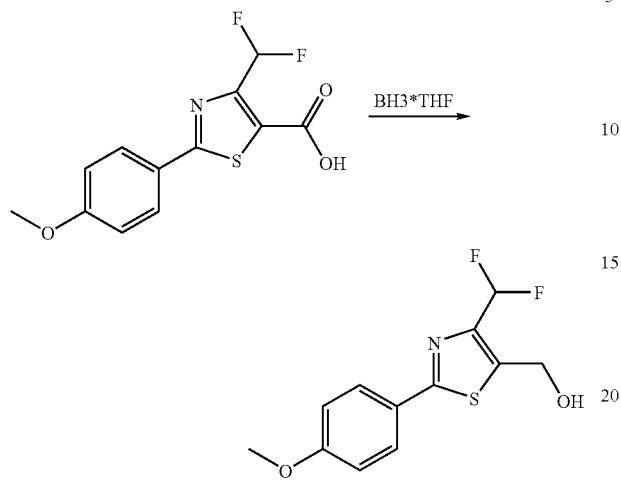

2.73 g 4-Difluoromethyl-2-(4-methoxy-phenyl)-thiazole-5-carboxylic acid were dissolved in 30 ml tetrahydrofuran. 23 ml of a one molar solution of borane tetrahydrofuran complex were added and the reaction mixture stirred at 40° C. for three hours. The cooled reaction mixture was poured on ice water and extracted three times with portions of 100 ml ethyl acetate. The combined organic layers were dried over MgSO4. Then the solvent was removed in vacuo to obtain 2.70 g [4-difluoromethyl-2-(4-methoxy-phenyl)-thiazol-5-yl]-methanol.

C12H11F2NO2S (271.29), MS (ESI): 272.0 (M+H$^+$).

5-Chloromethyl-4-difluoromethyl-2-(4-methoxy-phenyl)-thiazole

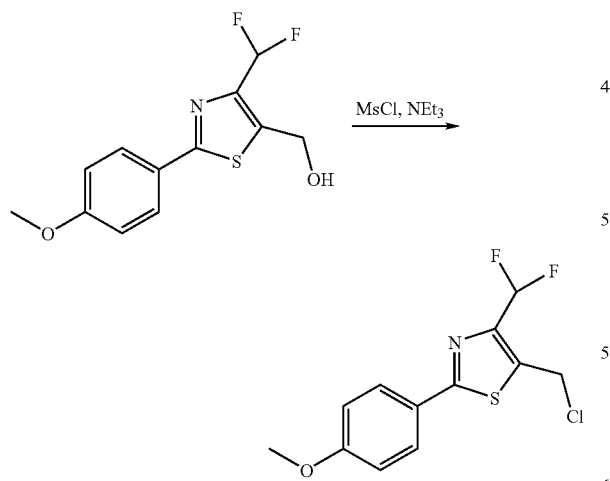

2.70 g [4-Difluoromethyl-2-(4-methoxy-phenyl)-thiazol-5-yl]-methanol were dissolved in 15 ml dichloromethane and cooled in an ice bath. 2.07 ml triethylamine were added, followed by the addition of 0.92 ml methanesulfonylchloride. The ice bath was removed and the resulting mixture stirred at room temperature over night. Then 2.07 ml triethylamine and 0.92 ml methanesulfonylchloride were added again and the reaction mixture stirred at room temperature for additional four hours. The reaction mixture was then washed with water and brine, dried over MgSO4 and the solvent removed in vacuo to obtain 3.0 g crude 5-chloromethyl-4-difluoromethyl-2-(4-methoxy-phenyl)-thiazole as an oil which was used without further purification.

C12H10ClF2NOS (289.73), MS (ESI): 289.9 (M+H$^+$), Rf (ethyl acetate:n-heptane=1:1)=0.76.

Building Block Synthesis According to Process J

[2-(4-Methoxy-phenyl)-4-(tetrahydro-pyran-2-yloxymethyl)-oxazol-5-yl]-methanol and 5-chloromethyl-2-(4-methoxy-phenyl)-4-(tetrahydro-pyran-2-yloxymethyl)-oxazole

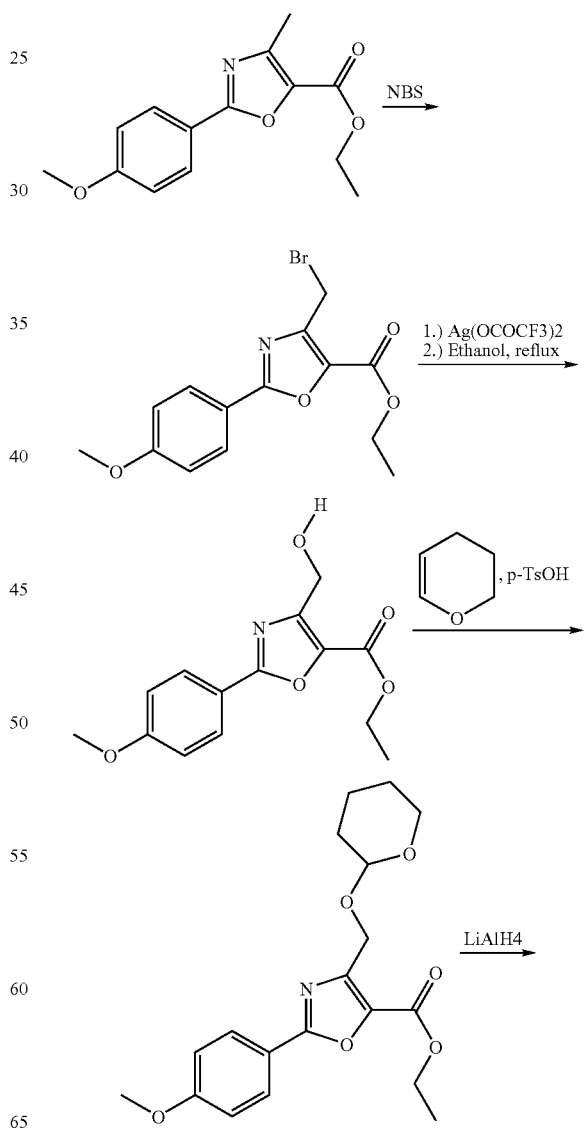

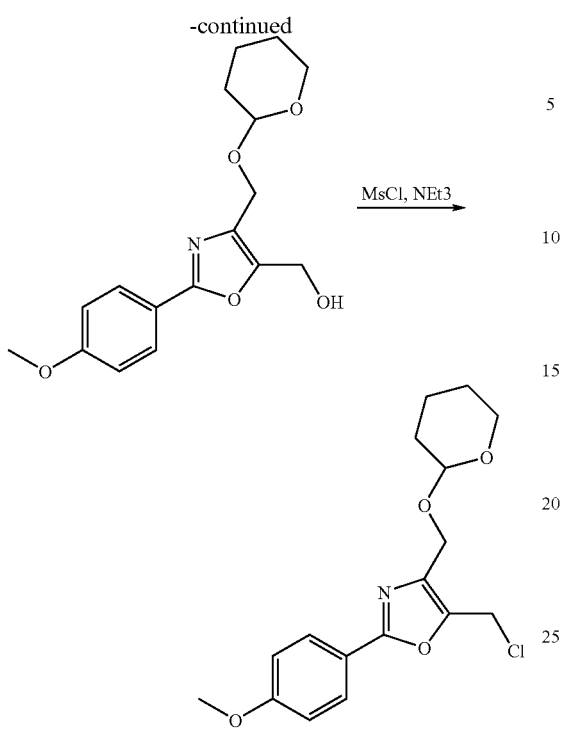

4-Bromomethyl-2-(4-methoxy-phenyl)-oxazole-5-carboxylic acid ethyl ester

To a boiling solution of 23.5 g 2-(4-methoxy-phenyl)-4-methyl-oxazole-5-carboxylic acid ethyl ester in 250 ml tetrachloro-methane were added portionwise a mixture of 5.92 g 2,2'-azobis(2-methylpropionitrile) and 19.3 g N-bromosuccinimide. The reaction mixture was refluxed for seven hours. The cooled reaction mixture was filtered over a celite pad and the solvent removed in vacuo to obtain 30.7 g of crude 4-bromomethyl-2-(4-methoxy-phenyl)-oxazole-5-carboxylic acid ethyl ester. The material was used without further purification in the next step.

C14H14BrNO4 (340.18), MS (ESI): 340.0 and 342.0 (M+H$^+$), Rf (ethyl acetate:n-heptane=7:3)=0.43).

4-Hydroxymethyl-2-(4-methoxy-phenyl)-oxazole-5-carboxylic acid ethyl ester

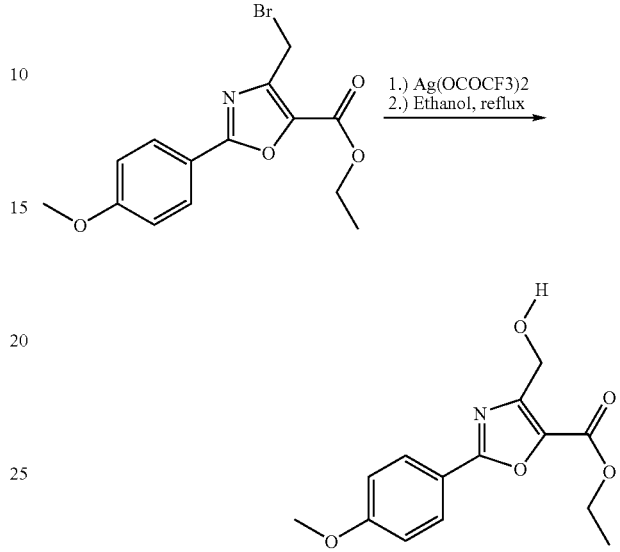

30.7 g of crude 4-Bromomethyl-2-(4-methoxy-phenyl)-oxazole-5-carboxylic acid ethyl ester were dissolved in 170 ml dry dimethylformamide. 29.95 g Silver trifluoroacetate were added and the mixture was stirred at room temperature overnight. 100 ml brine was added and the mixture was stirred for one hour. The reaction mixture was filtered through a pad of celite, the solvent removed in vacuo and the resulting residue dissolved in 200 ml ethanol. The mixture was heated to reflux for three hours. Then the solvent was removed in vacuo and the residue dissolved in water and extracted five times with ethyl acetate. The combined organic layers were dried over MgSO4, the solvent removed in vacuo and the residue purified by flash chromatography on silica gel (eluting with n-heptane:ethyl acetate=5:1=>ethylacetate) to obtain 17.8 g 4-hydroxymethyl-2-(4-methoxy-phenyl)-oxazole-5-carboxylic acid ethyl ester as a solid.

C14H15NO5 (277.28), MS (ESI): 278.1 (M+H$^+$), Rf (ethyl acetate:n-heptane=1:2)=0.11.

2-(4-Methoxy-phenyl)-4-(tetrahydro-pyran-2-yloxymethyl)-oxazole-5-carboxylic acid ethyl ester

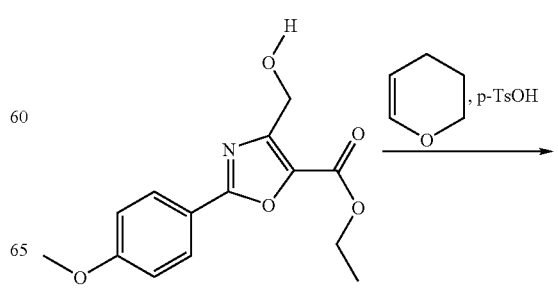

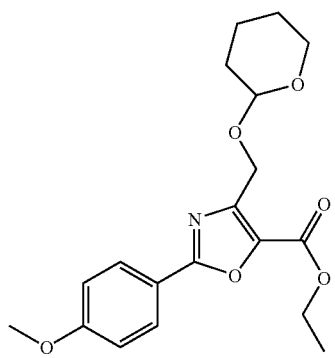

10.0 g 4-Hydroxymethyl-2-(4-methoxy-phenyl)-oxazole-5-carboxylic acid ethyl ester were dissolved in 85 ml dichloromethane. 4.0 ml 3,4-dihydro-2H-pyran and 1.85 mg pyridinium p-toluenesulfonate were added and the reaction mixture stirred at room temperature overnight. The solvent was removed in vacuo and the residue purified by flash chromatography on silica gel (eluting with n-heptane:ethyl acetate=4:1=>1:1) to obtain 12.3 g 2-(4-methoxy-phenyl)-4-(tetrahydro-pyran-2-yloxymethyl)-oxazole-5-carboxylic acid ethyl ester as an oil.

C19H23NO6 (361.40), MS (ESI): 362.2 (M+H$^+$), 278.2 (M-THP+H$^+$), Rf (ethyl acetate:n-heptane=1:1)=0.56.

[2-(4-Methoxy-phenyl)-4-(tetrahydro-pyran-2-yloxymethyl)-oxazol-5-yl]-methanol

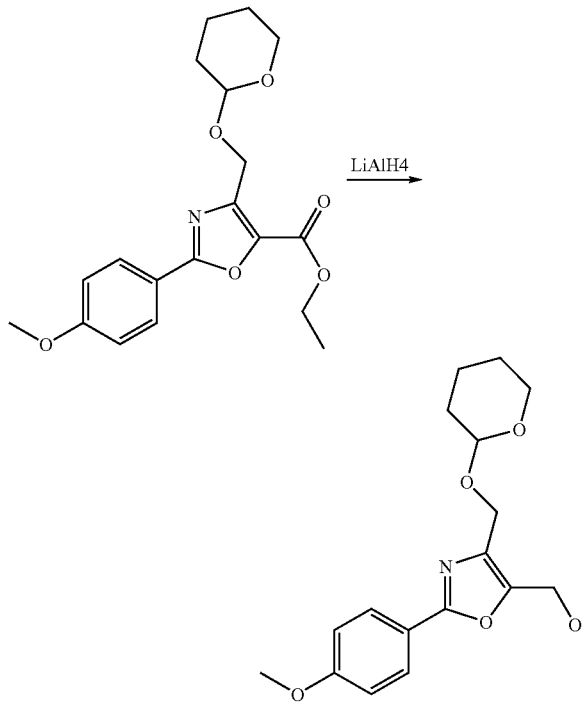

To a cooled suspension of 2.73 g lithium aluminium hydride in 180 ml tetrahydrofuran a solution of 12.3 g 2-(4-methoxy-phenyl)-4-(tetrahydro-pyran-2-yloxymethyl)-oxazole-5-carboxylic acid ethyl ester in 120 ml tetrahydrofuran were added at 0° C. The ice bath was removed and the reaction mixture stirred at room temperature for one hour. The reaction mixture was cooled in an ice bath again and 100 ml ethyl acetate were added followed by the addition of 300 ml methyl-tert-butyl ether. Then a solution of 10.92 g sodium hydroxide in 12.3 ml water was added. Solid precipitate was filtered off through a plug of celite. The filtrate was dried over MgSO4 and then the solvent was removed in vacuo to obtain 11.8 g [2-(4-methoxy-phenyl)-4-(tetrahydro-pyran-2-yloxymethyl)-oxazol-5-yl]-methanol as a solid.

C17H21NO5 (319.36), MS (ESI): 320.2 (M+H$^+$), Rf (ethyl acetate:n-heptane=1:1)=0.18.

5-Chloromethyl-2-(4-methoxy-phenyl)-4-(tetrahydro-pyran-2-yloxymethyl)-oxazole

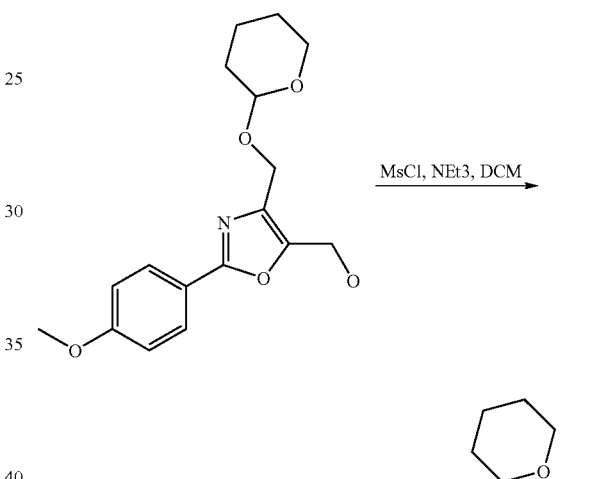

2.0 g [2-(4-Methoxy-phenyl)-4-(tetrahydro-pyran-2-yloxymethyl)-oxazol-5-yl]-methanol were dissolved in 30 ml dichloromethane and cooled in an ice bath. 0.88 ml triethylamine were added, followed by the addition of 0.49 ml methanesulfonylchloride. The ice bath was removed and the resulting mixture stirred at room temperature over night. The reaction mixture was then washed with water and brine, dried over MgSO4 and the solvent removed in vacuo to obtain 2.5 g of 5-chloromethyl-2-(4-methoxy-phenyl)-4-(tetrahydro-pyran-2-yloxymethyl)-oxazole as an oil which was used without further purification.

C17H20ClNO4 (337.81), MS (ESI): 338.2 (M+H$^+$), Rf (ethyl acetate:n-heptane=1:1)=0.42.

127
Building Block Synthesis According to Process K
[2-(4-Methoxy-phenyl)-5-(tetrahydro-pyran-2-yloxymethyl)-oxazol-4-yl]-methanol and methanesulfonic acid 2-(4-methoxy-phenyl)-5-(tetrahydro-pyran-2-yloxymethyl)-oxazol-4-ylmethyl ester
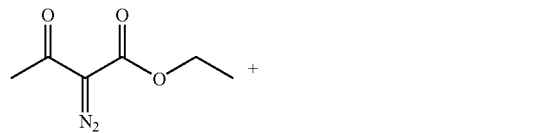
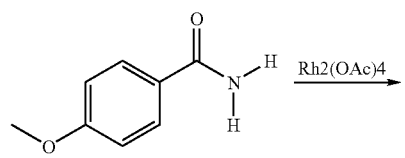
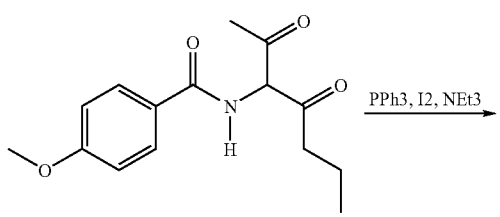
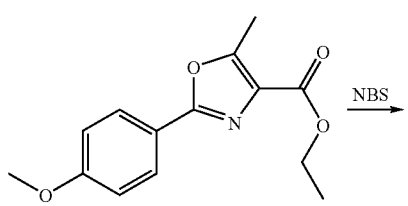
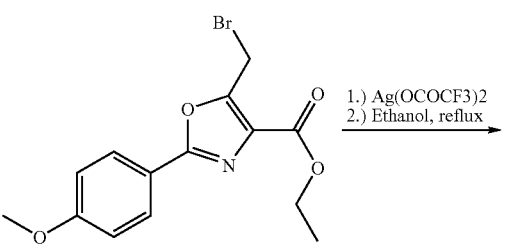
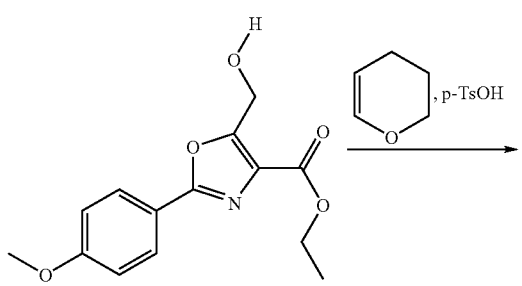
128
-continued
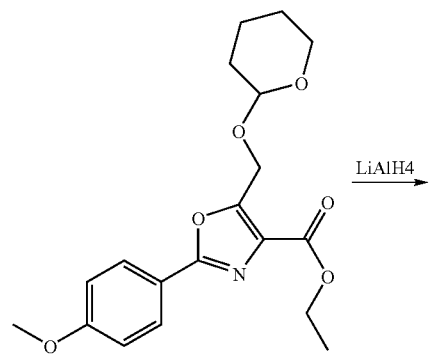
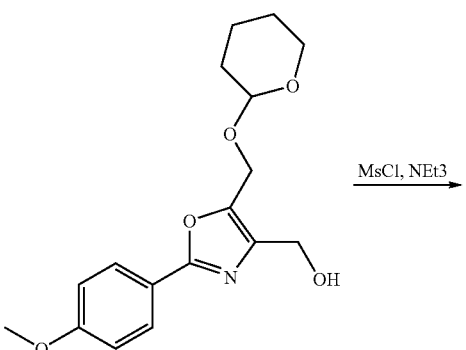
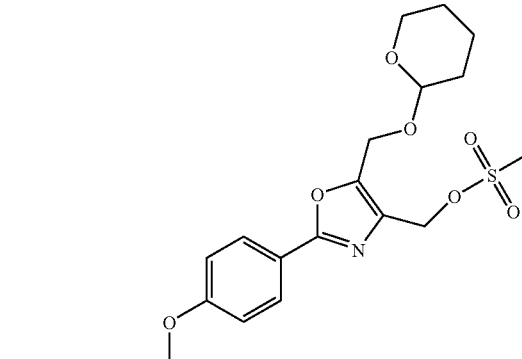
2-(4-Methoxy-benzoylamino)-3-oxo-butyric acid ethyl ester
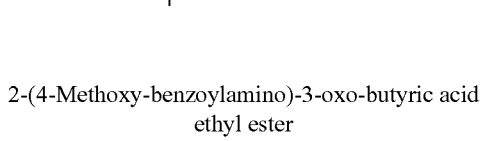
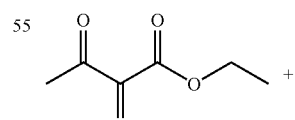
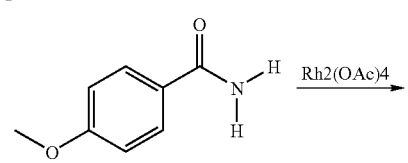

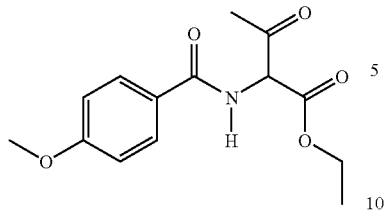

A solution of 12.1 g ethyl-2-diazo-3-oxobutanoate[3] in 100 ml 1,2-dichloroethane was added dropwise over 5 hours to a boiling solution of 9.0 g 4-methoxybenzamide and 1.05 g rhodium(II) acetate dimer in 200 ml dry 1,2-dichloroethane. The mixture was refluxed for thirty minutes, allowed to cool, evaporated in vacuo and purified by flash chromatography on silica gel to obtain 11.3 g 2-(4-methoxy-benzoylamino)-3-oxo-butyric acid ethyl ester.

[3] J. Chem. Soc., Perkin Trans. 1, 1998, 591-600.

C14H17NO5 (279.30), MS (ESI): 280.2 (M+H$^+$), Rf (ethyl acetate:n-heptane=1:1)=0.32.

2-(4-Methoxy-phenyl)-5-methyl-oxazole-4-carboxylic acid ethyl ester

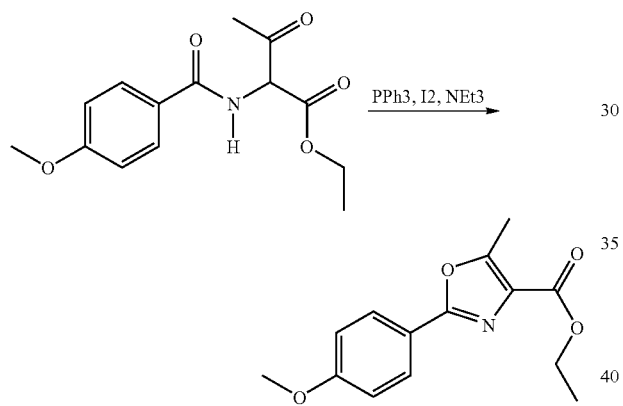

23.2 ml Triethylamine and a solution of 11.3 g 2-(4-methoxy-benzoylamino)-3-oxo-butyric acid ethyl ester in 200 ml dichloromethane were added sequentially to a stirred solution of 20.5 g iodine and 21.2 g triphenylphosphine in 500 ml dry dichloromethane. The reaction mixture was stirred at room temperature overnight. The solvent was evaporated in vacuo and the resulting residue purified by flash chromatography on silica gel to obtain 6.0 g 2-(4-methoxy-phenyl)-5-methyl-oxazole-4-carboxylic acid ethyl ester as pale yellow solid.

C14H15NO4 (261.28), MS (ESI): 262.2 (M+H$^+$), Rf (ethyl acetate:n-heptane=2:1)=0.31.

5-Bromomethyl-2-(4-methoxy-phenyl)-oxazole-4-carboxylic acid ethyl ester

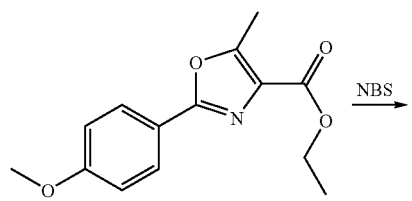

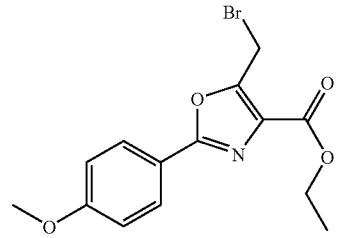

To a boiling solution of 6.0 g 2-(4-methoxy-phenyl)-5-methyl-oxazole-4-carboxylic acid ethyl ester in 100 ml tetrachloro-methane were added portionwise a mixture of 1.51 g 2,2'-azobis(2-methylpropionitrile) and 4.9 g N-bromosuccinimide. The reaction mixture was refluxed for three hours. The cooled reaction mixture was filtered over a celite pad and the solvent removed in vacuo to obtain 10.6 g of crude 5-bromomethyl-2-(4-methoxy-phenyl)-oxazole-4-carboxylic acid ethyl ester, which contains to some extend the dibrominated byproduct. The material was used without further purification in the next step.

C14H14BrNO4 (340.18), MS (ESI): 340.0 and 342.0 (M+H$^+$), Rf (ethyl acetate:n-heptane=2:1)=0.27).

5-Hydroxymethyl-2-(4-methoxy-phenyl)-oxazole-4-carboxylic acid ethyl ester

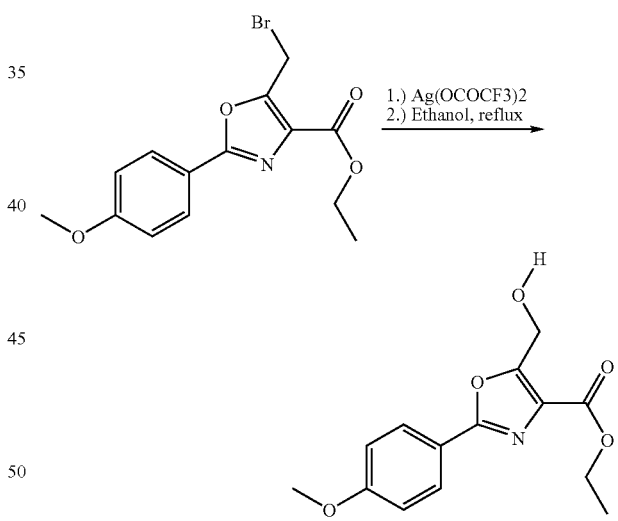

8.0 g 5-Bromomethyl-2-(4-methoxy-phenyl)-oxazole-4-carboxylic acid ethyl ester were dissolved in 50 ml dry dimethylformamide. 7.8 g Silver trifluoroacetate were added and the mixture was stirred at room temperature for two hours. 30 ml brine were added and the mixture was stirred for two hours. The reaction mixture was filtered through a pad of celite, the solvent removed in vacuo and the resulting residue dissolved in 200 ml ethanol. The mixture was heated to reflux for three hours. Then the solvent was removed in vacuo and the residue dissolved in water and extracted five times with ethyl acetate. The combined organic layers were dried over MgSO4, the solvent removed in vacuo and the residue purified by flash chromatography on silica gel (eluting with n-heptane:ethyl acetate=2:3=>ethylacetate) to obtain 4.8 g 5-hydroxymethyl-2-(4-methoxy-phenyl)-oxazole-4-carboxylic acid ethyl ester as a solid.

C14H15NO5 (277.28), MS (ESI): 278.1 (M+H⁺), Rf (ethyl acetate:n-heptane=1:2)=0.09.

2-(4-Methoxy-phenyl)-5-(tetrahydro-pyran-2-yloxymethyl)-oxazole-4-carboxylic acid ethyl ester

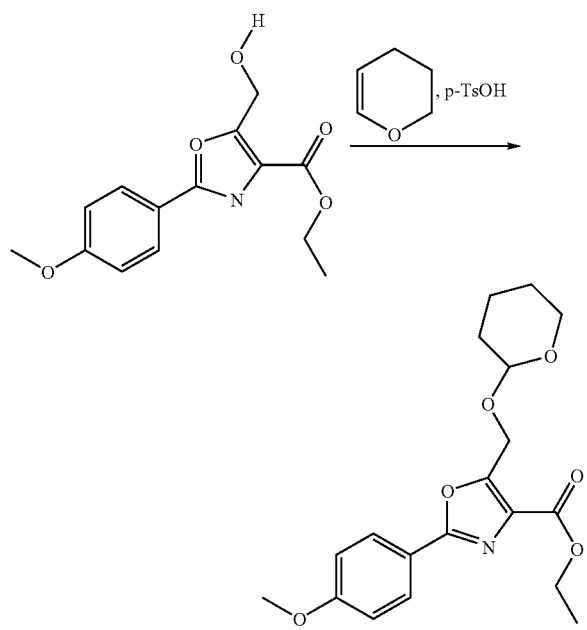

4.8 g 5-Hydroxymethyl-2-(4-methoxy-phenyl)-oxazole-4-carboxylic acid ethyl ester were dissolved in 75 ml dichloromethane. 1.9 ml 3,4-dihydro-2H-pyran and 870 mg pyridinium p-toluenesulfonate were added and the reaction mixture stirred at room temperature over night. The solvent was removed in vacuo and the residue purified by flash chromatography on silica gel (eluting with n-heptane:ethyl acetate=3:1=>1:1) to obtain 5.3 g 2-(4-methoxy-phenyl)-5-(tetrahydro-pyran-2-yloxymethyl)-oxazole-4-carboxylic acid ethyl ester.

C19H23NO6 (361.40), MS (ESI): 362.2 (M+H⁺), 278.1 (M-THP+H⁺).

[2-(4-Methoxy-phenyl)-5-(tetrahydro-pyran-2-yloxymethyl)-oxazol-4-yl]-methanol

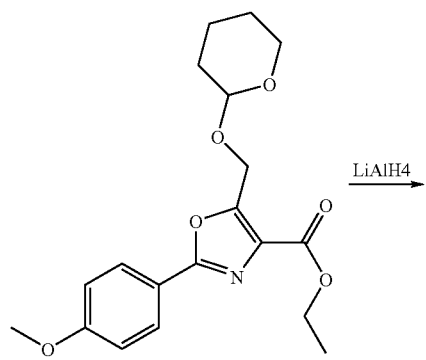

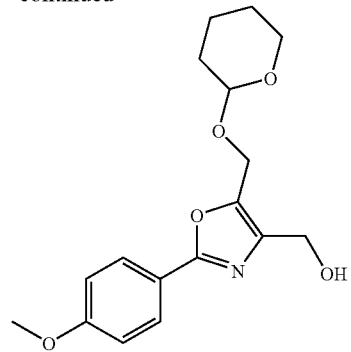

5.3 g 2-(4-Methoxy-phenyl)-5-(tetrahydro-pyran-2-yloxymethyl)-oxazole-4-carboxylic acid ethyl ester were dissolved in 100 ml tetrahydrofuran and cooled in an ice bath. 21.8 ml of a one molar solution of lithium aluminium hydride in tetrahydrofuran were added. The cooling bath was removed and the reaction mixture stirred at room temperature for thirty minutes. The reaction mixture was cooled in an ice bath again and sequentially added 6 ml water, 12 ml 15% NaOH and 18 ml water. After being stirred for one hour at room temperature the reaction mixture was filtered over a pad of celite and washed with ethyl acetate. The filtrate was dried over MgSO4 and the solvent was removed in vacuo and the residue purified by flash chromatography on silica gel (eluting with n-heptane:ethyl acetate=6:4=>9:1=>ethyl acetate) to obtain 3.0 g [2-(4-methoxy-phenyl)-5-(tetrahydro-pyran-2-yloxymethyl)-oxazol-4-yl]-methanol.

C17H21NO5 (319.36), MS (ESI): 320.2 (M+H⁺).

Methanesulfonic acid 2-(4-methoxy-phenyl)-5-(tetrahydro-pyran-2-yloxymethyl)-oxazol-4-ylmethyl ester

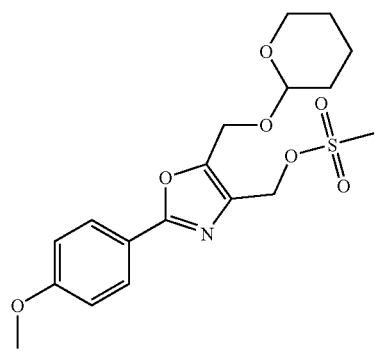

0.44 g [2-(4-Methoxy-phenyl)-5-(tetrahydro-pyran-2-yloxymethyl)-oxazol-4-yl]-methanol were dissolved in 30 ml dichloromethane and cooled in an ice bath. 0.29 ml triethylamine were added, followed by the addition of 0.13 ml methanesulfonylchloride. The reaction mixture was stirred at 0° C. for one hour then the ice bath was removed and the resulting mixture stirred at room temperature for an additional hour. The reaction mixture was then washed with water and brine, dried over MgSO4 and the solvent removed in vacuo to obtain 0.55 mg of methanesulfonic acid 2-(4-methoxy-phenyl)-5-(tetrahydro-pyran-2-yloxymethyl)-oxazol-4-ylmethyl ester as an oil which was used without further purification.

C18H23NO7S (397.45), MS (ESI): 398.2 (M+H⁺).

Building Block Synthesis According to Process N

2-Difluoromethoxy-4-fluoro-benzonitrile

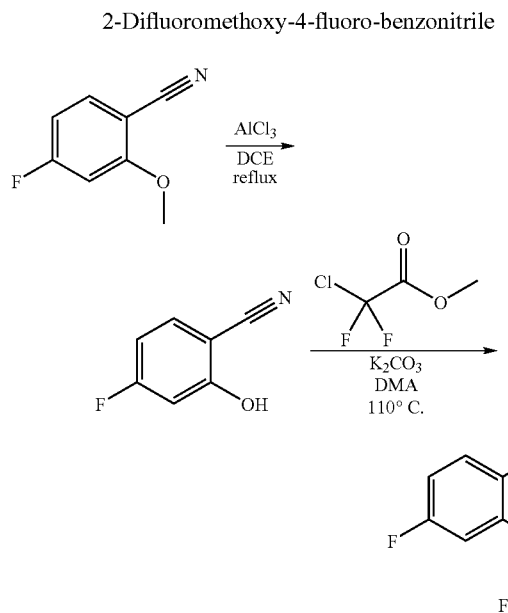

4-Fluoro-2-methoxy-benzonitrile was prepared according to a previous publication:[4] To a solution of 1 g of 4-fluoro-2-methoxy-benzonitrile in 15 mL of dichloroethane was added 1.1 g of aluminium trichloride. The resulting mixture was refluxed for 1 day then poured slowly into water and extracted with ethyl acetate. The organic extracts were washed twice with 10% aqueous solution of sodium hydroxide. The combined basic layers were washed twice with ethyl acetate, acidified with concentrated aqueous solution of hydrochloric acid and extracted three times with ethyl acetate. The combined organic extracts were washed with water, with brine, dried over magnesium sulfate, filtered and concentrated under reduced pressure to give 0.78 g of 4-fluoro-2-hydroxy-benzonitrile as a white solid.

[4] JP9143139

C7H4FNO (137.11), MS (ESI): 138.17 (M+H⁺).

To a solution of 4.6 g of 4-fluoro-2-hydroxy-benzonitrile in 15 mL of anhydrous dimethylacetamide were added 6.8 g of methyl chlorodifluororacetate and 6.5 g of potassium carbonate. The resulting mixture was degassed by bubbling argon through it and heated to 110° C. for 2 h then an additional 6.5 g of methyl chlorodifluororacetate and 6.5 g of potassium carbonate were added. The resulting mixture was heated to 110° C. for another hour then concentrated under reduced pressure. The residue was taken into ethyl acetate, washed twice with a molar aqueous solution of sodium hydroxide, with water and brine, dried over magnesium sulfate, filtered and concentrated under reduced pressure. The crude product was purified by column chromatography on silica gel (gradient from heptane 100 to heptane 80/ethyl acetate 20) to give 4.78 g of 2-difluoromethoxy-4-fluoro-benzonitrile as a yellowish liquid.

C8H4F3NO (187.12), MS (ESI): 188.0 (M+H⁺).

2-Difluoromethoxy-4,5-difluoro-benzonitrile

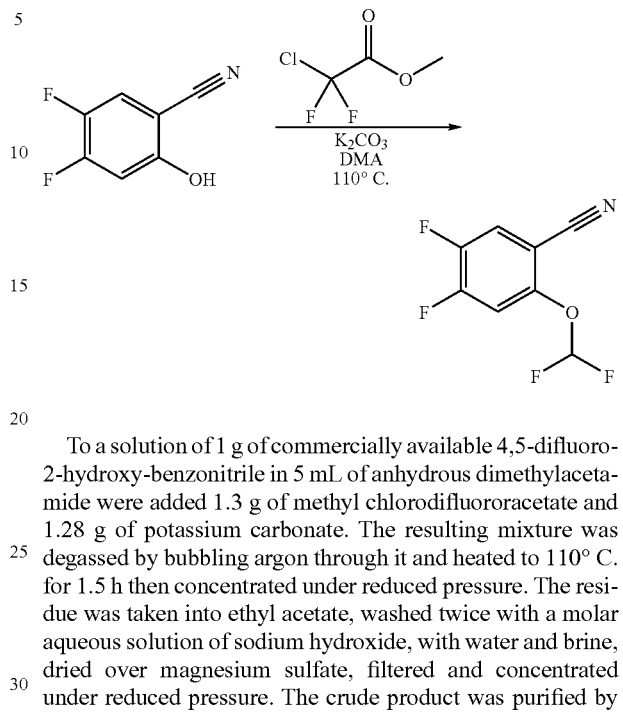

To a solution of 1 g of commercially available 4,5-difluoro-2-hydroxy-benzonitrile in 5 mL of anhydrous dimethylacetamide were added 1.3 g of methyl chlorodifluororacetate and 1.28 g of potassium carbonate. The resulting mixture was degassed by bubbling argon through it and heated to 110° C. for 1.5 h then concentrated under reduced pressure. The residue was taken into ethyl acetate, washed twice with a molar aqueous solution of sodium hydroxide, with water and brine, dried over magnesium sulfate, filtered and concentrated under reduced pressure. The crude product was purified by column chromatography on silica gel (gradient from heptane 100 to heptane 80/ethyl acetate 20) to give 0.42 g of 2-difluoromethoxy-4,5-difluoro-benzonitrile as a yellowish liquid.

C8H3F4NO (205.11), MS (EI): 205 (M⁺).

Building Block Synthesis According to Process M

4-Fluoro-2-(2,2,2-trifluoro-ethoxy)-benzonitrile

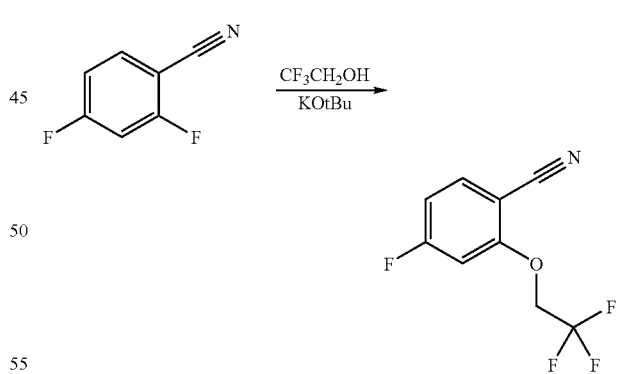

To a solution of 359 mg of trifluoroethanol in 3 mL of anhydrous tetrahydrofuran at 5° C. was slowly added 3.6 mL of a molar solution of potassium tert-butoxide in tert-butanol. The resulting solution was stirred for 30 minutes at 5° C. and slowly added to a solution of 500 mg of 2,4-difluoro-benzonitrile in 3 mL of anhydrous tetrahydrofuran at 5° C. The resulting mixture was stirred for 1 h at 5° C., then poured into water and extracted with ethyl acetate. The organic extracts were dried over magnesium sulfate, filtered and concentrated under reduced pressure. The crude product was purified by column chromatography on silica gel (gradient from heptane 100 to heptane 90/ethyl acetate 10) to give 640 mg of 4-fluoro-2-(2,2,2-trifluoro-ethoxy)-benzonitrile as a white solid.

C9H5F4NO (219.14), MS (ESI): 220 (M+H⁺).

4-Fluoro-2-isopropoxy-benzonitrile

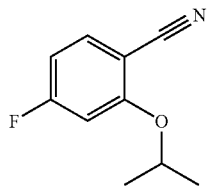

According to the method described for 4-fluoro-2-(2,2,2-trifluoro-ethoxy)-benzonitrile, 4-fluoro-2-isopropoxy-benzonitrile was obtained from 2,4-difluoro-benzonitrile and isopropanol.

C10H10FNO (179.20), MS (ESI): 180 (M+H⁺).

2-Cyclopropylmethoxy-4-fluoro-benzonitrile

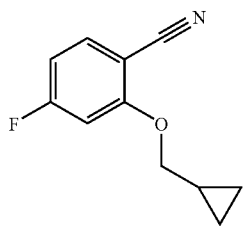

According to the method described for 4-fluoro-2-(2,2,2-trifluoro-ethoxy)-benzonitrile, 2-cyclopropylmethoxy-4-fluoro-benzonitrile was obtained from 2,4-difluoro-benzonitrile and cyclopropylmethanol.

C11H10FNO (191.21), MS (EI): 205 (M⁺).

The following examples were prepared according to process B:

Example 1

3-{2-Methoxy-4-[2-(4-trifluoromethyl-phenyl)-4-(4-trifluoromethyl-piperidin-1-ylmethyl)-thiazol-5-yl-methoxy]-phenyl}-4H-[1,2,4]oxadiazol-5-one

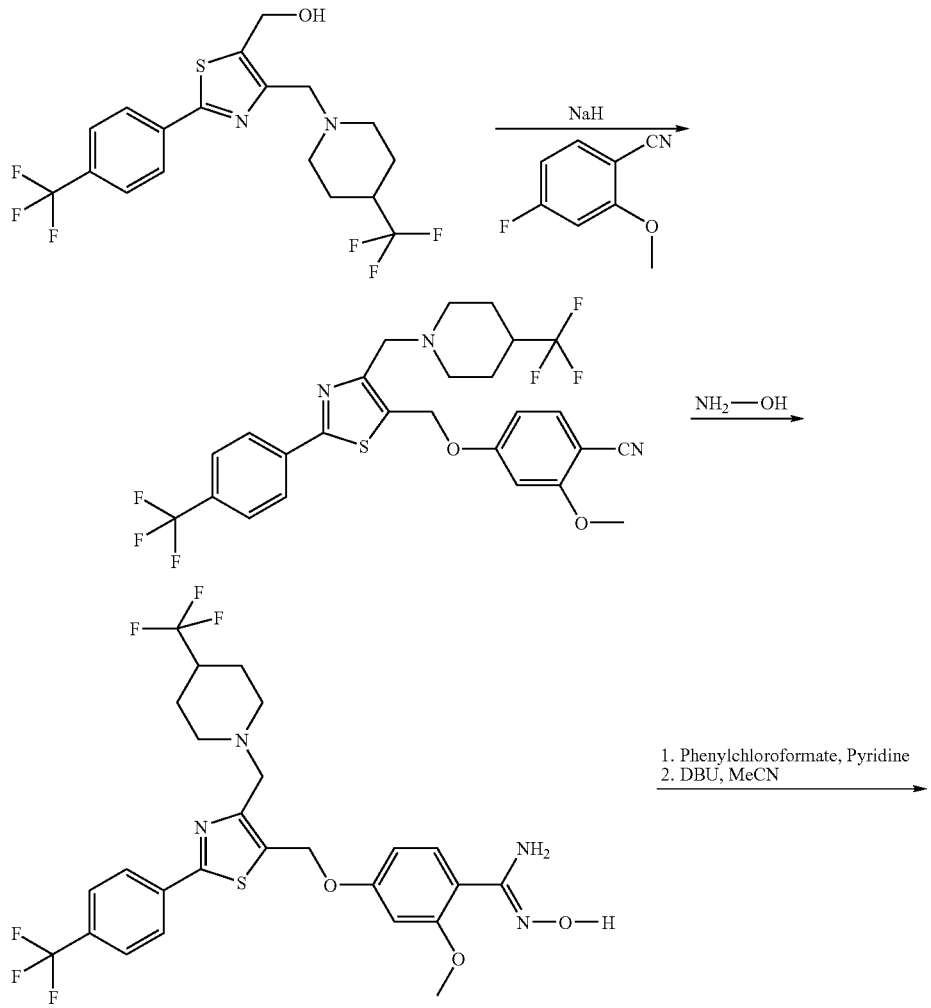

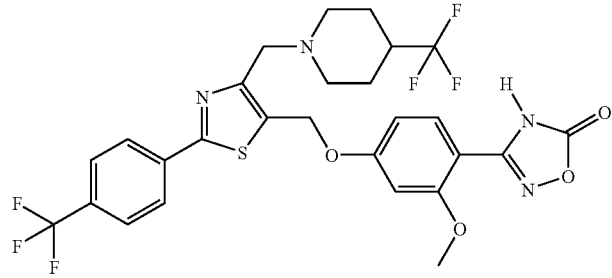

| 2-Methoxy-4-[2-(4-trifluoromethyl-phenyl)-4-(4-trifluoromethyl-piperidin-1-ylmethyl)-thiazol-5-yl-methoxy]-benzonitrile | N-hydroxy-2-methoxy-4-[2-(4-trifluoromethyl-phenyl)-4-(4-trifluoromethyl-piperidin-1-ylmethyl)-thiazol-5-ylmethoxy]-benzamidine |

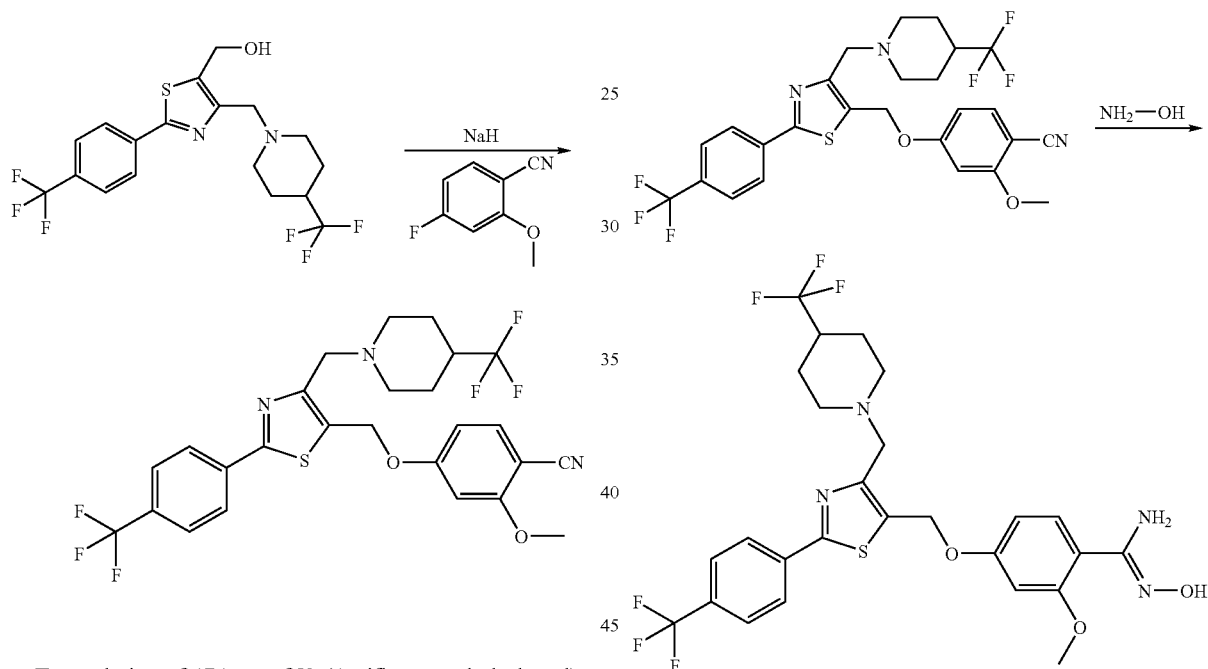

To a solution of 474 mg of [2-(4-trifluoromethyl-phenyl)-4-(4-trifluoromethyl-piperidin-1-ylmethyl)-thiazol-5-yl]-methanol in 2.9 mL of dimethylformamide was added 60 mg of sodium hydride. The resulting mixture was stirred for 30 minutes at 0° C. then 208 mg of 4-fluoro-2-methoxybenzonitrile was added. After stirring for 30 minutes at 0° C., the temperature was allowed to warm up to room temperature and the reaction mixture was stirred for 30 minutes. The solvent was removed under reduced pressure and dichloromethane/water was added to the residue. The organic layer was separated and the aqueous layer extracted three times with dichloromethane. The combined organic extracts were dried over magnesium sulfate, filtered, and concentrated under reduced pressure. The crude product was purified by column chromatography on silica gel (dichloromethane 95/methanol 5) to give 279 mg of 2-methoxy-4-[2-(4-trifluoromethyl-phenyl)-4-(4-trifluoromethyl-piperidin-1-ylmethyl)-thiazol-5-yl-methoxy]-benzonitrile.

C26H23F6N3O2S (555.55), MS (ESI): 556 (M+H+).

To a solution of 279 mg of 2-methoxy-4-[2-(4-trifluoromethyl-phenyl)-4-(4-trifluoromethyl-piperidin-1-ylmethyl)-thiazol-5-ylmethoxy]-benzonitrile in 3 mL of tetrahydrofuran and 1.5 mL of methanol was added 333 mg of hydroxylamine hydrochloride followed by 0.69 mL of triethylamine. The resulting mixture was heated to 60° C. overnight. After allowing it to cool down to room temperature, the mixture was poured into water and extracted with dichloromethane. The organic extracts were dried over magnesium sulfate, filtered, and concentrated under reduced pressure. The crude product was purified by column chromatography on silica gel (gradient from dichloromethane 100 to dichloromethane 95/methanol 5) to give 154 mg of N-hydroxy-2-methoxy-4-[2-(4-trifluoromethyl-phenyl)-4-(4-trifluoromethyl-piperidin-1-ylmethyl)-thiazol-5-ylmethoxy]-benzamidine.

C26H26F6N4O3S (588.58), MS (ESI): 589 (M++H).

3-{2-Methoxy-4-[2-(4-trifluoromethyl-phenyl)-4-(4-trifluoromethyl-piperidin-1-ylmethyl)-thiazol-5-ylmethoxy]-phenyl}-4H-[1,2,4]oxadiazol-5-one

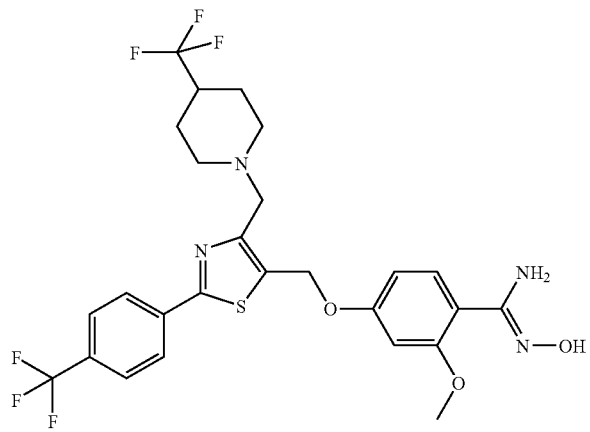

1. Phenylchloroformate, Pyridine
2. DBU, MeCN

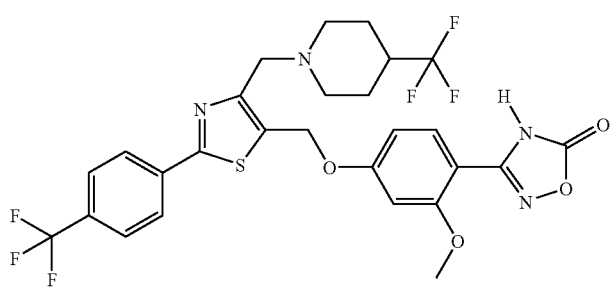

To a solution of 150 mg of N-hydroxy-2-methoxy-4-[2-(4-trifluoromethyl-phenyl)-4-(4-trifluoromethyl-piperidin-1-ylmethyl)-thiazol-5-ylmethoxy]-benzamidine in 5 mL of anhydrous dichloromethane at 0° C. were dropwise added 50 µL of pyridine followed by 40 µL of phenylchloroformate. The resulting mixture was stirred at room temperature for 1 h then water and dichloromethane were added. The aqueous layer was separated and extracted with dichloromethane. The combined organic extracts were dried over magnesium sulfate, filtered, and concentrated under reduced pressure. To a solution of the resulting residue in 2.7 mL of acetonitrile was added 60 µL of 1,8-diazabicyclo[5.4.0]undec-7-ene. The mixture was stirred at room temperature overnight. The solvent was removed under vacuo. The resulting residue was taken into tetrahydrofuran/ethyl acetate 50/50, washed with water, dried over magnesium sulfate, filtered, and concentrated under reduced pressure. The crude product was purified by column chromatography on silica gel (gradient from dichloromethane 100 to dichloromethane 90/methanol 10) to give 105 mg of 3-{2-methoxy-4-[2-(4-trifluoromethyl-phenyl)-4-(4-trifluoromethyl-piperidin-1-ylmethyl)-thiazol-5-ylmethoxy]-phenyl}-4H-[1,2,4]oxadiazol-5-one.

C27H24F6N4O4S (614.57), MS (EI): 614 (M+).

Example 2

3-{2-Chloro-4-[4-morpholin-4-ylmethyl-2-(4-trifluoromethyl-phenyl)-thiazol-5-ylmethoxy]-phenyl}-4H-[1,2,4]oxadiazol-5-one

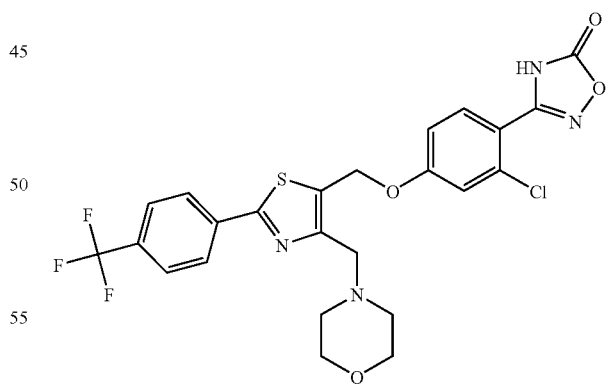

According to the method described in Example 1, 3-{2-chloro-4-[4-morpholin-4-ylmethyl-2-(4-trifluoromethyl-phenyl)-thiazol-5-ylmethoxy]-phenyl}-4H-[1,2,4]oxadiazol-5-one was obtained from [4-morpholin-4-ylmethyl-2-(4-trifluoromethyl-phenyl)-thiazol-5-yl]-methanol and commercially available 2-chloro-4-fluoro-benzonitrile.

C24H20ClF3N4O4S (552.96), MS (EI): 552 (M+).

Example 3

3-{2-Methoxy-4-[4-morpholin-4-ylmethyl-2-(4-trifluoromethyl-phenyl)-thiazol-5-ylmethoxy]-phenyl}-4H-[1,2,4]oxadiazol-5-one

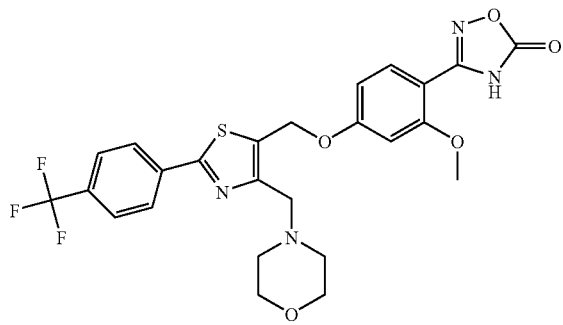

According to the method described in Example 1, 3-{2-methoxy-4-[4-morpholin-4-ylmethyl-2-(4-trifluoromethyl-phenyl)-thiazol-5-ylmethoxy]-phenyl}-4H-[1,2,4]oxadiazol-5-one was obtained from [4-morpholin-4-ylmethyl-2-(4-trifluoromethyl-phenyl)-thiazol-5-yl]-methanol and commercially available 4-fluoro-2-methoxybenzonitrile.

C25H23F3N4O5S (548.54), MS (ESI): 549 (M+H$^+$).

Example 4

3-{4-[4-(4,4-Difluoro-piperidin-1-ylmethyl)-2-(4-trifluoromethyl-phenyl)-thiazol-5-ylmethoxy]-2-methoxy-phenyl}-4H-[1,2,4]oxadiazol-5-one

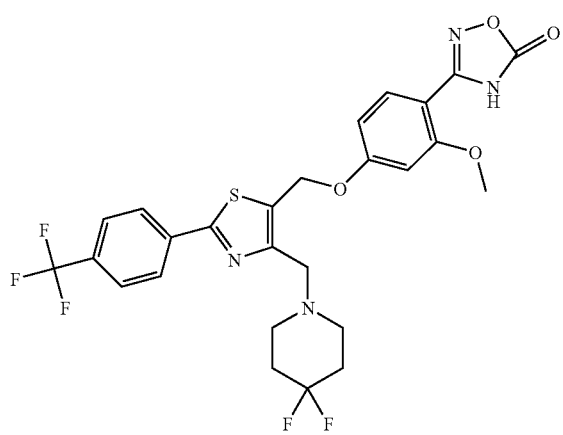

According to the method described in Example 1, 3-{4-[4-(4,4-difluoro-piperidin-1-ylmethyl)-2-(4-trifluoromethyl-phenyl)-thiazol-5-ylmethoxy]-2-methoxy-phenyl}-4H-[1,2,4]oxadiazol-5-one was obtained from 4-(4,4-difluoro-piperidin-1-ylmethyl)-2-(4-trifluoromethyl-phenyl)-thiazol-5-yl]-methanol and commercially available 4-fluoro-2-methoxybenzonitrile.

C26H23F5N4O4S (582.55), MS (ESI): 583 (M+H$^+$).

Example 5

3-{2-Methoxy-4-[4-(4-methyl-piperazin-1-ylmethyl)-2-(4-trifluoromethyl-phenyl)-thiazol-5-ylmethoxy]-phenyl}-4H-[1,2,4]oxadiazol-5-one

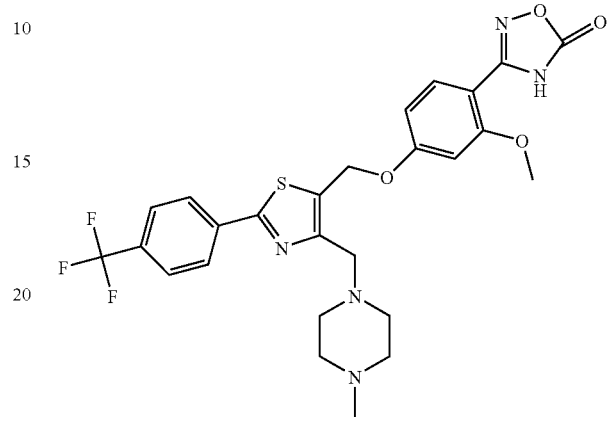

According to the method described in Example 1, 3-{2-methoxy-4-[4-(4-methyl-piperazin-1-ylmethyl)-2-(4-trifluoromethyl-phenyl)-thiazol-5-ylmethoxy]-phenyl}-4H-[1,2,4]oxadiazol-5-one was obtained from [4-(4-methyl-piperazin-1-ylmethyl)-2-(4-trifluoromethyl-phenyl)-thiazol-5-yl]-methanol and commercially available 4-fluoro-2-methoxybenzonitrile.

C26H26F3N5O4S (561.59), MS (ESI): 562 (M+H$^+$).

Example 6

3-{2-Methoxy-4-[4-pyrrolidin-1-ylmethyl-2-(4-trifluoromethyl-phenyl)-thiazol-5-ylmethoxy]-phenyl}-4H-[1,2,4]oxadiazol-5-one

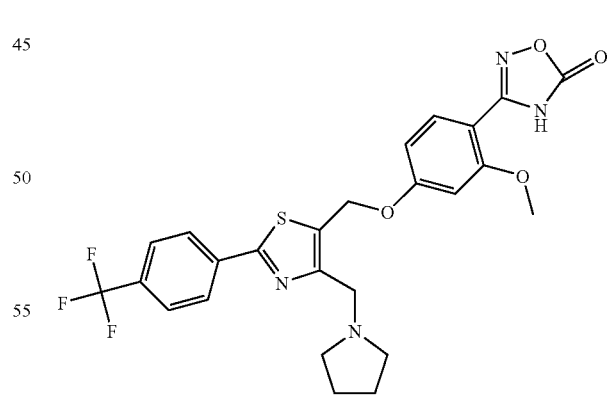

According to the method described in Example 1, 3-{2-methoxy-4-[4-pyrrolidin-1-ylmethyl-2-(4-trifluoromethyl-phenyl)-thiazol-5-ylmethoxy]-phenyl}-4H-[1,2,4]oxadiazol-5-one was obtained from [4-pyrrolidin-1-ylmethyl-2-(4-trifluoromethyl-phenyl)-thiazol-5-yl]-methanol and commercially available 4-fluoro-2-methoxybenzonitrile.

C25H23F3N4O4S (532.54), MS (ESI): 533 (M+H$^+$).

Example 7

3-{4-[4-(4-Fluoro-piperidin-1-ylmethyl)-2-(4-trifluoromethyl-phenyl)-thiazol-5-ylmethoxy]-2-methoxy-phenyl}-4H-[1,2,4]oxadiazol-5-one

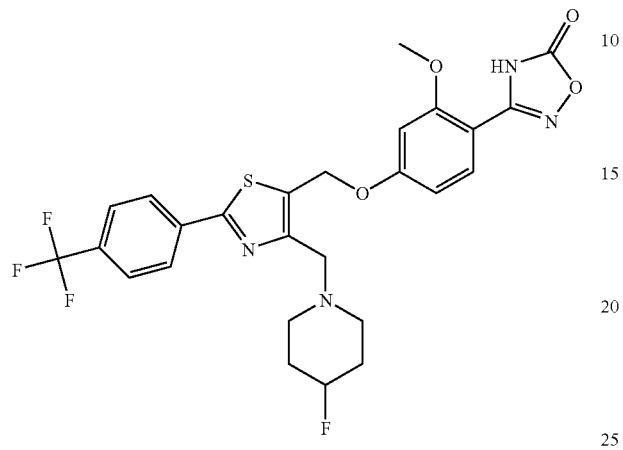

According to the method described in Example 1, 3-{4-[4-(4-fluoro-piperidin-1-ylmethyl)-2-(4-trifluoromethyl-phenyl)-thiazol-5-ylmethoxy]-2-methoxy-phenyl}-4H-[1,2,4]oxadiazol-5-one was obtained from [4-(4-fluoro-piperidin-1-ylmethyl)-2-(4-trifluoromethyl-phenyl)-thiazol-5-yl]-methanol and commercially available 4-fluoro-2-methoxybenzonitrile.

C26H24F4N4O4S (564.56), MS (ESI): 565 (M+H$^+$).

Example 8

3-{4-[4-Diethylaminomethyl-2-(4-trifluoromethyl-phenyl)-thiazol-5-ylmethoxy]-2-methoxy-phenyl}-4H-[1,2,4]oxadiazol-5-one

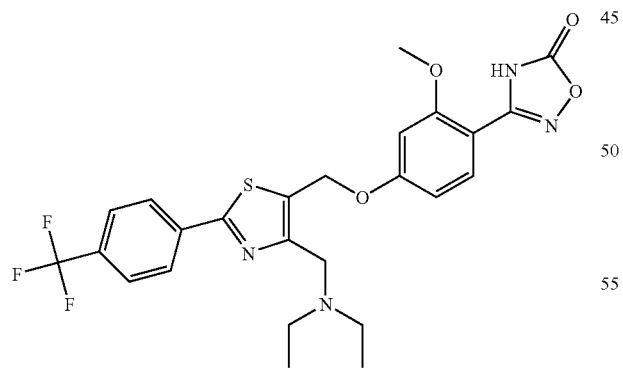

According to the method described in Example 1, 3-{4-[4-diethylaminomethyl-2-(4-trifluoromethyl-phenyl)-thiazol-5-ylmethoxy]-2-methoxy-phenyl}-4H-[1,2,4]oxadiazol-5-one was obtained from [4-diethylaminomethyl-2-(4-trifluoromethyl-phenyl)-thiazol-5-yl]-methanol and commercially available 4-fluoro-2-methoxybenzonitrile.

C25H25F3N4O4S (534.56), MS (ESI): 535 (M+H$^+$).

Example 9

3-{2-Methoxy-4-[2-(4-trifluoromethyl-phenyl)-4-(3-trifluoromethyl-pyrrolidin-1-ylmethyl) thiazol-5-ylmethoxy]-phenyl}-4H-[1,2,4]oxadiazol-5-one

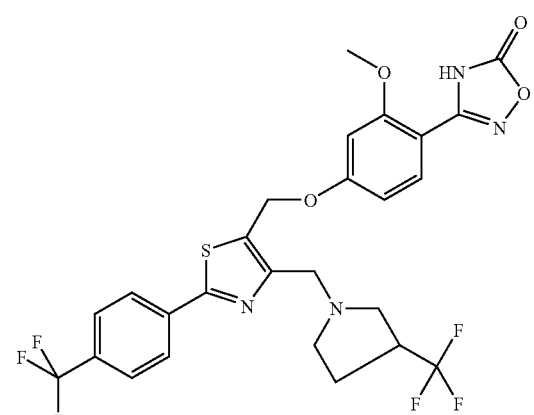

According to the method described in Example 1, racemic 3-{2-methoxy-4-[2-(4-trifluoromethyl-phenyl)-4-(3-trifluoromethyl-pyrrolidin-1-ylmethyl)-thiazol-5-ylmethoxy]-phenyl}-4H-[1,2,4]oxadiazol-5-one was obtained from racemic [2-(4-trifluoromethyl-phenyl)-4-(3-trifluoromethyl-pyrrolidin-1-ylmethyl)-thiazol-5-yl]-methanol and commercially available 4-fluoro-2-methoxybenzonitrile.

C26H22F6N4O4S (600.54), MS (ESI): 601 (M+H$^+$).

Example 10

3-{4-[4-{[Ethyl-(2-methoxy-ethyl)-amino]-methyl}-2-(4-trifluoromethyl-phenyl)-thiazol-5-ylmethoxy]-2-methoxy-phenyl}-4H-[1,2,4]oxadiazol-5-one

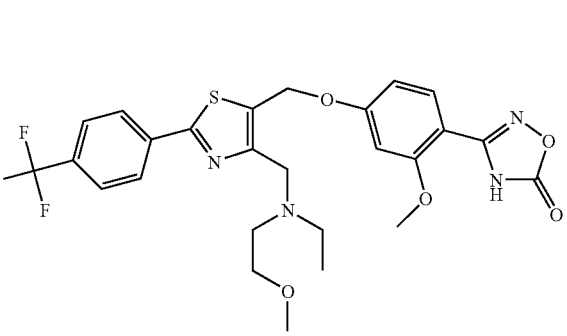

According to the method described in Example 1, 3-{4-[4-{[ethyl-(2-methoxy-ethyl)-amino]-methyl}-2-(4-trifluoromethyl-phenyl)-thiazol-5-ylmethoxy]-2-methoxy-phenyl}-4H-[1,2,4]oxadiazol-5-one was obtained from [4-{[ethyl-(2-methoxy-ethyl)-amino]-methyl}-2-(4-trifluoromethyl-phenyl)-thiazol-5-yl]-methanol and commercially available 4-fluoro-2-methoxybenzonitrile.

C26H27F3N4O5S (564.59), MS (CI): 565 (M+H$^+$).

Example 11

3-{4-[4-[([1,4]Dioxan-2-ylmethyl-methyl-amino)-methyl]-2-(4-trifluoromethyl-phenyl)-thiazol-5-ylmethoxy]-2-methoxy-phenyl}-4H-[1,2,4]oxadiazol-5-one

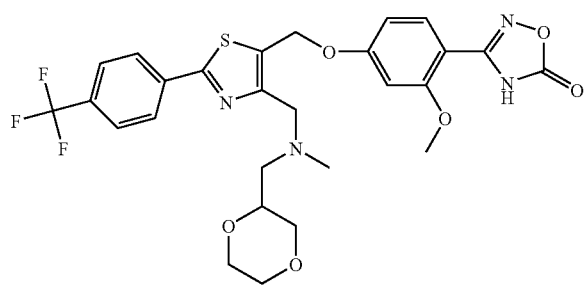

According to the method described in Example 1, racemic 3-{4-[4-[([1,4]dioxan-2-ylmethyl-methyl-amino)-methyl]-2-(4-trifluoromethyl-phenyl)-thiazol-5-ylmethoxy]-2-methoxy-phenyl}-4H-[1,2,4]oxadiazol-5-one was obtained from racemic [4-[([1,4]dioxan-2-ylmethyl-methyl-amino)-methyl]-2-(4-trifluoromethyl-phenyl)-thiazol-5-yl]-methanol and commercially available 4-fluoro-2-methoxybenzonitrile.

C27H27F3N4O6S (592.60), MS (ESI): 593 (M+H$^+$).

Example 12

3-{2-Methoxy-4-[4-(4-methoxy-piperidin-1-ylmethyl)-2-(4-trifluoromethyl-phenyl)-thiazol-5-ylmethoxy]-phenyl}-4H-[1,2,4]oxadiazol-5-one

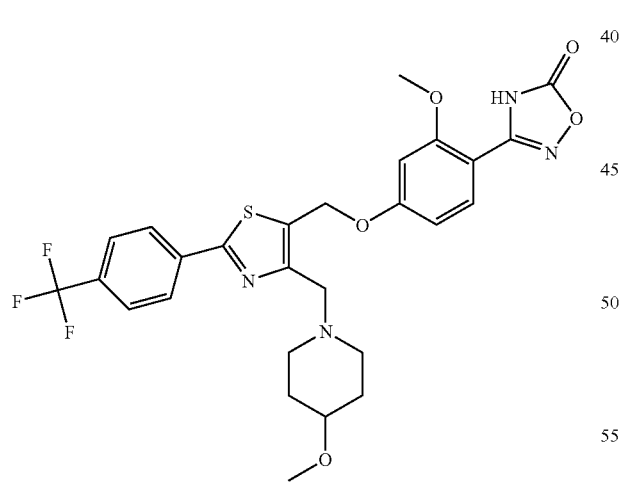

According to the method described in Example 1, 3-{2-methoxy-4-[4-(4-methoxy-piperidin-1-ylmethyl)-2-(4-trifluoromethyl-phenyl)-thiazol-5-ylmethoxy]-phenyl}-4H-[1,2,4]oxadiazol-5-one was obtained from [4-(4-methoxy-piperidin-1-ylmethyl)-2-(4-trifluoromethyl-phenyl)-thiazol-5-yl]-methanol and commercially available 4-fluoro-2-methoxybenzonitrile.

C27H27F3N4O5S (576.60), MS (ESI): 577 (M+H$^+$).

Example 13

3-{4-[4-(4-Ethyl-piperazin-1-ylmethyl)-2-(4-trifluoromethyl-phenyl)-thiazol-5-ylmethoxy]-2-methoxy-phenyl}-4H-[1,2,4]oxadiazol-5-one

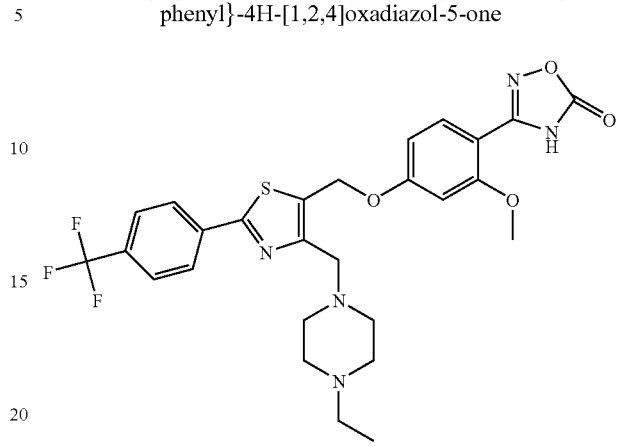

According to the method described in Example 1, 3-{4-[4-(4-ethyl-piperazin-1-ylmethyl)-2-(4-trifluoromethyl-phenyl)-thiazol-5-ylmethoxy]-2-methoxy-phenyl}-4H-[1,2,4]oxadiazol-5-one was obtained from [4-(4-ethyl-piperazin-1-ylmethyl)-2-(4-trifluoromethyl-phenyl)-thiazol-5-yl]-methanol and commercially available 4-fluoro-2-methoxybenzonitrile.

C27H28F3N5O4S (575.61), MS (ESI): 576 (M+H$^+$).

Example 14

Cyclopropyl-[5-[3-methoxy-4-(5-oxo-4,5-dihydro-[1,2,4]oxadiazol-3-yl)-phenoxymethyl]-2-(4-trifluoromethyl-phenyl)-thiazol-4-ylmethyl]-carbamic acid phenyl ester

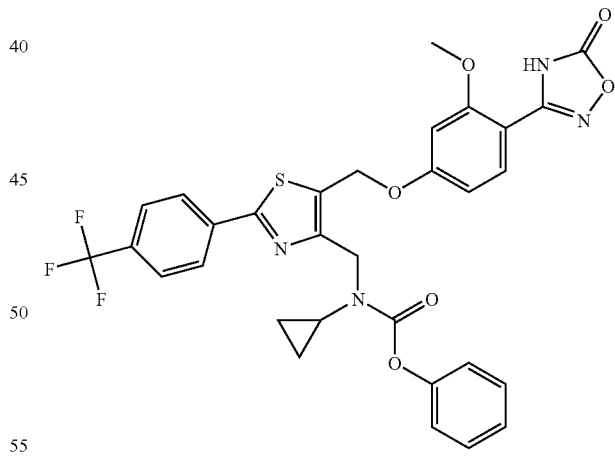

According to the method described in Example 1, cyclopropyl-[5-[3-methoxy-4-(5-oxo-4,5-dihydro-[1,2,4]oxadiazol-3-yl)-phenoxymethyl]-2-(4-trifluoromethyl-phenyl)-thiazol-4-ylmethyl]-carbamic acid phenyl ester was obtained from [4-cyclopropylaminomethyl-2-(4-trifluoromethyl-phenyl)-thiazol-5-yl]-methanol and commercially available 4-fluoro-2-methoxybenzonitrile. During the formation of the oxadiazolone ring, the secondary cyclopropylamine reacted with phenyl chloroformate to give the cited phenyl carbamate.

C31H25F3N4O6S (638.63), MS (CI): 639 (M+H$^+$).

Example 15

3-{4-[4-Cyclopropylaminomethyl-2-(4-trifluoromethyl-phenyl)-thiazol-5-ylmethoxy]-2-methoxy-phenyl}-4H-[1,2,4]oxadiazol-5-one

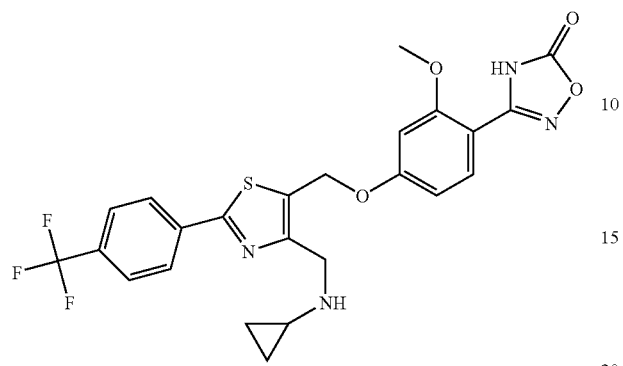

To a solution of 32.6 mg of cyclopropyl-[5-[3-methoxy-4-(5-oxo-4,5-dihydro-[1,2,4]oxadiazol-3-yl)-phenoxymethyl]-2-(4-trifluoromethyl-phenyl)-thiazol-4-ylmethyl]-carbamic acid phenyl ester in 2 mL of ethylene glycol was added 2 mL of a saturated solution of potassium hydroxide in water. The resulting mixture was stirred in a sealed tube under microwave irradiation for 25 minutes to 100° C., then 10 additional minutes to 120° C. and finally 15 more minutes to 140° C. It was then extracted with dichloromethane. The organic extracts were washed water, dried over magnesium sulfate, filtered, and concentrated under reduced pressure. The crude product was purified by column chromatography on silica gel (gradient from dichloromethane 100 to dichloromethane 90/methanol 10) to give 9.5 mg of 3-{4-[4-cyclopropylaminomethyl-2-(4-trifluoromethyl-phenyl)-thiazol-5-ylmethoxy]-2-methoxy-phenyl}-4H-[1,2,4]oxadiazol-5-one.

C24H21F3N4O4S (518.52), MS (ESI): 519 (M+H⁺).

The following examples were prepared according to process D, whereby the first two reaction steps were performed according to process B:

Example 16

3-{4-[4-(3-Azetidin-1-yl-propyl)-2-(4-trifluoromethyl-phenyl)-thiazol-5-ylmethoxy]-2-methoxy-phenyl}-4H-[1,2,4]oxadiazol-5-one

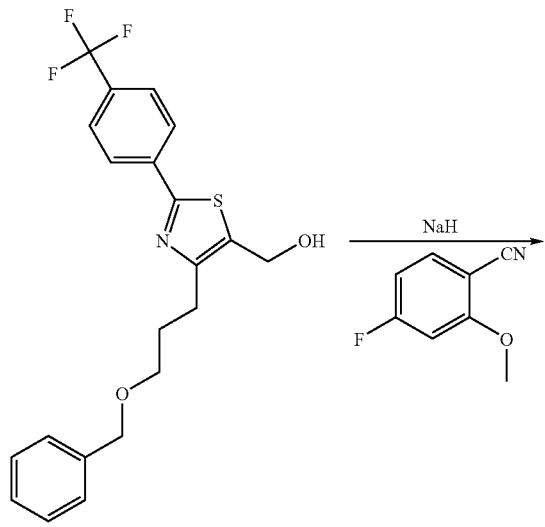

-continued

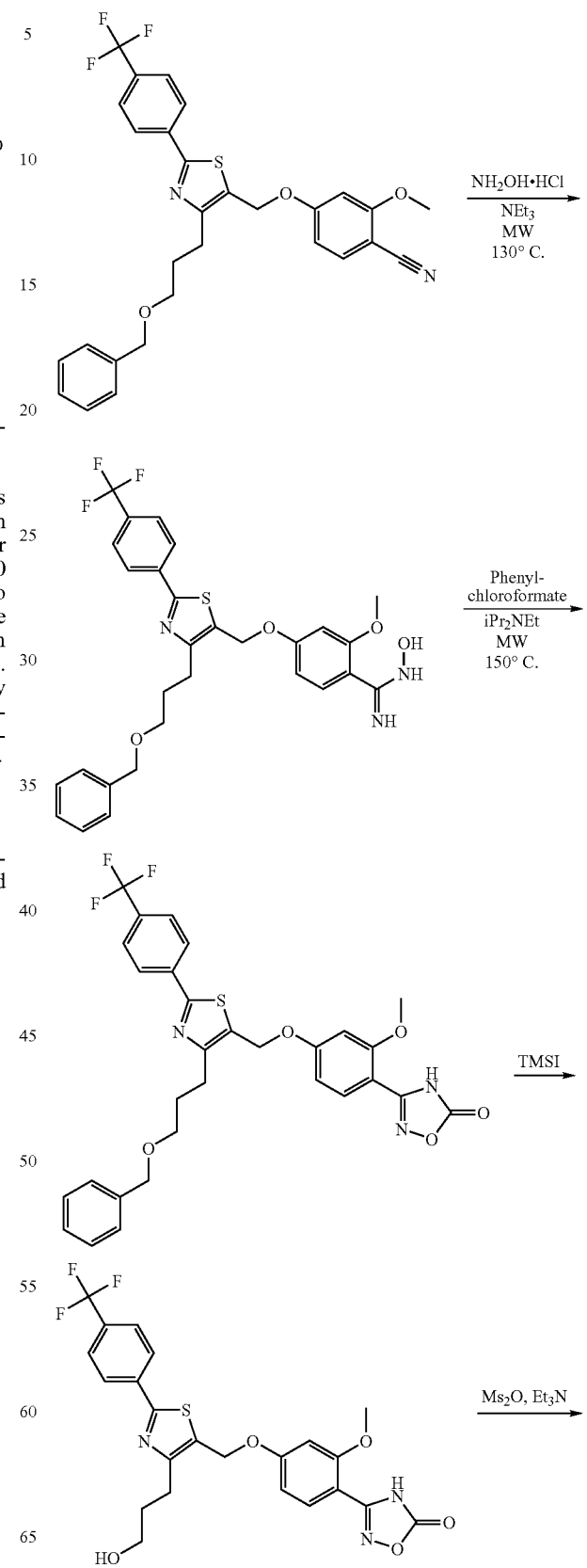

-continued

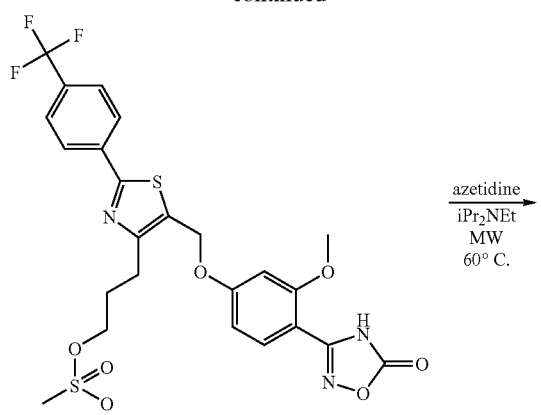

azetidine
iPr₂NEt
MW
60° C.

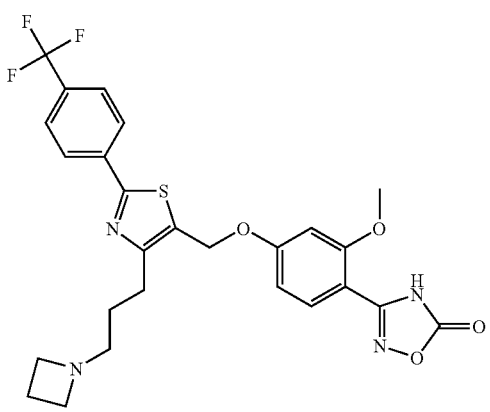

4-[4-(3-Benzyloxy-propyl)-2-(4-trifluoromethyl-phenyl)-thiazol-5-ylmethoxy]-2-methoxy-benzonitrile -continued

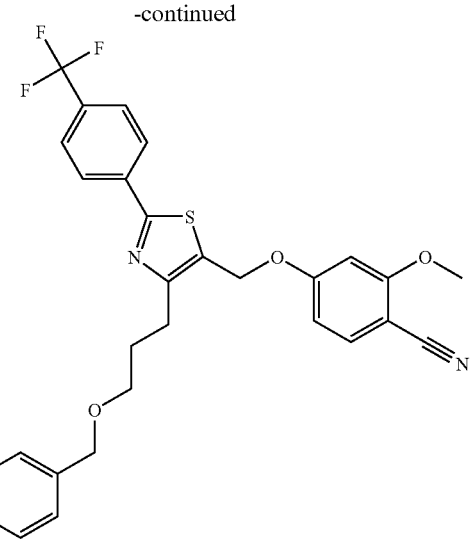

To a solution of 1.34 g of [4-(3-benzyloxy-propyl)-2-(4-trifluoromethyl-phenyl)-thiazol-5-yl]-methanol in 20 mL of dimethylformamide at 0° C. was added 158 mg of a 60% suspension of sodium hydride in mineral oil. The resulting mixture was stirred for 10 minutes at 0° C. then 497 mg of 4-fluoro-2-methoxybenzonitrile were added. After stirring for 30 minutes at 0° C., the temperature was allowed to warm up to room temperature and the reaction mixture was stirred until completion. The solvent was removed under reduced pressure and dichloromethane/water were added to the residue. The organic layer was separated and the aqueous layer extracted three times with dichloromethane. The combined organic extracts were washed with brine, dried over magnesium sulfate, filtered, and concentrated under reduced pressure to give 1.82 g of crude product as a yellow oil. A 1/1 solution of heptane/diisopropyl ether was added to the residue and the solidified product was filtered off to provide a first crop of 1.26 g of desired product. The mother liquor was concentrated and purified by column chromatography on silica gel (heptane 60/ethyl acetate 40) to give an additional 110 mg. The two fractions were combined to obtain 1.37 g of 4-[4-(3-benzyloxy-propyl)-2-(4-trifluoromethyl-phenyl)-thiazol-5-ylmethoxy]-2-methoxy-benzonitrile.

C29H25F3N2O3S (538.59), MS (ESI): 539 (M+H⁺).

4-[4-(3-Benzyloxy-propyl)-2-(4-trifluoromethyl-phenyl)-thiazol-5-ylmethoxy]-N-hydroxy-2-methoxy-benzamidine

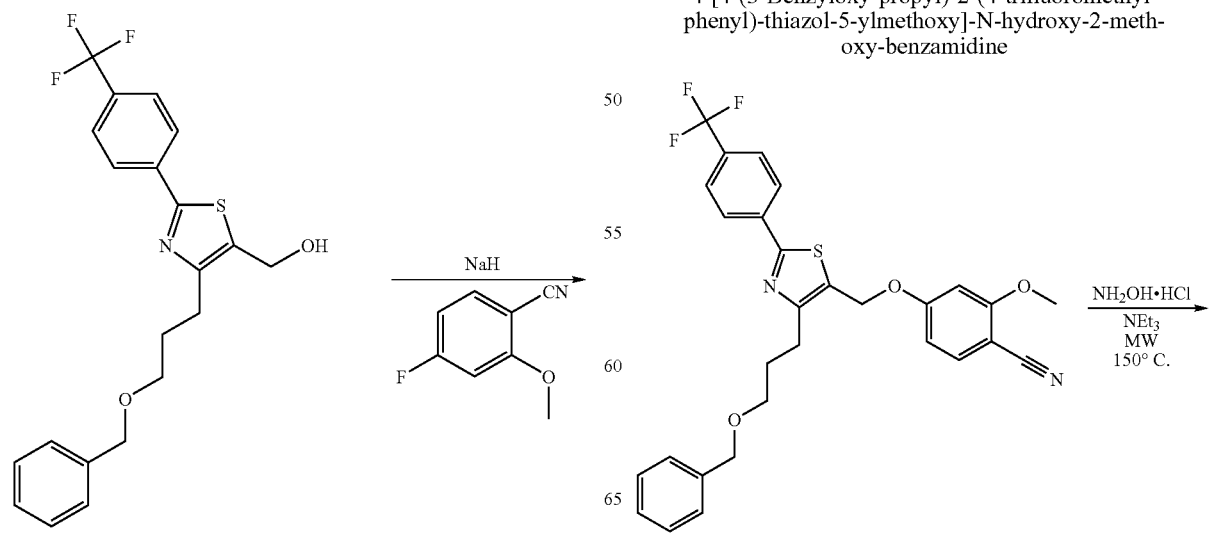

-continued

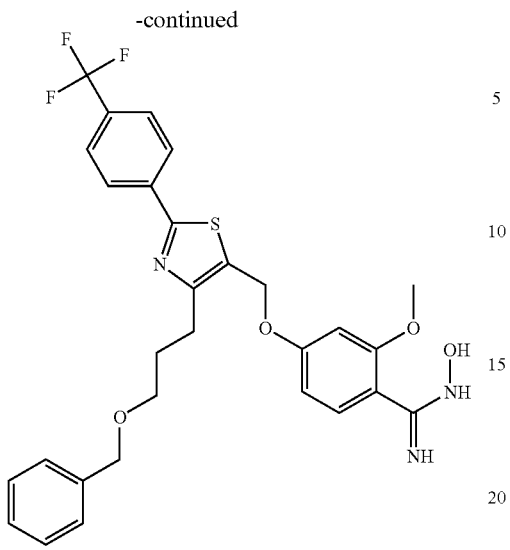

To a solution of 300 mg of 4-[4-(3-benzyloxy-propyl)-2-(4-trifluoromethyl-phenyl)-thiazol-5-ylmethoxy]-2-methoxy-benzonitrile in 1.8 mL of tetrahydrofuran and 2 mL of methanol was added 387 mg of hydroxylamine hydrochloride followed by 0.62 mL of triethylamine. The resulting mixture was heated to 150° C. under microwave irradiation for 10 minutes. After allowing it to cool down to room temperature, the mixture was concentrated under reduced pressure and dichloromethane/water were added to the residue. The organic layer was separated and the aqueous layer extracted three times with dichloromethane. The combined organic extracts were dried over magnesium sulfate, filtered, and concentrated under reduced pressure. The crude product was purified by column chromatography on silica gel (heptane 50/ethyl acetate 50) to give 162 mg of 4-[4-(3-benzyloxy-propyl)-2-(4-trifluoromethyl-phenyl)-thiazol-5-ylmethoxy]-N-hydroxy-2-methoxy-benzamidine.

C29H28F3N3O4S (571.62), MS (ESI): 572 (M+H+).

3-{4-[4-(3-Benzyloxy-propyl)-2-(4-trifluoromethyl-phenyl)-thiazol-5-ylmethoxy]-2-methoxy-phenyl}-4H-[1,2,4]oxadiazol-5-one -continued

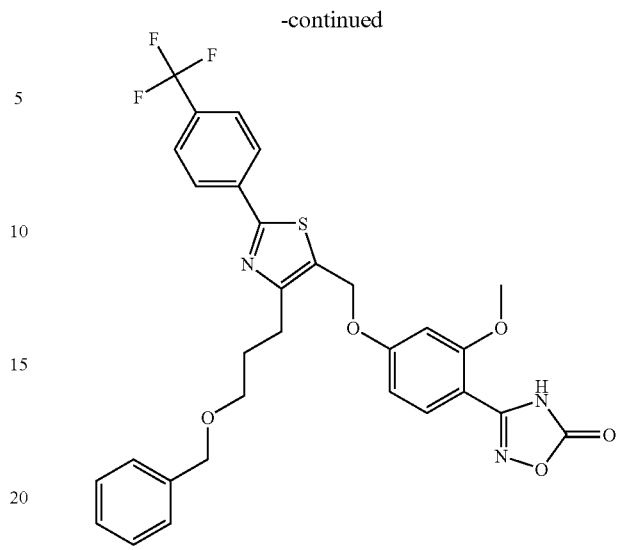

To a solution of 1.05 g of 4-[4-(3-benzyloxy-propyl)-2-(4-trifluoromethyl-phenyl)-thiazol-5-ylmethoxy]-N-hydroxy-2-methoxy-benzamidine in 5 mL of tetrahydrofuran were added 254 µL of phenyl chloroformate and 607 µL of diisopropylethylamine. The resulting mixture was heated to 150° C. under microwave irradiation for 20 minutes. After allowing it to cool down to room temperature, the mixture was concentrated under reduced pressure and dichloromethane/water were added to the residue. The organic layer was separated and the aqueous layer extracted three times with dichloromethane. The combined organic extracts were dried over magnesium sulfate, filtered, and concentrated under reduced pressure. Diisopropyl ether was added to the residue and the solid was collected by filtration and washed with diisopropyl ether to give 558 mg of 3-{4-[4-(3-benzyloxy-propyl)-2-(4-trifluoromethyl-phenyl)-thiazol-5-ylmethoxy]-2-methoxy-phenyl}-4H-[1,2,4]oxadiazol-5-one.

C30H26F3N3O5S (597.62), MS (ESI): 598 (M+H+).

3-{4-[4-(3-Hydroxy-propyl)-2-(4-trifluoromethyl-phenyl)-thiazol-5-ylmethoxy]-2-methoxy-phenyl}-4H-[1,2,4]oxadiazol-5-one

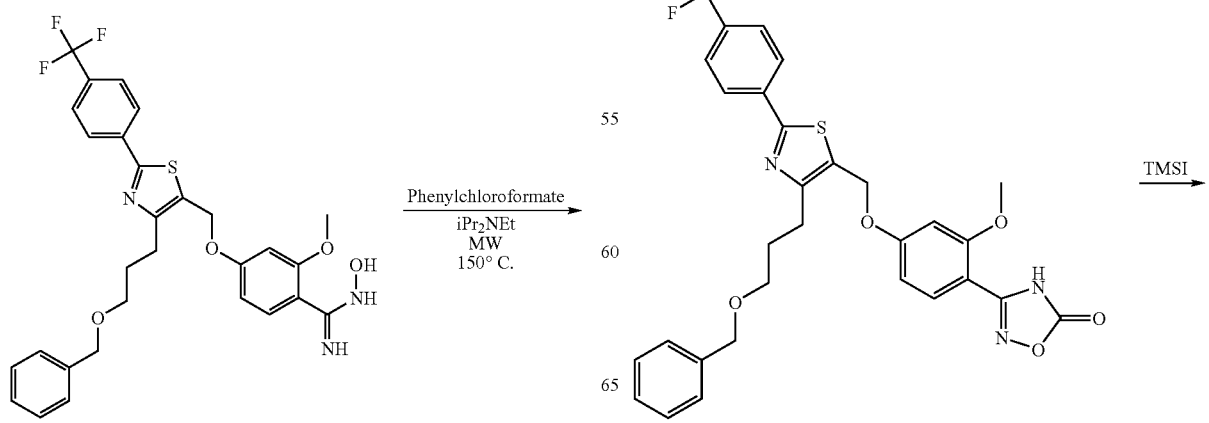

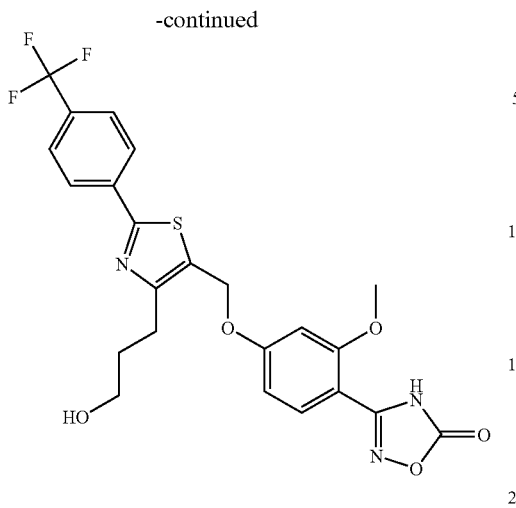

118 mg of 3-{4-[4-(3-benzyloxy-propyl)-2-(4-trifluoromethyl-phenyl)-thiazol-5-ylmethoxy]-2-methoxy-phenyl}-4H-[1,2,4]oxadiazol-5-one were dissolved in 14 mL of dichloromethane by heating and allowing to cool down to room temperature. To the resulting solution was added 144 µL of iodotrimethylsilane. The resulting mixture was stirred at room temperature for 6.5 h and 6 mL of methanol were added followed by a saturated aqueous solution of sodium bicarbonate. The mixture was stirred for 1 h, filtered and concentrated under reduced pressure. Dichloromethane/water were added to the residue. The organic layer was separated and the aqueous layer extracted three times with dichloromethane. The combined organic extracts were dried over magnesium sulfate, filtered, and concentrated under reduced pressure. The crude product was purified by column chromatography on silica gel (dichloromethane 90/methanol 10) to give 40 mg of 3-{4-[4-(3-hydroxy-propyl)-2-(4-trifluoromethyl-phenyl)-thiazol-5-ylmethoxy]-2-methoxy-phenyl}-4H-[1,2,4]oxadiazol-5-one.

C23H20F3N3O5S (507.49), MS (ESI): 508 (M+H$^+$).

Methanesulfonic acid 3-[5-[3-methoxy-4-(5-oxo-4,5-dihydro-[1,2,4]oxadiazol-3-yl)-phenoxymethyl]-2-(4-trifluoromethyl-phenyl)-thiazol-4-yl]-propyl ester

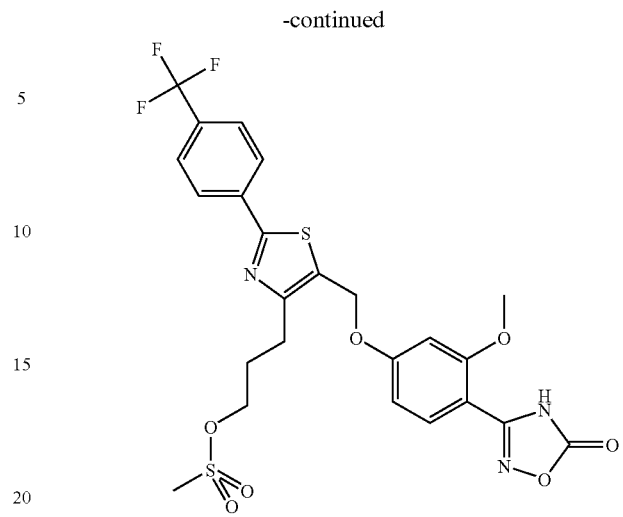

To a solution of 300 mg of 3-{4-[4-(3-hydroxy-propyl)-2-(4-trifluoromethyl-phenyl)-thiazol-5-ylmethoxy]-2-methoxy-phenyl}-4H-[1,2,4]oxadiazol-5-one in 15 mL of dichloromethane was added 1.2 mL of triethylamine and 217 mg of methanesulfonic anhydride. The resulting mixture was stirred at room temperature for 1 hour. A saturated aqueous solution of ammonium chloride was added. The organic layer was separated and the aqueous layer extracted three times with dichloromethane. The combined organic extracts were dried over magnesium sulfate, filtered, and concentrated under reduced pressure to give 228 mg of methanesulfonic acid 3-[5-[3-methoxy-4-(5-oxo-4,5-dihydro-[1,2,4]oxadiazol-3-yl)-phenoxymethyl]-2-(4-trifluoromethyl-phenyl)-thiazol-4-yl]-propyl ester which was used in the next step without further purification.

C24H22F3N3O7S2 (585.58), MS (ESI): 586 (M+H$^+$).

3-{4-[4-(3-Azetidin-1-yl-propyl)-2-(4-trifluoromethyl-phenyl)-thiazol-5-ylmethoxy]-2-methoxy-phenyl}-4H-[1,2,4]oxadiazol-5-one

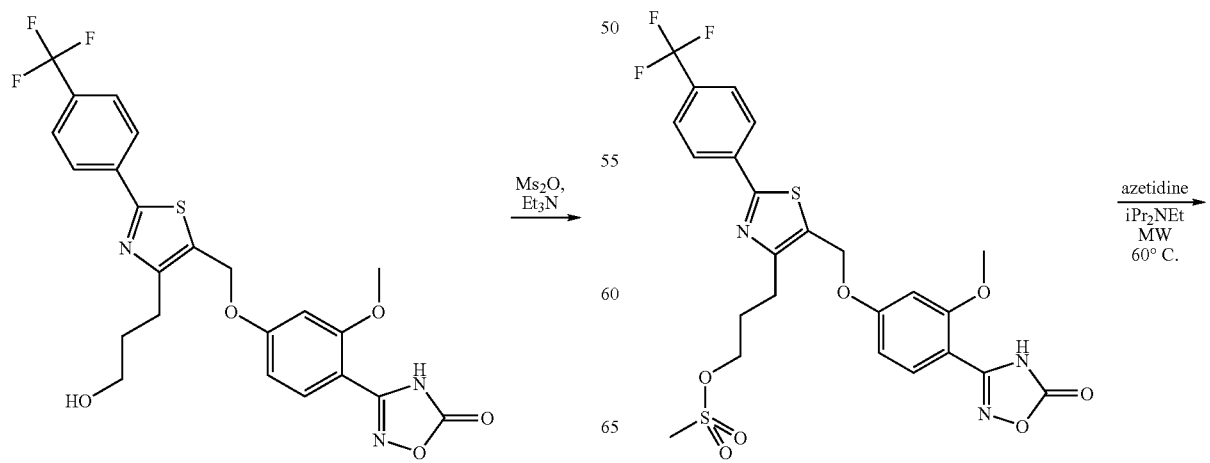

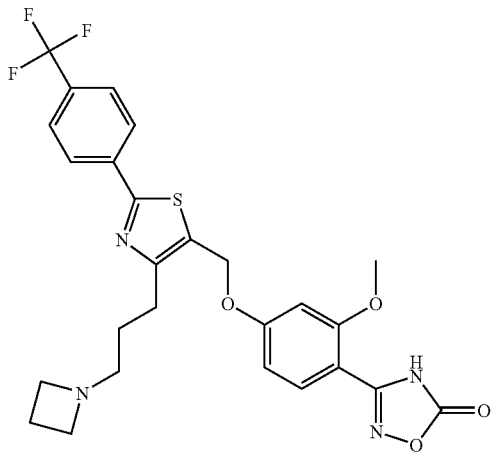

To a suspension of 130 mg of methanesulfonic acid 3-[5-[3-methoxy-4-(5-oxo-4,5-dihydro-[1,2,4]oxadiazol-3-yl)-phenoxymethyl]-2-(4-trifluoromethyl-phenyl)-thiazol-4-yl]-propyl ester in 7 mL of acetonitrile was added 25 µL of azetidine and 57 mg of diisopropylethyl amine. The resulting mixture was heated in a sealed tube to 60° C. under microwave irradiation for 30 minutes and then concentrated under reduced pressure. The residue was purified by column chromatography on silica gel (gradient from dichloromethane 100 to dichloromethane 90/methanol 10/water 1/acetic acid 1) followed by a 2 g SCX Waters column with gradient CH2Cl2/MeOH 30/70 to 7N NH3 in MeOH and another column chromatography on silica gel (eluting with dichloromethane 90/methanol 10) to give 3.5 mg of 3-{4-[4-(3-azetidin-1-yl-propyl)-2-(4-trifluoromethyl-phenyl)-thiazol-5-ylmethoxy]-2-methoxy-phenyl}-4H-[1,2,4]oxadiazol-5-one.

C26H25F3N4O4S (546.57), MS (ESI): 547 (M+H+).

The following examples were prepared according to process F:

Example 17

3-{2-Fluoro-4-[2-(4-trifluorométhyl-phényl)-4-(4-trifluorométhyl-pipéridin-1-ylméthyl)-thiazol-5-yl-méthoxy]-phényl}-4H-1,2,4-oxadiazol-5-one

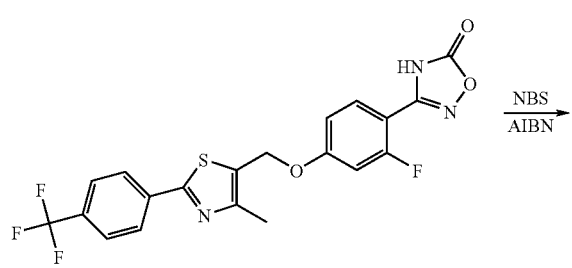

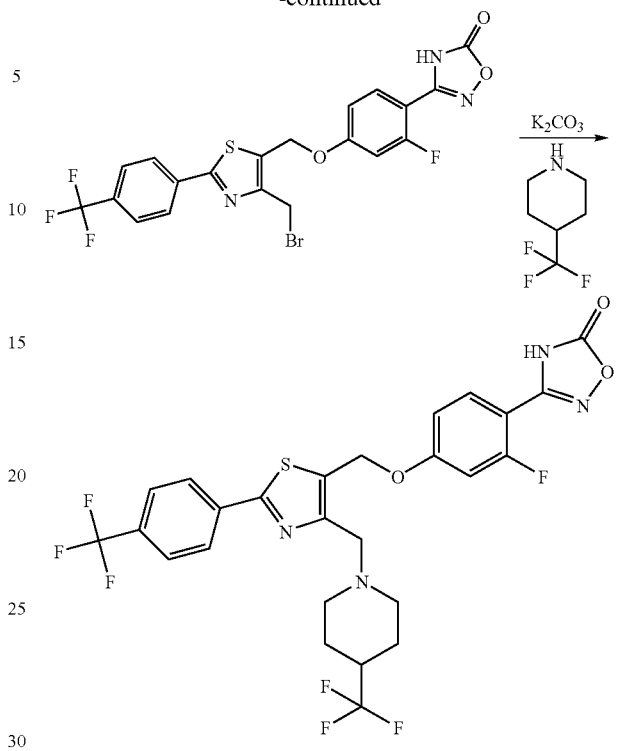

3-{4-[4-Bromomethyl-2-(4-trifluoromethyl-phenyl)-thiazol-5-ylmethoxy]-2-fluoro-phenyl}-4H-[1,2,4]oxadiazol-5-one

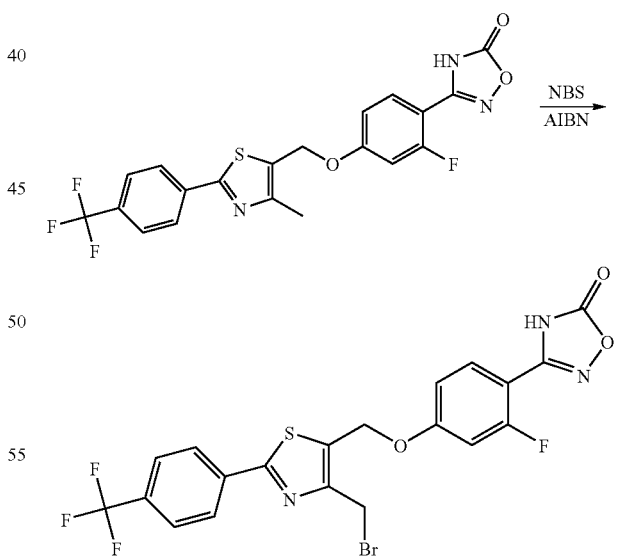

To a mixture of 100 mg of 3-{2-fluoro-4-[4-methyl-2-(4-trifluoromethyl-phenyl)-thiazole-5-ylmethoxy]-phenyl}-4H-[1,2,4]oxadiazole-5-one[5] in 3 mL of carbon tetrachloride and 2 mL of hexafluoroisopropanol at reflux was added 100 mg of N-bromosuccinimide and 10 mg of AIBN. The resulting mixture was refluxed for 1 h. It was then poured into water and extracted with dichloromethane. The organic extracts were dried over magnesium sulfate, filtered, and concentrated under reduced pressure. The solid was taken into dichloromethane, precipitated by adding diisopropyl ether, filtered and washed with diisopropyl ether. The white solid was purified by column chromatography on silica gel (gradient of dichloromethane/methanol from 100/0 to 80/20) to give 59 mg of 3-{4-[4-bromomethyl-2-(4-trifluoromethyl-phenyl)-thiazol-5-ylmethoxy]-2-fluoro-phenyl}-4H-[1,2,4]oxadiazol-5-one as a white solid.

[5] Example 1 from application WO2005/097786

C20H12BrF4N3O3S (530.29), MS (CI): 530 (M+H$^+$).

3-{2-Fluoro-4-[2-(4-trifluoromethyl-phenyl)-4-(4-trifluoromethyl-piperidin-1-ylmethyl)-thiazol-5-ylmethoxy]-phenyl}-4H-[1,2,4]oxadiazol-5-one

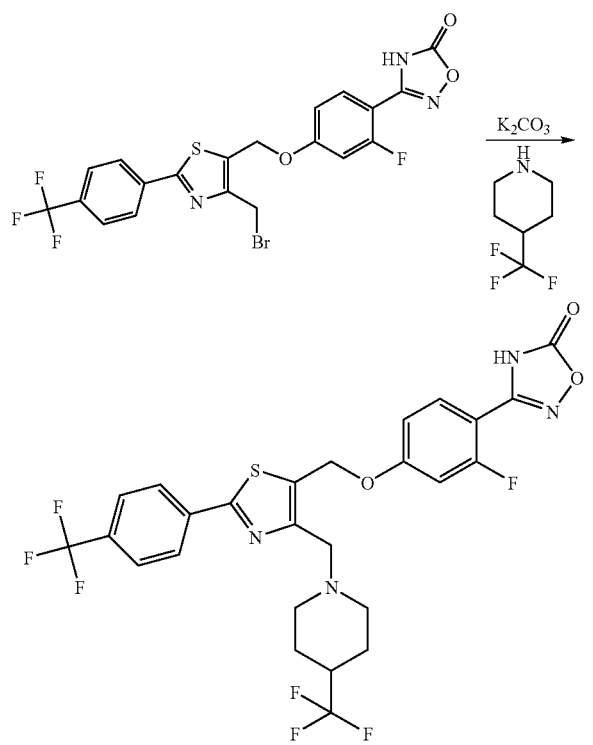

To a mixture of 136 mg of 3-{4-[4-bromomethyl-2-(4-trifluoromethyl-phenyl)-thiazol-5-ylmethoxy]-2-fluoro-phenyl}-4H-[1,2,4]oxadiazol-5-one in 17 mL of acetonitrile was added 48.6 mg of 4-trifluoropiperidine hydrochloride and 70 mg of potassium carbonate. The resulting mixture was stirred overnight and then concentrated under reduced pressure. It was then taken into dichloromethane and washed with water. The aqueous layer was extracted with dichloromethane. The combined organic extracts were dried over magnesium sulfate, filtered, and concentrated under reduced pressure. The crude product was purified by column chromatography on silica gel (dichloromethane 98/methanol 2) to give 51.6 mg of 3-{2-fluoro-4-[2-(4-trifluoromethyl-phenyl)-4-(4-trifluoromethyl-piperidin-1-ylmethyl)-thiazol-5-ylmethoxy]-phenyl}-4H-[1,2,4]oxadiazol-5-one as a white solid.

C26H21F7N4O3S (602.53), MS (ESI): 603 (M+H$^+$).

Example 18

3-{4-[4-(4,4-Difluoro-piperidin-1-ylmethyl)-2-(4-trifluoromethyl-phenyl)-thiazol-5-ylmethoxy]-2-fluoro-phenyl}-4H-[1,2,4]oxadiazol-5-one

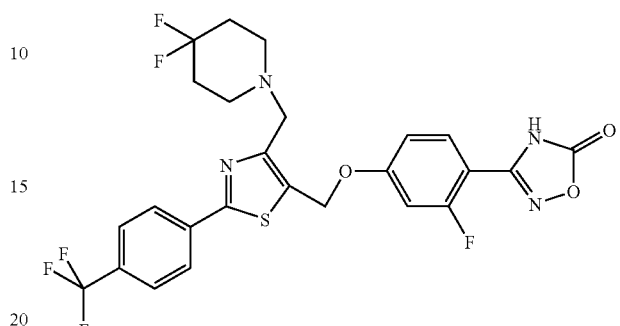

According to the method described for 3-{2-fluoro-4-[2-(4-trifluoromethyl-phenyl)-4-(4-trifluoromethyl-piperidin-1-ylmethyl)-thiazol-5-ylmethoxy]-phenyl}-4H-[1,2,4]oxadiazol-5-one, 3-{4-[4-butyl-2-(4-trifluoromethyl-phenyl)-thiazol-5-ylmethoxy]-2,6-difluoro-phenyl}-4H-[1,2,4]oxadiazol-5-one was obtained from 3-{2-fluoro-4-[4-methyl-2-(4-trifluoromethyl-phenyl)-thiazole-5-ylmethoxy]-phenyl}-4H-[1,2,4]oxadiazole-5-one and 4,4-difluoro-piperidine hydrochloride.

C25H20F6N4O3S (570.51), MS (ESI): 571 (M+H$^+$).

Example 19

3-{2-Fluoro-4-[4-{[(2-hydroxy-ethyl)-methyl-amino]-methyl}-2-(4-trifluoromethyl-phenyl)-thiazol-5-ylmethoxy]-phenyl}-4H-[1,2,4]oxadiazol-5-one

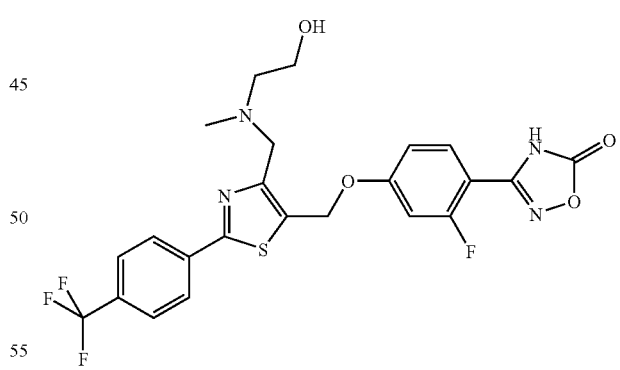

According to the method described for 3-{2-fluoro-4-[2-(4-trifluoromethyl-phenyl)-4-(4-trifluoromethyl-piperidin-1-ylmethyl)-thiazol-5-ylmethoxy]-phenyl}-4H-[1,2,4]oxadiazol-5-one, 3-{2-fluoro-4-[4-{[(2-hydroxy-ethyl)-methyl-amino]-methyl}-2-(4-trifluoromethyl-phenyl)-thiazol-5-ylmethoxy]-phenyl}-4H-[1,2,4]oxadiazol-5-one was obtained from 3-{2-fluoro-4-[4-methyl-2-(4-trifluoromethyl-phenyl)-thiazole-5-ylmethoxy]-phenyl}-4H-[1,2,4]oxadiazole-5-one and 2-methylaminoethanol.

C23H20F4N4O4S (524.49), MS (ESI): 525 (M+H$^+$).

Example 20

3-{2-Fluoro-4-[4-(4-methyl-piperazin-1-ylmethyl)-2-(4-trifluoromethyl-phenyl)-thiazol-5-ylmethoxy]-phenyl}-4H-[1,2,4]oxadiazol-5-one

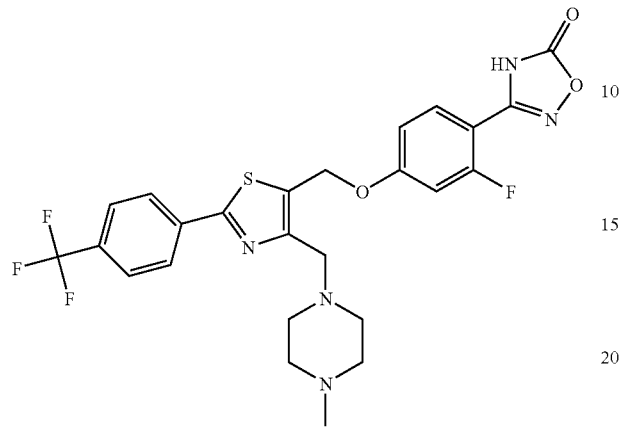

According to the method described for 3-{2-fluoro-4-[2-(4-trifluoromethyl-phenyl)-4-(4-trifluoromethyl-piperidin-1-ylmethyl)-thiazol-5-ylmethoxy]-phenyl}-4H-[1,2,4]oxadiazol-5-one, 3-{2-fluoro-4-[4-(4-methyl-piperazin-1-ylmethyl)-2-(4-trifluoromethyl-phenyl)-thiazol-5-ylmethoxy]-phenyl}-4H-[1,2,4]oxadiazol-5-one was obtained from 3-{2-fluoro-4-[4-methyl-2-(4-trifluoromethyl-phenyl)-thiazole-5-ylmethoxy]-phenyl}-4H-[1,2,4]oxadiazole-5-one and 4-methyl-piperazine.

C25H23F4N5O3S (549.55), MS (ESI): 550 (M+H$^+$).

Example 21

3-{2-Fluoro-4-[4-morpholin-4-ylmethyl-2-(4-trifluoromethyl-phenyl)-thiazol-5-ylmethoxy]-phenyl}-4H-[1,2,4]oxadiazol-5-one

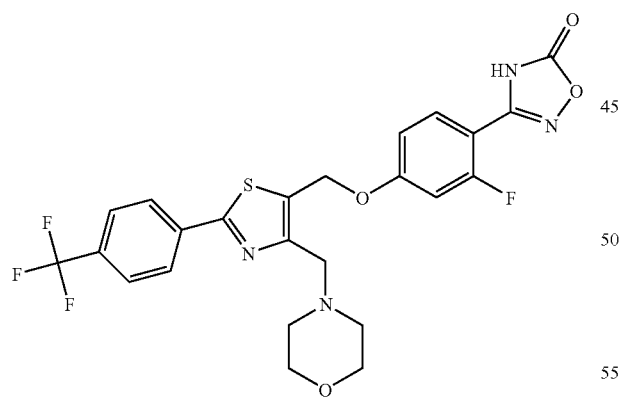

According to the method described for 3-{2-fluoro-4-[2-(4-trifluoromethyl-phenyl)-4-(4-trifluoromethyl-piperidin-1-ylmethyl)-thiazol-5-ylmethoxy]-phenyl}-4H-[1,2,4]oxadiazol-5-one, 3-{2-fluoro-4-[4-morpholin-4-ylmethyl-2-(4-trifluoromethyl-phenyl)-thiazol-5-ylmethoxy]-phenyl}-4H-[1,2,4]oxadiazol-5-one was obtained from 3-{2-fluoro-4-[4-methyl-2-(4-trifluoromethyl-phenyl)-thiazole-5-ylmethoxy]-phenyl}-4H-[1,2,4]oxadiazole-5-one and morpholine.

C24H20F4N4O4S (536.50), MS (ESI): 537 (M+H$^+$).

Example 22

3-{4-[4-(1,3-Dihydro-isoindol-2-ylmethyl)-2-(4-trifluoromethyl-phenyl)-thiazol-5-ylmethoxy]-2-fluoro-phenyl}-4H-[1,2,4]oxadiazol-5-one

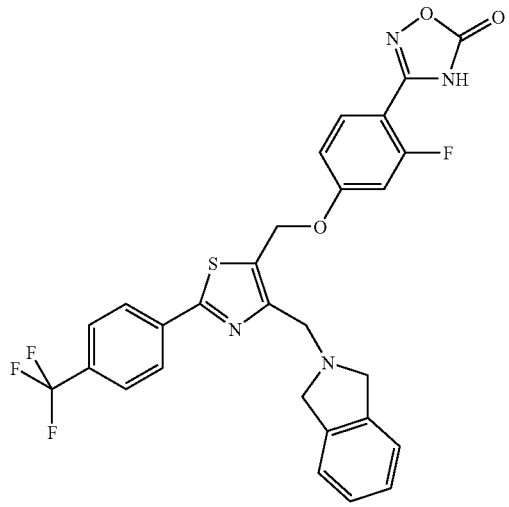

According to the method described for 3-{2-fluoro-4-[2-(4-trifluoromethyl-phenyl)-4-(4-trifluoromethyl-piperidin-1-ylmethyl)-thiazol-5-ylmethoxy]-phenyl}-4H-[1,2,4]oxadiazol-5-one, 3-{4-[4-(1,3-dihydro-isoindol-2-ylmethyl)-2-(4-trifluoromethyl-phenyl)-thiazol-5-ylmethoxy]-2-fluoro-phenyl}-4H-[1,2,4]oxadiazol-5-one was obtained from 3-{2-fluoro-4-[4-methyl-2-(4-trifluoromethyl-phenyl)-thiazole-5-ylmethoxy]-phenyl}-4H-[1,2,4]oxadiazole-5-one and 2,3-dihydro-1H-isoindole.

C28H20F4N4O3S (568.55), MS (ESI): 569 (M+H$^+$).

Example 23

3-{2-Fluoro-4-[4-[(4-fluoro-benzylamino)-methyl]-2-(4-trifluoromethyl-phenyl)-thiazol-5-ylmethoxy]-phenyl}-4H-[1,2,4]oxadiazol-5-one

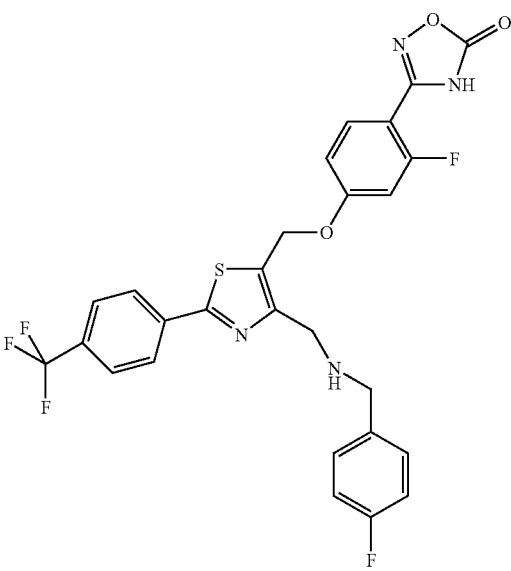

According to the method described for 3-{2-fluoro-4-[2-(4-trifluoromethyl-phenyl)-4-(4-trifluoromethyl-piperidin-1-ylmethyl)-thiazol-5-ylmethoxy]-phenyl}-4H-[1,2,4]oxadiazol-5-one, 3-{2-fluoro-4-[4-[(4-fluoro-benzylamino)-methyl]-2-(4-trifluoromethyl-phenyl)-thiazol-5-ylmethoxy]-phenyl}-4H-[1,2,4]oxadiazol-5-one was obtained from 3-{2-fluoro-4-[4-methyl-2-(4-trifluoromethyl-phenyl)-thiazole-5-ylmethoxy]-phenyl}-4H-[1,2,4]oxadiazole-5-one and 4-fluoro-benzylamine.

C27H19F5N4O3S (574.53), MS (ESI): 575 (M+H+).

Example 24

3-{2-Fluoro-4-[4-(2-hydroxymethyl-pyrrolidin-1-ylmethyl)-2-(4-trifluoromethyl-phenyl)-thiazol-5-ylmethoxy]-phenyl}-4H-[1,2,4]oxadiazol-5-one

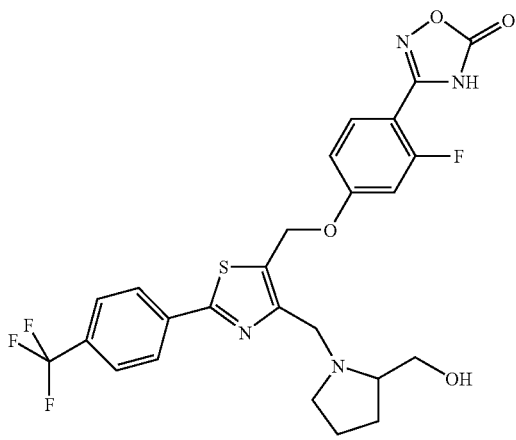

According to the method described for 3-{2-fluoro-4-[2-(4-trifluoromethyl-phenyl)-4-(4-trifluoromethyl-piperidin-1-ylmethyl)-thiazol-5-ylmethoxy]-phenyl}-4H-[1,2,4]oxadiazol-5-one, racemic 3-{2-fluoro-4-[4-(2-hydroxymethyl-pyrrolidin-1-ylmethyl)-2-(4-trifluoromethyl-phenyl)-thiazol-5-ylmethoxy]-phenyl}-4H-[1,2,4]oxadiazol-5-one was obtained from 3-{2-fluoro-4-[4-methyl-2-(4-trifluoromethyl-phenyl)-thiazole-5-ylmethoxy]-phenyl}-4H-[1,2,4]oxadiazole-5-one and racemic 2-hydroxymethyl-pyrrolidine.

C25H22F4N4O4S (550.53), MS (ESI): 551 (M+H+).

Example 25

3-{2-Fluoro-4-[4-{[(furan-2-ylmethyl)-amino]-methyl}-2-(4-trifluoromethyl-phenyl)-thiazol-5-ylmethoxy]-phenyl}-4H-[1,2,4]oxadiazol-5-one To a solution of 50 mg of 3-{4-[4-bromomethyl-2-(4-trifluoromethyl-phenyl)-thiazol-5

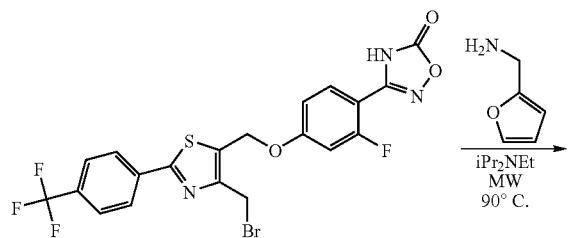

-ylmethoxy]-2-fluoro-phenyl}-4H-[1,2,4]oxadiazol-5-one in 2.5 mL of acetonitrile was added 12 mg of furfurylamine and 25 mg of diisopropylethyl amine. The resulting mixture was heated in a sealed tube to 90° C. under microwave irradiation for 5 minutes and then concentrated under reduced pressure. The residue was purified by column chromatography on silica gel (gradient from dichloromethane 100 to dichloromethane 90/methanol 10/water 1/acetic acid 1) followed by washings with diisopropyl ether to give 18 mg of 3-{2-fluoro-4-[4-{[(furan-2-ylmethyl)-amino]-methyl}-2-(4-trifluoromethyl-phenyl)-thiazol-5-ylmethoxy]-phenyl}-4H-[1,2,4]oxadiazol-5-one.

C25H18F4N4O4S (546.50), MS (ESI): 547 (M+H+).

Example 26

3-{2-Fluoro-4-[4-[(3-methylsulfanyl-propylamino)-methyl]-2-(4-trifluoromethyl-phenyl)-thiazol-5-ylmethoxy]-phenyl}-4H-[1,2,4]oxadiazol-5-one

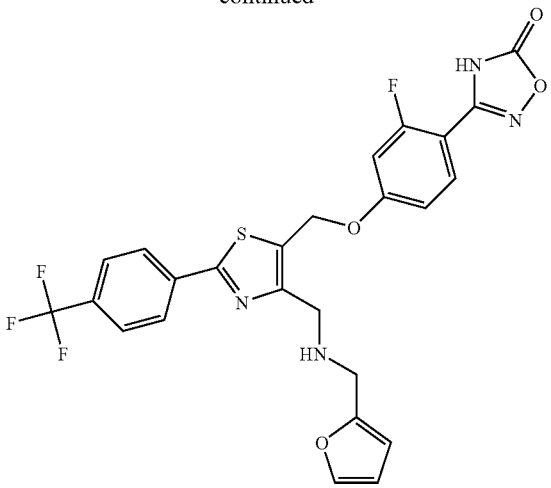

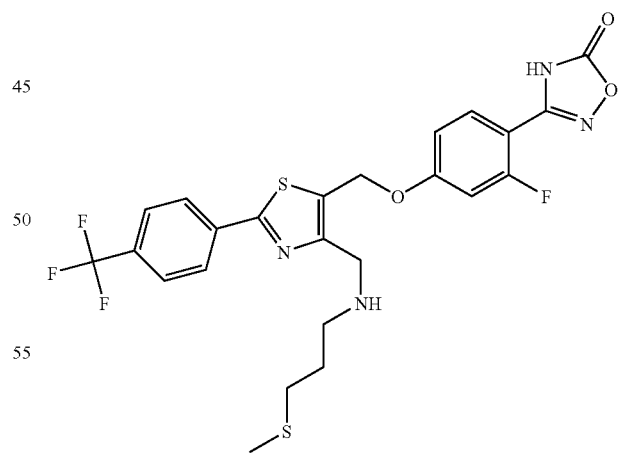

According to the method described for 3-{2-fluoro-4-[2-(4-trifluoromethyl-phenyl)-4-(4-trifluoromethyl-piperidin-1-ylmethyl)-thiazol-5-ylmethoxy]-phenyl}-4H-[1,2,4]oxadiazol-5-one, 3-{2-fluoro-4-[4-[(3-methylsulfanyl-propylamino)-methyl]-2-(4-trifluoromethyl-phenyl)-thiazol-5-ylmethoxy]-phenyl}-4H-[1,2,4]oxadiazol-5-one was obtained from 3-{2-fluoro-4-[4-methyl-2-(4-trifluoromethyl-phenyl)-thiazole-5-ylmethoxy]-phenyl}-4H-[1,2,4]oxadiazole-5-one and 3-methylsulfanyl-propylamine.
C24H22F4N4O3S2 (554.59), MS (ESI): 555 (M+H+).

Example 27

4-[5-[3-Fluoro-4-(5-oxo-4,5-dihydro-[1,2,4]oxadiazol-3-yl)-phenoxymethyl]-2-(4-trifluoromethyl-phenyl)-thiazol-4-ylmethyl]-piperazin-2-one

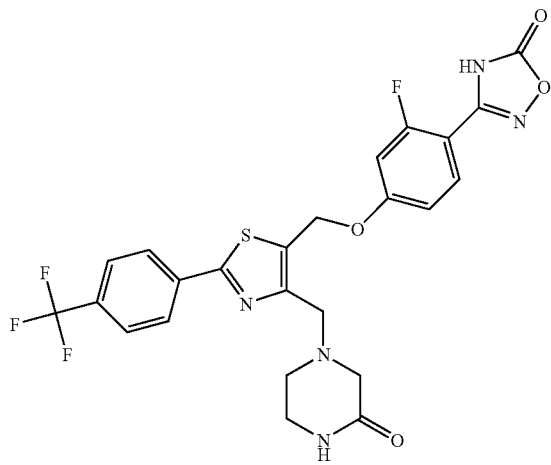

According to the method described for 3-{2-fluoro-4-[2-(4-trifluoromethyl-phenyl)-4-(4-trifluoromethyl-piperidin-1-ylmethyl)-thiazol-5-ylmethoxy]-phenyl}-4H-[1,2,4]oxadiazol-5-one, 4-[5-[3-fluoro-4-(5-oxo-4,5-dihydro-[1,2,4] oxadiazol-3-yl)-phenoxymethyl]-2-(4-trifluoromethyl-phenyl)-thiazol-4-ylmethyl]-piperazin-2-one was obtained from 3-{2-fluoro-4-[4-methyl-2-(4-trifluoromethyl-phenyl)-thiazole-5-ylmethoxy]-phenyl}-4H-[1,2,4]oxadiazole-5-one and piperazin-2-one.
C24H19F4N5O4S (549.50), MS (ESI): 550 (M+H+).

Example 28

3-{2-Fluoro-4-[4-[(4-methoxy-benzylamino)-methyl]-2-(4-trifluoromethyl-phenyl)-thiazol-5-ylmethoxy]-phenyl}-4H-[1,2,4]oxadiazol-5-one

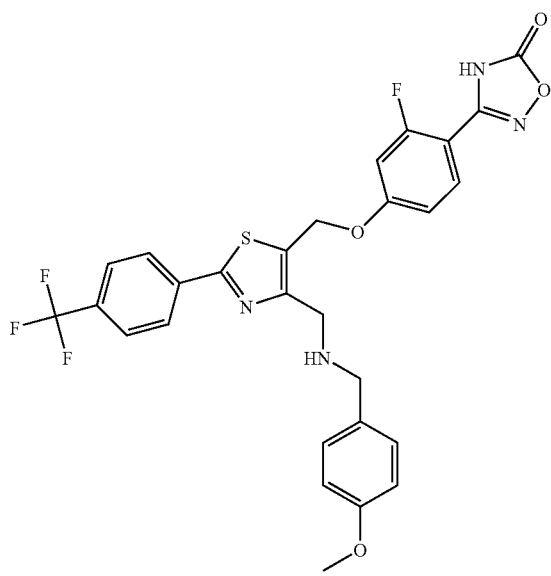

According to the method described for 3-{2-fluoro-4-[2-(4-trifluoromethyl-phenyl)-4-(4-trifluoromethyl-piperidin-1-ylmethyl)-thiazol-5-ylmethoxy]-phenyl}-4H-[1,2,4]oxadiazol-5-one, 3-{2-fluoro-4-[4-[(4-methoxy-benzylamino)-methyl]-2-(4-trifluoromethyl-phenyl)-thiazol-5-ylmethoxy]-phenyl}-4H-[1,2,4]oxadiazol-5-one was obtained from 3-{2-fluoro-4-[4-methyl-2-(4-trifluoromethyl-phenyl)-thiazole-5-ylmethoxy]-phenyl}-4H-[1,2,4] oxadiazole-5-one and 4-methoxy-benzylamine.
C28H22F4N4O4S (586.56), MS (ESI): 587 (M+H+).

Example 29

3-{4-[4-[(1R,4R)-1-(2,5-Diaza-bicyclo[2.2.1]hept-2-yl)methyl]-2-(4-trifluoromethyl-phenyl)-thiazol-5-ylmethoxy]-2-fluoro-phenyl}-4H-[1,2,4]oxadiazol-5-one

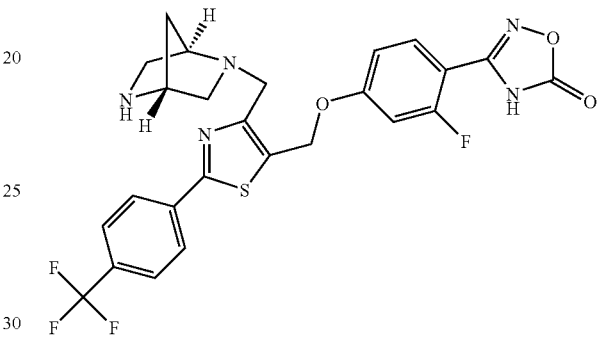

According to the method described for 3-{2-fluoro-4-[2-(4-trifluoromethyl-phenyl)-4-(4-trifluoromethyl-piperidin-1-ylmethyl)-thiazol-5-ylmethoxy]-phenyl}-4H-[1,2,4]oxadiazol-5-one, 3-{4-[4-[(1R,4R)-1-(2,5-diaza-bicyclo[2.2.1] hept-2-yl)methyl]-2-(4-trifluoromethyl-phenyl)-thiazol-5-ylmethoxy]-2-fluoro-phenyl}-4H-[1,2,4]oxadiazol-5-one was obtained from 3-{2-fluoro-4-[4-methyl-2-(4-trifluoromethyl-phenyl)-thiazole-5-ylmethoxy]-phenyl}-4H-[1,2,4] oxadiazole-5-one and (1R,4R)-2,5-diaza-bicyclo[2.2.1]heptane.
C25H21F4N5O3S (547.53), MS (ESI): 548 (M+H+).

Example 30

3-{2-Fluoro-4-[4-(3-hydroxymethyl-piperidin-1-ylmethyl)-2-(4-trifluoromethyl-phenyl)-thiazol-5-ylmethoxy]-phenyl}-4H-[1,2,4]oxadiazol-5-one

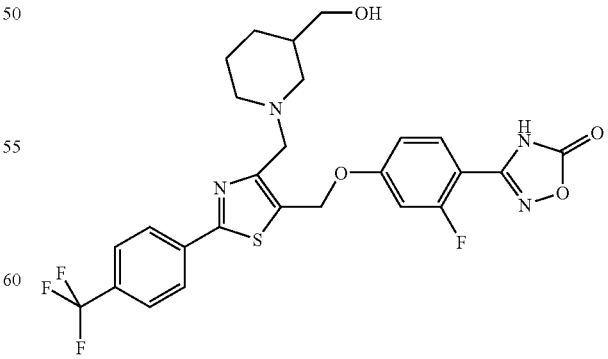

According to the method described for 3-{2-fluoro-4-[2-(4-trifluoromethyl-phenyl)-4-(4-trifluoromethyl-piperidin-1-ylmethyl)-thiazol-5-ylmethoxy]-phenyl}-4H-[1,2,4]oxadiazol-5-one, racemic 3-{2-fluoro-4-[4-(3-hydroxymethyl-piperidin-1-ylmethyl)-2-(4-trifluoromethyl-phenyl)-thiazol-5-ylmethoxy]-phenyl}-4H-[1,2,4]oxadiazol-5-one was obtained from 3-{2-fluoro-4-[4-methyl-2-(4-trifluoromethyl-phenyl)-thiazole-5-ylmethoxy]-phenyl}-4H-[1,2,4]oxadiazole-5-one and racemic 3-hydroxymethyl-piperidine.

C26H24F4N4O4S (564.56), MS (ESI): 565 (M+H$^+$).

Example 31

3-{5-Bromo-2-methoxy-4-[4-piperidin-1-ylmethyl-2-(4-trifluoromethyl-phenyl)-thiazol-5-ylmethoxy]-phenyl}-4H-[1,2,4]oxadiazol-5-one

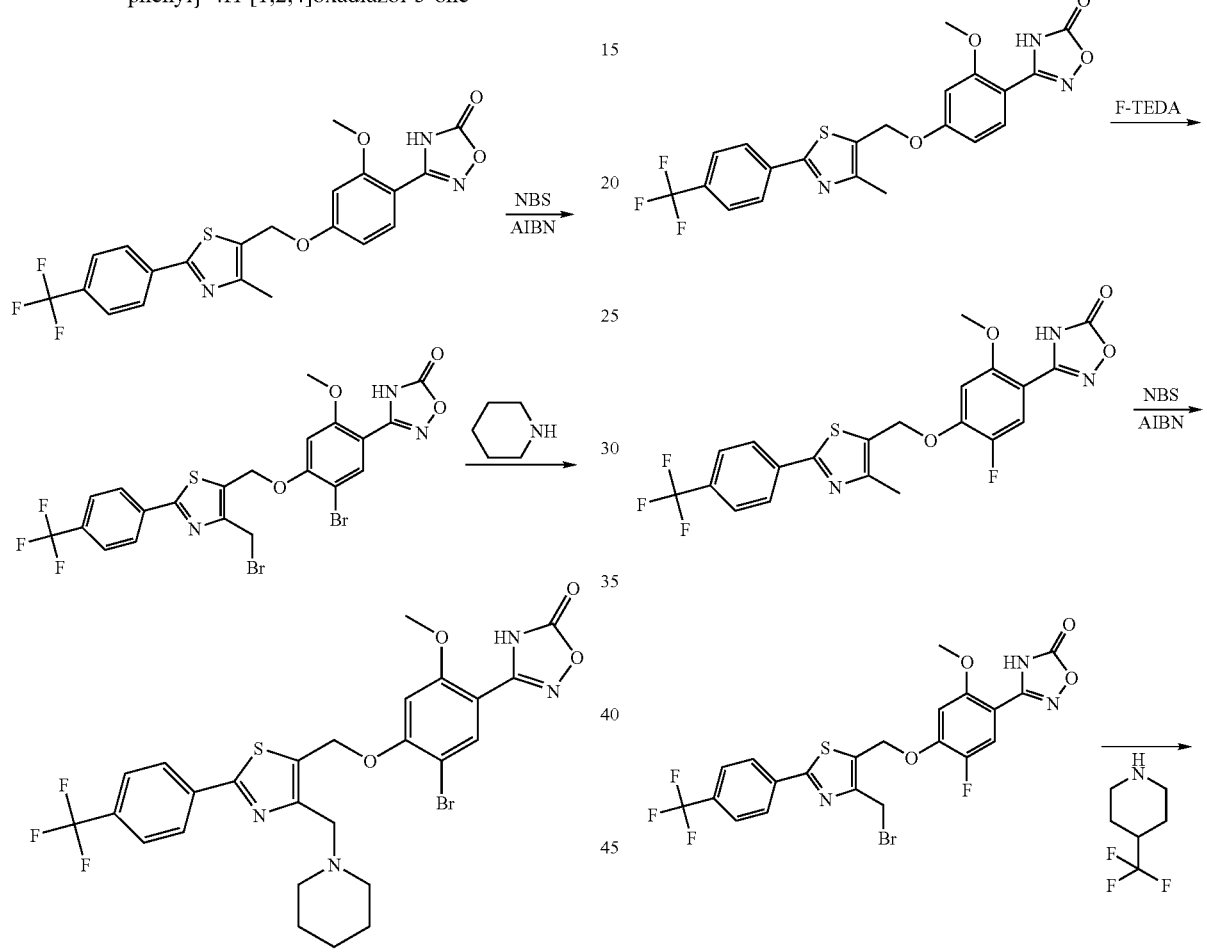

According to the method described for 3-{2-fluoro-4-[2-(4-trifluoromethyl-phenyl)-4-(4-trifluoromethyl-piperidin-1-ylmethyl)-thiazol-5-ylmethoxy]-phenyl}-4H-[1,2,4]oxadiazol-5-one, 3-{5-bromo-2-methoxy-4-[4-piperidin-1-ylmethyl-2-(4-trifluoromethyl-phenyl)-thiazol-5-ylmethoxy]-phenyl}-4H-[1,2,4]oxadiazol-5-one was obtained from 3-{2-methoxy-4-[4-methyl-2-(4-trifluoromethyl-phenyl)-thiazol-5-ylmethoxy]-phenyl}-4H-[1,2,4]oxadiazol-5-one[6] and piperidine. During the bromination step on 3-{2-methoxy-4-[4-methyl-2-(4-trifluoromethyl-phenyl)-thiazol-5-ylmethoxy]-phenyl}-4H-[1,2,4]oxadiazol-5-one, 3-{5-bromo-4-[4-bromomethyl-2-(4-trifluoromethyl-phenyl)-thiazol-5-ylmethoxy]-2-methoxy-phenyl}-4H-[1,2,4]oxadiazol-5-one was obtained. It was then converted to the cited product upon reaction with piperidine.

[6] Example 11 from application WO2005/097786

C26H24BrF3N4O4S (625.46), MS (ESI): 625 (M+H$^+$).

Example 32

3-{5-Fluoro-2-methoxy-4-[2-(4-trifluoromethyl-phenyl)-4-(4-trifluoromethyl-piperidin-1-ylmethyl)-thiazol-5-ylmethoxy]-phenyl}-4H-[1,2,4]oxadiazol-5-one

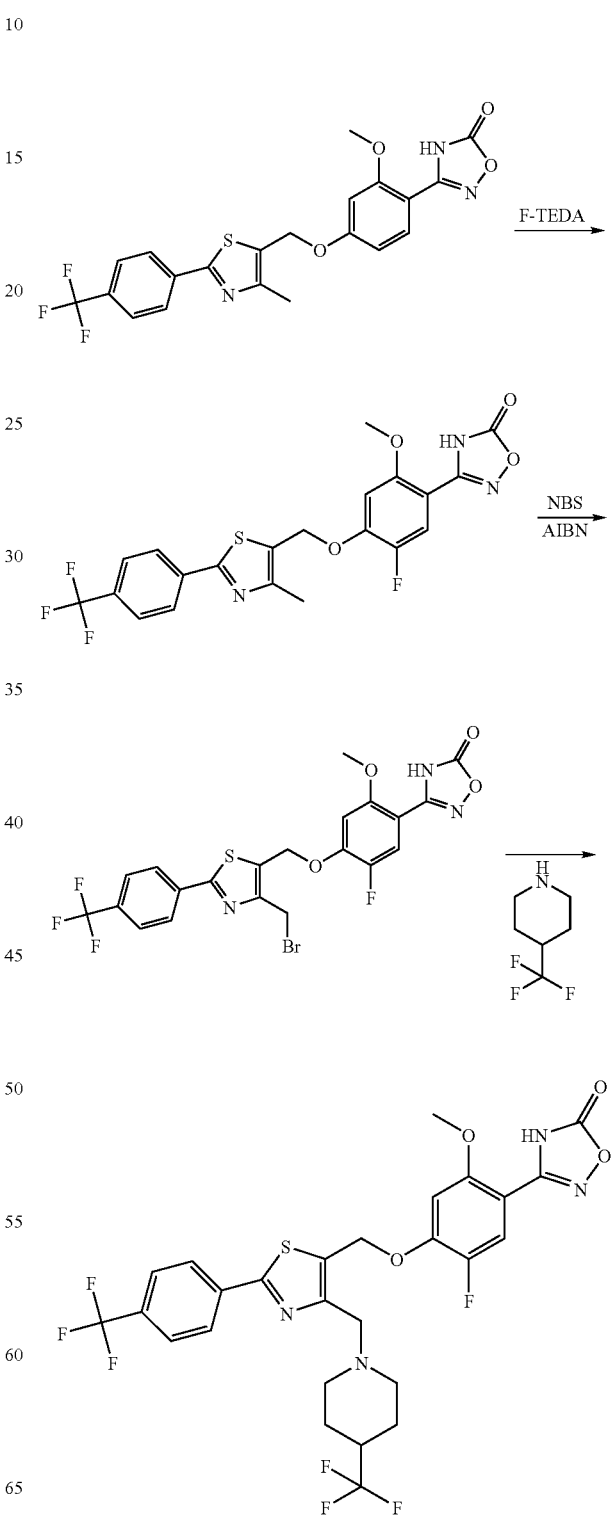

3-{5-Fluoro-2-methoxy-4-[4-methyl-2-(4-trifluoromethyl-phenyl)-thiazol-5-ylmethoxy]-phenyl}-4H-[1,2,4]oxadiazol-5-one

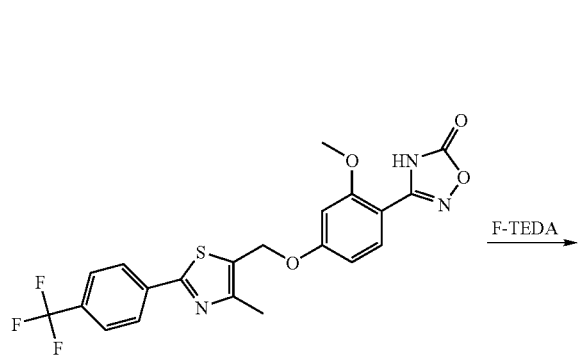

To a solution of 1.13 g of 3-{2-methoxy-4-[4-methyl-2-(4-trifluoromethyl-phenyl)-thiazol-5-ylmethoxy]-phenyl}-4H-[1,2,4]oxadiazol-5-one in 40 mL of trifluoroacetic acid was added 738 mg of 1-chloromethyl-4-fluoro-1,4-diazoniabicyclo[2.2.2]octane bis(tetrafluoroborate) (F-TEDA). The resulting mixture was heated to 70° C. for 6 h then poured into water and extracted with dichloromethane. The organic extracts were dried over magnesium sulfate, filtered, and concentrated under reduced pressure. The crude product was purified by column chromatography on silica gel (gradient from dichloromethane 100 to dichloromethane 80/methanol 20) to give 164 mg of a 1/1 mixture of 3-{5-fluoro-2-methoxy-4-[4-methyl-2-(4-trifluoromethyl-phenyl)-thiazol-5-ylmethoxy]-phenyl}-4H-[1,2,4]oxadiazol-5-one and starting material which was used in the next step without further purification.

C21H15F4N3O4S (481.42), MS (ESI): 482 (M+H+).

3-{5-Fluoro-2-methoxy-4-[2-(4-trifluoromethyl-phenyl)-4-(4-trifluoromethyl-piperidin-1-ylmethyl)-thiazol-5-ylmethoxy]-phenyl}-4H-[1,2,4]oxadiazol-5-one

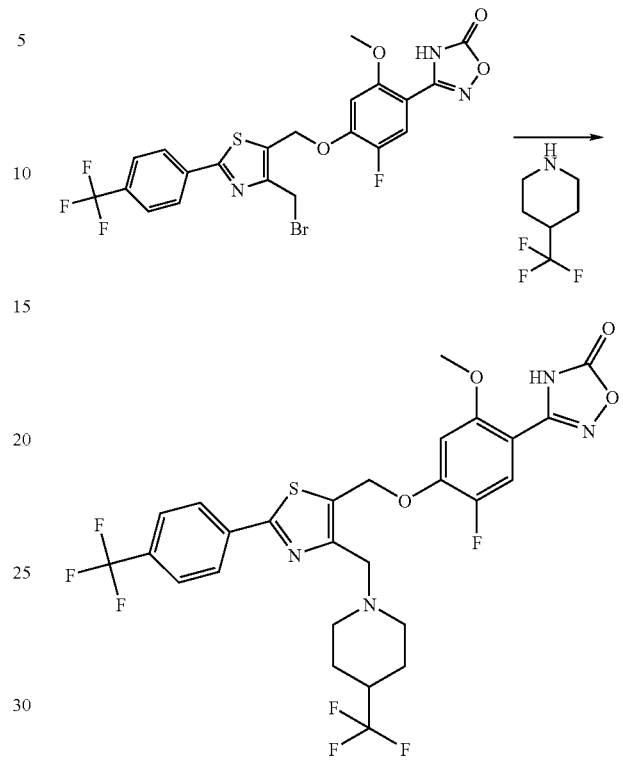

According to the method described for 3-{2-fluoro-4-[2-(4-trifluoromethyl-phenyl)-4-(4-trifluoromethyl-piperidin-1-ylmethyl)-thiazol-5-ylmethoxy]-phenyl}-4H-[1,2,4]oxadiazol-5-one, 3-{5-fluoro-2-methoxy-4-[2-(4-trifluoromethyl-phenyl)-4-(4-trifluoromethyl-piperidin-1-ylmethyl)-thiazol-5-ylmethoxy]-phenyl}-4H-[1,2,4]oxadiazol-5-one was obtained from 3-{5-fluoro-2-methoxy-4-[4-methyl-2-(4-trifluoromethyl-phenyl)-thiazol-5-ylmethoxy]-phenyl}-4H-[1,2,4]oxadiazol-5-one and 4-trifluoromethyl-piperidine.

C27H23F7N4O4S (632.55), MS (ESI): 633 (M+H+).

The following examples were prepared according to process G:

Example 33

Acetic acid 5-[3-fluoro-4-(5-oxo-4,5-dihydro-[1,2,4]oxadiazol-3-yl)-phenoxymethyl]-2-(4-trifluoromethyl-phenyl)-thiazol-4-ylmethyl ester

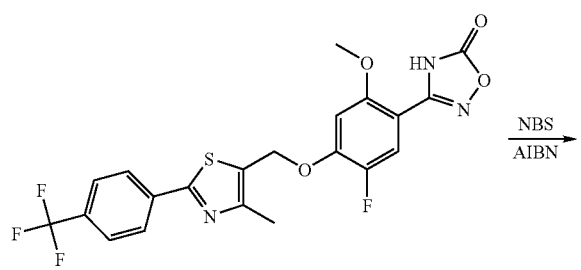

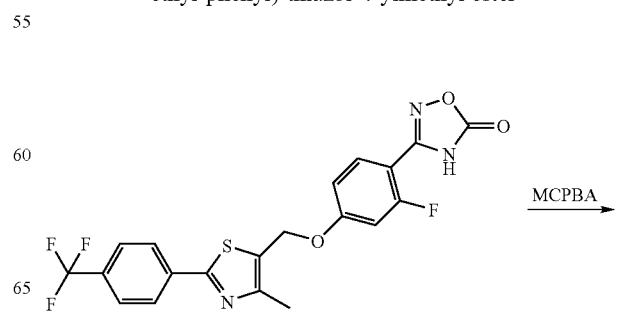

-continued

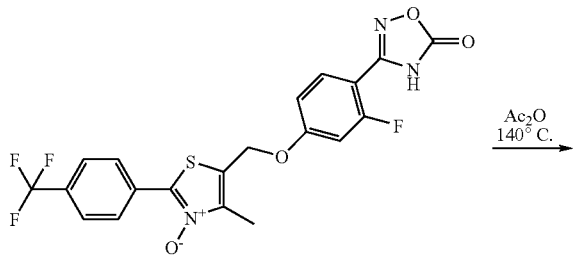

3-{2-Fluoro-4-[4-methyl-3-oxy-2-(4-trifluoromethyl-phenyl)-thiazol-5-ylmethoxy]-phenyl}-4H-[1,2,4]oxadiazol-5-one

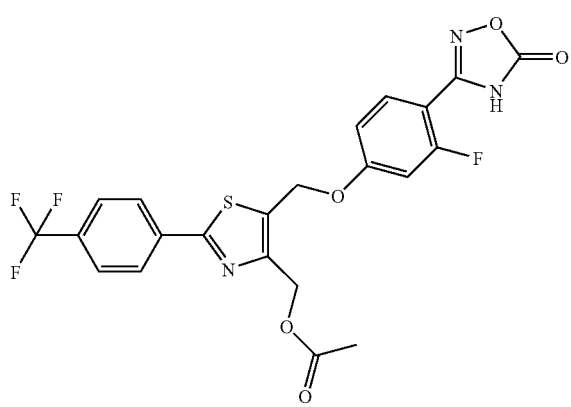

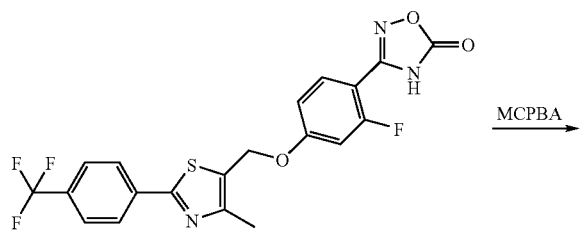

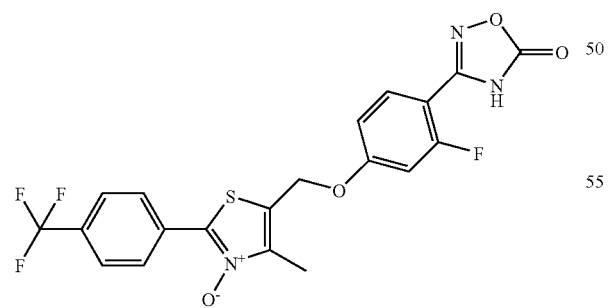

1 g of 3-{2-fluoro-4-[4-methyl-3-oxy-2-(4-trifluoromethyl-phenyl)-thiazol-5-ylmethoxy]-phenyl}-4H-[1,2,4]oxadiazol-5-one were dissolved in 23 mL of hexafluoroisopropanol. To the resulting solution was added 2.1 g of MCPBA (70% pure). The resulting mixture was heated to 50° C. for 6 h and stirred at room temperature overnight. The precipitate is filtered. The filtrate is concentrated under reduced pressure and 8 mL of ethyl acetate was added to the residue. The solid was filtered and washed with ethyl acetate to give 0.48 g of a first crop of desired product as a white solid. The filtrate was concentrated and recrystallized in methanol to provide an additional 0.19 g of desired product as a white solid. The mother liquor was concentrated and purified by column chromatography on silica gel (heptane 1/ethyl acetate 3 then dichloromethane 95/methanol 5). The crops were combined to give 0.67 g of 3-{2-fluoro-4-[4-methyl-3-oxy-2-(4-trifluoromethyl-phenyl)-thiazol-5-ylmethoxy]-phenyl}-4H-[1,2,4]oxadiazol-5-one as a white solid.

C20H13F4N3O4S (467.40), MS (ESI): 468 (M+H$^+$).

Acetic acid 5-[3-fluoro-4-(5-oxo-4,5-dihydro-[1,2,4]oxadiazol-3-yl)-phenoxymethyl]-2-(4-trifluoromethyl-phenyl)-thiazol-4-ylmethyl ester

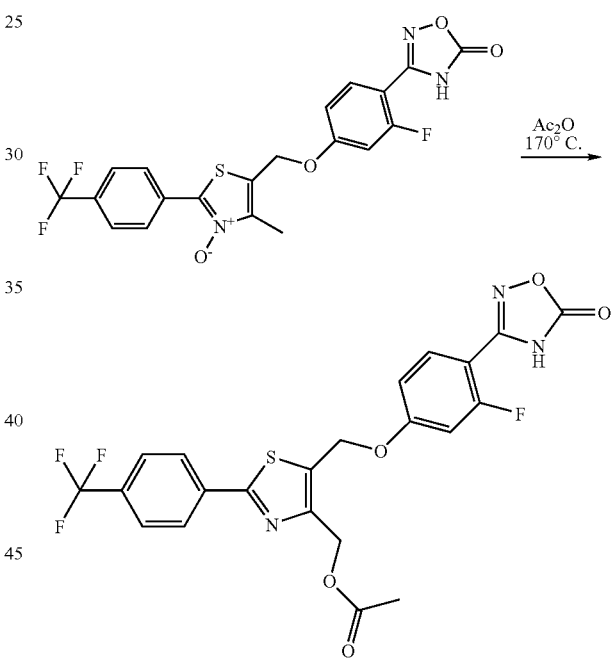

A mixture of 470 mg of 3-{2-fluoro-4-[4-methyl-3-oxy-2-(4-trifluoromethyl-phenyl)-thiazol-5-ylmethoxy]-phenyl}-4H-[1,2,4]oxadiazol-5-one in 5 mL of acetic anhydride was heated to 170° C. for 18 minutes. The mixture was poured into water/ethyl acetate. The organic layer was separated and the aqueous layer extracted three times with ethyl acetate. The combined organic extracts were dried over magnesium sulfate, filtered, and concentrated under reduced pressure. The crude product was purified by column chromatography on silica gel (gradient from heptane 4/ethyl acetate 1 to heptane 1/ethyl acetate 1) to give 180 mg of acetic acid 5-[3-fluoro-4-(5-oxo-4,5-dihydro-[1,2,4]oxadiazol-3-yl)-phenoxymethyl]-2-(4-trifluoromethyl-phenyl)-thiazol-4-ylmethyl ester as a beige solid.

C22H15F4N3O5S (509.43), MS (ESI): 510 (M+H$^+$).

Example 34

Acetic acid 5-[3-methoxy-4-(5-oxo-4,5-dihydro-[1,2,4]oxadiazol-3-yl)-phenoxymethyl]-2-(4-trifluoromethyl-phenyl)-thiazol-4-ylmethyl ester

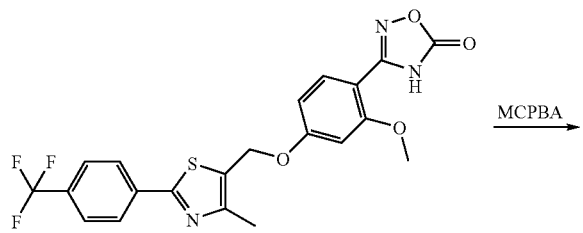

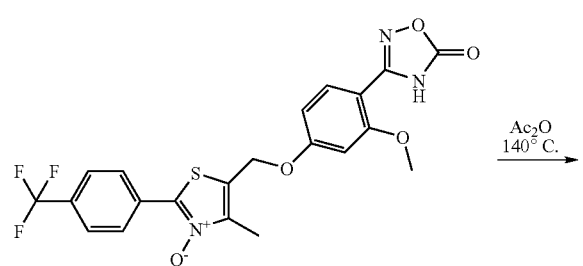

3-{2-Methoxy-4-[4-methyl-3-oxy-2-(4-trifluoromethyl-phenyl)-thiazol-5-ylmethoxy]-phenyl}-4H-[1,2,4]oxadiazol-5-one

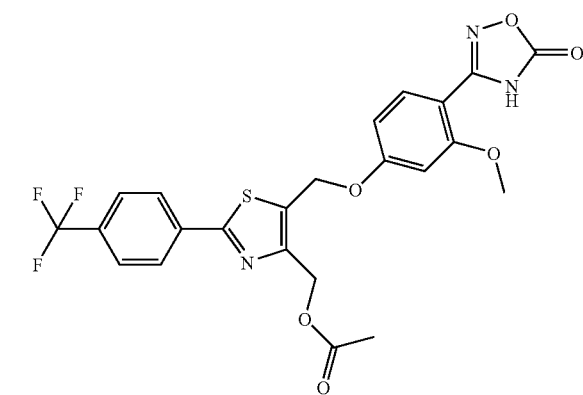

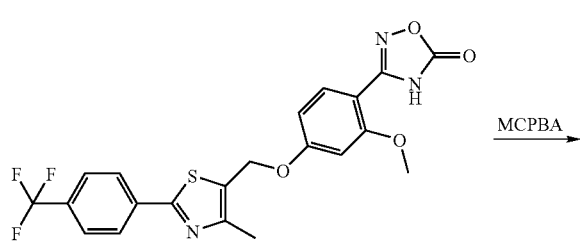

-continued

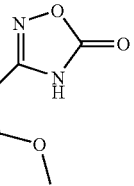

7.55 g of 3-{2-methoxy-4-[4-methyl-2-(4-trifluoromethyl-phenyl)-thiazol-5-ylmethoxy]-phenyl}-4H-[1,2,4]oxadiazol-5-one were dissolved by adding 210 mL of hexafluoroisopropanol followed by 2.5 mL of dichloromethane. To the resulting solution was added 16.3 g of MCPBA (70% pure). The resulting mixture was heated to 50° C. for 5 h and slowly stirred at room temperature over the weekend. The precipitate is filtered and washed with 3 mL of hexafluoroisopropanol. The filtrate is concentrated under reduced pressure and 250 mL of ethyl acetate was added to the residue. The resulting suspension was stirred at room temperature for 3 h then filtered and washed with a mixture of hexane and diisopropyl ether to give 4.77 g of 3-{2-methoxy-4-[4-methyl-3-oxy-2-(4-trifluoromethyl-phenyl)-thiazol-5-ylmethoxy]-phenyl}-4H-[1,2,4]oxadiazol-5-one as a white solid which was used in the next step without further purification.

C21H16F3N3O5S (479.43), MS (ESI): 480 (M+H$^+$).

Acetic acid 5-[3-methoxy-4-(5-oxo-4,5-dihydro-[1,2,4]oxadiazol-3-yl)-phenoxymethyl]-2-(4-trifluoromethyl-phenyl)-thiazol-4-ylmethyl ester

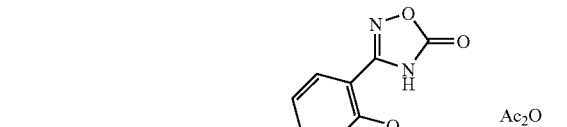

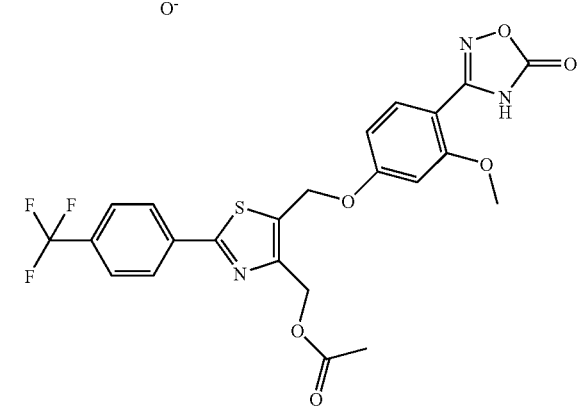

A suspension of 0.4 g of 3-{2-methoxy-4-[4-methyl-3-oxy-2-(4-trifluoromethyl-phenyl)-thiazol-5-ylmethoxy]- phenyl}-4H-[1,2,4]oxadiazol-5-one in 15 mL of acetic anhydride was heated to 140° C. for 1.5 h. The mixture was allowed to cool down to room temperature. 20 mL of Toluene was added and the mixture was concentrated under reduced pressure to give 0.5 g of acetic acid 5-[3-methoxy-4-(5-oxo-4,5-dihydro-[1,2,4]oxadiazol-3-yl)-phenoxymethyl]-2-(4-trifluoromethyl-phenyl)-thiazol-4-ylmethyl ester which was used in the next step without further purification.

C21H16F3N3O5S (479.43), MS (ESI): 478 (M−H⁺).

The following examples were prepared according to process E:

3-{2-Fluoro-4-[4-pyrrolidin-1-ylmethyl-2-(4-trifluoromethyl-phenyl)-thiazol-5-ylmethoxy]-phenyl}-4H-[1,2,4]oxadiazol-5-one

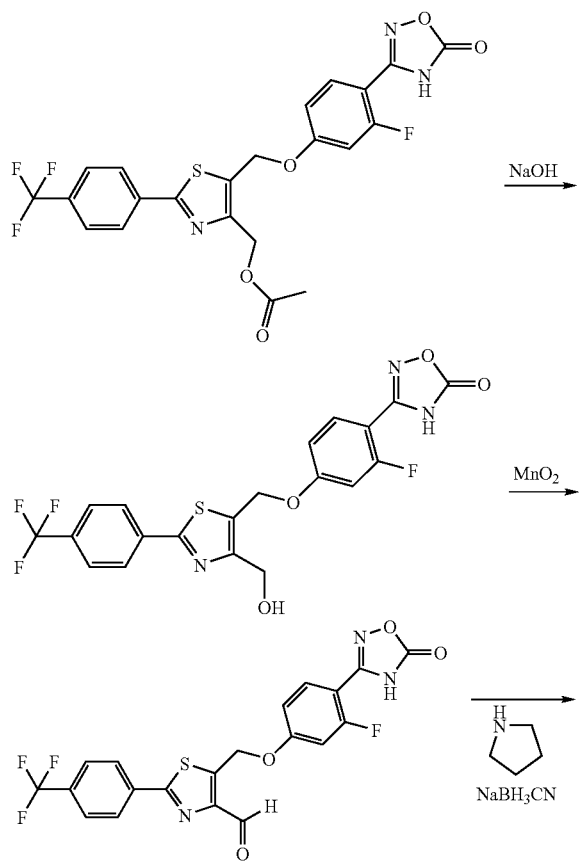

3-{2-Fluoro-4-[4-hydroxymethyl-2-(4-trifluoromethyl-phenyl)-thiazol-5-ylmethoxy]-phenyl}-4H-[1,2,4]oxadiazol-5-one

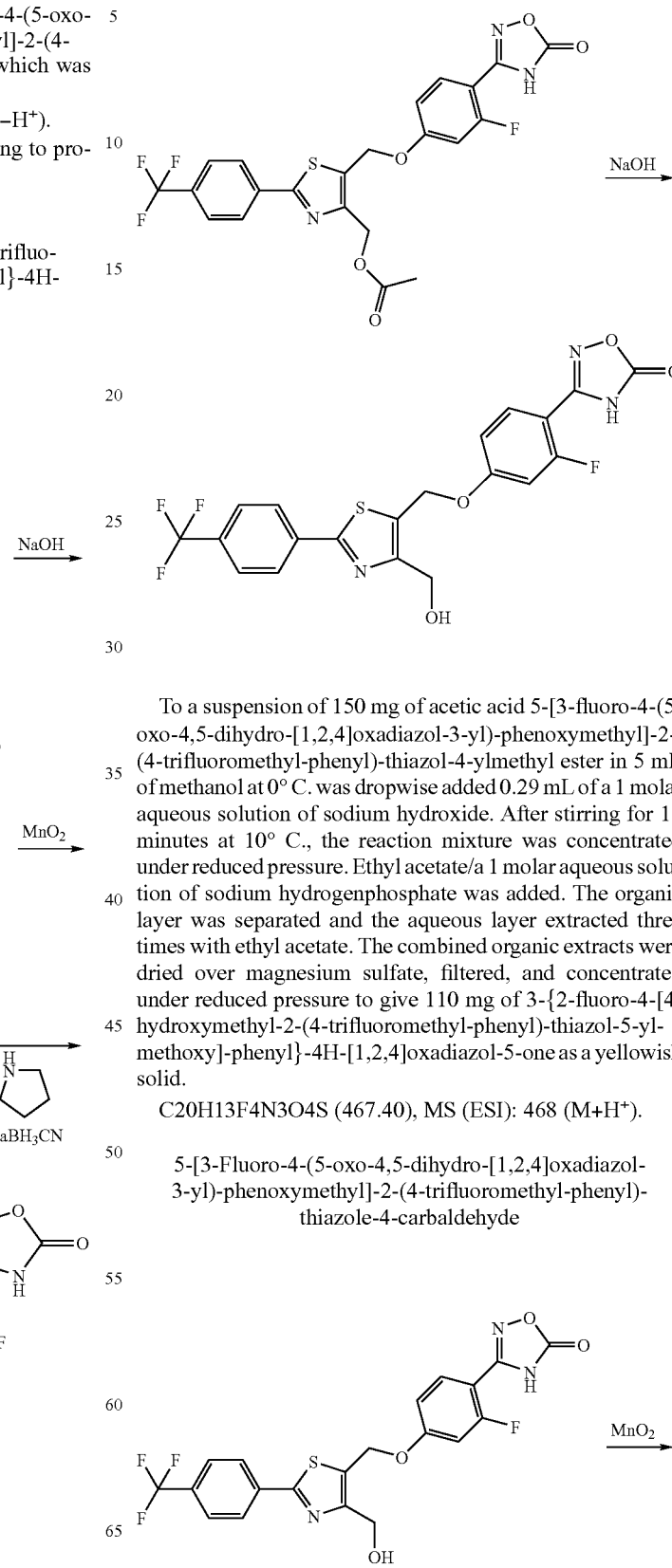

To a suspension of 150 mg of acetic acid 5-[3-fluoro-4-(5-oxo-4,5-dihydro-[1,2,4]oxadiazol-3-yl)-phenoxymethyl]-2-(4-trifluoromethyl-phenyl)-thiazol-4-ylmethyl ester in 5 mL of methanol at 0° C. was dropwise added 0.29 mL of a 1 molar aqueous solution of sodium hydroxide. After stirring for 15 minutes at 10° C., the reaction mixture was concentrated under reduced pressure. Ethyl acetate/a 1 molar aqueous solution of sodium hydrogenphosphate was added. The organic layer was separated and the aqueous layer extracted three times with ethyl acetate. The combined organic extracts were dried over magnesium sulfate, filtered, and concentrated under reduced pressure to give 110 mg of 3-{2-fluoro-4-[4-hydroxymethyl-2-(4-trifluoromethyl-phenyl)-thiazol-5-ylmethoxy]-phenyl}-4H-[1,2,4]oxadiazol-5-one as a yellowish solid.

C20H13F4N3O4S (467.40), MS (ESI): 468 (M+H⁺).

5-[3-Fluoro-4-(5-oxo-4,5-dihydro-[1,2,4]oxadiazol-3-yl)-phenoxymethyl]-2-(4-trifluoromethyl-phenyl)-thiazole-4-carbaldehyde

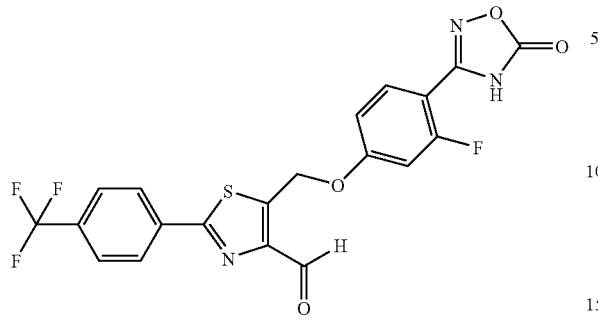

To a mixture of 20 mg of 3-{2-fluoro-4-[4-hydroxymethyl-2-(4-trifluoromethyl-phenyl)-thiazol-5-ylmethoxy]-phenyl}-4H-[1,2,4]oxadiazol-5-one in 10 mL of chloroform was added 23 mg of manganese dioxide. After stirring at room temperature overnight, the reaction mixture was filtered through celite and washed with dichloromethane/methanol. The filtrate was concentrated under reduced pressure to give 200 mg of 5-[3-fluoro-4-(5-oxo-4,5-dihydro-[1,2,4]oxadiazol-3-yl)-phenoxymethyl]-2-(4-trifluoromethyl-phenyl)-thiazole-4-carbaldehyde as a beige solid.

C20H11F4N3O4S (465.39), MS (CI): 483 (M+NH4+).

3-{2-Fluoro-4-[4-pyrrolidin-1-ylmethyl-2-(4-trifluoromethyl-phenyl)-thiazol-5-ylmethoxy]-phenyl}-4H-[1,2,4]oxadiazol-5-one

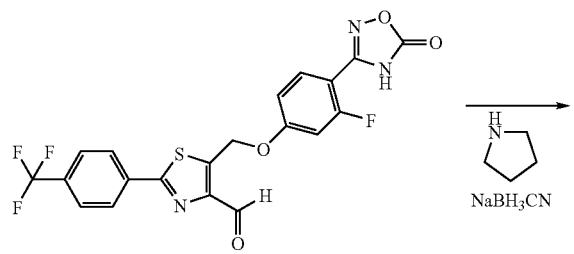

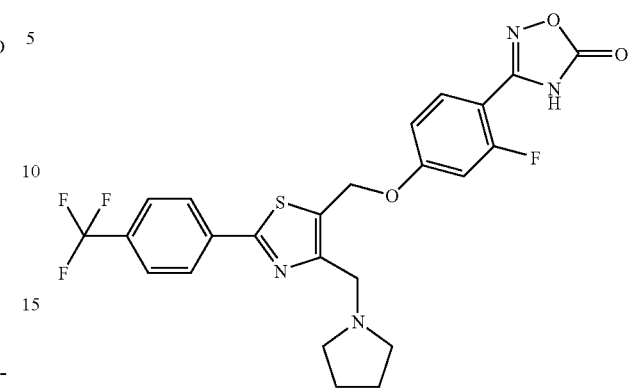

To a suspension of 50 mg of 5-[3-fluoro-4-(5-oxo-4,5-dihydro-[1,2,4]oxadiazol-3-yl)-phenoxymethyl]-2-(4-trifluoromethyl-phenyl)-thiazole-4-carbaldehyde in 2 mL of methanol was added 0.03 mL of pyrrolidine. The resulting solution was stirred at room temperature for 1.5 h then 13.5 mg of sodium cyanoborohydride was added. After stirring at room temperature for 4 h, the reaction mixture was concentrated under reduced pressure. Ethyl acetate/water was added to the residue. The organic layer was separated and the aqueous layer extracted three times with ethyl acetate. The combined organic extracts were dried over magnesium sulfate, filtered, and concentrated under reduced pressure. The crude product was purified by column chromatography on silica gel (dichloromethane 80/methanol 20) to give 9 mg of 3-{2-fluoro-4-[4-pyrrolidin-1-ylmethyl-2-(4-trifluoromethyl-phenyl)-thiazol-5-ylmethoxy]-phenyl}-4H-[1,2,4]oxadiazol-5-one as a beige solid.

C24H20F4N4O3S (520.51), MS (ESI): 521 (M+H+).

Example 36

3-(2-Methoxy-4-{2-(4-trifluoromethyl-phenyl)-4-[(3,3,3-trifluoro-propylamino)-methyl]-thiazol-5-ylmethoxy}-phenyl)-4H-[1,2,4]oxadiazol-5-one

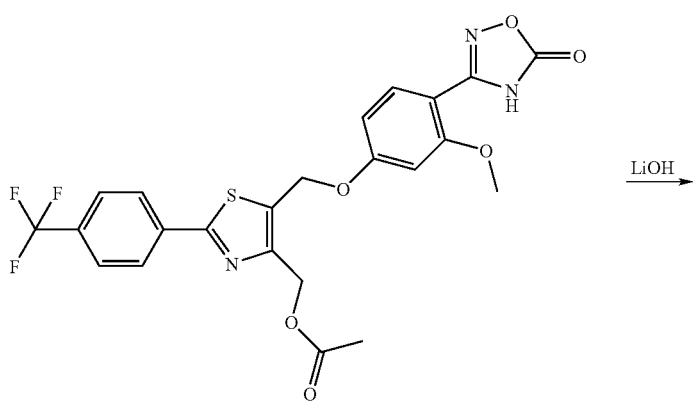

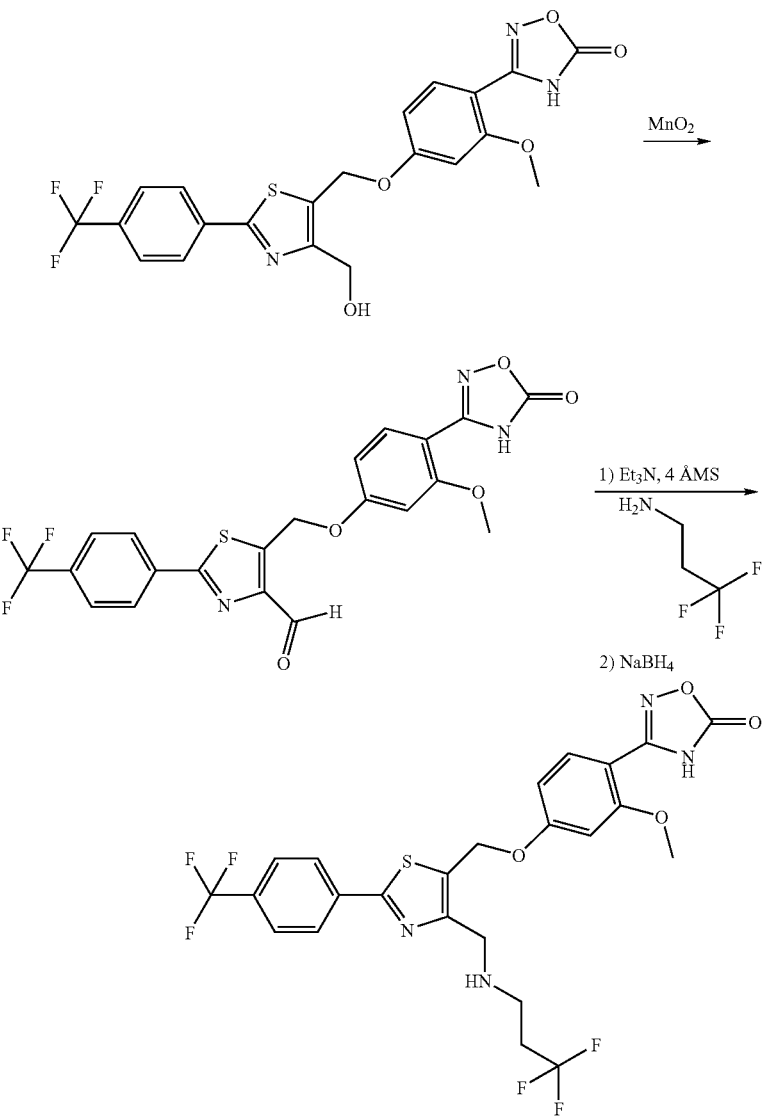
3-{4-[4-Hydroxymethyl-2-(4-trifluoromethyl-phenyl)-thiazol-5-ylmethoxy]-2-methoxy-phenyl}-4H-[1,2,4]oxadiazol-5-one
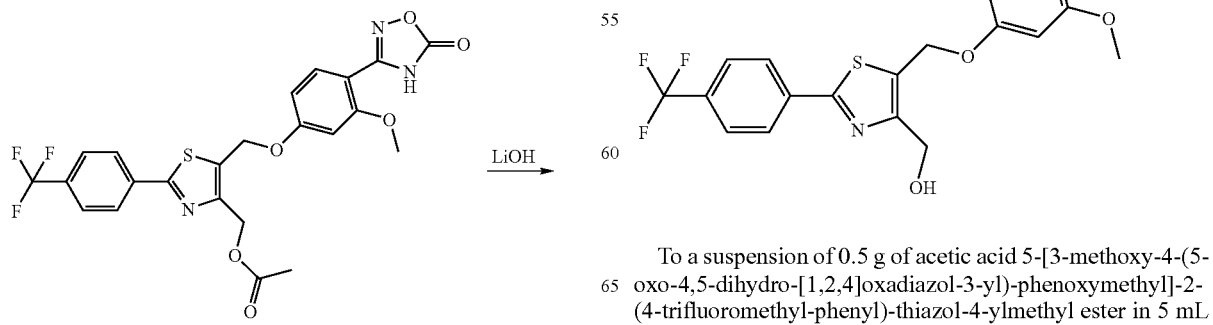
To a suspension of 0.5 g of acetic acid 5-[3-methoxy-4-(5-oxo-4,5-dihydro-[1,2,4]oxadiazol-3-yl)-phenoxymethyl]-2-(4-trifluoromethyl-phenyl)-thiazol-4-ylmethyl ester in 5 mL of methanol at 0° C. was added 0.22 g of lithium hydroxide.

The resulting solution was stirred for 45 minutes at 0° C. then it was allowed to warm up to room temperature. The solvent was partly removed under reduced pressure and ethyl acetate/1 molar aqueous solution of KH2PO4 was added. The organic layer was separated and the aqueous layer extracted three times with ethyl acetate. The combined organic extracts were dried over magnesium sulfate, filtered, and concentrated under reduced pressure. 40 mL of Ethyl acetate was added to the residue and, after stirring for 30 minutes, the resulting solid was collected by filtration to give 225 mg of 3-{4-[4-hydroxymethyl-2-(4-trifluoromethyl-phenyl)-thiazol-5-yl-methoxy]-2-methoxy-phenyl}-4H-[1,2,4]oxadiazol-5-one as a beige solid.

C21H16F3N3O5S (479.44), MS (ESI): 480 (M+H$^+$).

5-[3-Methoxy-4-(5-oxo-4,5-dihydro-[1,2,4]oxadiazol-3-yl)-phenoxymethyl]-2-(4-trifluoromethyl-phenyl)-thiazole-4-carbaldehyde

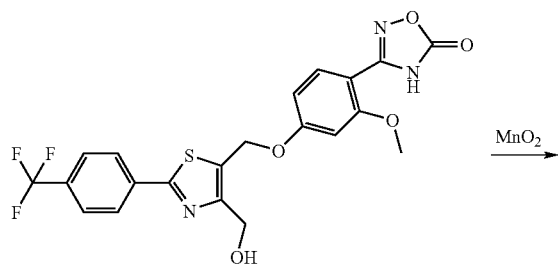

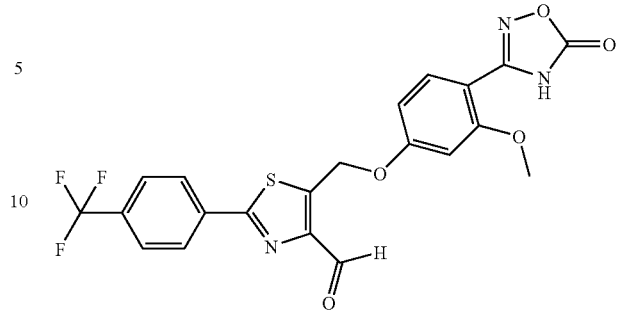

50 mg of 3-{4-[4-hydroxymethyl-2-(4-trifluoromethyl-phenyl)-thiazol-5-ylmethoxy]-2-methoxy-phenyl}-4H-[1,2,4]oxadiazol-5-one were dissolved in 2 mL of dimethylformamide by heating to 60° C. and 2 mL of dichloromethane was added. To the resulting solution was added 90 mg of manganese dioxide. The reaction mixture was heated to 60° C. overnight. 5 mL of dimethylformamide was added. The hot mixture was filtered through celite and washed with dichloromethane/methanol. The filtrate was concentrated under reduced pressure to give 30 mg of 5-[3-methoxy-4-(5-oxo-4,5-dihydro-[1,2,4]oxadiazol-3-yl)-phenoxymethyl]-2-(4-trifluoromethyl-phenyl)-thiazole-4-carbaldehyde which was used in the next step without further purification.

C21H14F3N3O5S (477.42), MS (ESI): 478 (M+H$^+$).

3-(2-Methoxy-4-{2-(4-trifluoromethyl-phenyl)-4-[(3,3,3-trifluoro-propylamino)-methyl]-thiazol-5-yl-methoxy}-phenyl)-4H-[1,2,4]oxadiazol-5-one

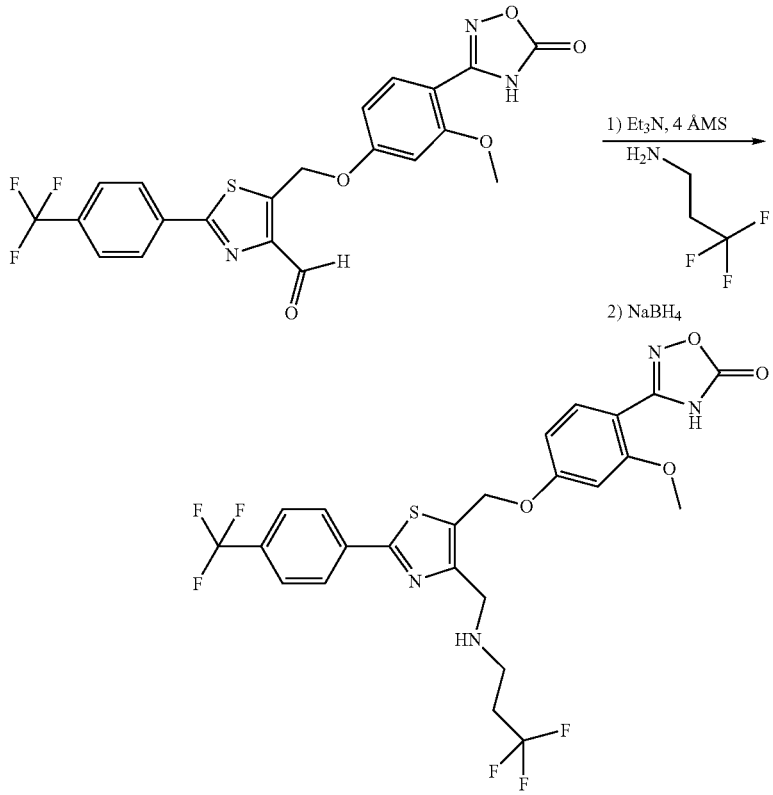

To a suspension of 30 mg of 5-[3-methoxy-4-(5-oxo-4,5-dihydro-[1,2,4]oxadiazol-3-yl)-phenoxymethyl]-2-(4-trifluoromethyl-phenyl)-thiazole-4-carbaldehyde in 1.5 mL of methanol were added 0.018 mL of triethylamine, 10 mg of 3,3,3-trifluoro-propylamine hydrochloride and 0.5 g of 4 Å powdered molecular sieves. The resulting mixture was stirred at room temperature for 1 h then 2.4 mg of sodium borohydride was added. After stirring at room temperature for 45 minutes, the reaction mixture was concentrated under reduced pressure. The crude product was purified by preparative thin layer chromatography on silica gel (dichloromethane 90/methanol 10/water 1/acetic acid 1) followed by azeotropal removal of traces of acetic acid with cyclohexane to give 6.5 mg of 3-(2-methoxy-4-{2-(4-trifluoromethyl-phenyl)-4-[(3,3,3-trifluoro-propylamino)-methyl]-thiazol-5-ylmethoxy}-phenyl)-4H-[1,2,4]oxadiazol-5-one as a white solid.

C24H20F6N4O4S (574.50), MS (ESI): 575 (M+H+).

Example 37

3-{4-[4-((1R,2R,4S)-Bicyclo[2.2.1]hept-2-ylaminomethyl)-2-(4-trifluoromethyl-phenyl)-thiazol-5-ylmethoxy]-2-methoxy-phenyl}-4H-[1,2,4]oxadiazol-5-one

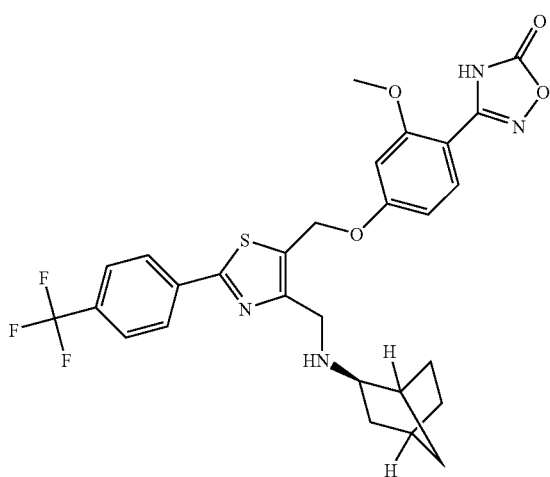

According to the method described for 3-(2-methoxy-4-{2-(4-trifluoromethyl-phenyl)-4-[(3,3,3-trifluoro-propylamino)-methyl]-thiazol-5-ylmethoxy}-phenyl)-4H-[1,2,4]oxadiazol-5-one, 3-{4-[4-((1R,2R,4S)-bicyclo[2.2.1]hept-2-ylaminomethyl)-2-(4-trifluoromethyl-phenyl)-thiazol-5-ylmethoxy]-2-methoxy-phenyl}-4H-[1,2,4]oxadiazol-5-one was obtained from 5-[3-methoxy-4-(5-oxo-4,5-dihydro-[1,2,4]oxadiazol-3-yl)-phenoxymethyl]-2-(4-trifluoromethyl-phenyl)-thiazole-4-carbaldehyde and exo-2-aminonorbornane.

C28H27F3N4O4S (572.61), MS (ESI): 573 (M+H+).

Example 38

3-{2-Methoxy-4-[4-({[(S)-1-(tetrahydro-furan-2-yl)methyl]-amino}-methyl)-2-(4-trifluoromethyl-phenyl)-thiazol-5-ylmethoxy]-phenyl}-4H-[1,2,4]oxadiazol-5-one

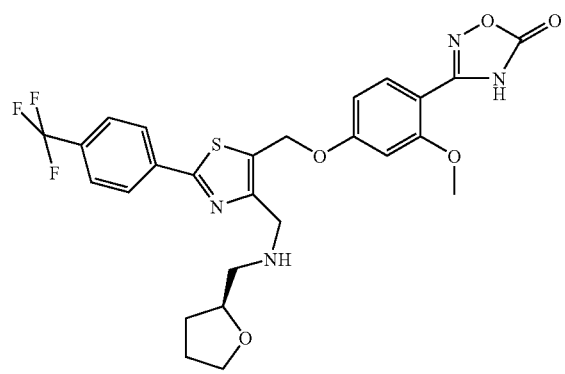

According to the method described for 3-(2-methoxy-4-{2-(4-trifluoromethyl-phenyl)-4-[(3,3,3-trifluoro-propylamino)-methyl]-thiazol-5-ylmethoxy}-phenyl)-4H-[1,2,4]oxadiazol-5-one, 3-{2-methoxy-4-[4-({[(S)-1-(tetrahydro-furan-2-yl)methyl]-amino}-methyl)-2-(4-trifluoromethyl-phenyl)-thiazol-5-ylmethoxy]-phenyl}-4H-[1,2,4]oxadiazol-5-one was obtained from 5-[3-methoxy-4-(5-oxo-4,5-dihydro-[1,2,4]oxadiazol-3-yl)-phenoxymethyl]-2-(4-trifluoromethyl-phenyl)-thiazole-4-carbaldehyde and (S)-(+)-tetrahydrofurfuryl amine.

C26H25F3N4O5S (562.57), MS (ESI): 563 (M+H+).

Example 39

3-{2-Methoxy-4-[4-({[(R)-1-(tetrahydro-furan-2-yl)methyl]-amino}-methyl)-2-(4-trifluoromethyl-phenyl)-thiazol-5-ylmethoxy]-phenyl}-4H-[1,2,4]oxadiazol-5-one

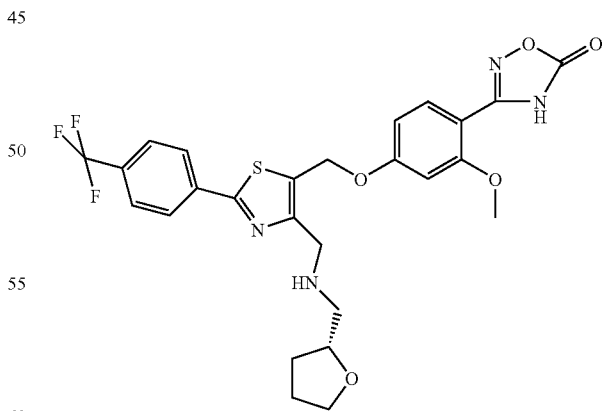

According to the method described for 3-(2-methoxy-4-{2-(4-trifluoromethyl-phenyl)-4-[(3,3,3-trifluoro-propylamino)-methyl]-thiazol-5-ylmethoxy}-phenyl)-4H-[1,2,4]oxadiazol-5-one, 3-{2-methoxy-4-[4-({[(R)-1-(tetrahydro-furan-2-yl)methyl]-amino}-methyl)-2-(4-trifluoromethyl-phenyl)-thiazol-5-ylmethoxy]-phenyl}-4H-[1,2,4]

oxadiazol-5-one was obtained from 5-[3-methoxy-4-(5-oxo-4,5-dihydro-[1,2,4]oxadiazol-3-yl)-phenoxymethyl]-2-(4-trifluoromethyl-phenyl)-thiazole-4-carbaldehyde and (R)-(–)-tetrahydrofurfuryl amine.

C26H25F3N4O5S (562.57), MS (ESI): 563 (M+H$^+$).

Example 40

3-{4-[4-[(Cyclopropylmethyl-amino)-methyl]-2-(4-trifluoromethyl-phenyl)-thiazol-5-ylmethoxy]-2-methoxy-phenyl}-4H-[1,2,4]oxadiazol-5-one

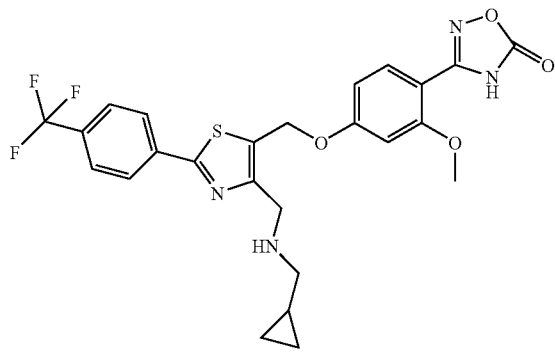

According to the method described for 3-(2-methoxy-4-{2-(4-trifluoromethyl-phenyl)-4-[(3,3,3-trifluoro-propylamino)-methyl]-thiazol-5-ylmethoxy}-phenyl)-4H-[1,2,4]oxadiazol-5-one, 3-{4-[4-[(cyclopropylmethyl-amino)-methyl]-2-(4-trifluoromethyl-phenyl)-thiazol-5-ylmethoxy]-2-methoxy-phenyl}-4H-[1,2,4]oxadiazol-5-one was obtained from 5-[3-methoxy-4-(5-oxo-4,5-dihydro-[1,2,4]oxadiazol-3-yl)-phenoxymethyl]-2-(4-trifluoromethyl-phenyl)-thiazole-4-carbaldehyde and cyclopropylmethyl amine.

C25H23F3N4O4S (532.54), MS (ESI): 533 (M+H$^+$).

Example 41

3-{4-[4-Cyclobutylaminomethyl-2-(4-trifluoromethyl-phenyl)-thiazol-5-ylmethoxy]-2-methoxy-phenyl}-4H-[1,2,4]oxadiazol-5-one

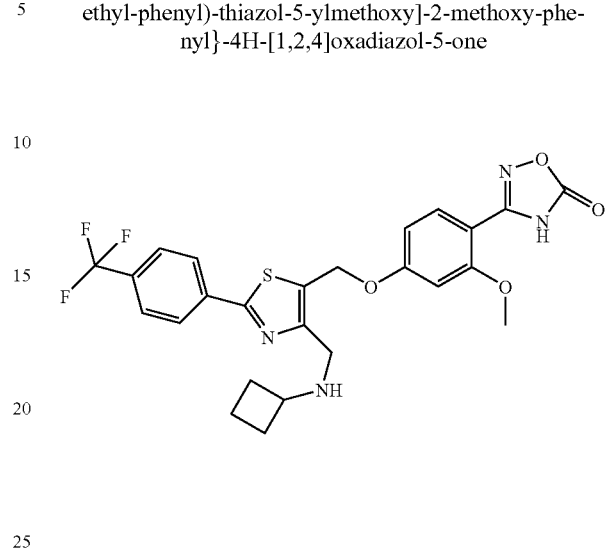

According to the method described for 3-(2-methoxy-4-{2-(4-trifluoromethyl-phenyl)-4-[(3,3,3-trifluoro-propylamino)-methyl]-thiazol-5-ylmethoxy}-phenyl)-4H-[1,2,4]oxadiazol-5-one, 3-{4-[4-cyclobutylaminomethyl-2-(4-trifluoromethyl-phenyl)-thiazol-5-ylmethoxy]-2-methoxy-phenyl}-4H-[1,2,4]oxadiazol-5-one was obtained from 5-[3-methoxy-4-(5-oxo-4,5-dihydro-[1,2,4]oxadiazol-3-yl)-phenoxymethyl]-2-(4-trifluoromethyl-phenyl)-thiazole-4-carbaldehyde and cyclobutylamine.

C25H23F3N4O4S (532.54), MS (ESI): 533 (M+H$^+$).

The following examples were prepared according to process D:

Example 42

3-{4-[4-(4-Methanesulfonyl-piperazin-1-ylmethyl)-2-(4-trifluoromethyl-phenyl)-thiazol-5-ylmethoxy]-2-methoxy-phenyl}-4H-[1,2,4]oxadiazol-5-one

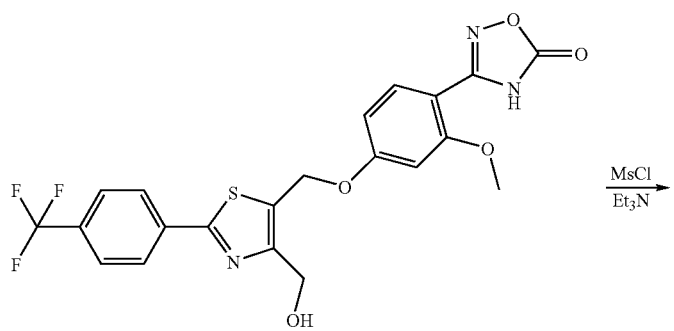

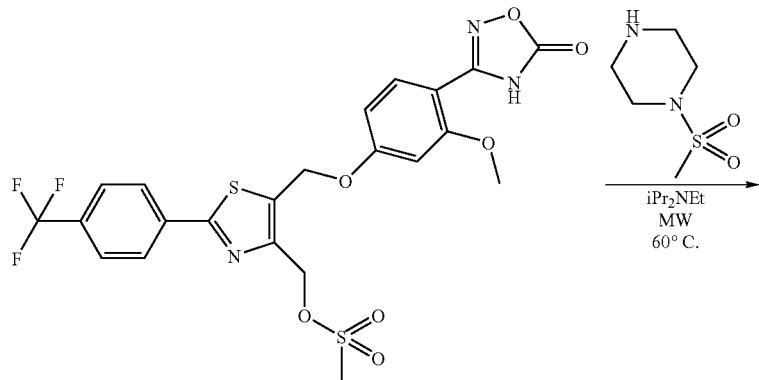
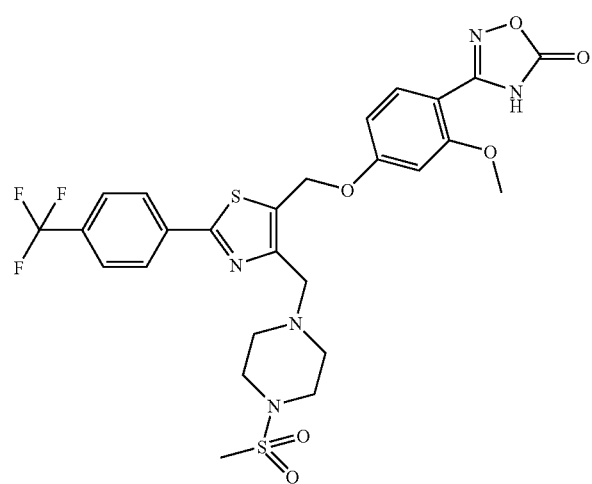
Methanesulfonic acid 5-[3-methoxy-4-(5-oxo-4,5-dihydro-[1,2,4]oxadiazol-3-yl)-phenoxymethyl]-2-(4-trifluoromethyl-phenyl)-thiazol-4-ylmethyl ester
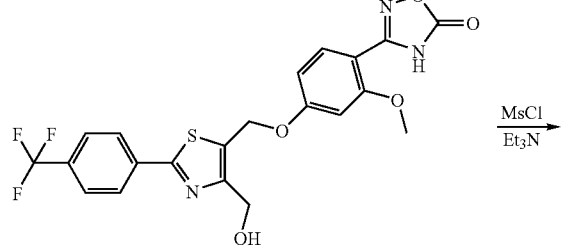
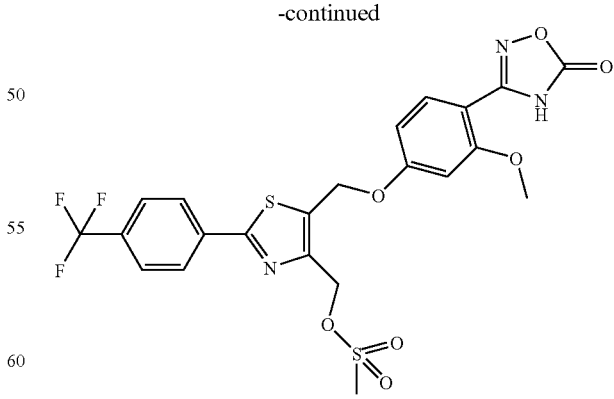
To a solution of 400 mg of 3-{4-[4-hydroxymethyl-2-(4-trifluoromethyl-phenyl)-thiazol-5-ylmethoxy]-2-methoxy-phenyl}-4H-[1,2,4]oxadiazol-5-one in 8 mL of dimethylformamide was added 0.42 mL of triethylamine followed by dropwise addition of 0.1 mL of methanesulfonyl chloride. The resulting mixture was stirred at room temperature for 45 minutes then concentrated under reduced pressure to give 830 mg of crude methanesulfonic acid 5-[3-methoxy-4-(5-oxo-4,5-dihydro-[1,2,4]oxadiazol-3-yl)-phenoxymethyl]-2-(4-trifluoromethyl-phenyl)-thiazol-4-ylmethyl ester which was used in the next step without further purification.

C22H18F3N3O7S2 (557.52), MS (ESI): 558 (M+H+).

3-{4-[4-(4-Methanesulfonyl-piperazin-1-ylmethyl)-2-(4-trifluoromethyl-phenyl)-thiazol-5-ylmethoxy]-2-methoxy-phenyl}-4H-[1,2,4]oxadiazol-5-one

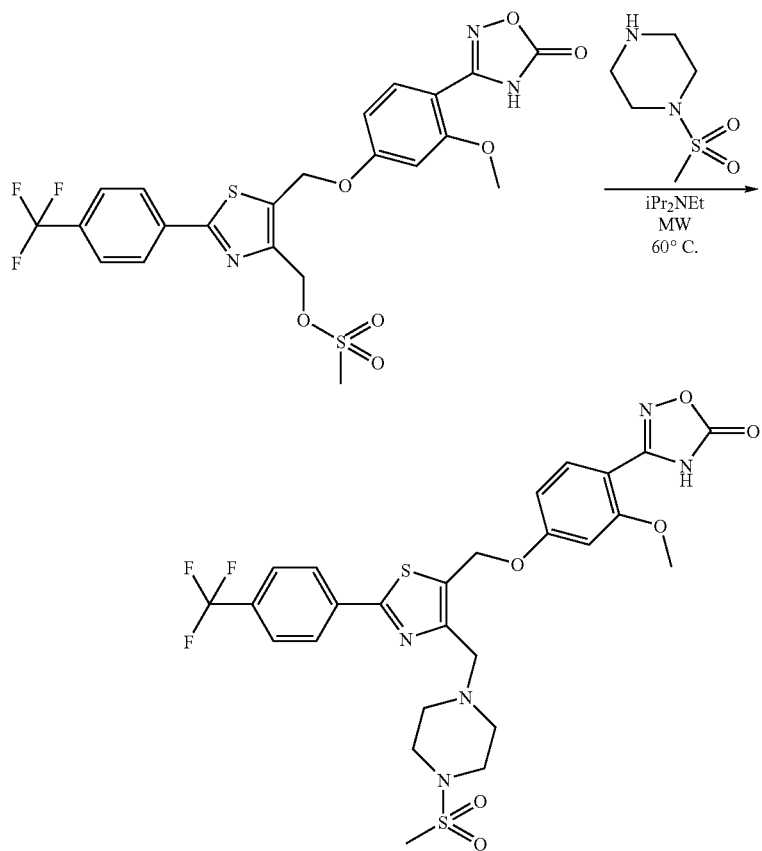

To a solution of 50 mg of methanesulfonic acid 5-[3-methoxy-4-(5-oxo-4,5-dihydro-[1,2,4]oxadiazol-3-yl)-phenoxymethyl]-2-(4-trifluoromethyl-phenyl)-thiazol-4-ylmethyl ester in 2 mL of dimethylformamide was added 80 μL of diisopropylethyl amine and 19.2 mg of 1-methylsulfonylpiperazine. The resulting mixture was heated in a sealed tube to 90° C. under microwave irradiation for 5 minutes and then concentrated under reduced pressure. The residue was purified by chromatography on a SCX Waters column with gradient CH2Cl2/MeOH 30/70 to 7N NH3 in MeOH followed by recrystallization in dichloromethane 9/methanol 1 to give 6.7 mg of 3-{4-[4-(4-methanesulfonyl-piperazin-1-ylm-ethyl)-2-(4-trifluoromethyl-phenyl)-thiazol-5-ylmethoxy]-2-methoxy-phenyl}-4H-[1,2,4]oxadiazol-5-one.

C26H26F3N5O6S2 (625.65), MS (ESI): 626.

Example 43

3-{4-[4-{[Bis-(2-hydroxy-ethyl)-amino]-methyl}-2-(4-trifluoromethyl-phenyl)-thiazol-5-ylmethoxy]-2-methoxy-phenyl}-4H-[1,2,4]oxadiazol-5-one

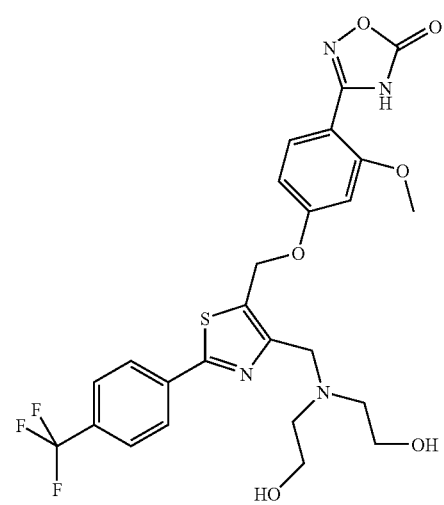

According to the method described for 3-{4-[4-(4-methanesulfonyl-piperazin-1-ylmethyl)-2-(4-trifluoromethyl-phenyl)-thiazol-5-ylmethoxy]-2-methoxy-phenyl}-4H-[1,2,4]oxadiazol-5-one, 3-{4-[4-{[bis-(2-hydroxy-ethyl)-amino]-methyl}-2-(4-trifluoromethyl-phenyl)-thiazol-5-ylmethoxy]-2-methoxy-phenyl}-4H-[1,2,4]oxadiazol-5-one was obtained from methanesulfonic acid 5-[3-methoxy-4-(5-oxo-4,5-dihydro-[1,2,4]oxadiazol-3-yl)-phenoxymethyl]-2-(4-trifluoromethyl-phenyl)-thiazol-4-ylmethyl ester and diethanolamine.

C25H25F3N4O6S (566.55), MS (ESI): 567.

Example 44

3-{4-[4-[(2-Methanesulfinyl-ethylamino)-methyl]-2-(4-trifluoromethyl-phenyl)-thiazol-5-ylmethoxy]-2-methoxy-phenyl}-4H-[1,2,4]oxadiazol-5-one

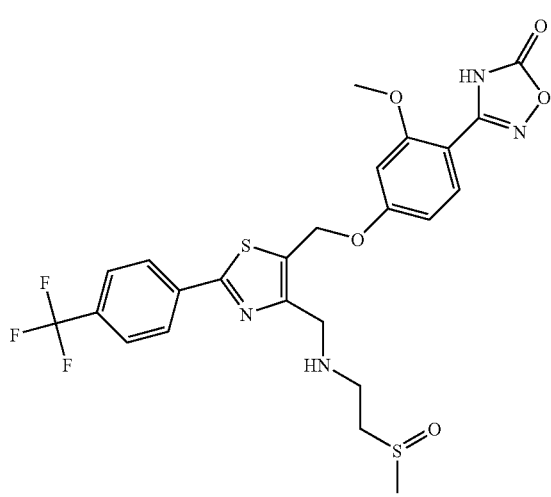

According to the method described for 3-{4-[4-(4-methanesulfonyl-piperazin-1-ylmethyl)-2-(4-trifluoromethyl-phenyl)-thiazol-5-ylmethoxy]-2-methoxy-phenyl}-4H-[1,2,4]oxadiazol-5-one, 3-{4-[4-[(2-methanesulfinyl-ethylamino)-methyl]-2-(4-trifluoromethyl-phenyl)-thiazol-5-ylmethoxy]-2-methoxy-phenyl}-4H-[1,2,4]oxadiazol-5-one was obtained from methanesulfonic acid 5-[3-methoxy-4-(5-oxo-4,5-dihydro-[1,2,4]oxadiazol-3-yl)-phenoxymethyl]-2-(4-trifluoromethyl-phenyl)-thiazol-4-ylmethyl ester and 2-methanesulfinyl-ethylamine.

C24H23F3N4O5S2 (568.59), MS (ESI): 569.

Example 45

3-{2-Methoxy-4-[4-thiomorpholin-4-ylmethyl-2-(4-trifluoromethyl-phenyl)-thiazol-5-ylmethoxy]-phenyl}-4H-[1,2,4]oxadiazol-5-one

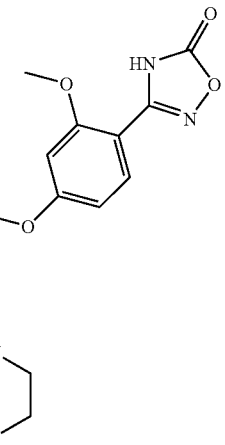

According to the method described for 3-{4-[4-(4-methanesulfonyl-piperazin-1-ylmethyl)-2-(4-trifluoromethyl-phenyl)-thiazol-5-ylmethoxy]-2-methoxy-phenyl}-4H-[1,2,4]oxadiazol-5-one, 3-{2-methoxy-4-[4-thiomorpholin-4-ylmethyl-2-(4-trifluoromethyl-phenyl)-thiazol-5-ylmethoxy]-phenyl}-4H-[1,2,4]oxadiazol-5-one was obtained from methanesulfonic acid 5-[3-methoxy-4-(5-oxo-4,5-dihydro-[1,2,4]oxadiazol-3-yl)-phenoxymethyl]-2-(4-trifluoromethyl-phenyl)-thiazol-4-ylmethyl ester and thiomorpholine.

C25H23F3N4O4S2 (564.61), MS (ESI): 565.

Example 46

3-{4-[4-(1,1-Dioxo-1$\lambda^6$-thiomorpholin-4-ylmethyl)-2-(4-trifluoromethyl-phenyl)-thiazol-5-ylmethoxy]-2-methoxy-phenyl}-4H-[1,2,4]oxadiazol-5-one

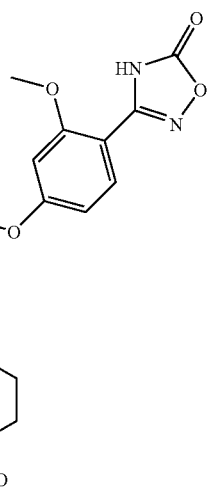

50 mg of 3-{2-Methoxy-4-[4-thiomorpholin-4-ylmethyl-2-(4-trifluoromethyl-phenyl)-thiazol-5-ylmethoxy]-phenyl}-4H-[1,2,4]oxadiazol-5-one were suspended in 3 mL of a 2N solution of hydrochloric acid in ether and 3 mL of methanol were added. The resulting solution was concentrated under reduced pressure. To a suspension of the resulting hydrochloride in 1.5 mL of acetonitrile and 0.5 mL of water was added 108 mg of Oxone® (potassium peroxymonosulfate). The resulting mixture was stirred at room temperature for 1 hour then poured into dichloromethane/water. The organic layer was separated, washed with a saturated aqueous solution of Na2S2O3, dried over magnesium sulfate, filtered, and concentrated under reduced pressure. The crude product was purified by preparative thin layer chromatography on silica gel (dichloromethane 95/acetone 5) to give 4.5 mg of 3-{4-[4-(1,1-dioxo-1λ$^6$-thiomorpholin-4-ylmethyl)-2-(4-trifluoromethyl-phenyl)-thiazol-5-ylmethoxy]-2-methoxyphenyl}-4H-[1,2,4]oxadiazol-5-one.

C25H23F3N4O6S2 (596.60), MS (ESI): 597.

The following examples were prepared according to process E, whereby the first two reaction steps were performed according to process B:

Example 47

3-{2-Methyl-4-[4-propylaminomethyl-2-(4-trifluoromethyl-phenyl)-thiazol-5-ylmethoxy]-phenyl}-4H-[1,2,4]oxadiazol-5-one

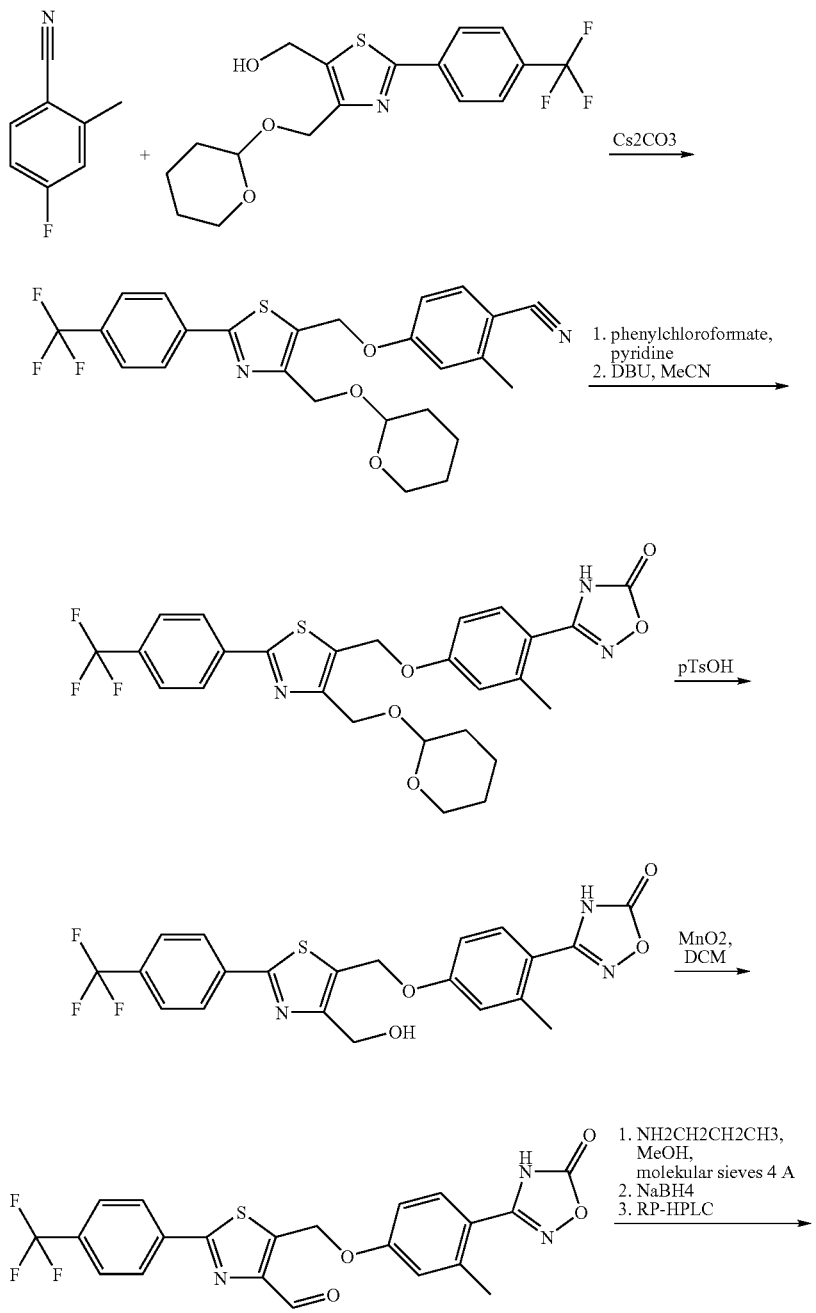

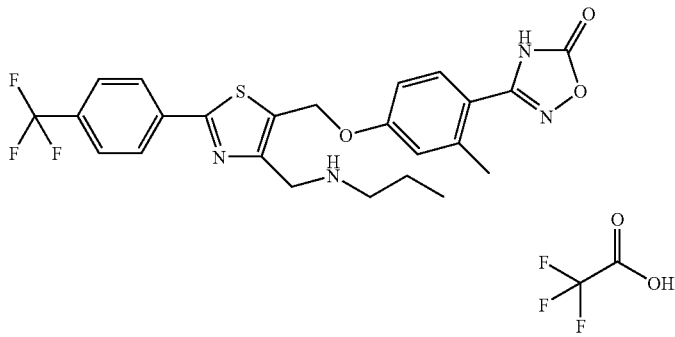

2-Methyl-4-[4-(tetrahydro-pyran-2-yloxymethyl)-2-(4-trifluoromethyl-phenyl)-thiazol-5-ylmethoxy]-benzonitrile

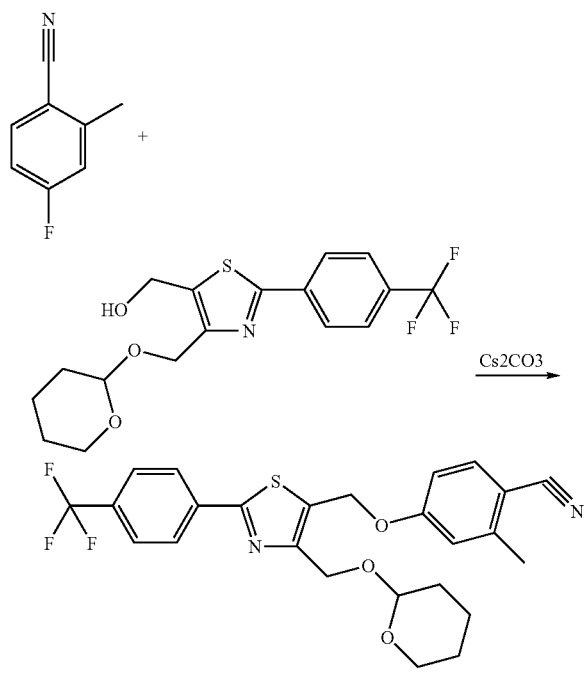

To a stirred solution of 1.09 g 4-fluoro-2-methylbenzonitrile in 50 ml dimethylformamide were given 3.0 g [4-(tetrahydro-pyran-2-yloxymethyl)-2-(4-trifluoromethyl-phenyl)-thiazol-5-yl]-methanol[7] and 2.62 g cesium carbonate. The reaction mixture was stirred at room temperature overnight. 250 ml ethyl acetate were added and the mixture washed five times with portions of 50 ml water and brine. The organic layer was dried over MgSO4, then the solvent was removed in vacuo. The residue was purified by silica gel chromatography with the eluent n-heptane:ethyl acetate=15:1=>2:1 to obtain 1.5 g 2-methyl-4-[4-(tetrahydro-pyran-2-yloxymethyl)-2-(4-trifluoromethyl-phenyl)-thiazol-5-ylmethoxy]-benzonitrile as pale yellow solid.

[7] WO 2002067912, WO 2002059098

C25H23F3N2O3S (488.53), MS (ESI): 489.2, 405.2, Rf (n-heptane:ethyl acetate=2:1)=0.36.

3-{2-Methyl-4-[4-(tetrahydro-pyran-2-yloxymethyl)-2-(4-trifluoromethyl-phenyl)-thiazol-5-ylmethoxy]-phenyl}-4H-[1,2,4]oxadiazol-5-one

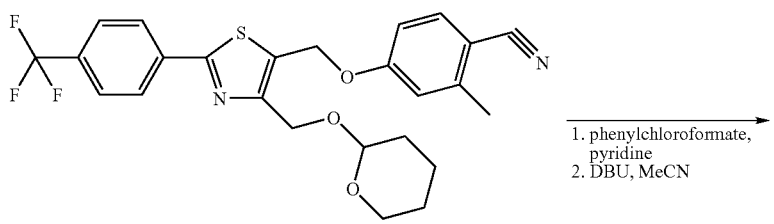

1. phenylchloroformate, pyridine
2. DBU, MeCN

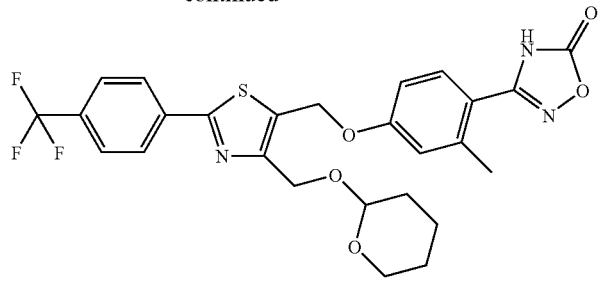

1.5 g 2-Methyl-4-[4-(tetrahydro-pyran-2-yloxymethyl)-2-(4-trifluoromethyl-phenyl)-thiazol-5-ylmethoxy]-benzonitrile were dissolved in a mixture of 10 ml tetrahydrofuran and 10 ml methanol. 2.12 g hydroxylamine hydrochloride were added followed by the addition of 5.08 ml triethylamine. The reaction mixture was stirred at 65° C. overnight. The solvents were removed in vacuo and the resulting residue poured into water and extracted five times with ethylacetate. The combined organic extracts were washed with brine, dried over MgSO4 and the solvent was evaporated in vacuo. The residue was dissolved in 10 ml dichloromethane. 0.32 ml pyridine and 0.49 ml phenylchloroformate were added and the mixture stirred at room temperature for fifteen minutes. The mixture was diluted by the addition of 50 ml acetonitrile and 2.28 ml 1,8-diazabicyclo[5.4.0]undec-7-ene were added. The mixture was stirred at room temperature for thirty minutes. The mixture was evaporated in vacuo and the resulting crude material was purified by silica gel chromatography with the eluent n-heptane: ethyl acetate=4:1=>ethyl acetate=>ethyl acetate:methanol=4:1 to obtain 1.05 g 3-{2-methyl-4-[4-(tetrahydro-pyran-2-yloxymethyl)-2-(4-trifluoromethyl-phenyl)-thiazol-5-ylmethoxy]-phenyl}-4H-[1,2,4]oxadiazol-5-one as pale yellow solid.

C26H24F3N3O5S (547.56), MS (ESI): 464.2.

5-[3-Methyl-4-(5-oxo-4,5-dihydro-[1,2,4]oxadiazol-3-yl)-phenoxymethyl]-2-(4-trifluoromethyl-phenyl)-thiazole-4-carbaldehyde

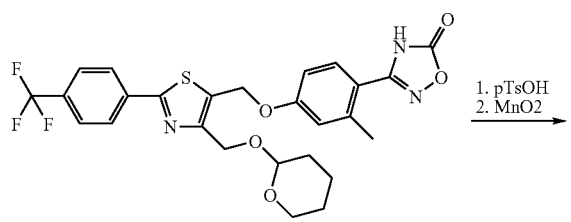

1.05 g 3-{2-Methyl-4-[4-(tetrahydro-pyran-2-yloxymethyl)-2-(4-trifluoromethyl-phenyl)-thiazol-5-ylmethoxy]-phenyl}-4H-[1,2,4]oxadiazol-5-one was suspended in 80 ml methanol. 66.0 mg p-Toluenesulfonic acid were added and the reaction mixture warmed to 60° C. until the reaction mixture became a clear solution. The cooled reaction mixture was evaporated in vacuo. The residue was dissolved in a mixture of 10 ml dimethylformamide and 40 ml dichloromethane. 3.76 g Manganese (IV) oxide on activated charcoil were added and the reaction mixture heated to reflux for two hours. The cooled reaction mixture was filtered through a celite pad. The filtrate was evaporated in vacuo to obtain 670 mg crude 5-[3-methyl-4-(5-oxo-4,5-dihydro-[1,2,4]oxadiazol-3-yl)-phenoxymethyl]-2-(4-trifluoromethyl-phenyl)-thiazole-4-carbaldehyde which was used without further purification.

C21H14F3N3O4S (461.42), MS (ESI): 462.0, Rf (ethyl acetate:methanol=19:1)=0.52.

3-{2-Methyl-4-[4-propylaminomethyl-2-(4-trifluoromethyl-phenyl)-thiazol-5-ylmethoxy]-phenyl}-4H-[1,2,4]oxadiazol-5-one

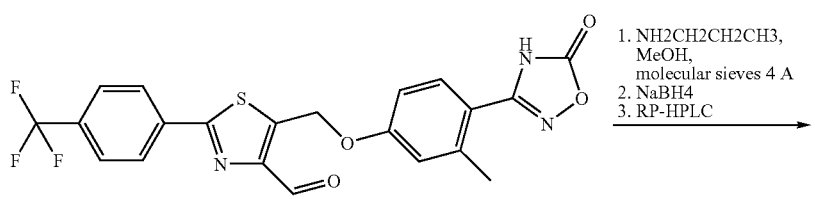

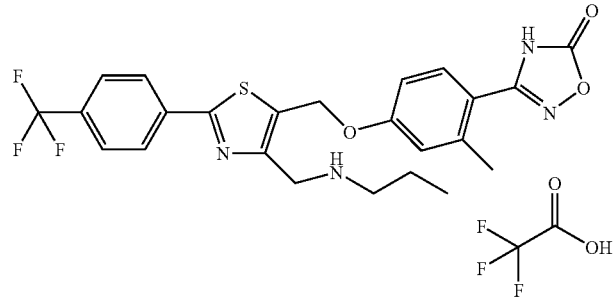

100 mg 5-[3-Methyl-4-(5-oxo-4,5-dihydro-[1,2,4]oxadiazol-3-yl)-phenoxymethyl]-2-(4-trifluoromethyl-phenyl)-thiazole-4-carbaldehyde and 12.8 mg propylamine were suspended in 3 ml methanol. 30.0 µl triethylamine were added upon the reaction mixture became a clear solution. 400 mg molecular sieves four angstrom were added and the reaction mixture stirred at room temperature for two hours. Then 8.2 mg sodium borohydride were added and the reaction mixture stirred at room temperature for thirty minutes. The reaction mixture was filtered through a celite pad. The filtrate was evaporated in vacuo and then evaporated in vacuo. The residue was purified by RP-HPLC to obtain 45.7 mg 3-{2-methyl-4-[4-propylaminomethyl-2-(4-trifluoromethyl-phenyl)-thiazol-5-ylmethoxy]-phenyl}-4H-[1,2,4]oxadiazol-5-one as its trifluoroacetate salt.

C24H23F3N4O3S.C2HF3O2 (618.56), MS (ESI): 505.1.

Example 48

3-{4-[4-[(2-Methoxy-ethylamino)-methyl]-2-(4-trifluoromethyl-phenyl)-thiazol-5-ylmethoxy]-2-methyl-phenyl}-4H-[1,2,4]oxadiazol-5-one

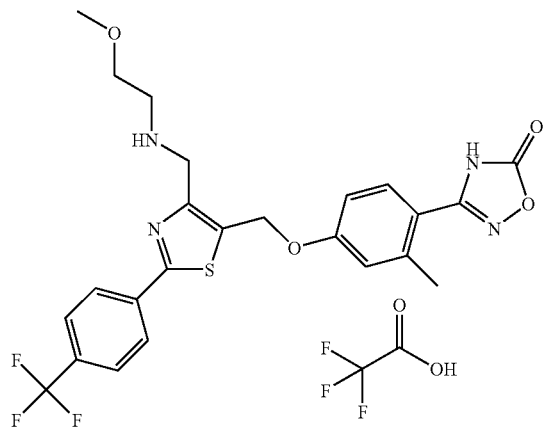

According to the method described for 3-{2-methyl-4-[4-propylaminomethyl-2-(4-trifluoromethyl-phenyl)-thiazol-5-ylmethoxy]-phenyl}-4H-[1,2,4]oxadiazol-5-one in example 47, 3-{4-[4-[(2-methoxy-ethylamino)-methyl]-2-(4-trifluoromethyl-phenyl)-thiazol-5-ylmethoxy]-2-methyl-phenyl}-4H-[1,2,4]oxadiazol-5-one was obtained from 5-[3-Methyl-4-(5-oxo-4,5-dihydro-[1,2,4]oxadiazol-3-yl)-phenoxymethyl]-2-(4-trifluoromethyl-phenyl)-thiazole-4-carbaldehyde and 2-methoxyethylamine. The compound was obtained as its trifluoroacetate salt.

C24H23F3N4O4S.C2HF3O2 (634.56), MS (ESI): 521.1.

Example 49

3-{2-Methyl-4-[4-{[2-(1-methyl-pyrrolidin-2-yl)-ethylamino]-methyl}-2-(4-trifluoromethyl-phenyl)-thiazol-5-ylmethoxy]-phenyl}-4H-[1,2,4]oxadiazol-5-one

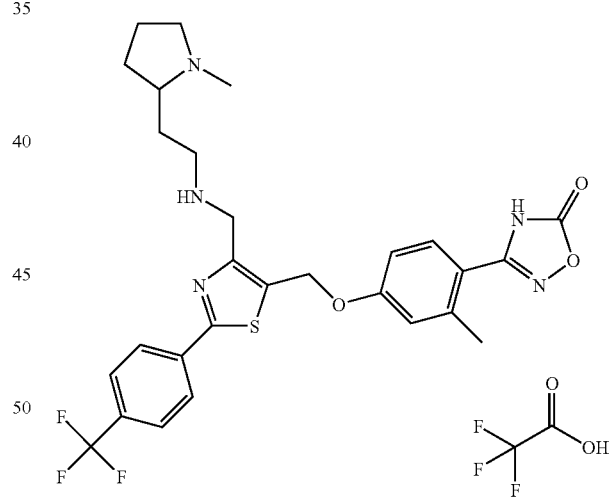

According to the method described for 3-{2-methyl-4-[4-propylaminomethyl-2-(4-trifluoromethyl-phenyl)-thiazol-5-ylmethoxy]-phenyl}-4H-[1,2,4]oxadiazol-5-one in example 47, 3-{2-methyl-4-[4-{[2-(1-methyl-pyrrolidin-2-yl)-ethylamino]-methyl}-2-(4-trifluoromethyl-phenyl)-thiazol-5-ylmethoxy]-phenyl}-4H-[1,2,4]oxadiazol-5-one was obtained from 5-[3-methyl-4-(5-oxo-4,5-dihydro-[1,2,4]oxadiazol-3-yl)-phenoxymethyl]-2-(4-trifluoromethyl-phenyl)-thiazole-4-carbaldehyde and 2-(2-aminoethyl)-1-methylpyrrolidine. The compound was obtained as its trifluoroacetate salt.

C24H23F3N4O3S.C2HF3O2 (618.56), MS (ESI): 574.2.

Example 50

3-{2-Methyl-4-[4-[(2-pyrrolidin-1-yl-ethylamino)-methyl]-2-(4-trifluoromethyl-phenyl)-thiazol-5-ylmethoxy]-phenyl}-4H-[1,2,4]oxadiazol-5-one

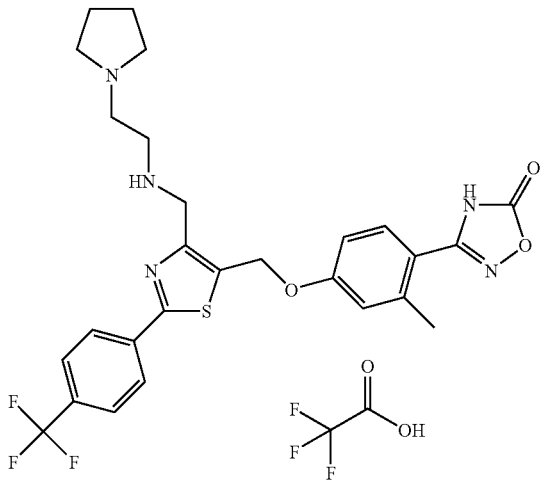

According to the method described for 3-{2-methyl-4-[4-propylaminomethyl-2-(4-trifluoromethyl-phenyl)-thiazol-5-ylmethoxy]-phenyl}-4H-[1,2,4]oxadiazol-5-one in example 47, 3-{2-methyl-4-[4-[(2-pyrrolidin-1-yl-ethylamino)-methyl]-2-(4-trifluoromethyl-phenyl)-thiazol-5-ylmethoxy]-phenyl}-4H-[1,2,4]oxadiazol-5-one was obtained from 5-[3-methyl-4-(5-oxo-4,5-dihydro-[1,2,4]oxadiazol-3-yl)-phenoxymethyl]-2-(4-trifluoromethyl-phenyl)-thiazole-4-carbaldehyde and N-(2-aminoethyl)pyrrolidine. The compound was obtained as its trifluoroacetate salt.

C27H28F3N5O3S.2C2HF3O2 (787.66), MS (ESI): 560.2.

Example 51

3-{2-Methyl-4-[4-[(2-morpholin-4-yl-ethylamino)-methyl]-2-(4-trifluoromethyl-phenyl)-thiazol-5-ylmethoxy]-phenyl}-4H-[1,2,4]oxadiazol-5-one

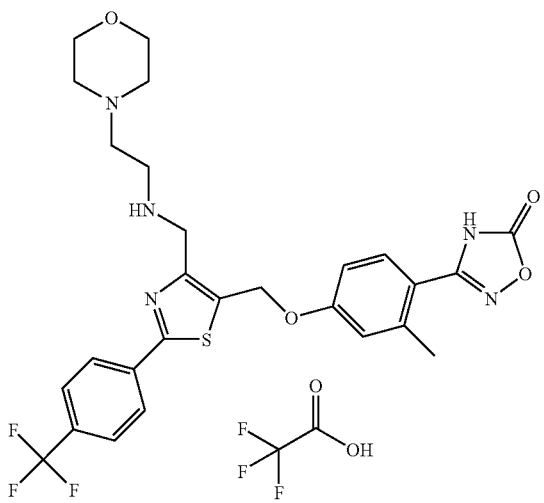

According to the method described for 3-{2-methyl-4-[4-propylaminomethyl-2-(4-trifluoromethyl-phenyl)-thiazol-5-ylmethoxy]-phenyl}-4H-[1,2,4]oxadiazol-5-one in example 47, 3-{2-methyl-4-[4-[(2-morpholin-4-yl-ethylamino)-methyl]-2-(4-trifluoromethyl-phenyl)-thiazol-5-ylmethoxy]-phenyl}-4H-[1,2,4]oxadiazol-5-one was obtained from 5-[3-methyl-4-(5-oxo-4,5-dihydro-[1,2,4]oxadiazol-3-yl)-phenoxymethyl]-2-(4-trifluoromethyl-phenyl)-thiazole-4-carbaldehyde and N-(2-aminoethyl)-morpholine. The compound was obtained as its trifluoroacetate salt.

C27H28F3N5O4S.C2HF3O2 (803.66), MS (ESI): 576.2.

Example 52

3-{2-Methyl-4-[4-[(2-piperidin-1-yl-ethylamino)-methyl]-2-(4-trifluoromethyl-phenyl)-thiazol-5-ylmethoxy]-phenyl}-4H-[1,2,4]oxadiazol-5-one

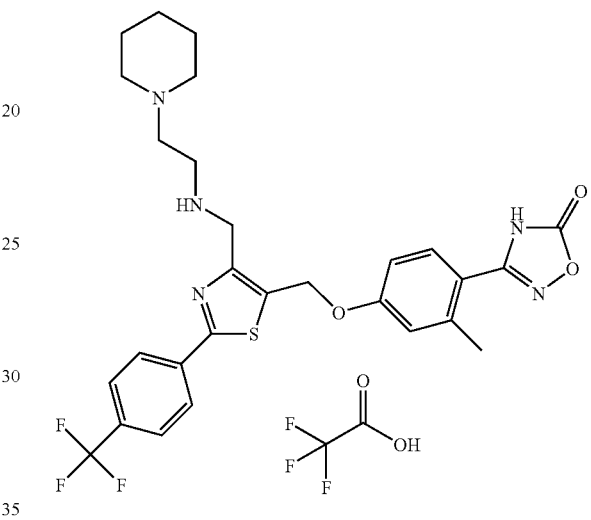

According to the method described for 3-{2-methyl-4-[4-propylaminomethyl-2-(4-trifluoromethyl-phenyl)-thiazol-5-ylmethoxy]-phenyl}-4H-[1,2,4]oxadiazol-5-one in example 47, 3-{2-methyl-4-[4-[(2-piperidin-1-yl-ethylamino)-methyl]-2-(4-trifluoromethyl-phenyl)-thiazol-5-ylmethoxy]-phenyl}-4H-[1,2,4]oxadiazol-5-one was obtained from 5-[3-methyl-4-(5-oxo-4,5-dihydro-[1,2,4]oxadiazol-3-yl)-phenoxymethyl]-2-(4-trifluoromethyl-phenyl)-thiazole-4-carbaldehyde and 1-(2-aminoethyl)piperidine. The compound was obtained as its trifluoroacetate salt.

C28H30F3N5O3S.C2HF3O2 (801.69), MS (ESI): 574.2.

Example 53

3-{4-[4-[(2-Dimethylamino-ethylamino)-methyl]-2-(4-trifluoromethyl-phenyl)-thiazol-5-ylmethoxy]-2-methyl-phenyl}-4H-[1,2,4]oxadiazol-5-one

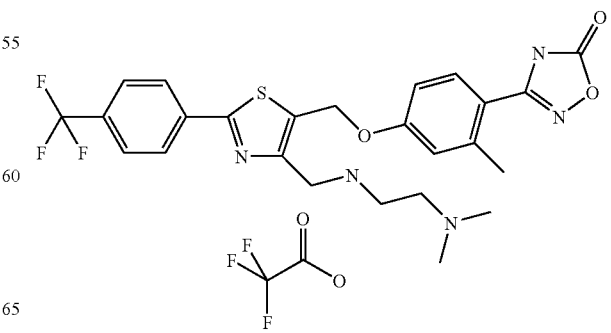

201

According to the method described for 3-{2-methyl-4-[4-propylaminomethyl-2-(4-trifluoromethyl-phenyl)-thiazol-5-ylmethoxy]-phenyl}-4H-[1,2,4]oxadiazol-5-one in example 47, 3-{4-[4-[(2-dimethylamino-ethylamino)-methyl]-2-(4-trifluoromethyl-phenyl)-thiazol-5-ylmethoxy]-2-methyl-phenyl}-4H-[1,2,4]oxadiazol-5-one was obtained from 5-[3-methyl-4-(5-oxo-4,5-dihydro-[1,2,4]oxadiazol-3-yl)-phenoxymethyl]-2-(4-trifluoromethyl-phenyl)-thiazole-4-carbaldehyde and N,N-dimethylethylenediamine. The compound was obtained as its trifluoroacetate salt.

C25H26F3N5O3S.C2HF3O2 (761.63), MS (ESI): 534.2.

The following examples were prepared according to process A:

Example 54

3-(2-Chloro-4-{4-methyl-2-[2-(4-trifluoromethyl-phenyl)-ethyl]-oxazol-5-ylmethoxy}-phenyl)-4H-[1,2,4]oxadiazol-5-one

202

2-Chloro-4-{4-methyl-2-[2-(4-trifluoromethyl-phenyl)-ethyl]-oxazol-5-ylmethoxy}-benzonitrile

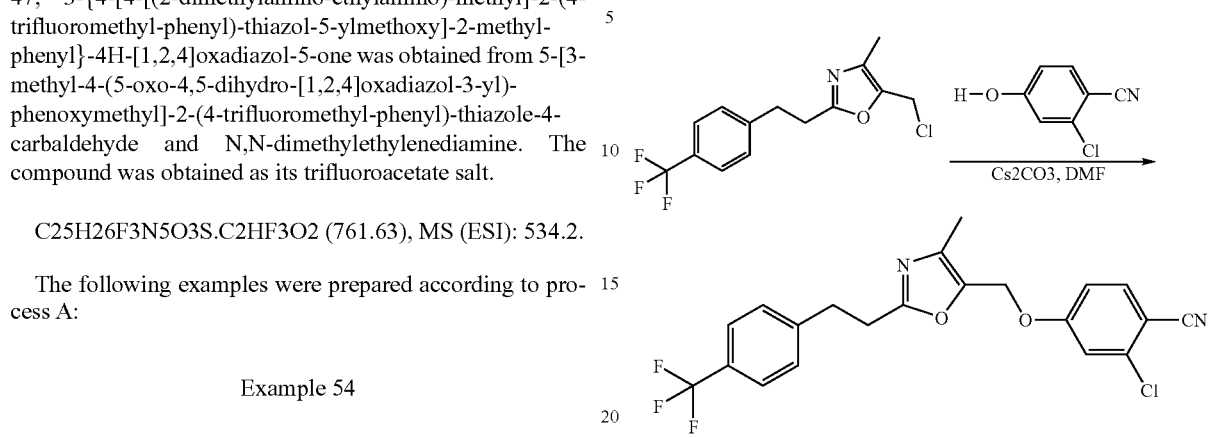

To a solution of 2.63 g 2-chloro-4-hydroxy-benzonitrile in 25 ml dimethylformamide were added 4.0 g 5-chloromethyl-

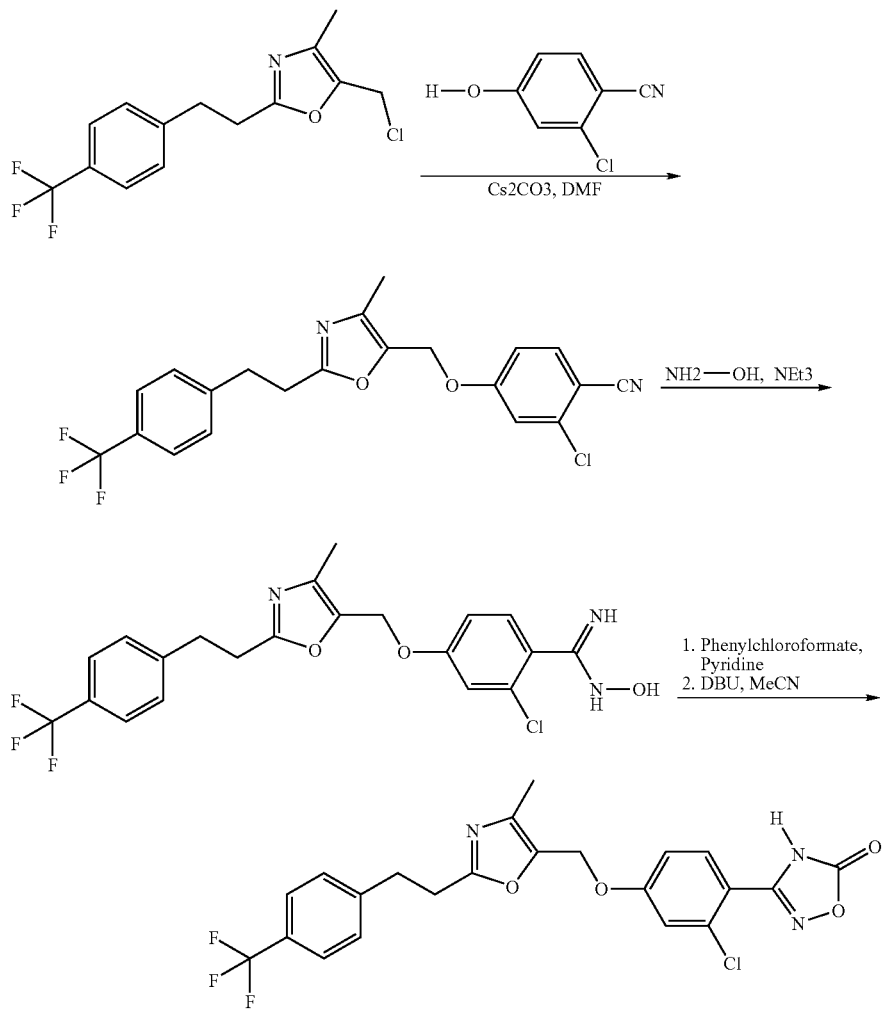

4-methyl-2-[2-(4-trifluoromethyl-phenyl)-ethyl]-oxazole and 8.58 g cesium carbonate. The mixture was stirred at room temperature overnight. Then 150 ml of ethyl acetate were added, the mixture washed with 40 ml water and brine and then dried over MgSO4. The solvent was removed in vacuo. The resulting crude material was purified by RP-HPLC to obtain 3.0 g 2-chloro-4-{4-methyl-2-[2-(4-trifluoromethyl-phenyl)-ethyl]-oxazol-5-ylmethoxy}-benzonitrile.

C21H16ClF3N2O2 (420.82), MS (ESI): 421.1 (M+H$^+$).

2-Chloro-N-hydroxy-4-{4-methyl-2-[2-(4-trifluoromethyl-phenyl)-ethyl]-oxazol-5-ylmethoxy}-benzamidine 3.0 g 2-Chloro-4-{4-methyl-2-[2-(4-trifluoromethyl-phenyl)-ethyl]-oxazol-5-ylmethoxy}-benzonitrile were dissolved in a mixture of 20 ml tetrahydrofuran and 20 ml methanol. 9.91 g hydroxylamine hydrochloride were added followed by the addition of 19.9 ml triethylamine. The reaction mixture was stirred at 65° C. overnight. The solvents were removed in vacuo and the resulting residue poured into water and extracted five times with ethylacetate. The combined organic extracts were washed with brine, dried over MgSO4 and the solvent was evaporated in vacuo to obtain 4.4 g crude 2-chloro-N-hydroxy-4-{4-methyl-2-[2-(4-trifluoromethyl-phenyl)-ethyl]-oxazol-5-ylmethoxy}-benzamidine which was used without further purification.

C21H19ClF3N3O3 (453.85), MS (ESI): 454.2 (M+H$^+$).

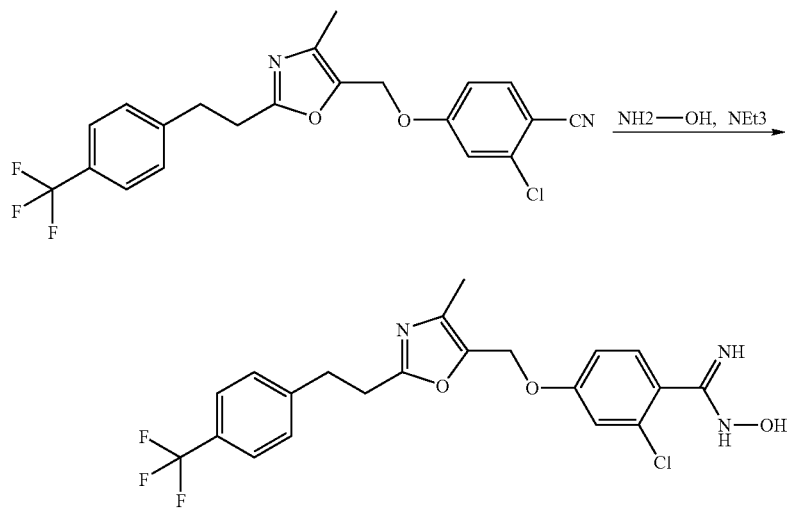

3-(2-Chloro-4-{4-methyl-2-[2-(4-trifluoromethyl-phenyl)-ethyl]-oxazol-5-ylmethoxy}-phenyl)-4H-[1,2,4]oxadiazol-5-one

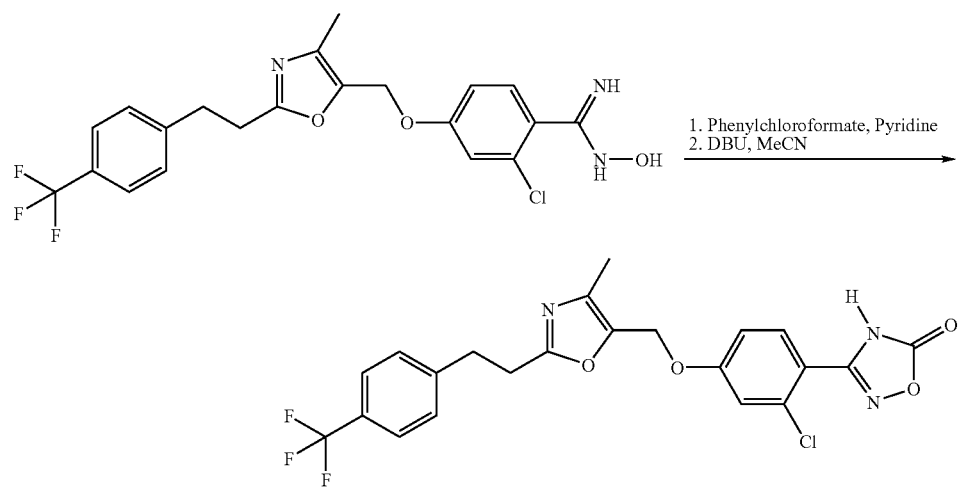

4.4 g crude 2-Chloro-N-hydroxy-4-{4-methyl-2-[2-(4-trifluoromethyl-phenyl)-ethyl]-oxazol-5-ylmethoxy}-benzamidine were dissolved in 20 ml dichloromethane. 0.94 ml pyridine and 1.46 ml phenylchloroformate were added and the mixture stirred at room temperature for ten minutes. The mixture was diluted by the addition of 40 ml acetonitrile and 7.25 ml 1,8-diazabicyclo[5.4.0]undec-7-ene were added. The mixture was stirred at room temperature for 10 minutes. The mixture was evaporated in vacuo and the resulting crude material was purified by reversed phase HPLC to obtain 460 mg 3-(2-chloro-4-{4-methyl-2-[2-(4-trifluoromethyl-phenyl)-ethyl]-oxazol-5-ylmethoxy}-phenyl)-4H-[1,2,4]oxadiazol-5-one.

C22H17ClF3N3O4 (479.85), MS (ESI): 479.98 (M+H⁺).

Example 55

3-(2-Chloro-4-[4-methoxymethyl-2-[2-(4-methoxy-phenyl)-vinyl]-oxazol-5-ylmethoxy]-phenyl)-4H-[1,2,4]oxadiazol-5-one

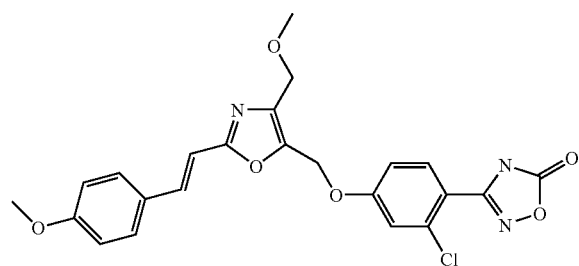

According to the method described for 3-(2-chloro-4-{4-methyl-2-[2-(4-trifluoromethyl-phenyl)-ethyl]-oxazol-5-ylmethoxy}-phenyl)-4H-[1,2,4]oxadiazol-5-one in example 54, 3-(2-chloro-4-{4-methoxymethyl-2-[2-(4-methoxy-phenyl)-vinyl]-oxazol-5-ylmethoxy}-phenyl)-4H-[1,2,4]oxadiazol-5-one was obtained from 5-chloromethyl-4-methoxymethyl-2-[2-(4-methoxy-phenyl)-vinyl]-oxazole and 2-chloro-4-hydroxy-benzonitrile.

C23H20ClN3O6 (469.88), MS (ESI): 470.0 (M+H⁺).

Example 56

3-[4-(2-Benzyloxymethyl-4-methyl-oxazol-5-ylmethoxy)-2-chloro-phenyl]-4H-[1,2,4]oxadiazol-5-one

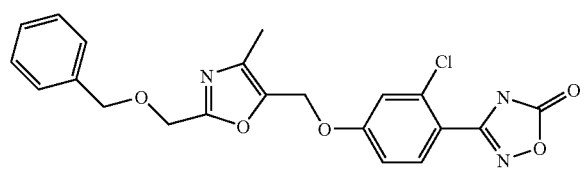

According to the method described for 3-(2-chloro-4-{4-methyl-2-[2-(4-trifluoromethyl-phenyl)-ethyl]-oxazol-5-ylmethoxy}-phenyl)-4H-[1,2,4]oxadiazol-5-one in example 54, 3-[4-(2-benzyloxymethyl-4-methyl-oxazol-5-ylmethoxy)-2-chloro-phenyl]-4H-[1,2,4]oxadiazol-5-one was obtained from 2-benzyloxymethyl-5-chloromethyl-4-methyl-oxazole and 2-chloro-4-hydroxy-benzonitrile.

C21H18ClN3O5 (427.85), MS (ESI): 428.4 (M+H⁺).

Example 57

3-{2-Chloro-4-[2-(4-methoxy-benzyl)-4-methyl-oxazol-5-ylmethoxy]-phenyl}-4H-[1,2,4]oxadiazol-5-one

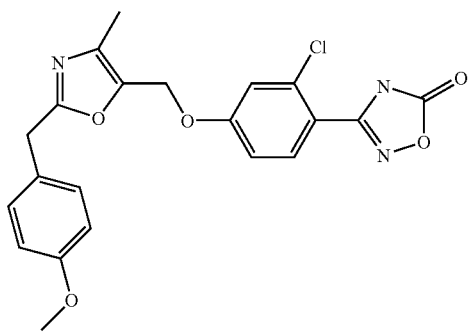

According to the method described for 3-(2-chloro-4-{4-methyl-2-[2-(4-trifluoromethyl-phenyl)-ethyl]-oxazol-5-ylmethoxy}-phenyl)-4H-[1,2,4]oxadiazol-5-one in example 54, 3-{2-chloro-4-[2-(4-methoxy-benzyl)-4-methyl-oxazol-5-ylmethoxy]-phenyl}-4H-[1,2,4]oxadiazol-5-one was obtained from 5-chloromethyl-2-(4-methoxy-benzyl)-4-methyl-oxazole and 2-chloro-4-hydroxy-benzonitrile.

C21H18ClN3O5 (427.85), MS (ESI): 428.2 (M+H⁺).

Example 58

3-(2-Chloro-4-{4-methoxymethyl-2-[2-(4-trifluoromethyl-phenyl)-vinyl]-thiazol-5-ylmethoxy}-phenyl)-4H-[1,2,4]oxadiazol-5-one

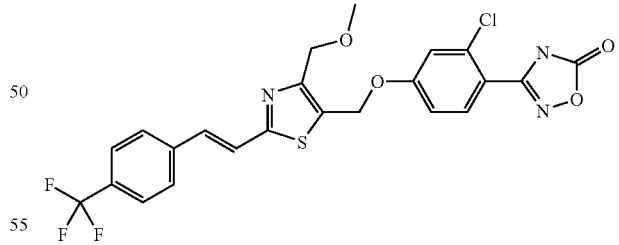

According to the method described for 3-(2-chloro-4-{4-methyl-2-[2-(4-trifluoromethyl-phenyl)-ethyl]-oxazol-5-ylmethoxy}-phenyl)-4H-[1,2,4]oxadiazol-5-one in example 54, 3-(2-chloro-4-{4-methoxymethyl-2-[2-(4-trifluoromethyl-phenyl)-vinyl]-thiazol-5-ylmethoxy}-phenyl)-4H-[1,2,4]oxadiazol-5-one was obtained from 5-chloromethyl-4-methoxymethyl-2-[2-(4-trifluoromethyl-phenyl)-vinyl]-thiazole and 2-chloro-4-hydroxy-benzonitrile.

C23H17ClF3N3O4S (523.92), MS (ESI): 524.0 (M+H⁺).

Example 59

3-{2-Chloro-4-[4-(2,2,2-trifluoro-ethoxymethyl)-2-(4-trifluoromethyl-phenyl)-oxazol-5-ylmethoxy]-phenyl}-4H-[1,2,4]oxadiazol-5-one

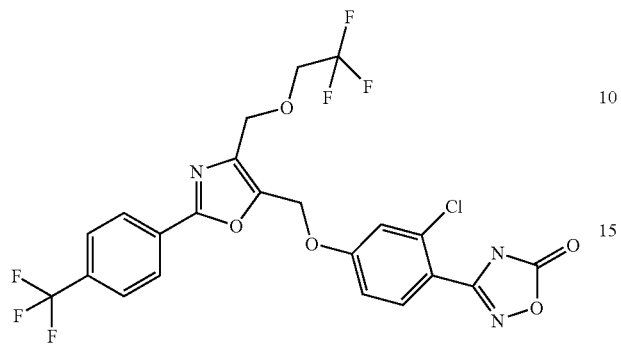

According to the method described for 3-(2-chloro-4-{4-methyl-2-[2-(4-trifluoromethyl-phenyl)-ethyl]-oxazol-5-yl-methoxy}-phenyl)-4H-[1,2,4]oxadiazol-5-one in example 54, 3-{2-chloro-4-[4-(2,2,2-trifluoro-ethoxymethyl)-2-(4-trifluoromethyl-phenyl)-oxazol-5-ylmethoxy]-phenyl}-4H-[1,2,4]oxadiazol-5-one was obtained from 5-chloromethyl-4-(2,2,2-trifluoro-ethoxymethyl)-2-(4-trifluoromethyl-phenyl)-oxazole and 2-chloro-4-hydroxy-benzonitrile.

C22H14ClF6N3O5 (549.82), MS (ESI): 550.2 (M+H$^+$).

The following examples were prepared according to process L, whereby the first reaction step was performed according to general process B [B1+B2=>B3]:

Example 60

3-{4-[4-{[Ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one

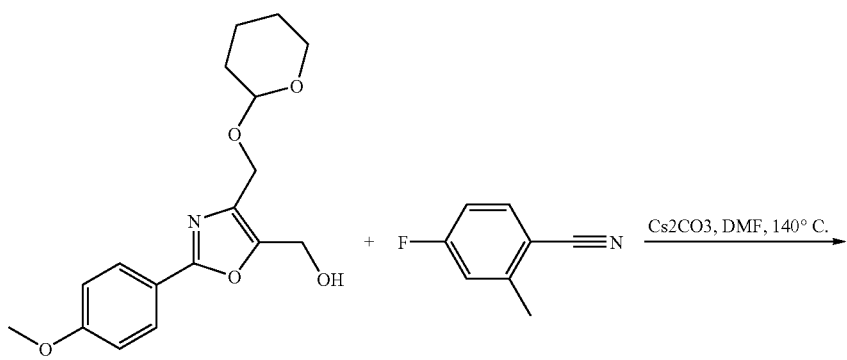

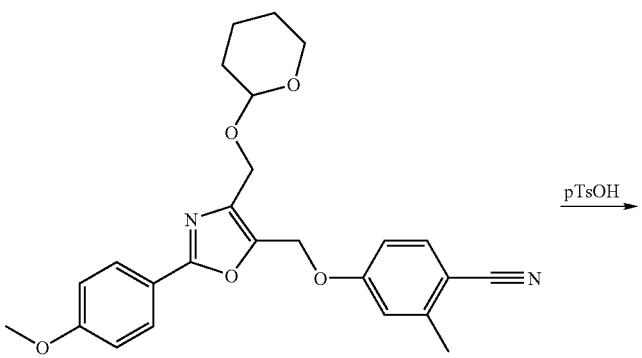

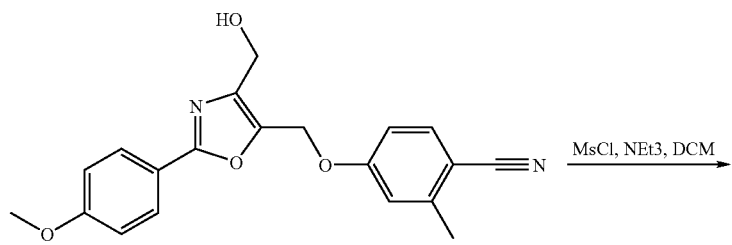

-continued
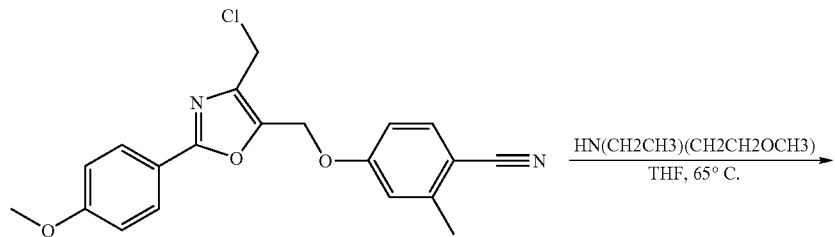
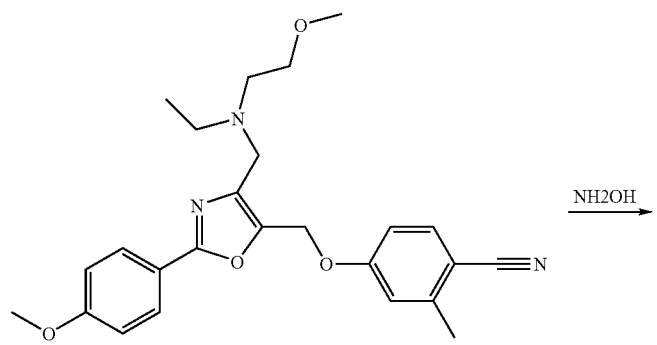
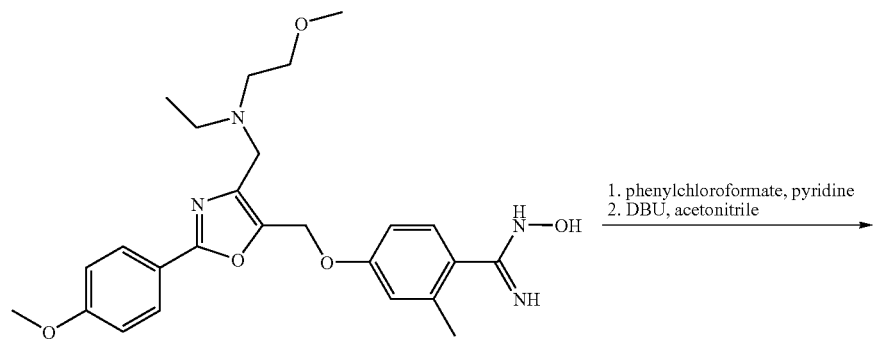
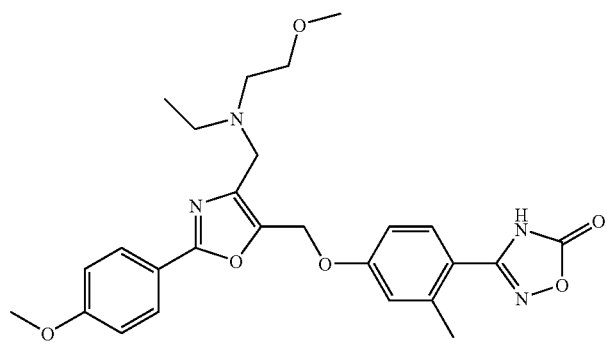

211

4-[2-(4-Methoxy-phenyl)-4-(tetrahydro-pyran-2-yloxymethyl)-oxazol-5-ylmethoxy]-2-methyl-benzonitrile

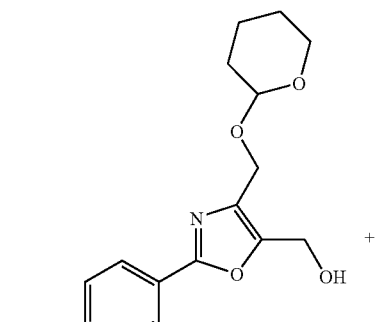

+

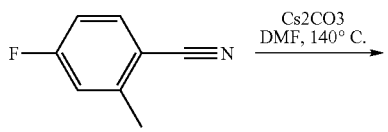

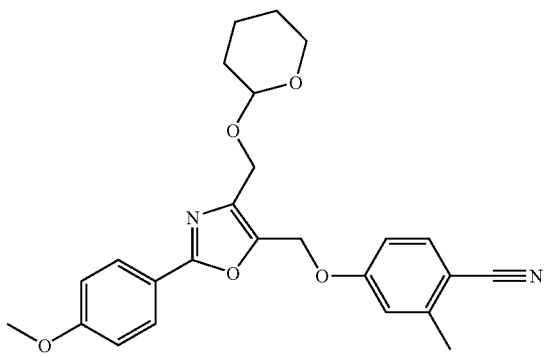

To a solution of 3.2 g 4-fluoro-2-methylbenzonitrile in 50 ml dimethylformamide 5.0 g [2-(4-methoxy-phenyl)-4-(tetrahydro-pyran-2-yloxymethyl)-oxazol-5-yl]-methanol were added followed by the addition of 10.2 g cesium carbonate. The reaction mixture was stirred at 140° C. overnight. The cooled reaction mixture was diluted with 200 ml ethyl acetate and washed five times with portions of 50 ml water and brine. The organic phase was dried over MgSO4 and the solvent was evaporated in vacuo. The residue was purified by chromatography on silica gel with the eluent n-heptane:ethyl acetate=5:1=>2:1 to obtain 5.96 g 4-[2-(4-Methoxy-phenyl)-4-(tetrahydro-pyran-2-yloxymethyl)-oxazol-5-ylmethoxy]-2-methyl-benzonitrile as an oil.

C25H26N2O5 (434.50), MS (ESI): 435.2 (M+H$^+$), Rf (n-heptane:ethyl acetate=1:1)=0.42.

212

4-[4-Hydroxymethyl-2-(4-methoxy-phenyl)-oxazol-5-ylmethoxy]-2-methyl-benzonitrile

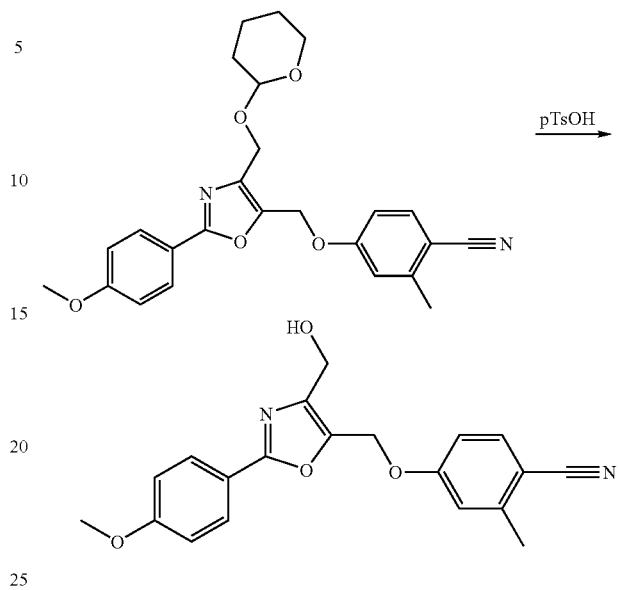

5.96 g 4-[2-(4-Methoxy-phenyl)-4-(tetrahydro-pyran-2-yloxymethyl)-oxazol-5-ylmethoxy]-2-methyl-benzonitrile were dissolved in 100 ml methanol. 522 mg p-toluenesulfonic acid monohydrate were added and the reaction mixture stirred at room temperature for one hour. The solvent was removed in vacuo. The residue was dissolved in 150 ml ethyl acetate and washed with 80 ml saturated NaHCO3 solution and brine. The organic phase was dried over MgSO4 and the solvent was evaporated in vacuo to obtain 4.1 g 4-[4-hydroxymethyl-2-(4-methoxy-phenyl)-oxazol-5-ylmethoxy]-2-methyl-benzonitrile as pale yellow solid.

C20H18N2O4 (350.38), MS (ESI): 351.2 (M+H$^+$).

4-[4-Chloromethyl-2-(4-methoxy-phenyl)-oxazol-5-ylmethoxy]-2-methyl-benzonitrile

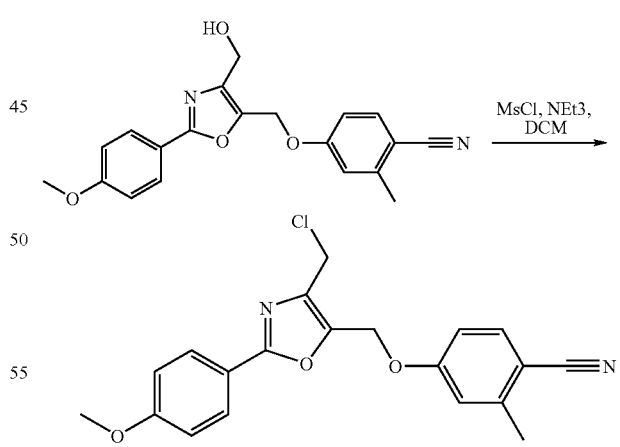

4.1 g 4-[4-Hydroxymethyl-2-(4-methoxy-phenyl)-oxazol-5-ylmethoxy]-2-methyl-benzonitrile were dissolved in 90 ml dichloromethane and cooled in an ice bath. 2.44 ml triethylamine were added, followed by the addition of 1.08 ml methanesulfonylchloride. The ice bath was removed and the resulting mixture stirred at room temperature over night. The reaction mixture was then washed with water and brine, dried over MgSO4 and the solvent removed in vacuo to obtain 2.5 g of 5-chloromethyl-2-(4-methoxy-phenyl)-4-(tetrahydro-pyran-2-yloxymethyl)-oxazole as an oil which was used without further purification.

C20H17ClN2O3 (368.82), MS (ESI): 369.1 (M+H$^+$), Rf (ethyl acetate:n-heptane=1:1)=0.59.

4-[4-{[Ethyl-(2-methoxy-ethyl)-amino]-methyl}-2-(4-methoxy-phenyl)-oxazol-5-ylmethoxy]-2-methyl-benzonitrile

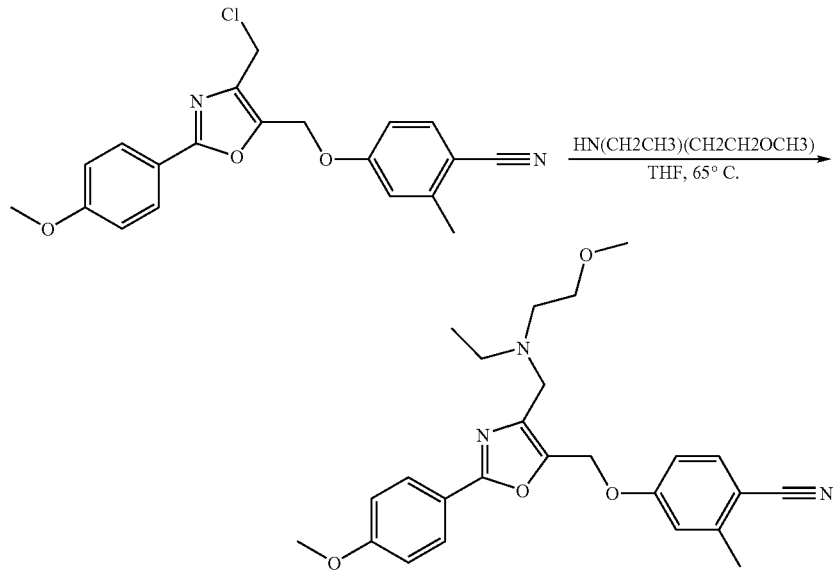

200 mg 5-chloromethyl-2-(4-methoxy-phenyl)-4-(tetrahydro-pyran-2-yloxymethyl)-oxazole and 224 mg N-(2-methoxyethyl)ethylamine were dissolved in 5 ml tetrahydrofuran and stirred at 60° C. for six hours. The cooled reaction mixture was diluted with 50 ml ethyl acetate and washed with portions of 20 ml water and brine, then dried over MgSO4. The solvent was removed in vacuo to obtain 158 mg 4-[4-{[ethyl-(2-methoxy-ethyl)-amino]-methyl}-2-(4-methoxy-phenyl)-oxazol-5-ylmethoxy]-2-methyl-benzonitrile as an oil.

C25H29N3O4 (435.53), MS (ESI): 436.3 (M+H$^+$).

3-{4-[4-{[Ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one

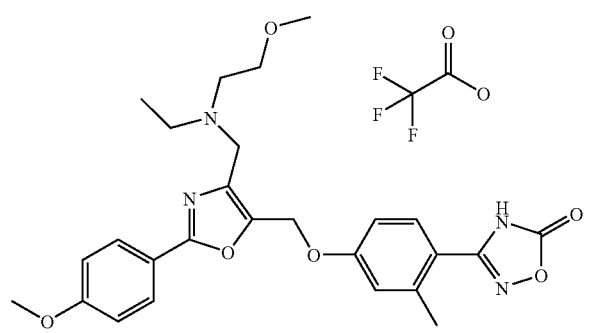

According to the method described for 3-(2-chloro-4-{4-methyl-2-[2-(4-trifluoromethyl-phenyl)-ethyl]-oxazol-5-ylmethoxy}-phenyl)-4H-[1,2,4]oxadiazol-5-one in example 54, 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one was obtained from 4-[4-{[ethyl-(2-methoxy-ethyl)-amino]-methyl}-2-(4-methoxy-phenyl)-oxazol-5-ylmethoxy]-2-methyl-benzonitrile. The compound was obtained as its trifluoro-acetate salt.

C26H30N4O6.C2HF3O2 (608.57), MS (ESI): 495.1 (M+H$^+$).

Example 61

3-{4-[4-Diethylaminomethyl-2-(4-methoxy-phenyl)-oxazol-5-ylmethoxy]-2-methyl-phenyl}-4H-[1,2,4]oxadiazol-5-one

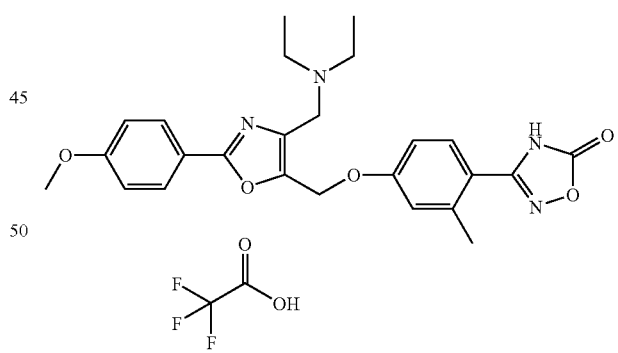

According to the method described for 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one in example 60, 3-{4-[4-diethylaminomethyl-2-(4-methoxy-phenyl)-oxazol-5-ylmethoxy]-2-methyl-phenyl}-4H-[1,2,4]oxadiazol-5-one was obtained from 5-chloromethyl-2-(4-methoxy-phenyl)-4-(tetrahydro-pyran-2-yloxymethyl)-oxazole and diethylamine. The compound was obtained as its trifluoro-acetate salt.

C25H28N4O5.C2HF3O2 (578.55), MS (ESI): 465.1 (M+H$^+$).

Example 62

3-{4-[2-(4-Methoxy-phenyl)-4-pyrrolidin-1-ylmethyl-oxazol-5-ylmethoxy]-2-methyl-phenyl}-4H-[1,2,4]oxadiazol-5-one

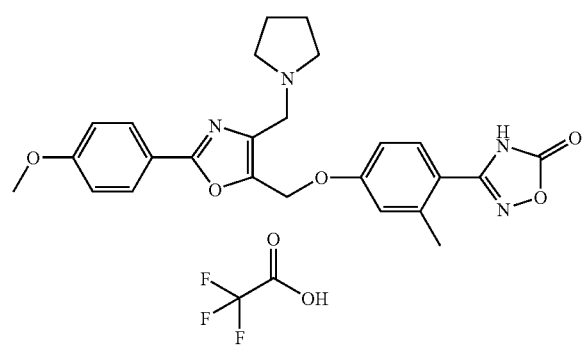

According to the method described for 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one in example 60, 3-{4-[2-(4-methoxy-phenyl)-4-pyrrolidin-1-ylmethyl-oxazol-5-ylmethoxy]-2-methyl-phenyl}-4H-[1,2,4]oxadiazol-5-one was obtained from 5-chloromethyl-2-(4-methoxy-phenyl)-4-(tetrahydro-pyran-2-yloxymethyl)-oxazole and pyrrolidine. The compound was obtained as its trifluoro-acetate salt.

C25H26N4O5.C2HF3O2 (576.53), MS (ESI): 463.2 (M+H⁺).

Example 63

3-{4-[2-(4-Methoxy-phenyl)-4-morpholin-4-ylmethyl-oxazol-5-ylmethoxy]-2-methyl-phenyl}-4H-[1,2,4]oxadiazol-5-one

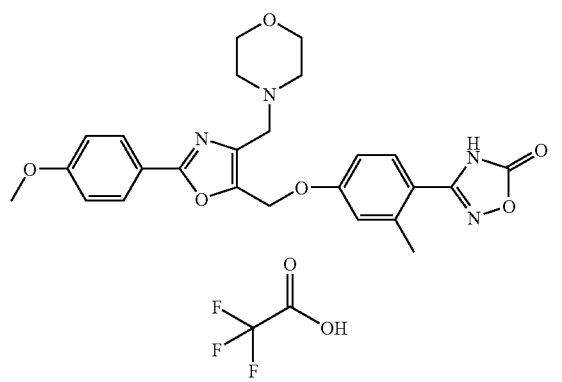

According to the method described for 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one in example 60, 3-{4-[2-(4-methoxy-phenyl)-4-morpholin-4-ylmethyl-oxazol-5-ylmethoxy]-2-methyl-phenyl}-4H-[1,2,4]oxadiazol-5-one was obtained from 5-chloromethyl-2-(4-methoxy-phenyl)-4-(tetrahydro-pyran-2-yloxymethyl)-oxazole and morpholine. The compound was obtained as its trifluoro-acetate salt.

C25H26N4O6.C2HF3O2 (592.53), MS (ESI): 479.3 (M+H⁺).

Example 64

3-{4-[4-{[Bis-(2-methoxy-ethyl-amino]-methyl}-2-(4-methoxy-phenyl)-oxazol-5-ylmethoxy]-2-methyl-phenyl}-4H-[1,2,4]oxadiazol-5-one

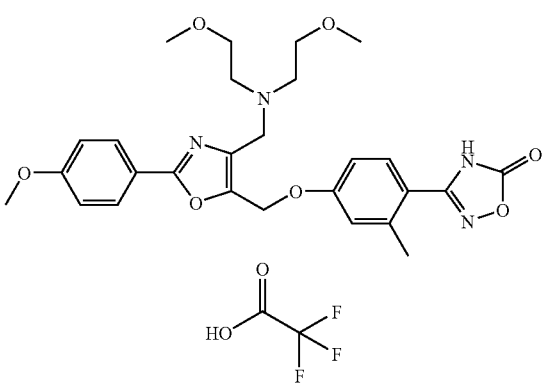

According to the method described for 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one in example 60, 3-{4-[4-{[bis-(2-methoxy-ethyl)-amino]-methyl}-2-(4-methoxy-phenyl)-oxazol-5-ylmethoxy]-2-methyl-phenyl}-4H-[1,2,4]oxadiazol-5-one was obtained from 5-chloromethyl-2-(4-methoxy-phenyl)-4-(tetrahydro-pyran-2-yloxymethyl)-oxazole and bis-(2-methoxy-ethyl)-amine. The compound was obtained as its trifluoro-acetate salt.

C27H32N4O7.C2HF3O2 (638.60), MS (ESI): 525.1 (M+H⁺).

Example 65

3-{4-[2-(4-Methoxy-phenyl)-4-piperidin-1-ylmethyl-oxazol-5-ylmethoxy]-2-methyl-phenyl}-4H-[1,2,4]oxadiazol-5-one

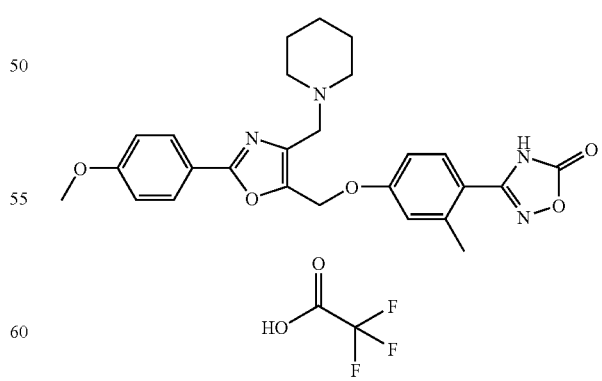

According to the method described for 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one in example 60, 3-{4-[2-(4-methoxy-phenyl)-4- piperidin-1-ylmethyl-oxazol-5-ylmethoxy]-2-methyl-phenyl}-4H-[1,2,4]oxadiazol-5-one was obtained from 5-chloromethyl-2-(4-methoxy-phenyl)-4-(tetrahydro-pyran-2-yloxymethyl)-oxazole and piperidine. The compound was obtained as its trifluoro-acetate salt.

C26H28N4O5.C2HF3O2 (590.56), MS (ESI): 477.2 (M+H$^+$).

Example 66

3-{4-[2-(4-Methoxy-phenyl)-5-piperidin-1-ylmethyl-oxazol-4-ylmethoxy]-2-methyl-phenyl}-4H-[1,2,4]oxadiazol-5-one

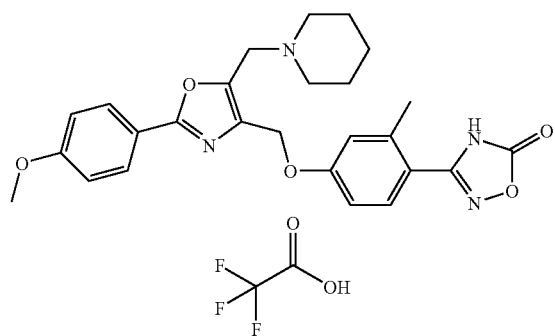

According to the method described for 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one in example 60, 3-{4-[2-(4-methoxy-phenyl)-5-piperidin-1-ylmethyl-oxazol-4-ylmethoxy]-2-methyl-phenyl}-4H-[1,2,4]oxadiazol-5-one was obtained from methanesulfonic acid 2-(4-methoxy-phenyl)-5-(tetrahydro-pyran-2-yloxymethyl)-oxazol-4-ylmethyl ester, 4-fluoro-2-methylbenzonitrile and piperidine. The compound was obtained as its trifluoro-acetate salt.

C26H28N4O5.C2HF3O2 (590.56), MS (ESI): 477.3 (M+H$^+$).

Example 67

3-{4-[2-(4-Methoxy-phenyl)-5-pyrrolidin-1-ylmethyl-oxazol-4-ylmethoxy]-2-methyl-phenyl}-4H-[1,2,4]oxadiazol-5-one

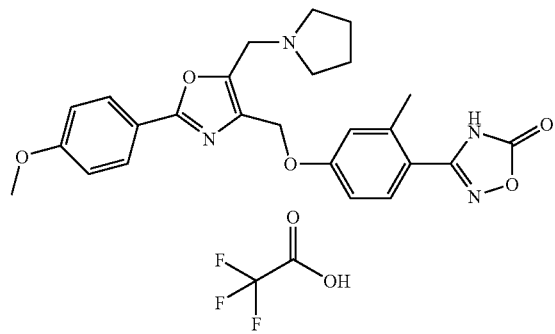

According to the method described for 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one in example 60, 3-{4-[2-(4-methoxy-phenyl)-5-pyrrolidin-1-ylmethyl-oxazol-4-ylmethoxy]-2-methyl-phenyl}-4H-[1,2,4]oxadiazol-5-one was obtained from methanesulfonic acid 2-(4-methoxy-phenyl)-5-(tetrahydro-pyran-2-yloxymethyl)-oxazol-4-ylmethyl ester, 4-fluoro-2-methylbenzonitrile and pyrrolidine. The compound was obtained as its trifluoro-acetate salt.

C25H26N4O5.C2HF3O2 (576.53), MS (ESI): 463.3 (M+H$^+$).

Example 68

3-{4-[2-(4-Methoxy-phenyl)-5-morpholin-4-ylmethyl-oxazol-4-ylmethoxy]-2-methyl-phenyl}-4H-[1,2,4]oxadiazol-5-one

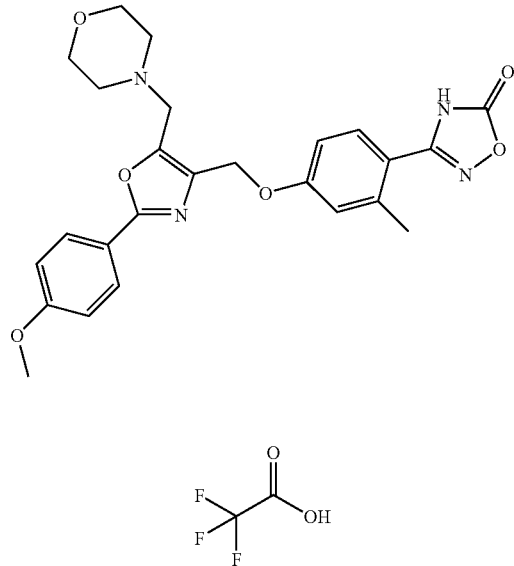

According to the method described for 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one in example 60, 3-{4-[2-(4-methoxy-phenyl)-5-morpholin-4-ylmethyl-oxazol-4-ylmethoxy]-2-methyl-phenyl}-4H-[1,2,4]oxadiazol-5-one was obtained from methanesulfonic acid 2-(4-methoxy-phenyl)-5-(tetrahydro-pyran-2-yloxymethyl)-oxazol-4-ylmethyl ester, 4-fluoro-2-methylbenzonitrile and morpholine. The compound was obtained as its trifluoro-acetate salt.

C25H26N4O6.C2HF3O2 (592.53), MS (ESI): 479.2 (M+H$^+$).

Example 69

3-{4-[5-{[Bis-(2-methoxy-ethyl)-amino]-methyl}-2-(4-methoxy-phenyl)-oxazol-4-ylmethoxy]-2-methyl-phenyl}-4H-[1,2,4]oxadiazol-5-one

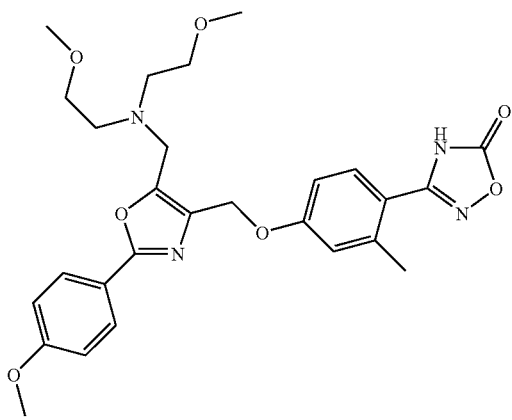

According to the method described for 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one in example 60, 3-{4-[5-{[bis-(2-methoxy-ethyl)-amino]-methyl}-2-(4-methoxy-phenyl)-oxazol-4-ylmethoxy]-2-methyl-phenyl}-4H-[1,2,4]oxadiazol-5-one was obtained from methanesulfonic acid 2-(4-methoxy-phenyl)-5-(tetrahydro-pyran-2-yloxymethyl)-oxazol-4-ylmethyl ester, 4-fluoro-2-methylbenzonitrile and bis-(2-methoxy-ethyl)-amine.

C27H32N4O7 (524.57), MS (ESI): 525.2 (M+H$^+$).

The following examples were prepared according to process L, whereby the first reaction step was performed according to general process A [A1+A2=>A3]:

Example 70

3-{2-Chloro-4-[2-(4-methoxy-phenyl)-4-morpholin-4-ylmethyl-oxazol-5-ylmethoxy]-phenyl}-4H-[1,2,4]oxadiazol-5-one

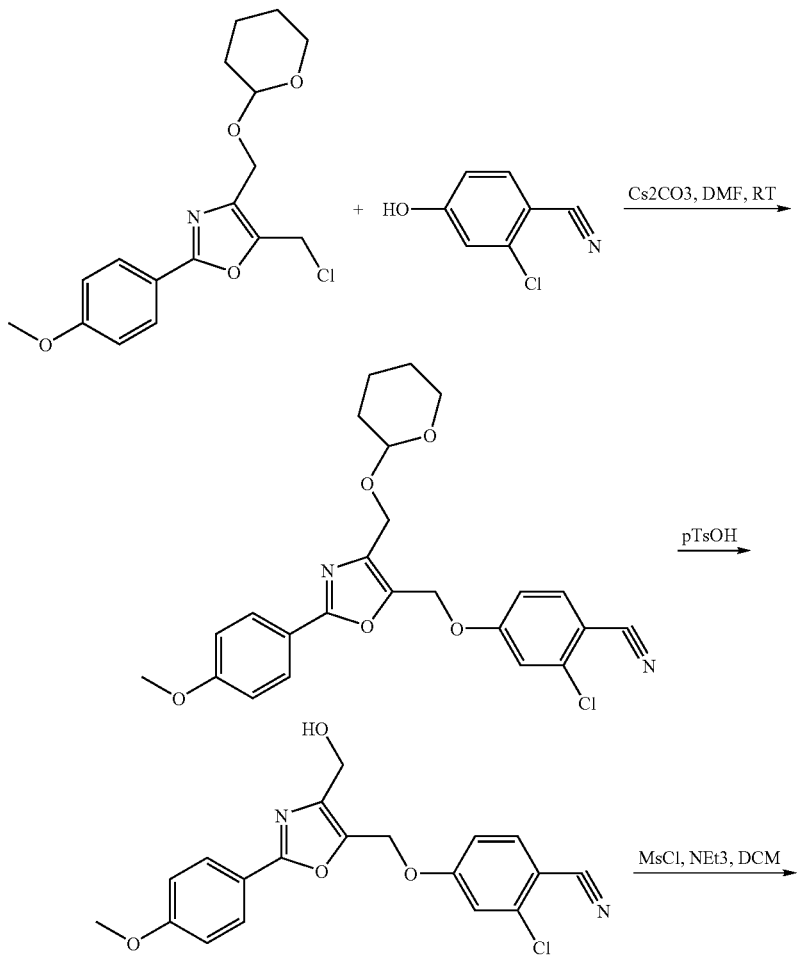

-continued
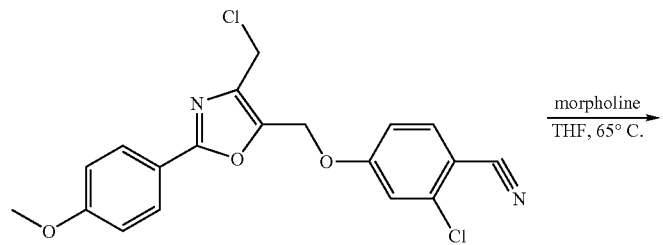
morpholine
THF, 65° C.
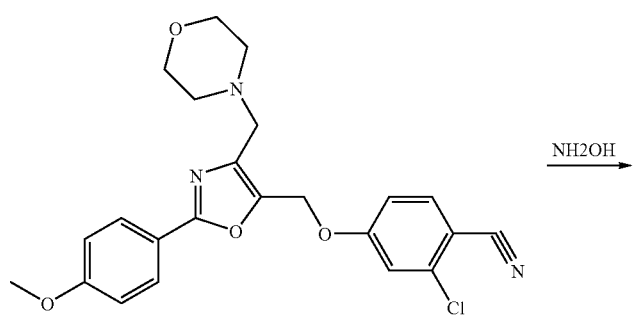
NH2OH
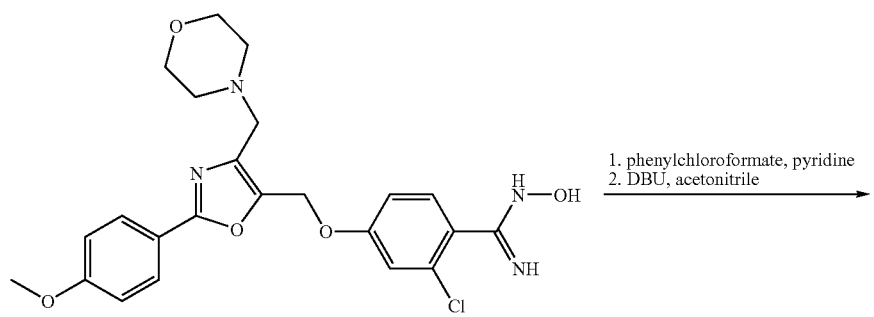
1. phenylchloroformate, pyridine
2. DBU, acetonitrile
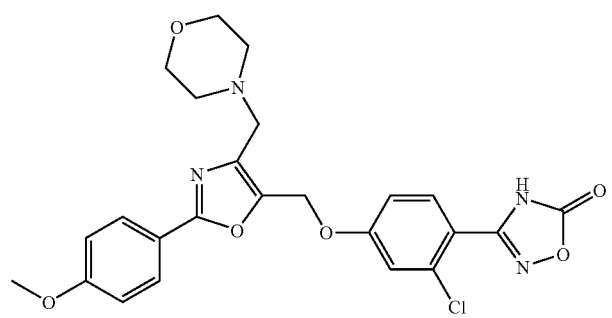

223

2-Chloro-4-[2-(4-methoxy-phenyl)-4-(tetrahydro-pyran-2-yloxymethyl)-oxazol-5-ylmethoxy]-benzonitrile

224

3-{2-Chloro-4-[2-(4-methoxy-phenyl)-4-morpholin-4-ylmethyl-oxazol-5-ylmethoxy]-phenyl}-4H-[1,2,4]oxadiazol-5-one

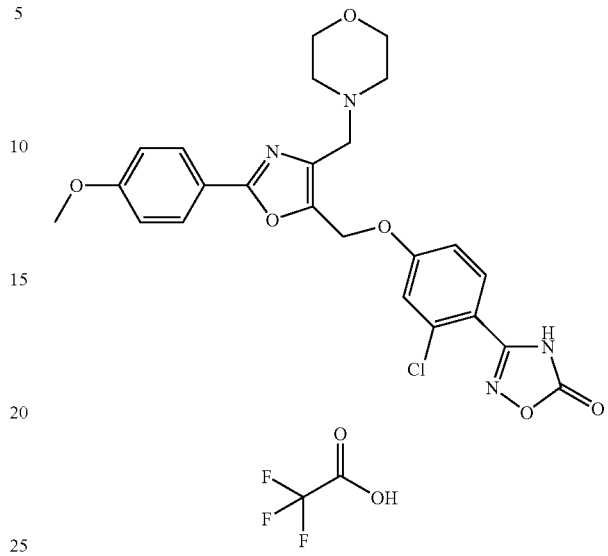

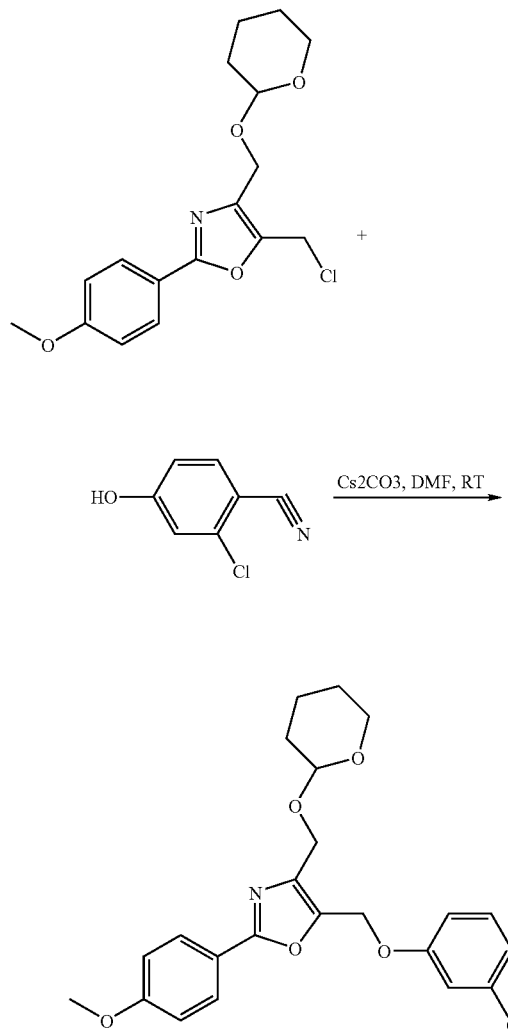

According to the method described for 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one in example 60, 3-{2-chloro-4-[2-(4-methoxy-phenyl)-4-morpholin-4-ylmethyl-oxazol-5-ylmethoxy]-phenyl}-4H-[1,2,4]oxadiazol-5-one was obtained from 2-chloro-4-[2-(4-methoxy-phenyl)-4-(tetrahydro-pyran-2-yloxymethyl)-oxazol-5-ylmethoxy]-benzonitrile and morpholine. The compound was obtained as its trifluoro-acetate salt.

C24H23ClN4O6.C2HF3O2 (612.95), MS (ESI): 499.2 (M+H$^+$).

Example 71

3-{2-Chloro-4-[4-{[ethyl-(2-methoxy-ethyl)-amino]-methyl}-2-(4-methoxy-phenyl)-oxazol-5-ylmethoxy]-phenyl}-4H-[1,2,4]oxadiazol-5-one

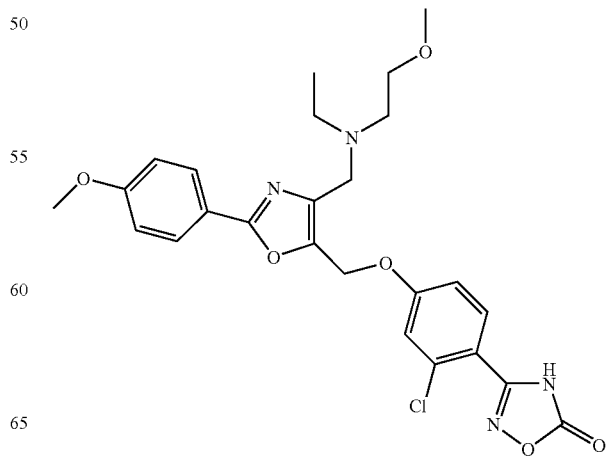

2.5 g 5-Chloromethyl-2-(4-methoxy-phenyl)-4-(tetrahydro-pyran-2-yloxymethyl)-oxazole and 1.48 g 2-chloro-4-hydroxybenzonitrile were dissolved in 20 ml dimethylformamide. 4.82 g Cesium carbonate were added and the reaction mixture stirred at room temperature overnight. The reaction mixture was diluted with 200 ml ethyl acetate and washed five times with portions of 50 ml water and brine. The organic phase was dried over MgSO4 and the solvent was evaporated in vacuo to obtain 4.0 g crude 2-chloro-4-[2-(4-methoxy-phenyl)-4-(tetrahydro-pyran-2-yloxymethyl)-oxazol-5-ylmethoxy]-benzonitrile. This material was used without further purification.

C24H23ClN2O5 (454.91), MS (ESI): 455.2 (M+H$^+$).

-continued

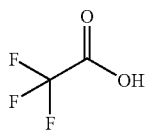

According to the method described for 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one in example 60, 3-{2-chloro-4-[4-{[ethyl-(2-methoxy-ethyl)-amino]-methyl}-2-(4-methoxy-phenyl)-oxazol-5-ylmethoxy]-phenyl}-4H-[1,2,4]oxadiazol-5-one was obtained from 2-chloro-4-[2-(4-methoxy-phenyl)-4-(tetrahydro-pyran-2-yloxymethyl)-oxazol-5-ylmethoxy]-benzonitrile and ethyl-(2-methoxy-ethyl)-amine. The compound was obtained as its trifluoro-acetate salt.

C25H27ClN4O6.C2HF3O2 (628.99), MS (ESI): 515.2 (M+H⁺).

Example 72

3-{4-[4-{[Bis-(2-methoxy-ethyl)-amino]-methyl}-2-(4-methoxy-phenyl)-oxazol-5-ylmethoxy]-2-chloro-phenyl}-4H-[1,2,4]oxadiazol-5-one

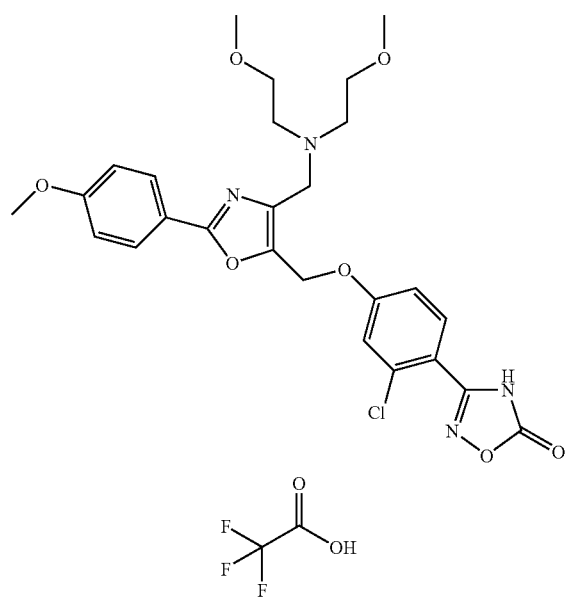

According to the method described for 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one in example 60, 3-{4-[4-{[bis-(2-methoxy-ethyl)-amino]-methyl}-2-(4-methoxy-phenyl)-oxazol-5-ylmethoxy]-2-chloro-phenyl}-4H-[1,2,4]oxadiazol-5-one was obtained from 2-chloro-4-[2-(4-methoxy-phenyl)-4-(tetrahydro-pyran-2-yloxymethyl)-oxazol-5-ylmethoxy]-benzonitrile and bis-(2-methoxy-ethyl)-amine. The compound was obtained as its trifluoro-acetate salt.

C26H29ClN4O7.C2HF3O2 (659.02), MS (ESI): 545.3 (M+H⁺).

Example 73

3-{2-Chloro-4-[4-piperidin-1-ylmethyl-2-(4-trifluoromethyl-phenyl)-thiazol-5-ylmethoxy]-phenyl}-4H-[1,2,4]oxadiazol-5-one Methanesulfonic acid 5-(3-chloro-4-cyano-phenoxymethyl)-2-(4-trifluoromethyl-phenyl)-thiazol-4-ylmethyl ester

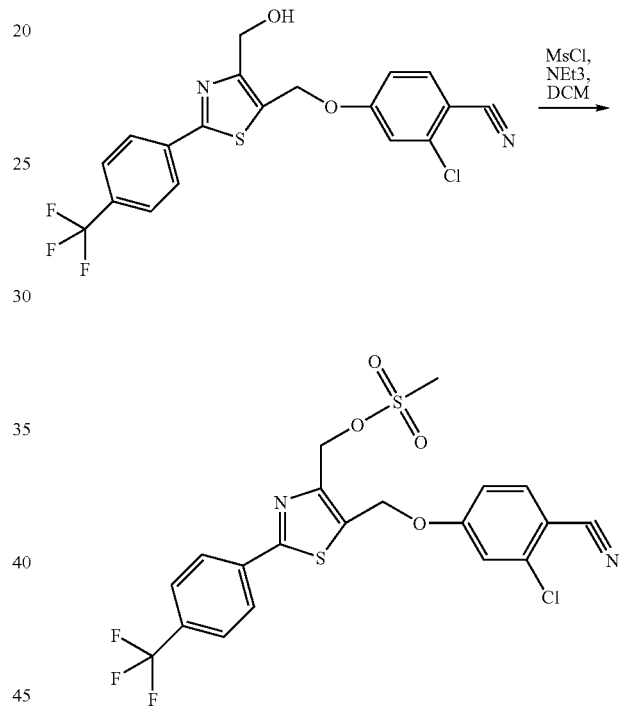

2.0 g 2-Chloro-4-[4-hydroxymethyl-2-(4-trifluoromethyl-phenyl)-thiazol-5-ylmethoxy]-benzonitrile [obtained from 5-chloromethyl-4-(tetrahydro-pyran-2-yloxymethyl)-2-(4-trifluoromethyl-phenyl)-thiazole[8] and 2-chloro-4-hydroxy-benzonitrile according to the method described in example 70] were suspended in 50 ml dichloromethane. At 0° C. 0.44 ml methanesulfonyl chloride and 0.98 ml triethylamine were added and the reaction mixture was stirred at 0° C. for one hour. The reaction mixture was diluted with 150 ml ethyl acetate and washed with 50 ml water and brine. The organic phase was dried over MgSO4, then the solvent was evaporated in vacuo to obtain 2.5 g methanesulfonic acid 5-(3-chloro-4-cyano-phenoxymethyl)-2-(4-trifluoromethyl-phenyl)-thiazol-4-ylmethyl ester as a pale yellow solid.

[8] WO 2002067912, WO 2002059098

C20H14ClF3N2O4S2 (502.92), MS (ESI): 503.1 (M+H⁺).

227

3-{2-Chloro-4-[4-piperidin-1-ylmethyl-2-(4-trifluoromethyl-phenyl)-thiazol-5-ylmethoxy]-phenyl}-4H-[1,2,4]oxadiazol-5-one

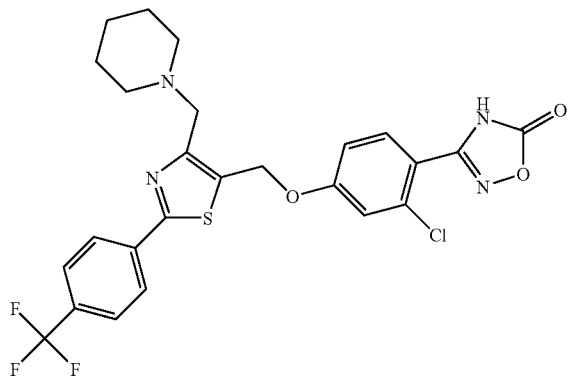

According to the method described for 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one in example 60, 3-{2-chloro-4-[4-piperidin-1-ylmethyl-2-(4-trifluoromethyl-phenyl)-thiazol-5-ylmethoxy]-phenyl}-4H-[1,2,4]oxadiazol-5-one was obtained from methanesulfonic acid 5-(3-chloro-4-cyano-phenoxymethyl)-2-(4-trifluoromethyl-phenyl)-thiazol-4-ylmethyl ester and piperidine.

C25H22ClF3N4O3S (550.99), MS (ESI): 551.1 (M+H$^+$).

Example 74

3-{4-[4-(4-Acetyl-piperazin-1-ylmethyl)-2-(4-trifluoromethyl-phenyl)-thiazol-5-ylmethoxy]-2-chloro-phenyl}-4H-[1,2,4]oxadiazol-5-one

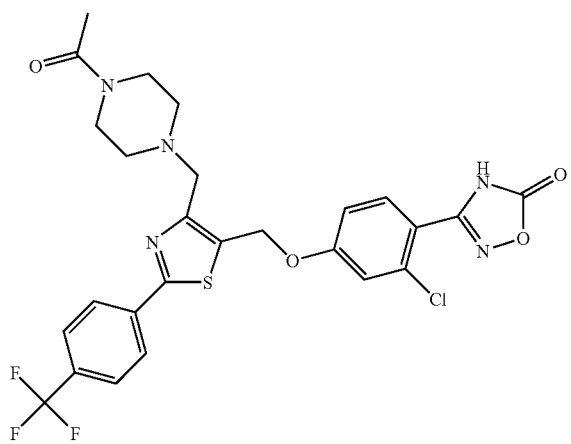

According to the method described for 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one in example 60, 3-{4-[4-(4-acetyl-piperazin-1-ylmethyl)-2-(4-trifluoromethyl-phenyl)-thiazol-5-ylmethoxy]-2-chloro-phenyl}-4H-[1,2,4]oxadiazol-5-one was obtained from methanesulfonic acid 5-(3-chloro-4-cyano-phenoxymethyl)-2-(4-trifluoromethyl-phenyl)-thiazol-4-ylmethyl ester and 4-acetylpiperazine.

C26H23ClF3N5O4S (594.02), MS (ESI): 594.2 (M+H$^+$).

228

Example 75

3-{2-Chloro-4-[4-(4-methyl-piperazin-1-ylmethyl)-2-(4-trifluoromethyl-phenyl)-thiazol-5-ylmethoxy]-phenyl}-4H-[1,2,4]oxadiazol-5-one

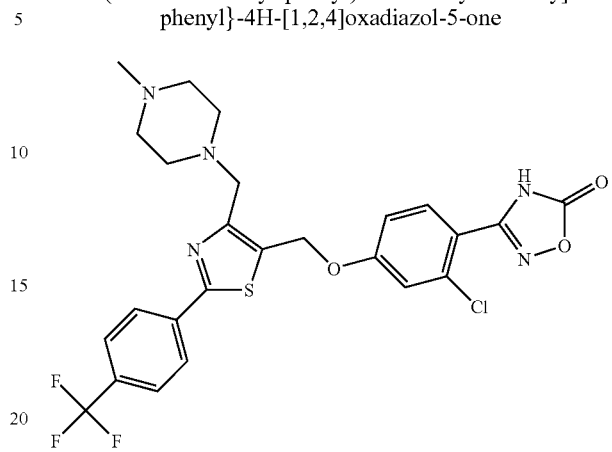

According to the method described for 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one in example 60, 3-{2-chloro-4-[4-(4-methyl-piperazin-1-ylmethyl)-2-(4-trifluoromethyl-phenyl)-thiazol-5-ylmethoxy]-phenyl}-4H-[1,2,4]oxadiazol-5-one was obtained from methanesulfonic acid 5-(3-chloro-4-cyano-phenoxymethyl)-2-(4-trifluoromethyl-phenyl)-thiazol-4-ylmethyl ester and 4-methyl-piperazine.

C25H23ClF3N5O3S (566.01), MS (ESI): 566.2 (M+H$^+$).

Example 76

3-{2-Chloro-4-[4-{[ethyl-(2-methoxy-ethyl)-amino]-methyl}-2-(4-trifluoromethyl-phenyl)-thiazol-5-ylmethoxy]-phenyl}-4H-[1,2,4]oxadiazol-5-one

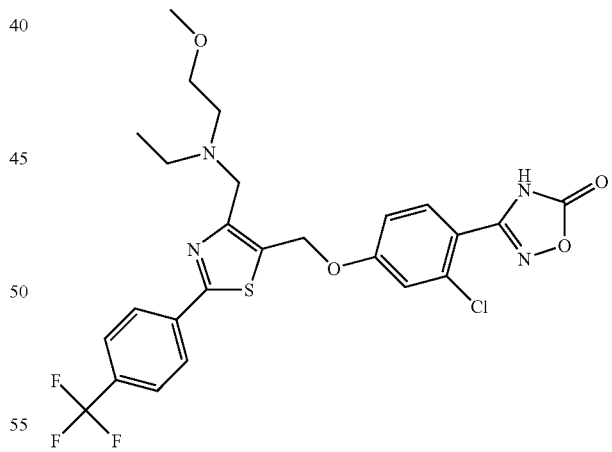

According to the method described for 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one in example 60, 3-{2-chloro-4-[4-{[ethyl-(2-methoxy-ethyl)-amino]-methyl}-2-(4-trifluoromethyl-phenyl)-thiazol-5-ylmethoxy]-phenyl}-4H-[1,2,4]oxadiazol-5-one was obtained from methanesulfonic acid 5-(3-chloro-4-cyano-phenoxymethyl)-2-(4-trifluoromethyl-phenyl)-thiazol-4-ylmethyl ester and N-(2-methoxyethyl)ethylamine.

C25H24ClF3N4O4S (569.01), MS (ESI): 569.1 (M+H$^+$).

Example 77

3-{4-[4-{[Bis-(2-methoxy-ethyl)-amino]-methyl}-2-(4-trifluoromethyl-phenyl)-thiazol-5-ylmethoxy]-2-chloro-phenyl}-4H-[1,2,4]oxadiazol-5-one

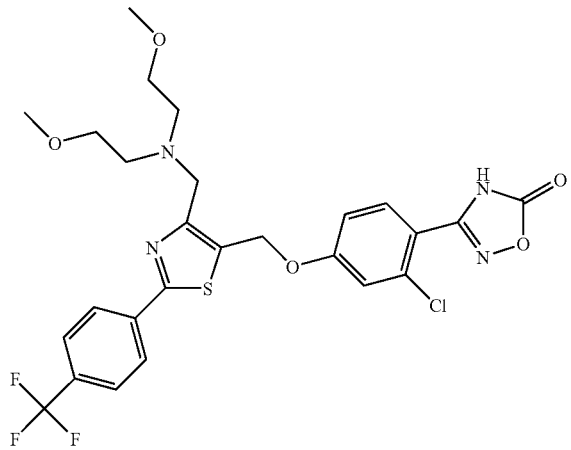

According to the method described for 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one in example 60, 3-{4-[4-{[bis-(2-methoxy-ethyl)-amino]-methyl}-2-(4-trifluoromethyl-phenyl)-thiazol-5-ylmethoxy]-2-chloro-phenyl}-4H-[1,2,4]oxadiazol-5-one was obtained from methanesulfonic acid 5-(3-chloro-4-cyano-phenoxymethyl)-2-(4-trifluoromethyl-phenyl)-thiazol-4-ylmethyl ester and bis-(2-methoxy-ethyl)-amine.

C26H26ClF3N4O5S (599.03), MS (ESI): 599.2 (M+H$^+$).

Example 78

3-{2-Chloro-4-[4-pyrrolidin-1-ylmethyl-2-(4-trifluoromethyl-phenyl)-thiazol-5-ylmethoxy]-phenyl}-4H-[1,2,4]oxadiazol-5-one

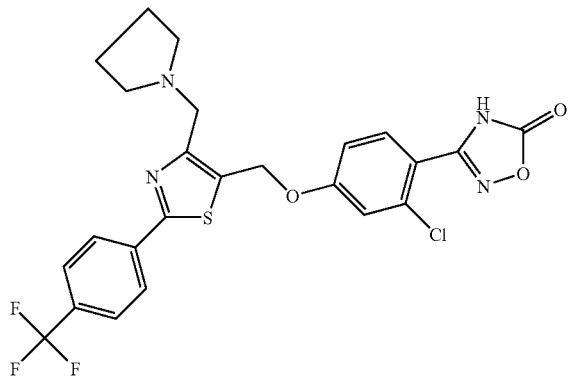

According to the method described for 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one in example 60, 3-{2-chloro-4-[4-pyrrolidin-1-ylmethyl-2-(4-trifluoromethyl-phenyl)-thiazol-5-ylmethoxy]-phenyl}-4H-[1,2,4]oxadiazol-5-one was obtained from methanesulfonic acid 5-(3-chloro-4-cyano-phenoxymethyl)-2-(4-trifluoromethyl-phenyl)-thiazol-4-ylmethyl ester and pyrrolidine.

C24H20ClF3N4O3S (536.96), MS (ESI): 537.2 (M+H$^+$).

Example 79

3-{2-Chloro-4-[4-diethylaminomethyl-2-(4-trifluoromethyl-phenyl)-thiazol-5-ylmethoxy]-phenyl}-4H-[1,2,4]oxadiazol-5-one

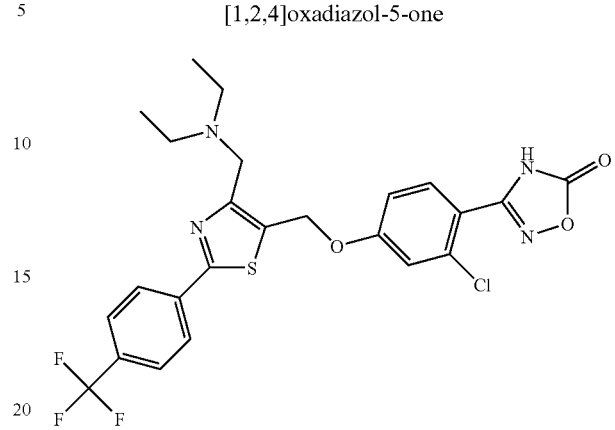

According to the method described for 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one in example 60, 3-{2-chloro-4-[4-diethylaminomethyl-2-(4-trifluoromethyl-phenyl)-thiazol-5-ylmethoxy]-phenyl}-4H-[1,2,4]oxadiazol-5-one was obtained from methanesulfonic acid 5-(3-chloro-4-cyano-phenoxymethyl)-2-(4-trifluoromethyl-phenyl)-thiazol-4-ylmethyl ester and diethylamine.

C24H22ClF3N4O3S (538.98), MS (ESI): 539.1 (M+H$^+$).

Example 80

3-{2-Chloro-4-[4-(4,4-difluoro-piperidin-1-ylmethyl)-2-(4-trifluoromethyl-phenyl)-thiazol-5-ylmethoxy]-phenyl}-4H-[1,2,4]oxadiazol-5-one

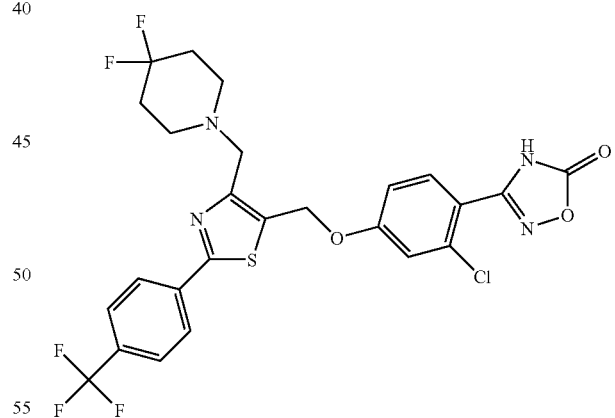

According to the method described for 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one in example 60, 3-{2-chloro-4-[4-(4,4-difluoro-piperidin-1-ylmethyl)-2-(4-trifluoromethyl-phenyl)-thiazol-5-ylmethoxy]-phenyl}-4H-[1,2,4]oxadiazol-5-one was obtained from methanesulfonic acid 5-(3-chloro-4-cyano-phenoxymethyl)-2-(4-trifluoromethyl-phenyl)-thiazol-4-ylmethyl ester and 4,4-difluoro-piperidine.

C25H20ClF5N4O3S (586.97), MS (ESI): 587.1 (M+H$^+$).

Example 81

3-{2-Chloro-4-[4-(4-phenyl-piperazin-1-ylmethyl)-2-(4-trifluoromethyl-phenyl)-thiazol-5-ylmethoxy]-phenyl}-4H-[1,2,4]oxadiazol-5-one

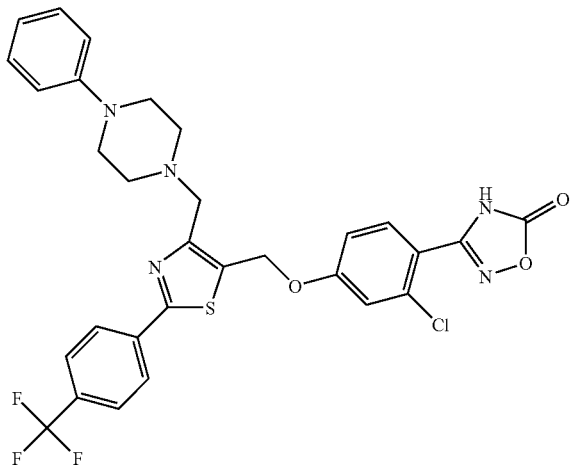

According to the method described for 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one in example 60, 3-{2-chloro-4-[4-(4-phenyl-piperazin-1-ylmethyl)-2-(4-trifluoromethyl-phenyl)-thiazol-5-ylmethoxy]-phenyl}-4H-[1,2,4]oxadiazol-5-one was obtained from methanesulfonic acid 5-(3-chloro-4-cyano-phenoxymethyl)-2-(4-trifluoromethyl-phenyl)-thiazol-4-yl-methyl ester and 4-phenyl-piperidine.

C30H25ClF3N5O3S (628.08), MS (ESI): 628.1 (M+H+).

Example 82

3-{2-Chloro-4-[4-(2-morpholin-4-yl-ethoxymethyl)-2-(4-trifluoromethyl-phenyl)-thiazol-5-ylmethoxy]-phenyl}-4H-[1,2,4]oxadiazol-5-one 2-Chloro-4-[4-(2-morpholin-4-yl-ethoxymethyl)-2-(4-trifluoromethyl-phenyl)-thiazol-5-ylmethoxy]-benzonitrile

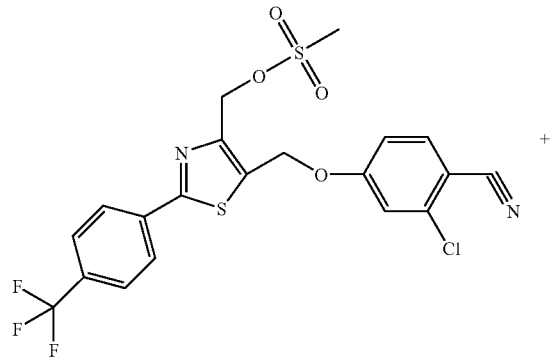

+

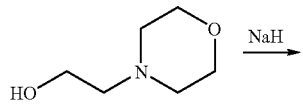 NaH →

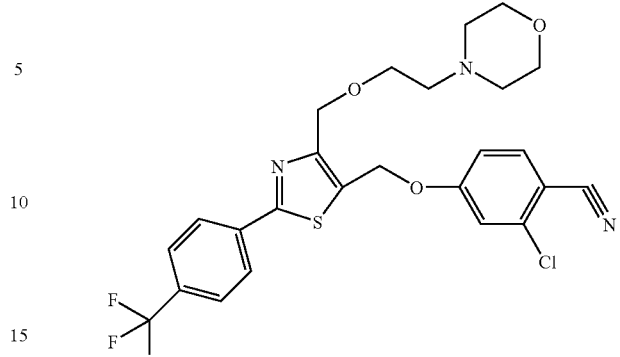

120 mg Methanesulfonic acid 5-(3-chloro-4-cyano-phenoxymethyl)-2-(4-trifluoromethyl-phenyl)-thiazol-4-ylmethyl ester was dissolved in 5 ml N-(2-hydroxyethyl)morpholine. 10 mg sodium hydride were added and the reaction mixture stirred at 50° C. for one hour. 10 ml water was added and the reaction mixture extracted 50 ml ethyl acetate. The organic layer was separated and washed twice with 20 ml brine. The organic layer was dried over MgSO4 and the solvent was then removed in vacuo. The residue was purified by RP-HPLC to obtain 40 mg 2-chloro-4-[4-(2-morpholin-4-yl-ethoxymethyl)-2-(4-trifluoromethyl-phenyl)-thiazol-5-ylmethoxy]-benzonitrile as its trifluoro-acetate salt.

C25H23ClF3N3O3S.C2HF3O2 (652.02), MS (ESI): 538.2 (M+H+).

3-{2-Chloro-4-[4-(2-morpholin-4-yl-ethoxymethyl)-2-(4-trifluoromethyl-phenyl)-thiazol-5-ylmethoxy]-phenyl}-4H-[1,2,4]oxadiazol-5-one

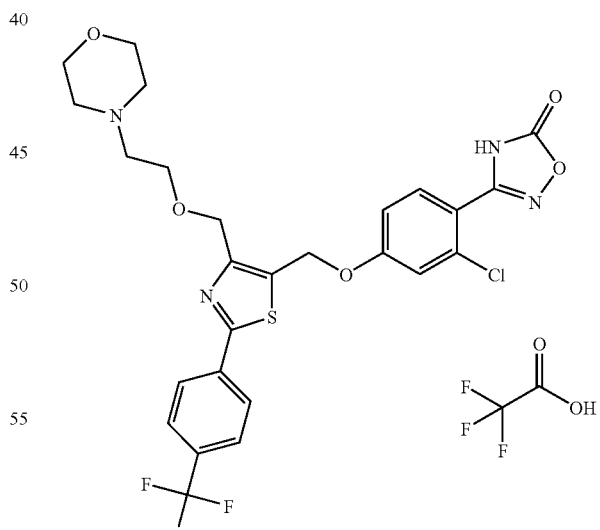

According to the method described for 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one in example 60, 3-{2-chloro-4-[4-(2-morpholin-4-yl-ethoxymethyl)-2-(4-trifluoromethyl-phenyl)-thiazol-5-ylmethoxy]-phenyl}-4H-[1,2,4]oxadiazol-5-one was obtained from 2-chloro-4-[4-(2-morpholin-4-yl-ethoxymethyl)-2-(4-trifluoromethyl-phenyl)-thiazol-5-ylmethoxy]-benzonitrile. The compound was obtained as its trifluoroacetate salt.

C26H24ClF3N4O5S.C2HF3O2 (711.04), MS (ESI): 597.3 (M+H$^+$).

Example 83

3-{2-Chloro-4-[4-(2-cyclohexyl-ethoxymethyl)-2-(4-trifluoromethyl-phenyl)-thiazol-5-ylmethoxy]-phenyl}-4H-[1,2,4]oxadiazol-5-one

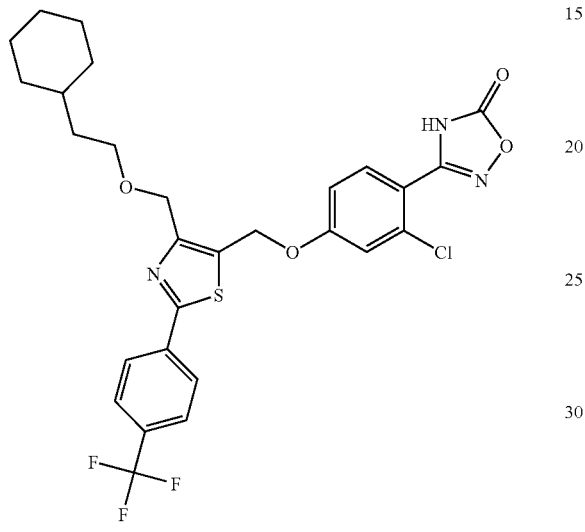

According to the method described for 3-{2-chloro-4-[4-(2-morpholin-4-yl-ethoxymethyl)-2-(4-trifluoromethyl-phenyl)-thiazol-5-ylmethoxy]-phenyl}-4H-[1,2,4]oxadiazol-5-one in example 82 and 3-{4-[4-{[ethyl-(2-methoxy-ethyl)-amino]-methyl}-2-(4-methoxy-phenyl)-oxazol-5-ylmethoxy]-2-methyl-phenyl}-4H-[1,2,4]oxadiazol-5-one in example 60, 3-{2-chloro-4-[4-(2-cyclohexyl-ethoxymethyl)-2-(4-trifluoromethyl-phenyl)-thiazol-5-ylmethoxy]-phenyl}-4H-[1,2,4]oxadiazol-5-one was obtained from methanesulfonic acid 5-(3-chloro-4-cyano-phenoxymethyl)-2-(4-trifluoromethyl-phenyl)-thiazol-4-ylmethyl ester and 2-cyclohexylethanol.

C28H27ClF3N3O4S (594.06), MS (ESI): 594.3 (M+H$^+$).

The following example was obtained according to process A:

Example 84

3-{2-Chloro-4-[4-difluoromethyl-2-(4-methoxy-phenyl)-thiazol-5-ylmethoxy]-phenyl}-4H-[1,2,4]oxadiazol-5-one

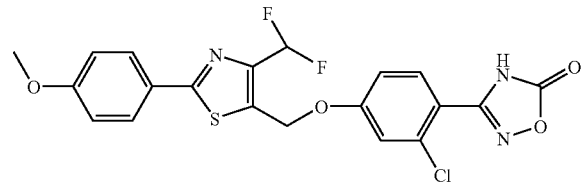

According to the method described for 3-(2-chloro-4-{4-methyl-2-[2-(4-trifluoromethyl-phenyl)-ethyl]-oxazol-5-ylmethoxy}-phenyl)-4H-[1,2,4]oxadiazol-5-one in example 54, 3-{2-chloro-4-[4-difluoromethyl-2-(4-methoxy-phenyl)-thiazol-5-ylmethoxy]-phenyl}-4H-[1,2,4]oxadiazol-5-one was obtained from 5-chloromethyl-4-difluoromethyl-2-(4-methoxy-phenyl)-thiazole and 2-Chloro-4-hydroxy-benzonitrile.

C20H14ClF2N3O4S (465.87), MS (ESI): 466.0 (M+H$^+$).

The following examples were prepared according to process D:

Example 85

3-{4-[4-(4-Hydroxy-piperidin-1-ylmethyl)-2-(4-trifluoromethyl-phenyl)-thiazol-5-ylmethoxy]-2-methoxy-phenyl}-4H-1,2,4-oxadiazol-5-one

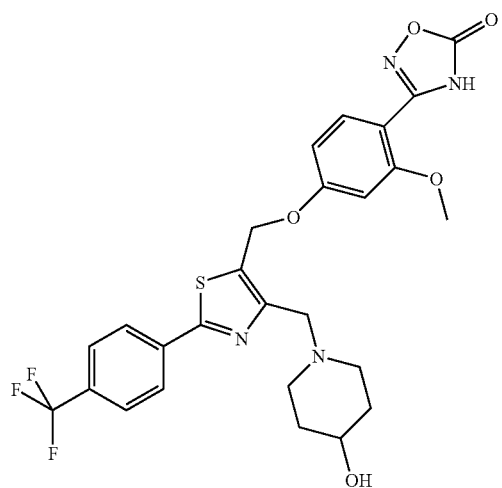

According to the method described for 3-{4-[4-(4-methanesulfonyl-piperazin-1-ylmethyl)-2-(4-trifluoromethyl-phenyl)-thiazol-5-ylmethoxy]-2-methoxy-phenyl}-4H-[1,2,4]oxadiazol-5-one, 3-{4-[4-(4-hydroxy-piperidin-1-ylmethyl)-2-(4-trifluoromethyl-phenyl)-thiazol-5-ylmethoxy]-2-methoxy-phenyl}-4H-1,2,4-oxadiazol-5-one was obtained from methanesulfonic acid 5-[3-methoxy-4-(5-oxo-4,5-dihydro-[1,2,4]oxadiazol-3-yl)-phenoxymethyl]-2-(4-trifluoromethyl-phenyl)-thiazol-4-ylmethyl ester and 4-hydroxy-piperidine.

C26H25F3N4O5S (562.57), MS (ESI): 563 (M+H$^+$).

Example 86

3-{4-[4-(1,4-Dioxa-8-aza-spiro[4.5]dec-8-ylmethyl)-2-(4-trifluoromethyl-phenyl)-thiazol-5-ylmethoxy]-2-methoxy-phenyl}-4H-1,2,4-oxadiazol-5-one

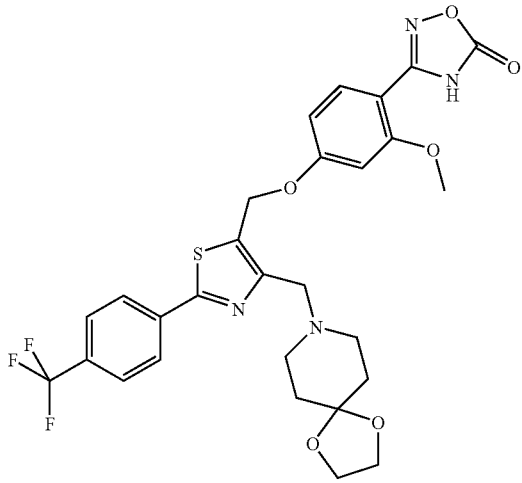

According to the method described for 3-{4-[4-(4-methanesulfonyl-piperazin-1-ylmethyl)-2-(4-trifluoromethyl-phenyl)-thiazol-5-ylmethoxy]-2-methoxy-phenyl}-4H-[1,2,4]oxadiazol-5-one, 3-{4-[4-(1,4-dioxa-8-aza-spiro[4.5]dec-8-ylmethyl)-2-(4-trifluoromethyl-phenyl)-thiazol-5-ylmethoxy]-2-methoxy-phenyl}-4H-1,2,4-oxadiazol-5-one was obtained from methanesulfonic acid 5-[3-methoxy-4-(5-oxo-4,5-dihydro-[1,2,4]oxadiazol-3-yl)-phenoxymethyl]-2-(4-trifluoromethyl-phenyl)-thiazol-4-ylmethyl ester and 1,4-dioxa-8-aza-spiro[4.5]decane.

$C_{28}H_{27}F_3N_4O_6S$ (604.61), MS (ESI): 605 (M+H$^+$).

Example 87

3-{4-[4-(4,4-Dihydroxy-piperidin-1-ylmethyl)-2-(4-trifluoromethyl-phenyl)-thiazol-5-ylmethoxy]-2-methoxy-phenyl}-4H-1,2,4-oxadiazol-5-one

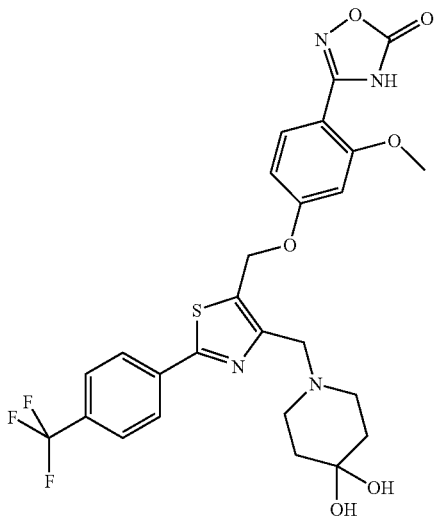

To a suspension of 10 mg of 3-{4-[4-(1,4-dioxa-8-aza-spiro[4.5]dec-8-ylmethyl)-2-(4-trifluoromethyl-phenyl)-thiazol-5-ylmethoxy]-2-methoxy-phenyl}-4H-1,2,4-oxadiazol-5-one in 2 mL of dioxane was added 0.5 mL of a 6N aqueous solution of hydrochloric acid. The resulting mixture was heated to 50° C. for 2 h and then poured into a saturated aqueous solution of sodium hydrogencarbonate and extracted with ethyl acetate. The organic extracts were washed with water, dried over magnesium sulfate, filtered and concentrated under reduced pressure. The crude product was recrystallized in acetonitrile to give 6 mg of 3-{4-[4-(4,4-dihydroxy-piperidin-1-ylmethyl)-2-(4-trifluoromethyl-phenyl)-thiazol-5-ylmethoxy]-2-methoxy-phenyl}-4H-1,2,4-oxadiazol-5-one as yellowish solid.

$C_{26}H_{25}F_3N_4O_6S$ (578.57), MS (ESI): 579 (M+H$^+$).

Example 88

3-{2-Methoxy-4-[4-(1-oxo-1$\lambda^4$-thiomorpholin-4-ylmethyl)-2-(4-trifluoromethyl-phenyl)-thiazol-5-ylmethoxy]-phenyl}-4H-1,2,4-oxadiazol-5-one

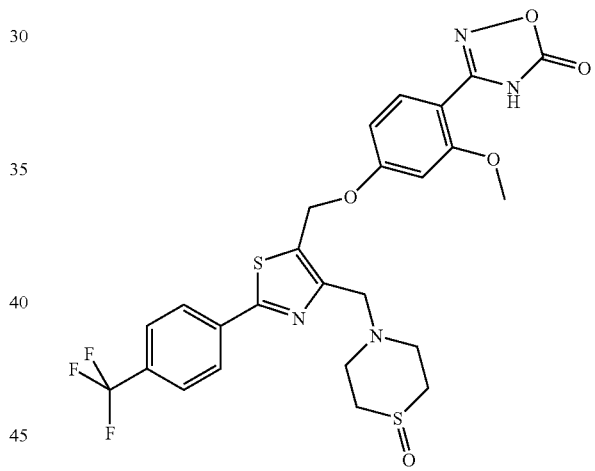

To a solution of 80 mg of 3-{2-methoxy-4-[4-thiomorpholin-4-ylmethyl-2-(4-trifluoromethyl-phenyl)-thiazol-5-ylmethoxy]-phenyl}-4H-[1,2,4]oxadiazol-5-one in 1 mL of methanol was added 2 mL of a 2N solution of hydrochloric acid in diethylether. The resulting mixture was concentrated under reduced pressure. To a solution of the residue in 1 mL of acetonitrile were added 1 mL of water and 88 mg of Oxone®. The resulting mixture was stirred at room temperature for 1 h, then poured into water and extracted with dichloromethane. The organic extracts were washed with water, dried over magnesium sulfate, filtered and concentrated under reduced pressure. The crude product was purified by column chromatography on silica gel (gradient of methanol in dichloromethane) to give 10.5 mg of 3-{2-methoxy-4-[4-(1-oxo-1$\lambda^4$-thiomorpholin-4-ylmethyl)-2-(4-trifluoromethyl-phenyl)-thiazol-5-ylmethoxy]-phenyl}-4H-1,2,4-oxadiazol-5-one as white solid.

$C_{25}H_{23}F_3N_4O_5S_2$ (580.61), MS (ESI): 581 (M+H$^+$).

Example 89

3-{2-Methoxy-4-[4-methylsulfanylmethyl-2-(4-trifluoromethyl-phenyl)-thiazol-5-ylmethoxy]-phenyl}-4H-1,2,4-oxadiazol-5-one

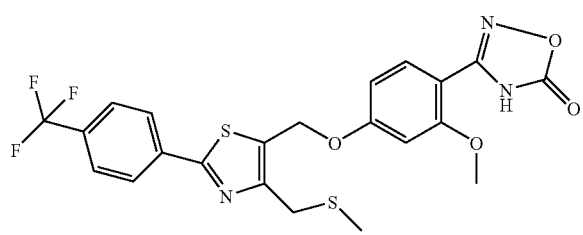

To a solution of 200 mg of methanesulfonic acid 5-[3-methoxy-4-(5-oxo-4,5-dihydro-[1,2,4]oxadiazol-3-yl)-phenoxymethyl]-2-(4-trifluoromethyl-phenyl)-thiazol-4-ylmethyl ester in 5 mL of dimethylformamide was added 50.3 mg of sodium methoxide. The resulting mixture was heated in a sealed tube to 90° C. under microwave irradiation for 5 minutes and concentrated under reduced pressure. The residue was taken into ethyl acetate, washed with water and concentrated under reduced pressure. The crude product was purified by column chromatography on silica gel (gradient of acetone in dichloromethane) to give 55 mg of 3-{2-methoxy-4-[4-methylsulfanylmethyl-2-(4-trifluoromethyl-phenyl)-thiazol-5-ylmethoxy]-phenyl}-4H-1,2,4-oxadiazol-5-one.

C22H18F3N3O4S2 (509.53), MS (ESI): 510 (M+H$^+$).

Example 90

3-{4-[4-Methanesulfinylmethyl-2-(4-trifluoromethyl-phenyl)-thiazol-5-ylmethoxy]-2-methoxy-phenyl}4H-1,2,4-oxadiazol-5-one

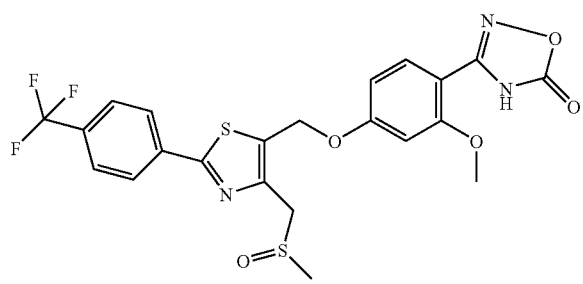

To a solution of 32 mg of 3-{2-methoxy-4-[4-methylsulfanylmethyl-2-(4-trifluoromethyl-phenyl)-thiazol-5-ylmethoxy]-phenyl}-4H-1,2,4-oxadiazol-5-one in 4 mL of dimethylformamide was added 15 mg of metachloroperbenzoic acid. The resulting mixture was stirred for 45 min at room temperature, then poured into water and extracted with dichloromethane. The organic extracts were washed with a saturated aqueous solution if sodium bicarbonate and concentrated under reduced pressure. The crude product was purified by column chromatography on silica gel (gradient of methanol in dichloromethane) to give 25 mg of 3-{4-[4-methanesulfinylmethyl-2-(4-trifluoromethyl-phenyl)-thiazol-5-ylmethoxy]-2-methoxy-phenyl}-4H-1,2,4-oxadiazol-5-one as a white solid which was further purified by trituration with diisopropyl ether.

C22H18F3N3O5S2 (525.53), MS (ESI): 526 (M+H$^+$).

Example 91

3-{4-[4-Methanesulfonylmethyl-2-(4-trifluoromethyl-phenyl)-thiazol-5-ylmethoxy]-2-methoxy-phenyl}-4H-1,2,4-oxadiazol-5-one

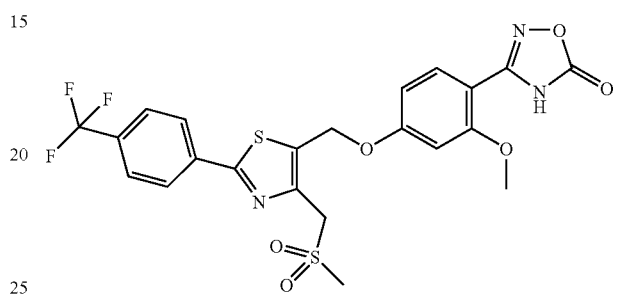

To a suspension of 35 mg of 3-{2-methoxy-4-[4-methylsulfanylmethyl-2-(4-trifluoromethyl-phenyl)-thiazol-5-ylmethoxy]-phenyl}-4H-1,2,4-oxadiazol-5-one in 4 mL of acetonitrile was added 1 mL of water and 84 mg of Oxone®. The resulting mixture was stirred overnight at room temperature, then poured into water and extracted with dichloromethane. The organic extracts were washed with a saturated aqueous solution if sodium bicarbonate and concentrated under reduced pressure. The crude product was triturated with dichloromethane/methanol/tetrahydrofuran/acetone to give 26 mg of 3-{4-[4-methanesulfonylmethyl-2-(4-trifluoromethyl-phenyl)-thiazol-5-ylmethoxy]-2-methoxy-phenyl}-4H-1,2,4-oxadiazol-5-one as a white solid.

C22H18F3N3O6S2 (541.53), MS (ESI): 542 (M+H$^+$).

The following examples were prepared according to process F:

Example 92

3-{4-[4-Aminomethyl-2-(4-trifluoromethyl-phenyl)-thiazol-5-ylmethoxy]-2-fluoro-phenyl}-4H-1,2,4-oxadiazol-5-one

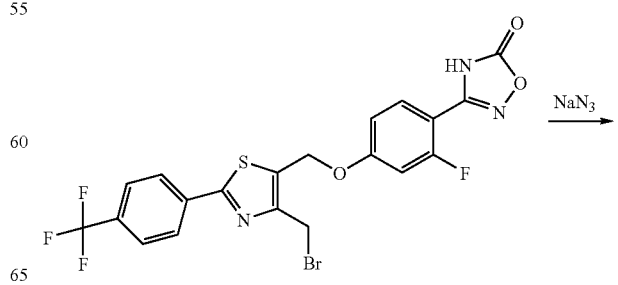

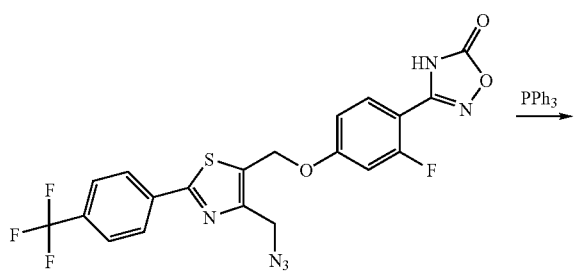

3-{4-[4-Azidomethyl-2-(4-trifluoromethyl-phenyl)-thiazol-5-ylmethoxy]-2-fluoro-phenyl}-4H-1,2,4-oxadiazol-5-one To a solution of 126 mg of 3-{4-[4-bromomethyl-2-(4-trifluoromethyl-phenyl)-thiazol-5-ylmethoxy]-2-fluoro-phenyl}-4H-[1,2,4]oxadiazol-5-one in 1.3 mL of dimethylformamide was added 43.5 mg of sodium azide. The resulting solution was stirred for 5 h and then concentrated under reduced pressure to give 118 mg of 3-{4-[4-azidomethyl-2-(4-trifluoromethyl-phenyl)-thiazol-5-ylmethoxy]-2-fluoro-phenyl}-4H-1,2,4-oxadiazol-5-one which was used in the next step without further purification.

3-{4-[4-Aminomethyl-2-(4-trifluoromethyl-phenyl)-thiazol-5-ylmethoxy]-2-fluoro-phenyl}-4H-1,2,4-oxadiazol-5-one

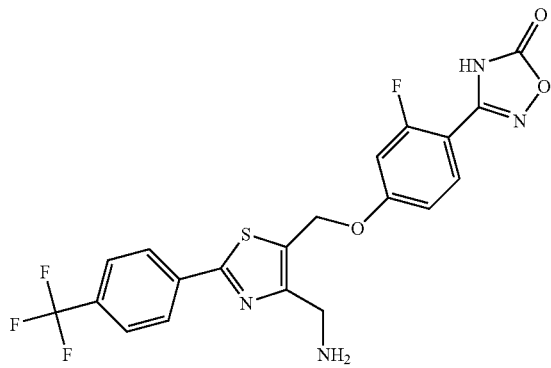

To a mixture of 118 mg of 3-{4-[4-azidomethyl-2-(4-trifluoromethyl-phenyl)-thiazol-5-ylmethoxy]-2-fluoro-phenyl}-4H-1,2,4-oxadiazol-5-one in 0.25 mL of dimethylformamide and 0.022 mL of water was added 31 mg of triphenylphosphine. The resulting mixture was stirred for 20 h at room temperature and then concentrated under reduced pressure. The crude product was purified by column chromatography on silica gel (gradient from dichloromethane 100 to dichloromethane 90/methanol 10/water 1/acetic acid 1) followed by chromatography on a SCX Waters column with gradient CH2Cl2/MeOH 30/70 to 7N NH3 in MeOH to give 5.5 mg of 3-{4-[4-aminomethyl-2-(4-trifluoromethyl-phenyl)-thiazol-5-ylmethoxy]-2-fluoro-phenyl}-4H-1,2,4-oxadiazol-5-one.

C20H14F4N4O3S (466.42), MS (ESI): 467 (M+H$^+$).

Example 93

N-[5-[3-Fluoro-4-(5-oxo-4,5-dihydro-1,2,4-oxadiazol-3-yl)-phenoxymethyl]-2-(4-trifluoromethyl-phenyl)-thiazol-4-ylmethyl]-acetamide

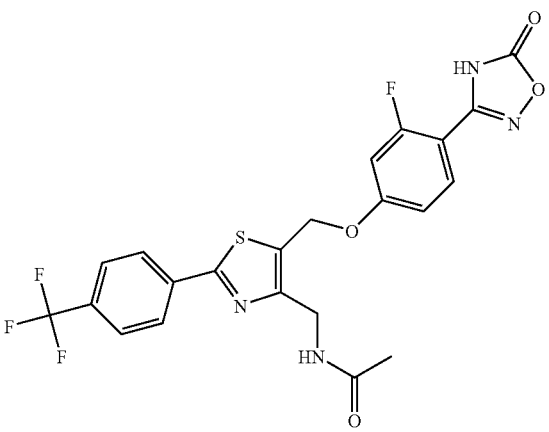

To a suspension of 53.3 mg of 3-{4-[4-aminomethyl-2-(4-trifluoromethyl-phenyl)-thiazol-5-ylmethoxy]-2-fluoro-phenyl}-4H-1,2,4-oxadiazol-5-one in 1 mL of dichloromethane was added 27 mg of pyridine and 19 mg of acetic anhydride. The resulting mixture was stirred for 1.5 h at room temperature and then a drop of pyridine and acetic anhydride were added. After stirring for 25 minutes at room temperature, it was poured into water and extracted with dichloromethane. The organic extracts were dried over magnesium sulfate, filtered, and concentrated under reduced pressure. The crude product was purified by column chromatography on silica gel (gradient from dichloromethane 100 to dichloromethane 90/methanol 10/water 1/acetic acid 1) to give 6.2 mg of N-[5-[3-fluoro-4-(5-oxo-4,5-dihydro-1,2,4-oxadiazol-3-yl)-phenoxymethyl]-2-(4-trifluoromethyl-phenyl)-thiazol-4-ylmethyl]-acetamide.

C22H16F4N4O4S (508.45), MS (ESI): 509 (M+H$^+$).

The following examples were prepared according B:

Example 94
3-{2-Difluoromethoxy-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one
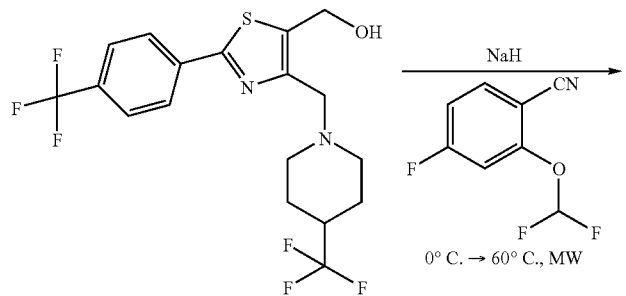
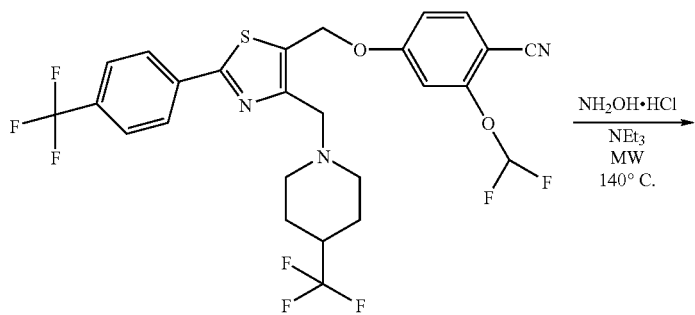
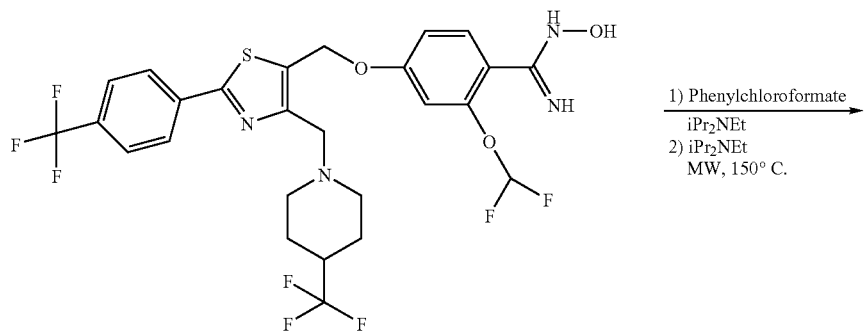
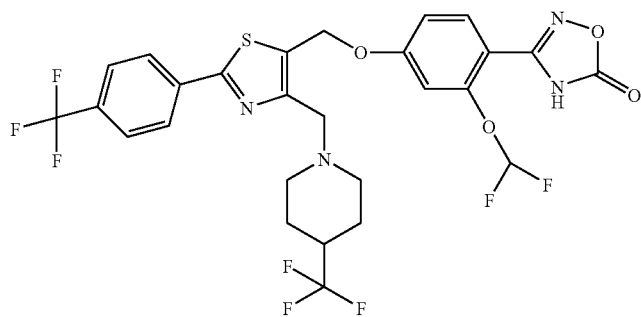

243

2-Difluoromethoxy-4-[2-(4-trifluoromethyl-phenyl)-4-(4-trifluoromethyl-piperidin-1-ylmethyl)-thiazol-5-ylmethoxy]-benzonitrile

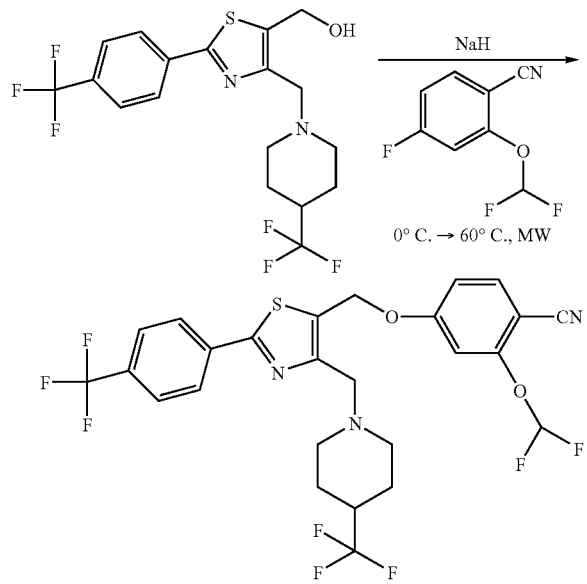

To a solution of 3 g of [2-(4-trifluoromethyl-phenyl)-4-(4-trifluoromethyl-piperidin-1-ylmethyl)-thiazol-5-yl]-methanol in 12 mL of dimethylformamide at 5° C. was added 319 mg of a 55% suspension of sodium hydride in mineral oil. The resulting mixture was stirred for 30 minutes at 5° C. 4.7 mL of the resulting solution was slowly added to a solution 319 mg of 2-difluoromethoxy-4-fluoro-benzonitrile in 1.2 mL of dimethylformamide at 5° C. The resulting mixture was stirred at 5° C. allowing the temperature to warm up to room temperature. It was then heated in a sealed tube to 60° C. under microwave irradiation for 15 minutes. After allowing it to cool down to room temperature, the mixture was poured into water and extracted with dichloromethane. The organic extracts were dried over magnesium sulfate, filtered and concentrated under reduced pressure. The crude product was purified by column chromatography on silica gel (gradient from heptane 100 to heptane 50/ethyl acetate 50) to give 0.83 g of 2-difluoromethoxy-4-[2-(4-trifluoromethyl-phenyl)-4-(4-trifluoromethyl-piperidin-1-ylmethyl)-thiazol-5-ylmethoxy]-benzonitrile.

C26H22F8N3O2S (592.54), MS (ESI): (M+H+) 593.1 (M+H+).

244

2-Difluoromethoxy-N-hydroxy-4-[2-(4-trifluoromethyl-phenyl)-4-(4-trifluoromethyl-piperidin-1-ylmethyl)-thiazol-5-ylmethoxy]-benzamidine

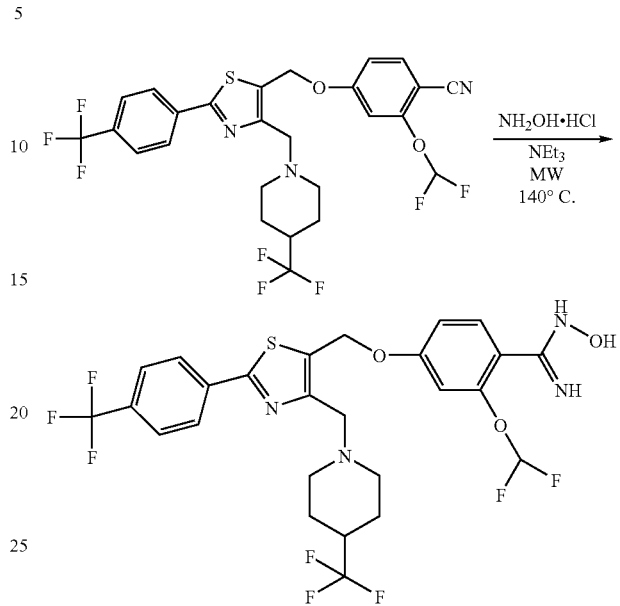

To a solution of 830 mg of 2-difluoromethoxy-4-[2-(4-trifluoromethyl-phenyl)-4-(4-trifluoromethyl-piperidin-1-ylmethyl)-thiazol-5-ylmethoxy]-benzonitrile in 13 mL of methanol was added 5.7 mL of triethylamine followed by 430 mg of hydroxylamine hydrochloride. The resulting mixture was heated in a sealed tube to 140° C. under microwave irradiation for 30 minutes. After allowing it to cool down to room temperature, the mixture was poured into water and extracted with dichloromethane. The organic extracts were dried over magnesium sulfate, filtered and concentrated under reduced pressure. The crude product was purified by column chromatography on silica gel (gradient from heptane 100 to heptane 60/ethyl acetate 40) to give 480 mg of 2-difluoromethoxy-N-hydroxy-4-[2-(4-trifluoromethyl-phenyl)-4-(4-trifluoromethyl-piperidin-1-ylmethyl)-thiazol-5-ylmethoxy]-benzamidine.

C26H24F8N4O3S (624.56), MS (ESI): 625.0 (M+H+).

3-{2-Difluoromethoxy-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one

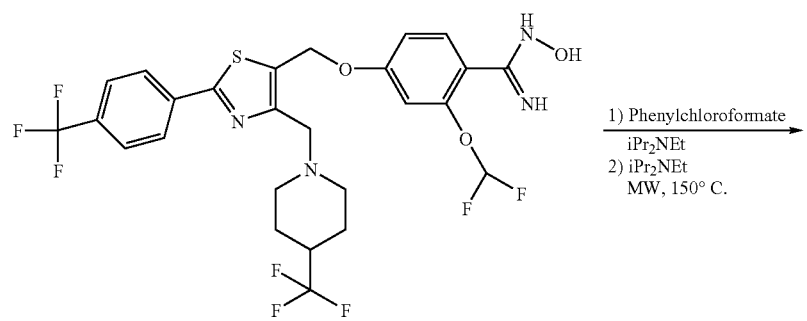

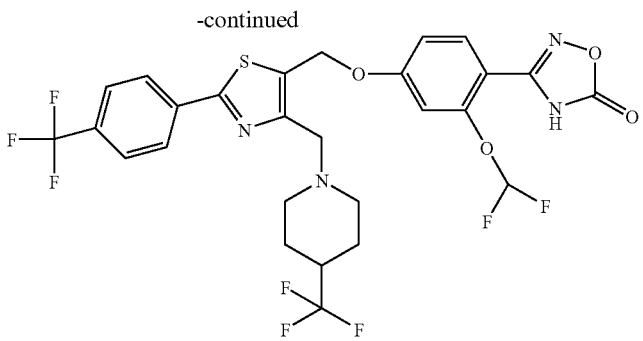

To a solution of 475 mg of 2-difluoromethoxy-N-hydroxy-4-[2-(4-trifluoromethyl-phenyl)-4-(4-trifluoromethyl-piperidin-1-ylmethyl)-thiazol-5-ylmethoxy]-benzamidine in 7.8 mL of tetrahydrofuran at 0° C. was added 1.8 mL of diisopropylethylamine followed by 0.1 mL of phenyl chloroformate. The resulting mixture was stirred for 5 minutes at 0° C. then poured into water and extracted with dichloromethane. The organic extracts were dried over magnesium sulfate, filtered and concentrated under reduced pressure. The residue was dissolved 7.8 mL of tetrahydrofuran and 0.33 mL of diisopropylethylamine. The resulting solution was heated in a sealed tube to 150° C. under microwave irradiation for 15 minutes. After allowing it to cool down to room temperature, the mixture was poured into water and extracted with dichloromethane. The organic extracts were dried over magnesium sulfate, filtered and concentrated under reduced pressure. The crude product was purified by column chromatography on silica gel (diisopropyl ether 100 followed by a gradient from dichloromethane 100 to dichloromethane 90/methanol 10) followed by another column chromatography on silica gel (gradient from dichloromethane 100 to dichloromethane 90/tetrahydrofuran 10) to give 70 mg of 3-{2-difluoromethoxy-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one.

C27H22F8N4O4S (650.55), MS (ESI): 651.2 (M+H$^+$).

Example 95

3-{2-Difluoromethoxy-5-fluoro-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one

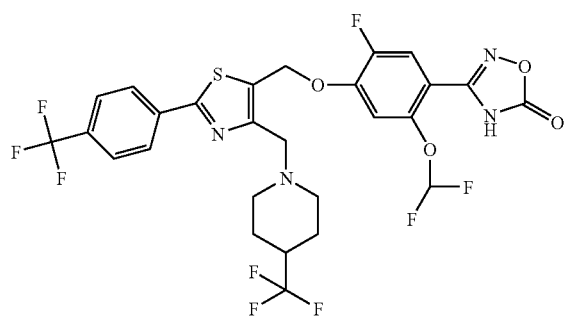

According to the method described for 3-{2-difluoromethoxy-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one, 3-{2-difluoromethoxy-5-fluoro-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one was obtained from [2-(4-trifluoromethyl-phenyl)-4-(4-trifluoromethyl-piperidin-1-ylmethyl)-thiazol-5-yl]-methanol and 2-difluoromethoxy-4,5-difluoro-benzonitrile.

C27H21F9N4O4S (668.54), MS (ESI): 669.9 (M+H$^+$).

Example 96

3-{2-Isopropoxy-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one

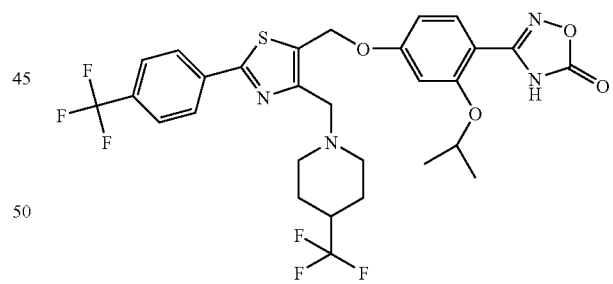

According to the method described for 3-{2-difluoromethoxy-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one, 3-{2-isopropoxy-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one was obtained from [2-(4-trifluoromethyl-phenyl)-4-(4-trifluoromethyl-piperidin-1-ylmethyl)-thiazol-5-yl]-methanol and 4-fluoro-2-isopropoxy-benzonitrile.

C29H28F6N4O4S (642.63), MS (ESI): 643.0 (M+H$^+$).

Example 97

3-{2-Cyclopropylmethoxy-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one

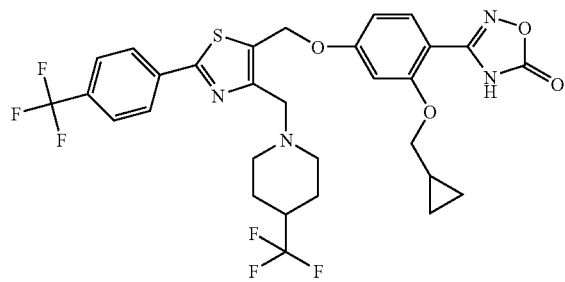

According to the method described for 3-{2-difluoromethoxy-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one, 3-{2-cyclopropylmethoxy-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one was obtained from [2-(4-trifluoromethyl-phenyl)-4-(4-trifluoromethyl-piperidin-1-ylmethyl)-thiazol-5-yl]-methanol and 2-cyclopropylmethoxy-4-fluoro-benzonitrile.

C30H28F6N4O4S (654.64), MS (ESI): 656.1 (M+H$^+$).

Example 98

3-{2-(2,2,2-Trifluoro-ethoxy)-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one

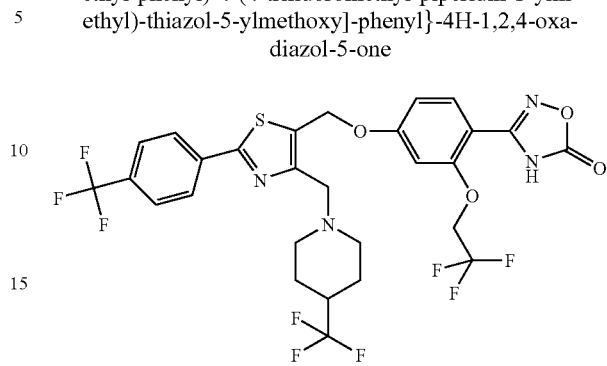

According to the method described for 3-{2-difluoromethoxy-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one, 3-{2-(2,2,2-trifluoro-ethoxy)-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one was obtained from [2-(4-trifluoromethyl-phenyl)-4-(4-trifluoromethyl-piperidin-1-ylmethyl)-thiazol-5-yl]-methanol and 4-fluoro-2-(2,2,2-trifluoro-ethoxy)-benzonitrile.

C28H23F9N4O4S (682.57), MS (ESI): 683.1 (M+H$^+$).

The following example was prepared according to process C:

Example 99

3-{5-Fluoro-2-(2,2,2-trifluoro-ethoxy)-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one

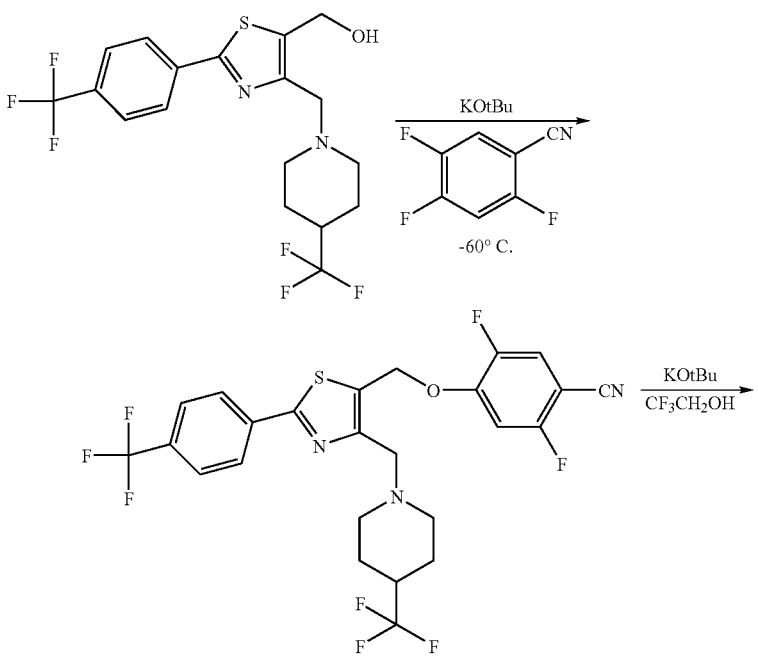

-continued
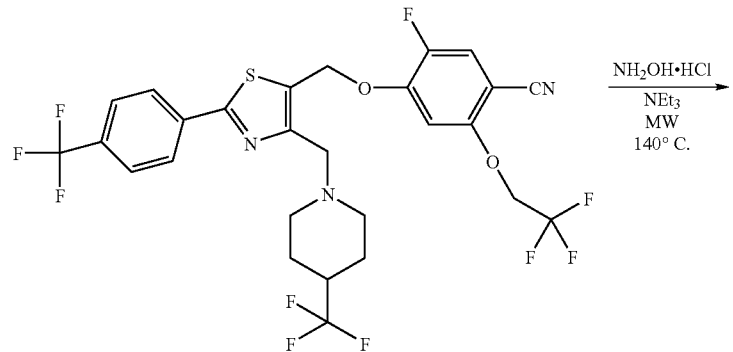
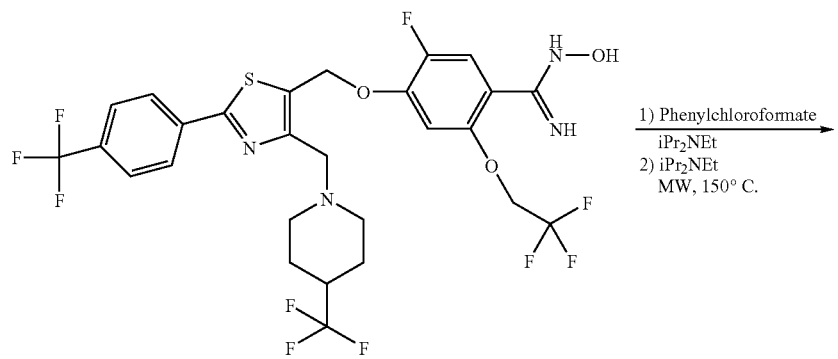
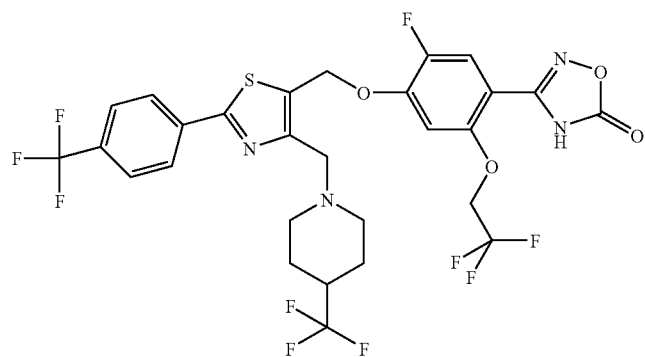
2,5-Difluoro-4-[2-(4-trifluoromethyl-phenyl)-4-(4-trifluoromethyl-piperidin-1-ylmethyl)-thiazol-5-yl-methoxy]-benzonitrile
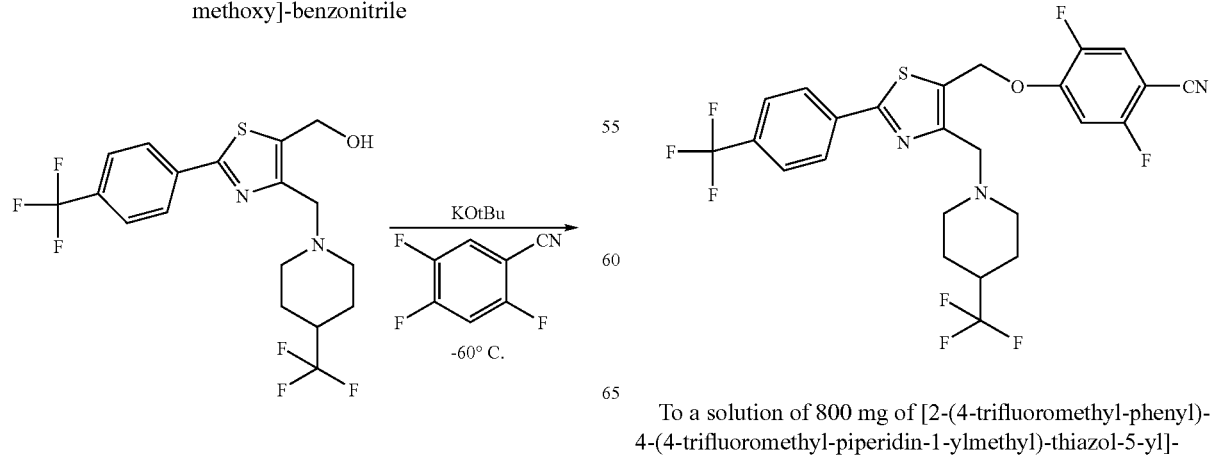
To a solution of 800 mg of [2-(4-trifluoromethyl-phenyl)-4-(4-trifluoromethyl-piperidin-1-ylmethyl)-thiazol-5-yl]- methanol in 4 mL of tetrahydrofuran at 5° C. was slowly added 2.13 mL of a molar solution of potassium tert-butoxide in tert-butanol. After stirring at 5° C. for 30 minutes, the resulting solution was slowly added to a solution of 296 mg of 2,4,5-trifluoro-benzonitrile in 1 mL of tetrahydrofuran at −60° C. The resulting mixture was stirred for 1 h at −60° C. then stirred overnight allowing the temperature to warm up to room temperature. It was then poured into water and extracted with dichloromethane. The organic extracts were dried over magnesium sulfate, filtered and concentrated under reduced pressure. The crude product was recrystallized from methanol and washed with diisopropyl ether to give 890 mg of 2,5-difluoro-4-[2-(4-trifluoromethyl-phenyl)-4-(4-trifluoromethyl-piperidin-1-ylmethyl)-thiazol-5-ylmethoxy]-benzonitrile.

C25H19F8N3OS (561.50), MS (ESI): 563.1 (M+H$^+$).

5-Fluoro-2-(2,2,2-trifluoro-ethoxy)-4-[2-(4-trifluoromethyl-phenyl)-4-(4-trifluoromethyl-piperidin-1-ylmethyl)-thiazol-5-ylmethoxy]-benzonitrile

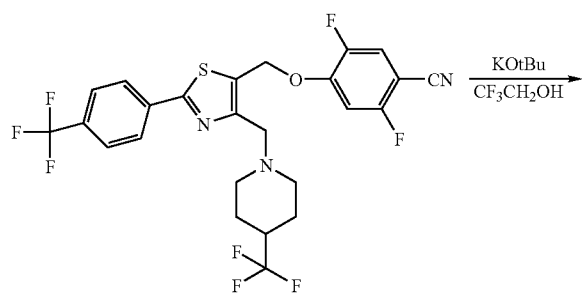

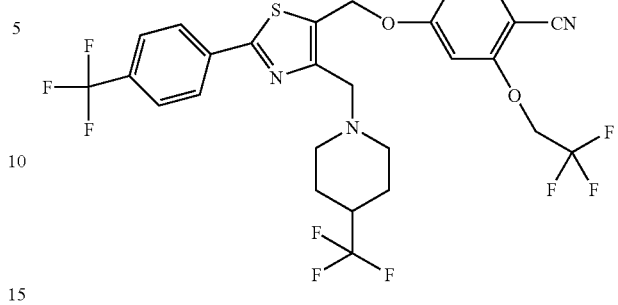

To a solution of 190 mg of trifluoroethanol in 1.16 mL of tetrahydrofuran at 5° C. was slowly added 2.2 mL of a molar solution of potassium tert-butoxide in tert-butanol. After stirring at 5° C. for 30 minutes, the resulting solution was slowly added to a solution of 890 mg of 2,5-difluoro-4-[2-(4-trifluoromethyl-phenyl)-4-(4-trifluoromethyl-piperidin-1-ylmethyl)-thiazol-5-ylmethoxy]-benzonitrile in 3.1 mL of tetrahydrofuran at −60° C. The resulting mixture was stirred overnight allowing the temperature to warm up to room temperature. It was then poured into water and extracted with dichloromethane. The organic extracts were dried over magnesium sulfate, filtered and concentrated under reduced pressure. The crude product was triturated with diisopropyl ether and filtered to give 410 mg of 5-fluoro-2-(2,2,2-trifluoroethoxy)-4-[2-(4-trifluoromethyl-phenyl)-4-(4-trifluoromethyl-piperidin-1-ylmethyl)-thiazol-5-ylmethoxy]-benzonitrile as a white solid.

C27H21F10N3O2S (641.54), MS (ESI): 642.1 (M+H$^+$).

3-{5-Fluoro-2-(2,2,2-trifluoro-ethoxy)-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one

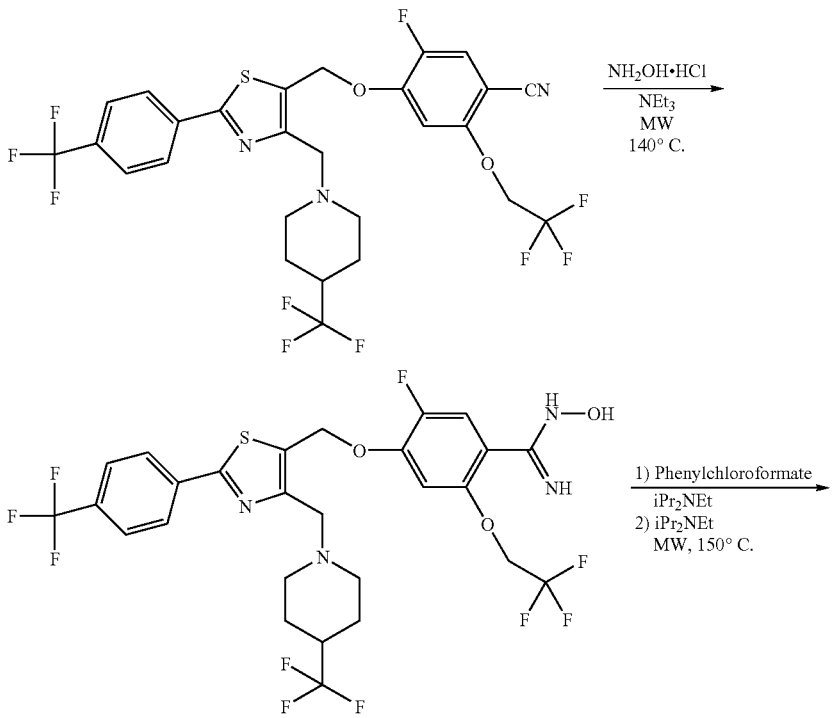

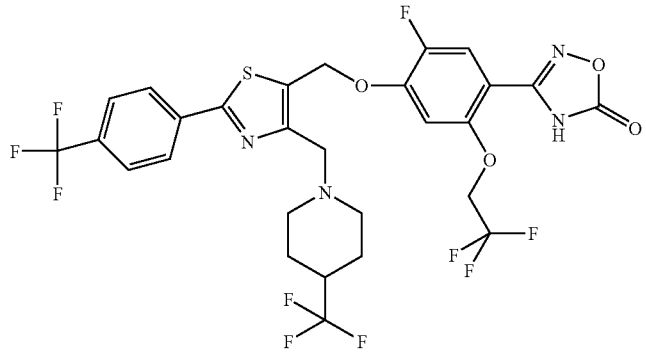

According to the method described for 3-{2-difluoromethoxy-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one, 3-{5-fluoro-2-(2,2,2-trifluoro-ethoxy)-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one was obtained from 5-fluoro-2-(2,2,2-trifluoro-ethoxy)-4-[2-(4-trifluoromethyl-phenyl)-4-(4-trifluoromethyl-piperidin-1-ylmethyl)-thiazol-5-ylmethoxy]-benzonitrile.

C28H22F10N4O4S (700.56), MS (ESI): 701.9 (M+H$^+$).

3-{5-fluoro-2-(2,2,2-trifluoro-ethoxy)-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one can also be prepared according to the method described for 3-{2-difluoromethoxy-4-[2-(4-trifluoromethyl-phenyl)-4-(4-trifluoromethyl-piperidin-1-ylmethyl)-thiazol-5-ylmethoxy]-phenyl}-4H-1,2,4-oxadiazol-5-one by starting from [2-(4-trifluoromethyl-phenyl)-4-(4-trifluoromethyl-piperidin-1-ylmethyl)-thiazol-5-yl]-methanol and 4,5-difluoro-2-(2,2,2-trifluoro-ethoxy)-benzonitrile.[9]

[9] WO2005/111003

The following example was prepared according to process B:

Example 100

3-{6-[4-Butyl-2-(4-trifluoromethyl-phenyl)-thiazol-5-ylmethoxy]-2-methyl-pyridin-3-yl}-4H-[1,2,4]oxadiazol-5-one

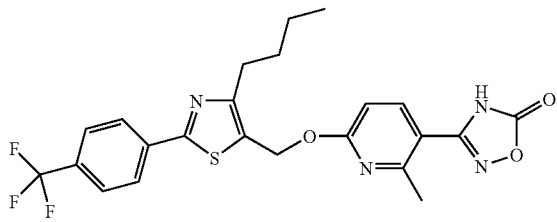

According to the method described in Example 1, 3-{6-[4-Butyl-2-(4-trifluoromethyl-phenyl)-thiazol-5-ylmethoxy]-2-methyl-pyridin-3-yl}-4H-[1,2,4]oxadiazol-5-one was obtained from [4-Butyl-2-(4-trifluoromethyl-phenyl)-thiazol-5-yl]-methanol[10] and commercially available 6-Fluoro-2-methyl-nicotinonitrile.

[10] EP1586573

C23H21F3N4O3S (490.51), MS (ESI): 491 (M+H$^+$).

The following examples were prepared according to process D:

Example 101

3-{2-Methoxy-4-[4-(3-methylsulfanyl-propyl)-2-(4-trifluoromethyl-phenyl)-thiazol-5-ylmethoxy]-phenyl}-4H-1,2,4-oxadiazol-5-one

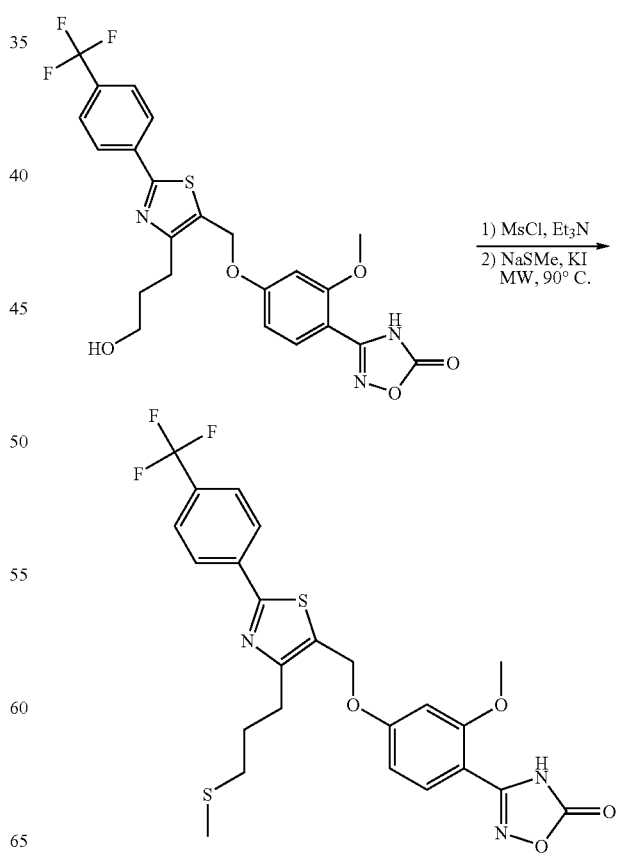

To a solution of 100 mg of 3-{4-[4-(3-hydroxy-propyl)-2-(4-trifluoromethyl-phenyl)-thiazol-5-ylmethoxy]-2-methoxy-phenyl}-4H-[1,2,4]oxadiazol-5-one in 1 mL of dimethylformamide at 0° C. were added 0.077 mL of triethylamine and 0.015 mL of methanesulfonyl chloride. The resulting mixture was stirred at 0° C. for 30 minutes and then concentrated under reduced pressure. The product was dissolved in 3 mL of dimethylformamide. To the resulting solution were added 5.5 mg of sodium methanethiolate and 13 mg of potassium iodide. The reaction mixture was heated for 10 minutes to 90° C. under microwave irradiation in a sealed tube. It was then concentrated under reduced pressure, taken into dichloromethane, washed with water, dried over magnesium sulfate, filtered, and concentrated under reduced pressure to give 20 mg of 3-{2-methoxy-4-[4-(3-methylsulfanyl-propyl)-2-(4-trifluoromethyl-phenyl)-thiazol-5-ylmethoxy]-phenyl}-4H-1,2,4-oxadiazol-5-one.

C24H22F3N3O4S2 (537.58), MS (ESI): 538 (M+H$^+$).

Example 102

3-{4-[4-(3-Methanesulfonyl-propyl)-2-(4-trifluoromethyl-phenyl)-thiazol-5-ylmethoxy]-2-methoxy-phenyl}-4H-1,2,4-oxadiazol-5-one

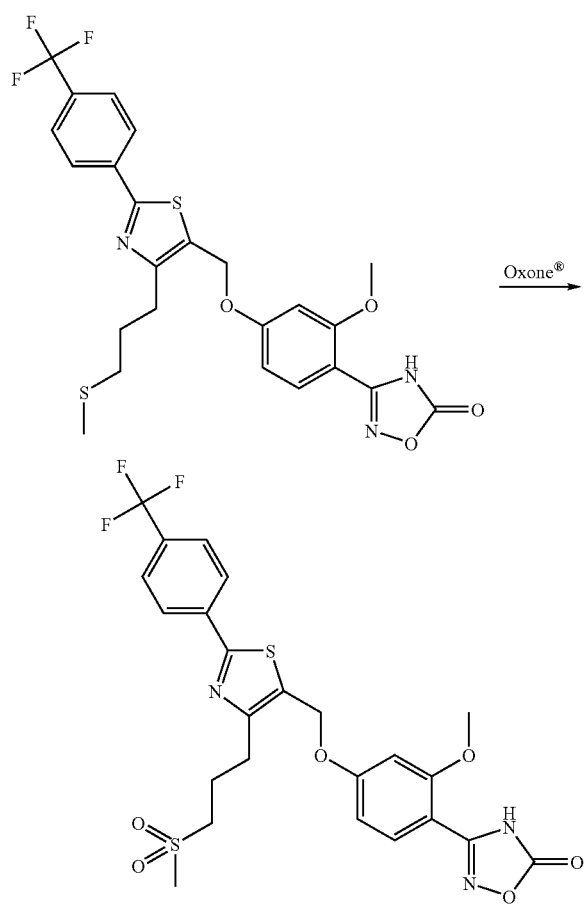

To a suspension of 60 mg of methoxy-4-[4-(3-methylsulfanyl-propyl)-2-(4-trifluoromethyl-phenyl)-thiazol-5-ylmethoxy]-phenyl}-4H-1,2,4-oxadiazol-5-one in 2 mL of acetonitrile and 0.5 mL of water was added 230 mg of Oxone® (potassium peroxymonosulfate). The resulting mixture was stirred at room temperature for 3 hour then poured into ethyl acetate/water. The organic layer was separated, washed with a saturated aqueous solution of Na2S2O3, dried over magnesium sulfate, filtered, and concentrated under reduced pressure. The residue was triturated with 1 mL of acetonitrile and filtered to give 16 mg of 3-{4-[4-(3-methanesulfonyl-propyl)-2-(4-trifluoromethyl-phenyl)-thiazol-5-ylmethoxy]-2-methoxy-phenyl}-4H-1,2,4-oxadiazol-5-one as beige solid.

C24H22F3N3O6S2 (569.58), MS (ESI): 570 (M+H$^+$).

Example 103

3-{2-Methoxy-4-[4-(3-thiomorpholin-4-yl-propyl)-2-(4-trifluoromethyl-phenyl)-thiazol-5-ylmethoxy]-phenyl}-4H-1,2,4-oxadiazol-5-one

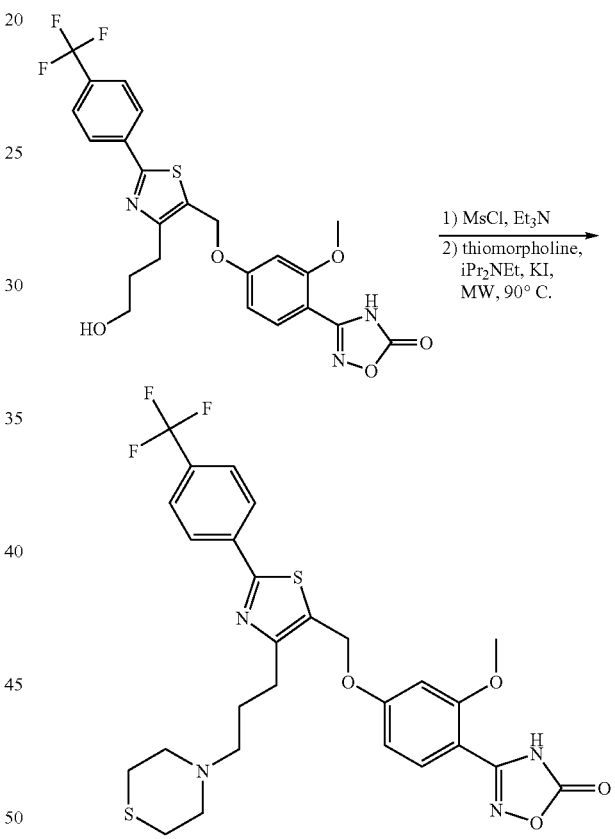

To a solution of 50 mg of 3-{4-[4-(3-hydroxy-propyl)-2-(4-trifluoromethyl-phenyl)-thiazol-5-ylmethoxy]-2-methoxy-phenyl}-4H-[1,2,4]oxadiazol-5-one in 1.5 mL of dimethylformamide at 0° C. were added 0.015 mL of triethylamine and 0.008 mL of methanesulfonyl chloride. The resulting mixture was stirred at 0° C. for 30 minutes and then concentrated under reduced pressure, taken into dichloromethane, washed with water, dried over magnesium sulfate, filtered, and concentrated under reduced pressure. The crude product was dissolved in 4 mL of dimethylformamide. To the resulting solution were added 0.012 mL of thiomorpholine, 0.017 mL of diisopropylethyl amine and 29 mg of potassium iodide. The reaction mixture was heated to 90° C. for 10 minutes under microwave irradiation in a sealed tube. It was then concentrated under reduced pressure, taken into dichloromethane, washed with water, dried over magnesium sulfate, filtered and concentrated under reduced pressure. The residue was purified by column chromatography on silica gel (gradient of methanol in dichloromethane), triturated in acetonitrile and filtered to give 5.3 mg of 3-{2-methoxy-4-[4-(3-thiomorpholin-4-yl-propyl)-2-(4-trifluoromethyl-phenyl)-thiazol-5-ylmethoxy]-phenyl}-4H-1,2,4-oxadiazol-5-one.

C27H27F3N4O4S2 (592.66), MS (ESI): 593 (M+H$^+$).

Example 104

3-{2-Methoxy-4-[4-(3-perhydro-azepin-1-yl-propyl)-2-(4-trifluoromethyl-phenyl)-thiazol-5-ylmethoxy]-phenyl}-4H-1,2,4-oxadiazol-5-one

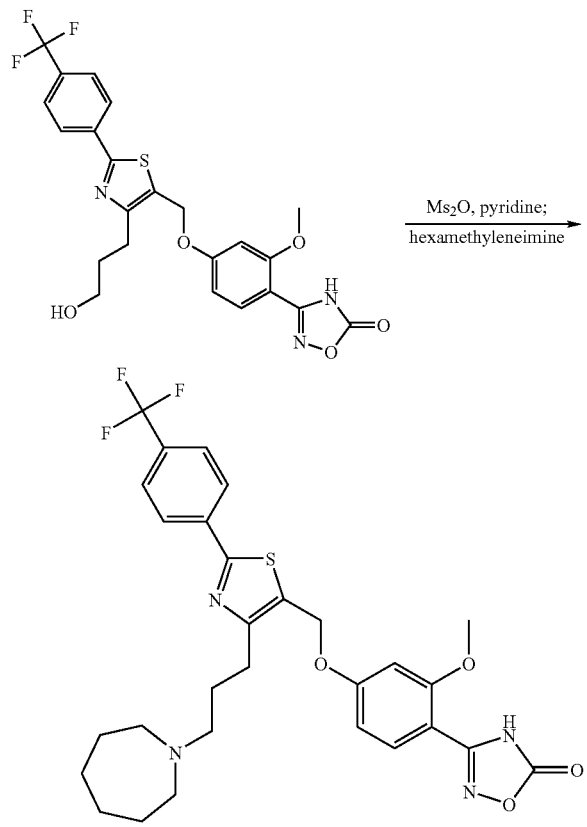

To a mixture of 150 mg of 3-{4-[4-(3-hydroxy-propyl)-2-(4-trifluoromethyl-phenyl)-thiazol-5-ylmethoxy]-2-methoxy-phenyl}-4H-[1,2,4]oxadiazol-5-one in 6 mL of acetonitrile were added 0.100 mL of pyridine and 0.200 mL of methanesulfonic anhydride. The resulting mixture was stirred at room temperature for 5 hour then 0.250 mL of hexamethyleneimine was added. The mixture was stirred at room temperature overnight and then concentrated under reduced pressure. The residue was purified by preparative HPLC on normal phase coupled to MS (gradient of methanol 5 in dichloromethane containing NH4OH), then precipitated from dichloromethane/pentane to give 26 mg of 3-{2-methoxy-4-[4-(3-perhydro-azepin-1-yl-propyl)-2-(4-trifluoromethyl-phenyl)-thiazol-5-ylmethoxy]-phenyl}-4H-1,2,4-oxadiazol-5-one as a white solid.

C29H31F3N4O4S (588.65), MS (ESI): 589 (M+H$^+$).

Example 105

3-{2-Methoxy-4-[4-(3-morpholin-4-yl-propyl)-2-(4-trifluoromethyl-phenyl)-thiazol-5-ylmethoxy]-phenyl}-4H-1,2,4-oxadiazol-5-one

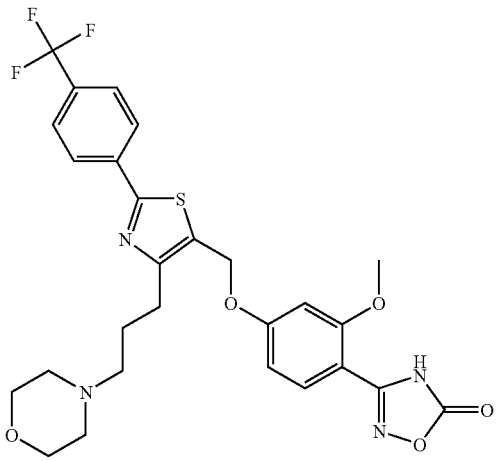

According to the method described 3-{2-methoxy-4-[4-(3-perhydro-azepin-1-yl-propyl)-2-(4-trifluoromethyl-phenyl)-thiazol-5-ylmethoxy]-phenyl}-4H-1,2,4-oxadiazol-5-one, 3-{2-methoxy-4-[4-(3-morpholin-4-yl-propyl)-2-(4-trifluoromethyl-phenyl)-thiazol-5-ylmethoxy]-phenyl}-4H-1,2,4-oxadiazol-5-one was obtained from 3-{4-[4-(3-hydroxy-propyl)-2-(4-trifluoromethyl-phenyl)-thiazol-5-ylmethoxy]-2-methoxy-phenyl}-4H-[1,2,4]oxadiazol-5-one and morpholine.

C27H27F3N4O5S (576.60), MS (ESI): 577 (M+H$^+$).

Example 106

3-{2-Methoxy-4-[4-[3-(4-methyl-piperazin-1-yl)-propyl]-2-(4-trifluoromethyl-phenyl)-thiazol-5-ylmethoxy]-phenyl}-4H-1,2,4-oxadiazol-5-one

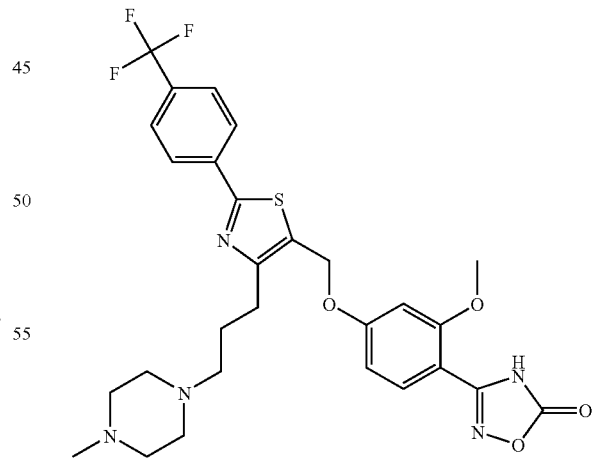

According to the method described 3-{2-methoxy-4-[4-(3-perhydro-azepin-1-yl-propyl)-2-(4-trifluoromethyl-phenyl)-thiazol-5-ylmethoxy]-phenyl}-4H-1,2,4-oxadiazol-5-one, 3-{2-methoxy-4-[4-[3-(4-methyl-piperazin-1-yl)-propyl]-2-(4-trifluoromethyl-phenyl)-thiazol-5-ylmethoxy]-phenyl}-4H-1,2,4-oxadiazol-5-one was obtained from 3-{4-[4-(3-hydroxy-propyl)-2-(4-trifluoromethyl-phenyl)-thiazol-5-ylmethoxy]-2-methoxy-phenyl}-4H-[1,2,4]oxadiazol-5-one and 1-methylpiperazine.

C28H30F3N5O4S (589.64), MS (ESI): 590 (M+H+).

Example 107

3-{2-Methoxy-4-[4-(3-piperidin-1-yl-propyl)-2-(4-trifluoromethyl-phenyl)-thiazol-5-ylmethoxy]-phenyl}-4H-1,2,4-oxadiazol-5-one

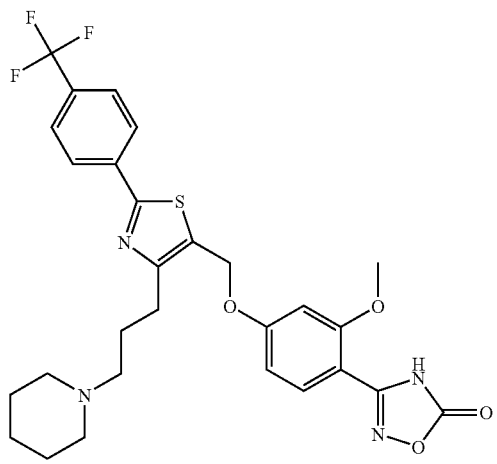

According to the method described 3-{2-methoxy-4-[4-(3-perhydro-azepin-1-yl-propyl)-2-(4-trifluoromethyl-phenyl)-thiazol-5-ylmethoxy]-phenyl}-4H-1,2,4-oxadiazol-5-one, 3-{2-methoxy-4-[4-(3-piperidin-1-yl-propyl)-2-(4-trifluoromethyl-phenyl)-thiazol-5-ylmethoxy]-phenyl}-4H-1,2,4-oxadiazol-5-one was obtained from 3-{4-[4-(3-hydroxy-propyl)-2-(4-trifluoromethyl-phenyl)-thiazol-5-ylmethoxy]-2-methoxy-phenyl}-4H-[1,2,4]oxadiazol-5-one and piperidine.

C28H29F3N4O4S (574.63), MS (ESI): 575 (M+H+).

Example 108

3-{2-Methoxy-4-[4-(3-pyrrolidin-1-yl-propyl)-2-(4-trifluoromethyl-phenyl)-thiazol-5-ylmethoxy]-phenyl}-4H-1,2,4-oxadiazol-5-one

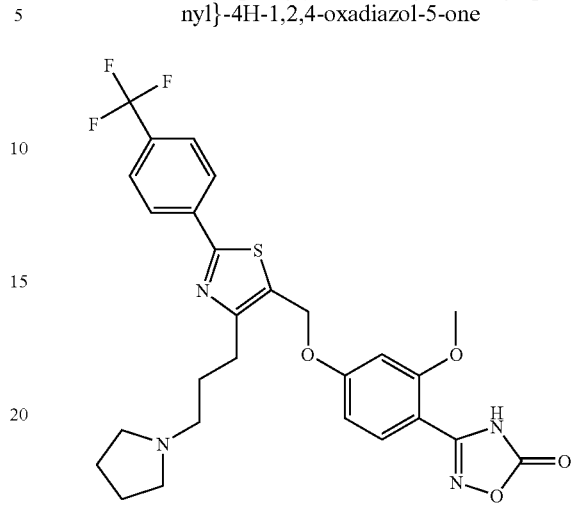

According to the method described 3-{2-methoxy-4-[4-(3-perhydro-azepin-1-yl-propyl)-2-(4-trifluoromethyl-phenyl)-thiazol-5-ylmethoxy]-phenyl}-4H-1,2,4-oxadiazol-5-one, 3-{2-methoxy-4-[4-(3-pyrrolidin-1-yl-propyl)-2-(4-trifluoromethyl-phenyl)-thiazol-5-ylmethoxy]-phenyl}-4H-1,2,4-oxadiazol-5-one was obtained from 3-{4-[4-(3-hydroxy-propyl)-2-(4-trifluoromethyl-phenyl)-thiazol-5-ylmethoxy]-2-methoxy-phenyl}-4H-[1,2,4]oxadiazol-5-one and pyrrolidine.

C27H27F3N4O4S (560.60), MS (ESI): 561 (M+H+).

The following examples were prepared according to process D, whereby the first two reaction steps were performed according to process B:

Example 109

3-{2-Fluoro-4-[4-(3-morpholin-4-yl-propyl)-2-(4-trifluoromethyl-phenyl)-thiazol-5-ylmethoxy]-phenyl}-4H-1,2,4-oxadiazol-5-one

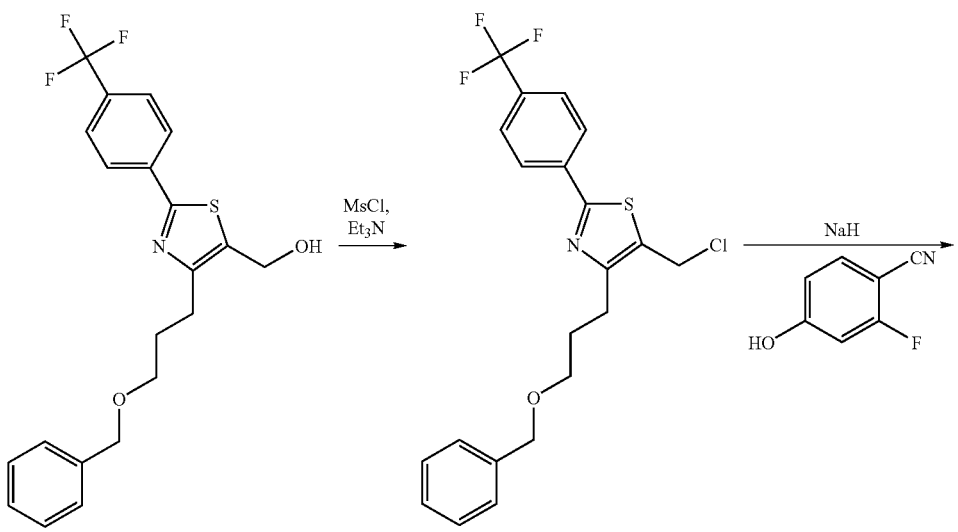

-continued
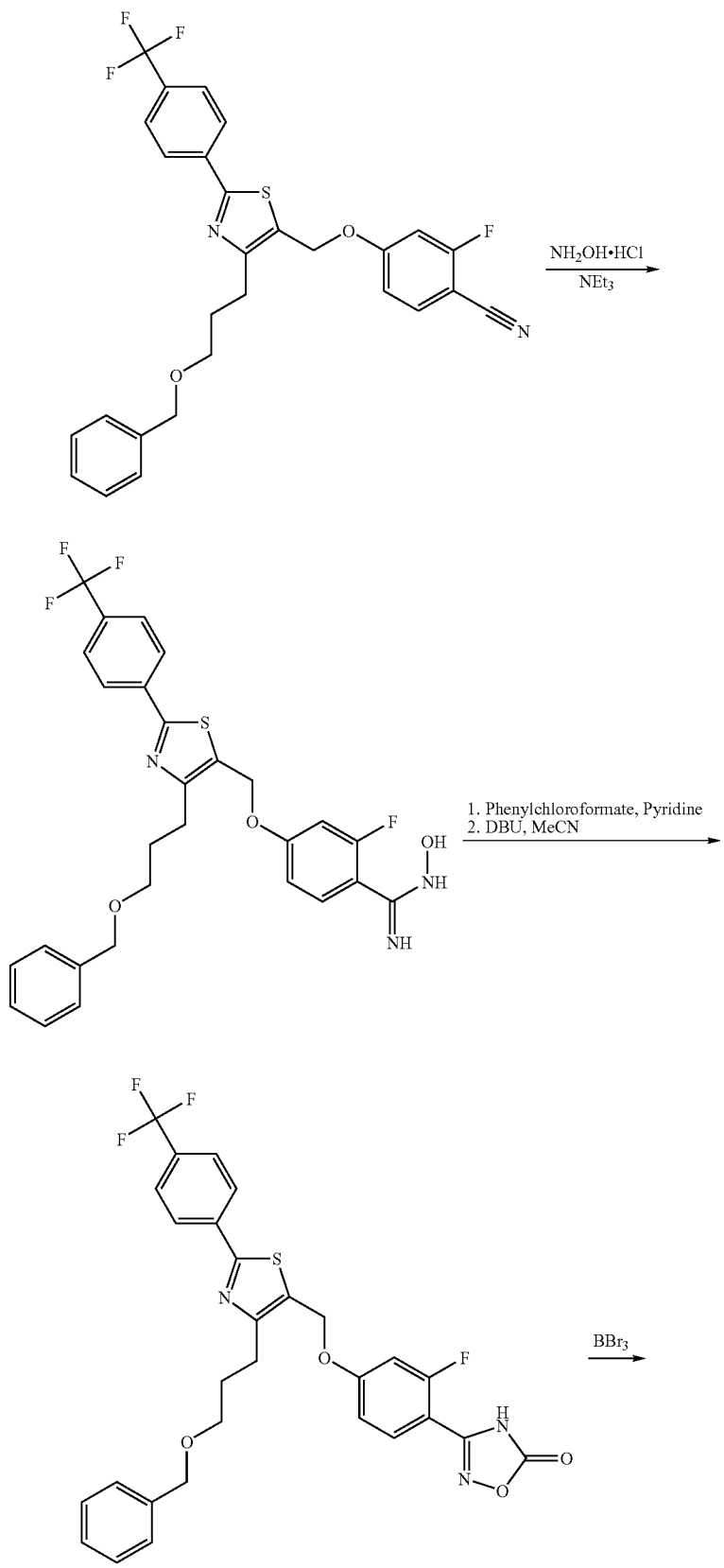

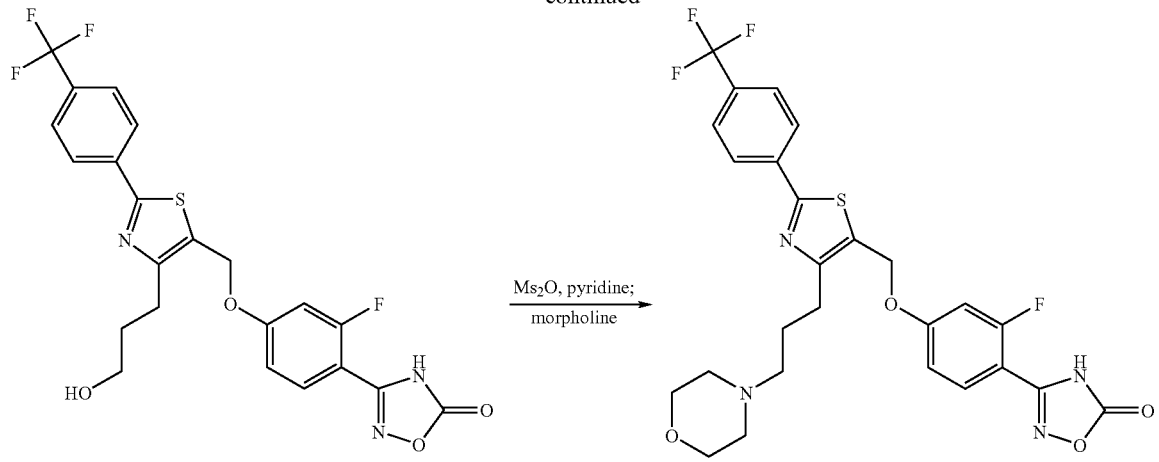

4-(3-Benzyloxy-propyl)-5-chloromethyl-2-(4-trifluoromethyl-phenyl)-thiazole

To a stirred solution of 1.5 g of {4-[3-(benzyloxy)propyl]-2-[4-(trifluoromethyl)phenyl]-1,3-thiazol-5-yl}methanol in 15 mL of dichloromethane were added 0.484 g of methanesulfonylchloride and 1.03 mL of triethylamine. The solution was stirred for 2 h at room temperature. The mixture was diluted with dichloromethane and poured into water. The aqueous layer was separated and extracted three times with dichloromethane. The combined organic layers were dried over magnesium sulfate, filtered and concentrated under reduced pressure to give 1.65 g of crude product as a yellow oil. Purification by column chromatography on silica gel (heptane 90/ethyl acetate 10) gave 0.840 g of 4-(3-benzyloxy-propyl)-5-chloromethyl-2-(4-trifluoromethyl-phenyl)-thiazole.

C21H19ClF3NOS (425.90), MS (ESI): 426 (M+H$^+$).

4-[4-(3-Benzyloxy-propyl)-2-(4-trifluoromethyl-phenyl)-thiazol-5-ylmethoxy]-2-fluoro-benzonitrile

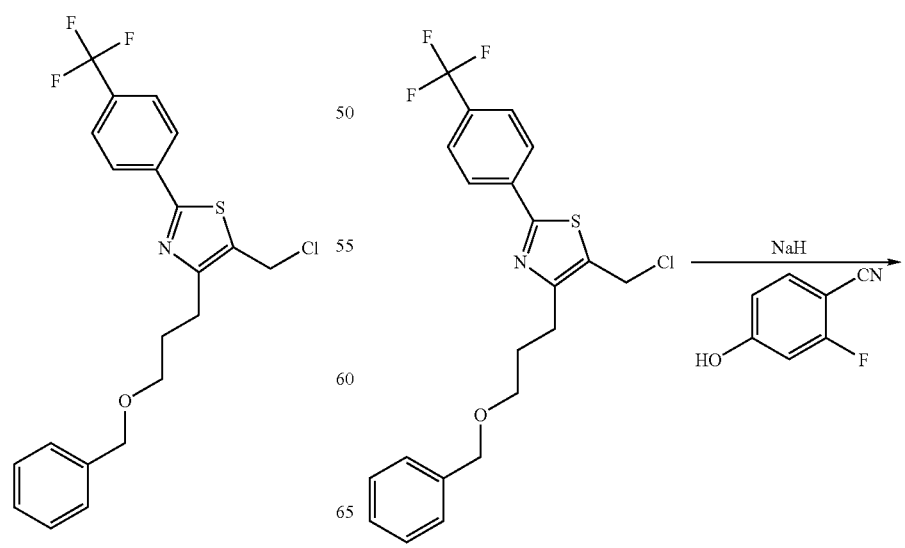

265

-continued

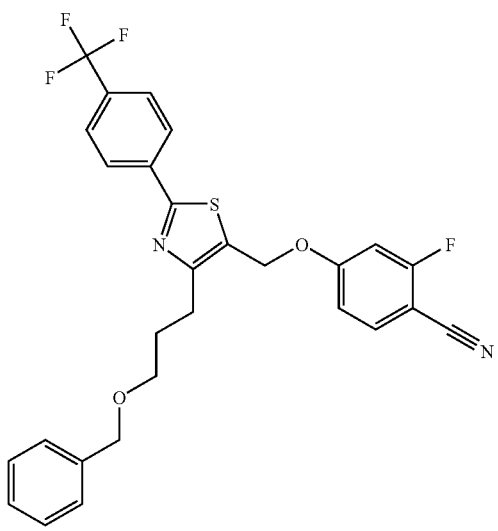

To a stirred solution of 0.82 g of 4-(3-benzyloxy-propyl)-5-chloromethyl-2-(4-trifluoromethyl-phenyl)-thiazole in 12 mL of DMF at 0° C. was added 0.1 g NaH 55%. The reaction mixture was stirred at 0° C. for 10 min then 2-0.264 g of fluoro-4-hydroxybenzonitrile was added at this temperature. The reaction mixture was stirred at 0° C. for 1 h30, allowed to warm up to room temperature and then stirred for 4 h at room temperature. The solvent was removed and the resulting residue was taken up into dichloromethane then water was added. After decantation and separation, the aqueous layer was extracted three times with dichloromethane. The combined organic layers were washed with water, dried over magnesium sulfate, filtered and concentrated under reduced pressure to give 0.91 g of crude product as a yellow oil. Purification by column chromatography on silica gel (heptane 1/ether 1) gave 840 mg of 4-[4-(3-benzyloxy-propyl)-2-(4-trifluoromethyl-phenyl)-thiazol-5-ylmethoxy]-2-fluoro-benzonitrile as a white foam.

C28H22F4N2O2S (526.56), MS (ESI): 527 (M+H$^+$).

266

4-[4-(3-Benzyloxy-propyl)-2-(4-trifluoromethyl-phenyl)-thiazol-5-ylmethoxy]-2-fluoro-N-hydroxy-benzamidine

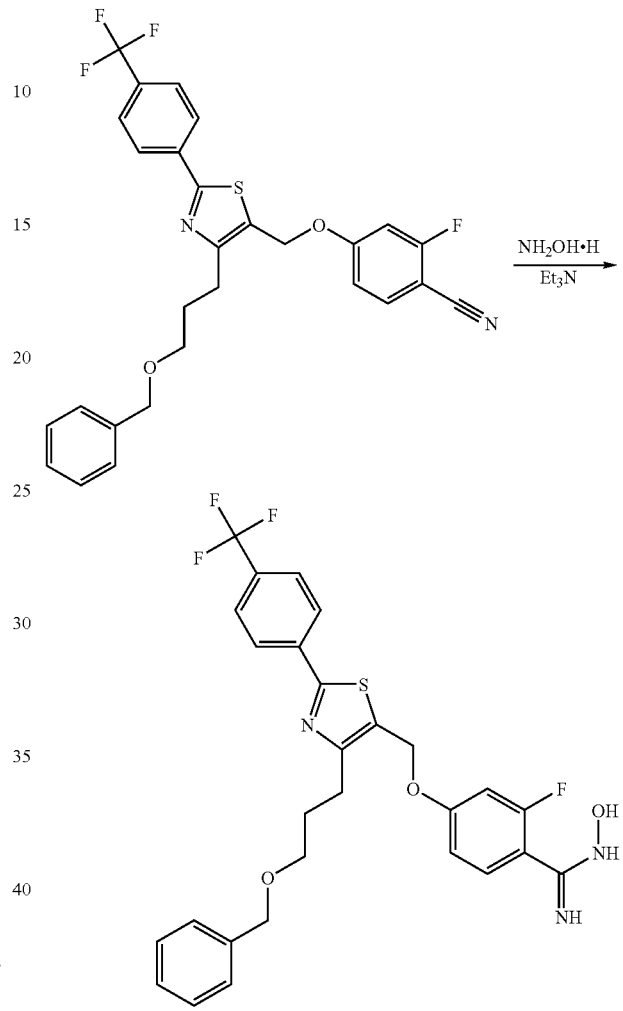

To a stirred solution of 0.84 g of 4-[4-(3-benzyloxy-propyl)-2-(4-trifluoromethyl-phenyl)-thiazol-5-ylmethoxy]-2-fluoro-benzonitrile in 5 mL of tetrahydrofuran and 5.6 mL of methanol were added 1.14 g of hydroxylamine hydrochloride followed by 1.8 mL of triethylamine. The reaction mixture was stirred at reflux temperature for 2 h and then at room temperature overnight. The reaction mixture was refluxed for an additional 2 h and then concentrated under reduced pressure. The residue was taken up into dichloromethane then water was added. The aqueous layer was separated and extracted three times with dichloromethane. The combined organic layers were washed with water, dried over magnesium sulfate, filtered and concentrated under reduced pressure to give 0.840 g of crude product as a yellow gum. Precipitation in heptane afforded 620 mg of 4-[4-(3-benzyloxy-propyl)-2-(4-trifluoromethyl-phenyl)-thiazol-5-ylmethoxy]-2-fluoro-N-hydroxy-benzamidine as a beige powder.

C28H25F4N3O3S (559.59), MS (ESI): 560 (M+H$^+$).

3-{4-[4-(3-Benzyloxy-propyl)-2-(4-trifluoromethyl-phenyl)-thiazol-5-ylmethoxy]-2-fluoro-phenyl}-4H-[1,2,4]oxadiazol-5-one

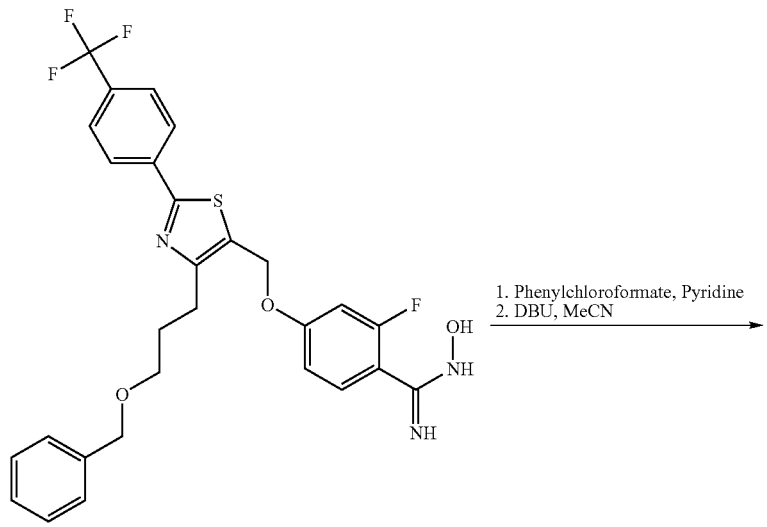

1. Phenylchloroformate, Pyridine
2. DBU, MeCN

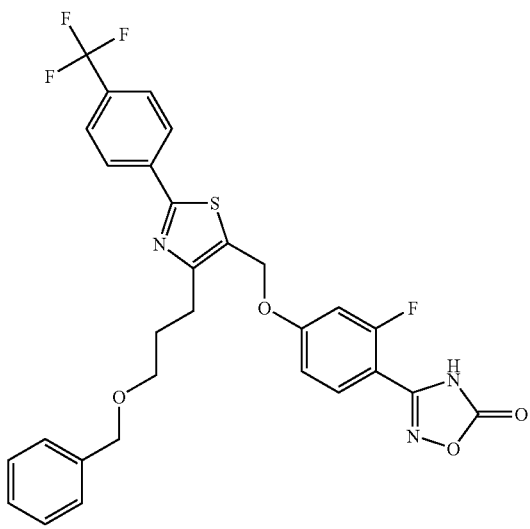

To a stirred suspension of 0.62 g of 4-[4-(3-benzyloxy-propyl)-2-(4-trifluoromethyl-phenyl)-thiazol-5-ylmethoxy]-2-fluoro-N-hydroxy-benzamidine in 17 mL of dichloromethane at 0° C., under argon, were added 0.23 mL of pyridine and 154 µL of phenyl chloroformate. The reaction mixture was stirred for 10 min at 0° C. followed by 1 h at room temperature. The reaction mixture was concentrated under reduced pressure and the resulting residue was taken up into 10 mL of acetonitrile under argon and 0.165 mL of 1,4-diazabicyclo[5.4.0]undec-7-ene (DBU) was added. The reaction mixture was stirred at room temperature overnight then warmed to 40° C. for 2 h. The reaction mixture was concentrated under reduced pressure. The residue was taken up into dichloromethane and a 1M aqueous solution of NaH2PO4 was added. The aqueous layer was separated and extracted three times with dichloromethane. The combined organic layers were washed with water, dried over magnesium sulfate, filtered and concentrated under reduced pressure to give 770 mg of crude product as a yellow powder. Purification by column chromatography on silica gel (heptane 1/ethyl acetate 1) gave 150 mg followed by column washing with 100% MeOH gave 320 mg of the title compound. In total, 470 mg of 3-{4-[4-(3-benzyloxy-propyl)-2-(4-trifluoromethyl-phenyl)-thiazol-5-ylmethoxy]-2-fluoro-phenyl}-4H-[1,2,4]oxadiazol-5-one as white powder was obtained.

C29H23F4N3O4S (585.58), MS (ESI): 586 (M+H$^+$).

3-{2-Fluoro-4-[4-(3-hydroxy-propyl)-2-(4-trifluoromethyl-phenyl)-thiazol-5-ylmethoxy]-phenyl}-4H-[1,2,4]oxadiazol-5-one

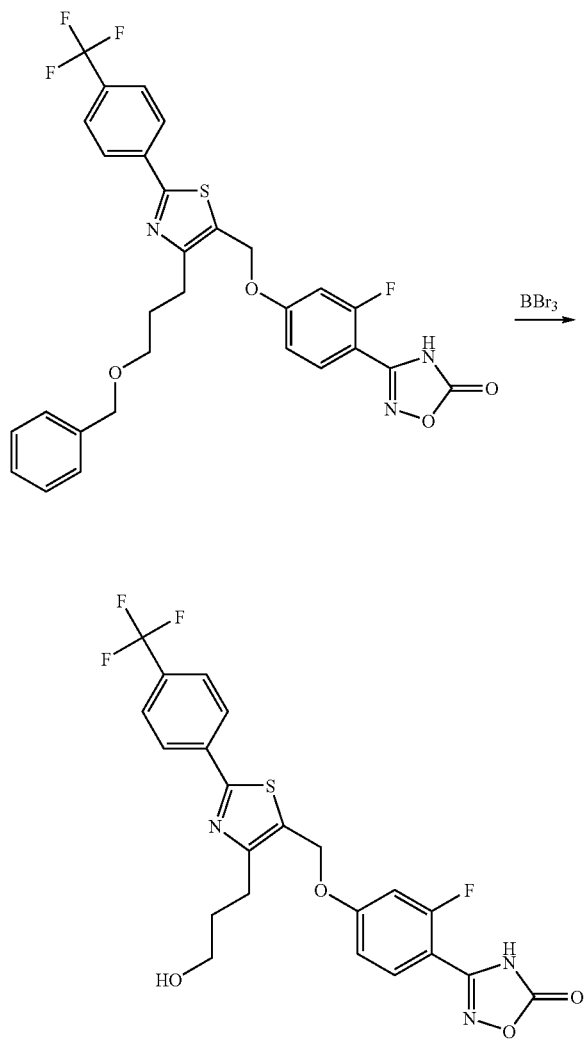

To a stirred solution of 100 mg of 3-{4-[4-(3-benzyloxy-propyl)-2-(4-trifluoromethyl-phenyl)-thiazol-5-ylmethoxy]-2-fluoro-phenyl}-4H-[1,2,4]oxadiazol-5-one in 3 mL of dichloromethane at −70° C. was added 0.34 mL of a 1M solution of boron tribromide in dichloromethane. After 1 h at −60° C., TLC monitoring (dichloromethane/acetone 8/2) showed remaining starting material so 1 mL of a 1M solution of boron tribromide in dichloromethane was added. After 10 min, the reaction mixture was poured into 30 mL of methanol and was neutralised with 5 mL of a saturated aqueous solution of NaHCO3. The suspension was filtered and the filtrate was concentrated under reduced pressure. The residue was taken up into dichloromethane then water added. The aqueous layer was separated and extracted three times with dichloromethane. The combined organic layers were dried over magnesium sulfate, filtered and concentrated under reduced pressure to give 60 mg of crude product. Purification by column chromatography on silica gel (dichloromethane 1/acetone 1) gave 13 mg of a first batch of the title compound (purity >95%) and 50 mg of a second batch of the title compound (purity >90%). The second batch was repurified by column chromatography on silica gel (dichloromethane 90/methanol 10). A total of 48 mg of 3-{2-fluoro-4-[4-(3-hydroxy-propyl)-2-(4-trifluoromethyl-phenyl)-thiazol-5-ylmethoxy]-phenyl}-4H-[1,2,4]oxadiazol-5-one was obtained.

C22H17F4N3O4S (495.46), MS (ESI): 496 (M+H$^+$).

3-{2-Fluoro-4-[4-(3-morpholin-4-yl-propyl)-2-(4-trifluoromethyl-phenyl)-thiazol-5-ylmethoxy]-phenyl}-4H-1,2,4-oxadiazol-5-one

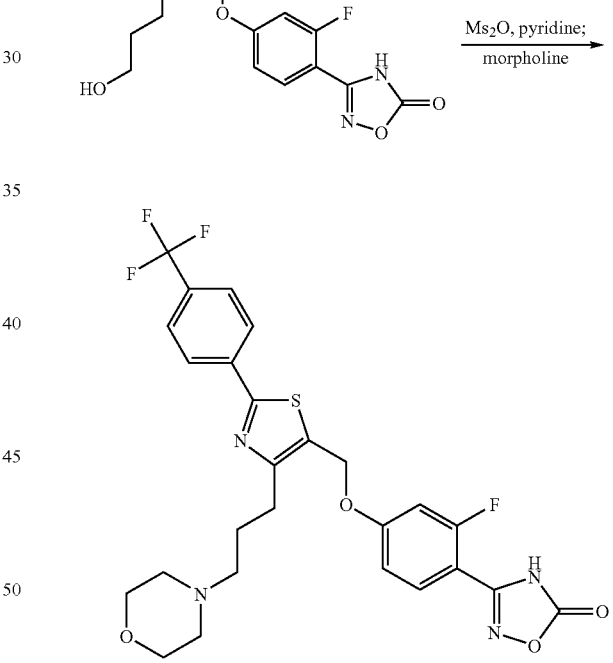

According to the method described 3-{2-methoxy-4-[4-(3-perhydro-azepin-1-yl-propyl)-2-(4-trifluoromethyl-phenyl)-thiazol-5-ylmethoxy]-phenyl}-4H-1,2,4-oxadiazol-5-one, 3-{2-fluoro-4-[4-(3-morpholin-4-yl-propyl)-2-(4-trifluoromethyl-phenyl)-thiazol-5-ylmethoxy]-phenyl}-4H-1,2,4-oxadiazol-5-one was obtained from 3-{2-fluoro-4-[4-(3-hydroxy-propyl)-2-(4-trifluoromethyl-phenyl)-thiazol-5-ylmethoxy]-phenyl}-4H-1,2,4-oxadiazol-5-one and morpholine.

C26H24F4N4O4S (564.56), MS (ESI): 565 (M+H$^+$).

Example 110

3-{2-Fluoro-4-[4-(3-pyrrolidin-1-yl-propyl)-2-(4-trifluoromethyl-phenyl)-thiazol-5-ylmethoxy]-phenyl}-4H-1,2,4-oxadiazol-5-one

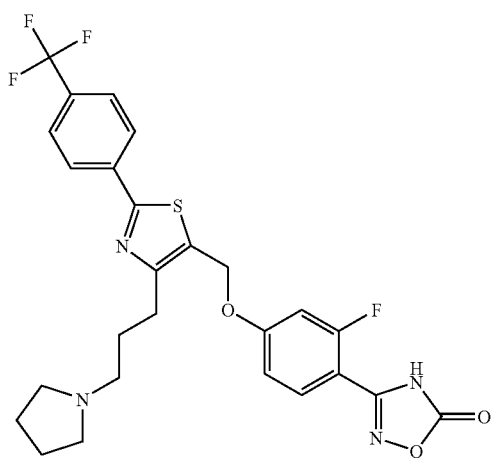

According to the method described 3-{2-methoxy-4-[4-(3-perhydro-azepin-1-yl-propyl)-2-(4-trifluoromethyl-phenyl)-thiazol-5-ylmethoxy]-phenyl}-4H-1,2,4-oxadiazol-5-one, 3-{2-fluoro-4-[4-(3-pyrrolidin-1-yl-propyl)-2-(4-trifluoromethyl-phenyl)-thiazol-5-ylmethoxy]-phenyl}-4H-1,2,4-oxadiazol-5-one was obtained from 3-{2-fluoro-4-[4-(3-hydroxy-propyl)-2-(4-trifluoromethyl-phenyl)-thiazol-5-ylmethoxy]-phenyl}-4H-1,2,4-oxadiazol-5-one and pyrrolidine.

C26H24F4N4O3S (548.56), MS (ESI): 549 (M+H⁺).

Example 111

3-{4-[4-[3-(Benzyl-methyl-amino)-propyl]-2-(4-trifluoromethyl-phenyl)-thiazol-5-ylmethoxy]-2-methoxy-phenyl}-4H-[1,2,4]oxadiazol-5-one

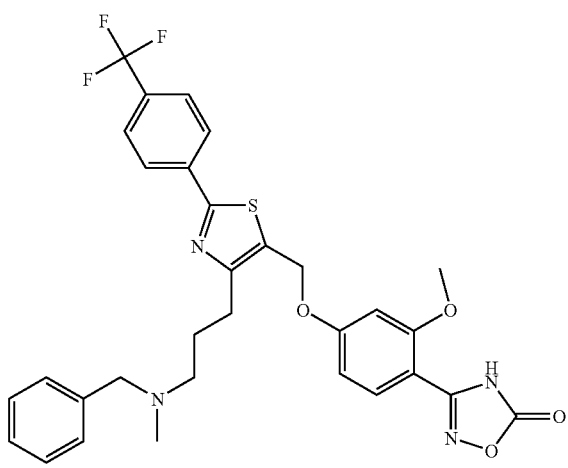

According to the method described 3-{2-methoxy-4-[4-(3-perhydro-azepin-1-yl-propyl)-2-(4-trifluoromethyl-phenyl)-thiazol-5-ylmethoxy]-phenyl}-4H-1,2,4-oxadiazol-5-one, 3-{4-[4-[3-(benzyl-methyl-amino)-propyl]-2-(4-trifluoromethyl-phenyl)-thiazol-5-ylmethoxy]-2-methoxy-phenyl}-4H-[1,2,4]oxadiazol-5-one was obtained from 3-{4-[4-(3-hydroxy-propyl)-2-(4-trifluoromethyl-phenyl)-thiazol-5-ylmethoxy]-2-methoxy-phenyl}-4H-[1,2,4]oxadiazol-5-one and benzyl-methyl-amine.

C31H29F3N4O4S (610.66), MS (ESI): 611 (M+H⁺).

Example 112

3-(2-Methoxy-4-{2-(4-trifluoromethyl-phenyl)-4-[3-(4-trifluoromethyl-piperidin-1-yl)-propyl]-thiazol-5-ylmethoxy}-phenyl)-4H-[1,2,4]oxadiazol-5-one

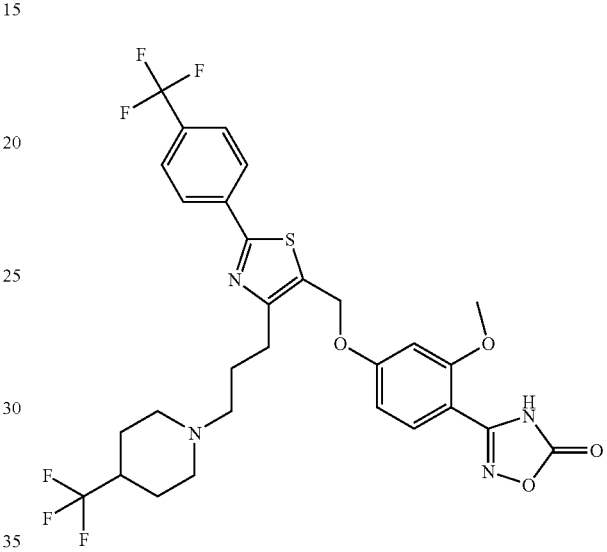

According to the method described for 3-{2-methoxy-4-[4-(3-perhydro-azepin-1-yl-propyl)-2-(4-trifluoromethyl-phenyl)-thiazol-5-ylmethoxy]-phenyl}-4H-1,2,4-oxadiazol-5-one, 3-(2-methoxy-4-{2-(4-trifluoromethyl-phenyl)-4-[3-(4-trifluoromethyl-piperidin-1-yl)-propyl]-thiazol-5-ylmethoxy}-phenyl)-4H-[1,2,4]oxadiazol-5-one was obtained from 3-{4-[4-(3-hydroxy-propyl)-2-(4-trifluoromethyl-phenyl)-thiazol-5-ylmethoxy]-2-methoxy-phenyl}-4H-[1,2,4]oxadiazol-5-one and 4-trifluoromethyl-piperidine.

C29H28F6N4O4S (642.63), MS (ESI): 643 (M+H⁺).

We claim:

1. A compound of formula I:

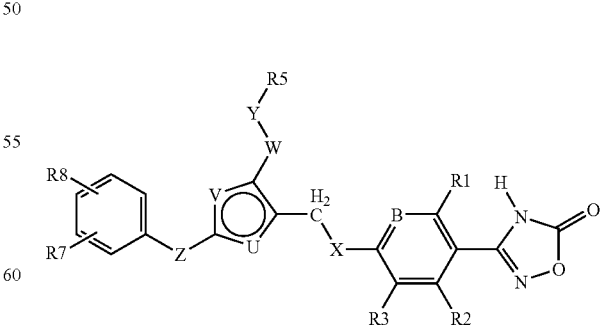

wherein
B is C(R4) or N;
R1 is H, halogen, (C1-C8) alkyl, (C0-C4) alkylene-O—(C0-C4) alkylene-H, (C0-C2) alkylene-O—(C0-C2)

alkylene-(C3-C6) cycloalkyl, SCH3, or CN, wherein the alkyl and alkylene are unsubstituted or mono, bi- or trisubstituted by F;

R2, R3, and R4 are independently
H, halogen, (C1-C8) alkyl, (C0-C4) alkylene-O—(C0-C4) alkylene-H, SCH3, or CN, wherein the alkyl and alkylene are unsubstituted or mono, bi- or trisubstituted by F;

X is O, S, S(O), S(O)2, O-CH2, S—CH2, CH2-O, or CH2-S;

one of U and V is N, and the other is S or O;

W is a bond, (C1-C8) alkylene, (C2-C8) alkenylene, (C0-C6) alkylene-(C3-C6) cycloalkylene, or (C3-C6) cycloalkylene-(C1-C6) alkylene, wherein the alkylene, alkenylene and cycloalkylene are unsubstituted or mono-, di- or trisubstituted by OH or F;

Y is S, S(O), S(O)2, or N(R6),

R5 is H, (C1-C8) alkyl, (C0-C4) alkylene-(C3-C13) cycloalkyl, (C0-C4) alkylene-(C6-C14) aryl, (C2-C8) alkenyl, (C0-C4) alkylene-(C3-C15) heterocycloalkyl, (C0-C4) alkylene-(C3-C15) heterocycloalkenyl, (C0-C4) alkylene-(C5-C15) heteroaryl, (C0-C4) alkylene-CO—(C1-C4) alkyl, (C0-C4) alkylene-CO—(C0-C4) alkylene-(C3-C13)cycloalkyl, (C0-C4) alkylene-CO—(C0-C4) alkylene-(C6-C10)aryl, (C0-C4) alkylene-CO—(C0-C4) alkylene-(C3-C15) heterocycloalkyl, (C0-C4) alkylene-CO—(C0-C4) alkylene-(C3-C15) heterocycloalkenyl, (C0-C4) alkylene-CO—(C0-C4) alkylene-(C5-C15) heteroaryl, SO2-(C1-C4) alkyl, SO2-(C0-C4) alkylene-(C3-C13)cycloalkyl, SO2-(C0-C4) alkylene-(C6-C10) aryl, SO2-(C0-C4) alkylene-(C3-C15) heterocycloalkyl, SO2-(C0-C4) alkylene-(C3-C15) heterocycloalkenyl, SO2-(C0-C4) alkylene-(C5-C15) heteroaryl, CO-O—(C0-C4) alkylene-(C6-C10) aryl, CO—O—(C1-C4) alkyl, CO—O—(C0-C4) alkylene-(C3-C13) cycloalkyl, CO—O—(C0-C4) alkylene-(C3-C15)heterocycloalkyl, CO—O—(C0-C4) alkylene-(C3-Cl5)heterocycloalkenyl, CO—O—(C0-C4) alkylene-(C5-C15)heteroaryl, CO—N((C0-C4) alkylene-H)-(C0-C4) alkylene-(C6-C10) aryl, CO—N((C0-C4) alkylene-H)-(C0-C4) alkylene-H, CO—N((C0-C4) alkylene-H)-(C0-C4) alkylene-(C3-C13)cycloalkyl, CO—N((C0-C4) alkylene-H)-(C0-C4) alkylene-(C3-C15) heterocycloalkyl, CO—N((C0-C4) alkylene-H)-(C0-C4) alkylene-(C3-C15) heterocycloalkenyl, CO—N((C0-C4) alkylene-H)-(C0-C4) alkylene-(C5-C15) heteroaryl, SO2-N((C0-C4)alkylene-H)-(C0-C4) alkylene-(C6-C10)aryl, SO2-N((C0-C4)alkylene-H)-(C0-C4)alkylene-H, SO2-N((C0-C4) alkylene-H)-(C0-C4)alkylene-(C3-C13)cycloalkyl, SO2-N((C0-C4)alkylene-H)-(C0-C4)alkylene-(C3-C15)heterocycloalkyl, SO2-N((C0-C4)alkylene-H)-(C0-C4)alkylene-(C3-C15)heterocycloalkenyl, or SO2-N((C0-C4)alkylene-H)-(C0-C4)alkylene-(C5-C15) heteroaryl, wherein the alkyl and alkylene are unsubstituted or mono-, di- or trisubstituted by F, S-(C1-C4) alkyl, SO-(C1-C4) alkyl, SO2-(C1-C4) alkyl, CO—N((C0-C4)alkylene-H)-(C0-C4) alkylene-H, N((C0-C4) alkylene-H)-(C0-C4) alkylene-H, CO-0(C1-C4) alkyl, (C1-C4) alkyl or O—(C0-C4) alkylene-H, and wherein the cycloalkyl, aryl, heterocycloalkyl, heterocycloalkenyl and heteroaryl are unsubstituted or mono-, di-or trisubstituted by F, Cl, Br, CF3, (C1-C4) alkyl or (C0-C4)-alkylen-O—(C0-C4)alkylene-H,
provided that:
when Y is S, S(O) or S(O)2, then R5 is not SO2-(C1-C4) alkyl, SO2-(C0-C4)alkylene-(C3-C13)cycloalkyl, SO2-(C0-C4)alkylene-(C6C10)aryl, SO2-(C0-C4) alkylene-(C3-C15)heterocycloalkyl, SO2-(C0-C4) alkylene-(C3-C15)heterocycloalkenyl, SO2-(C0-C4) alkylene-(C5-C15)heteroaryl, SO2-N((C0-C4) alkylene-H)-(C0-C4)alkylene-(C6-C10)aryl, SO2-N((C0-C4)alkylene-H)-(C0-C4)alkylene-H, SO2-N((C0-C4)alkylene-H)-(C0-C4)alkylene-(C3-C13)cycloalkyl, SO2-N((C0-C4)alkylene-H)-(C0-C4)alkylene-(C3-C15)heterocycloalkyl, SO2-N((C0-C4)alkylene-H)-(C0-C4)alkylene-(C3-C15)heterocycloalkenyl, or SO2-N((C0-C4)alkylene-H)-(C0-C4)alkylene-(C5-C15) heteroaryl;

R6 is H, (C1-C8)alkyl, (C2-C8)alkenyl, or (C0-C4)alkylene-(C3-C6)cycloalkyl, wherein the alkyl and alkenyl are unsubstituted or mono-, di- or trisubstituted by F or O—(C0-C4)-alkylene-H; or When Y is N(R6), R5 and R6 together with the nitrogen atom to which they are bonded may form a (C3-C15)-heterocycloalkyl, a (C3-C15)-heterocycloalkenyl or a (C5-C15)-heteroaryl, each of which can contain additionally 1 to 3 heteroatoms selected from N, O, and S, wherein the heteroatoms can be oxidized, and each of which is unsubstituted or mono-, di- or trisubstituted by halogen, CN, CF3, (C1-C4) alkyl, (C0-C4) alkylene-(C3-C6) cycloalkyl, (C0-C4) alkylene-O—(C0-C4) alkylene-H, (C0-C4) alkylene-O—(C0-C4) alkylene-(C3-C6) cycloalkyl, (C0-C4) alkylene-O—(C0-C4) alkylene-(C6-C10)aryl, (C0-C4) alkylene-O—(C0-C4) alkylene-(C3-C15) heterocycloalkyl, (C0-C4)alkylene-O—(C0-C4) alkylene-(C3-C15) heterocycloalkenyl, (C0-C4)alkylene-O—(C0-C4)alkylene-(C5-C15) heteroaryl, (C0-C4) alkylene-S-(C1-C4) alkyl, (C0-C4) alkylene-SO—(C1-C4) alkyl, (C0-C4) alkylene-SO2-(C1-C4) alkyl, (C0-C4) alkylene-O—(C1-C4) alkyl, (C0-C4) alkylene-CO—(C6-C10)aryl, (C0-C4) alkylene-O-(C3-C15)heterocycloalkyl, (C0-C4) alkylene-O—(C3-C15)heterocycloalkenyl, (C0-C4) alkylene-O—(C5-C15)heteroaryl, (C0-C4) alkylene-CO—N((C0-C4) alkylene-H)-(C0-C4) alkylene-H, (C0-C4) alkylene-CO—N((C0-C4)alkylene-H)-(C0-C4) alkylene-(C3-C6)cycloalkyl, (C0-C4)alkylene-CO—N((C0-C4)alkylene-H)-(C0-C4)alkylene-(C6-C10)aryl, (C0-C4)alkylene-CO—N((C0-C4)alkylene-H)-(C0-C4)alkylene-(C3-C15)heterocycloalkyl, (C0-C4)alkylene-CO—N((C0-C4)alkylene-H)-(C0-C4)alkylene-(C3-C15)heterocycloalkenyl, (C0-C4)alkylene-CO—N((C0-C4)alkylene-H)-(C0-C4)alkylene-(C5-C15)heteroaryl, (C0-C4) alkylene-N ((C0-C4) alkylene-H)—CO—(C1-C4) alkyl, (C0-C4) alkylene-N((C0-C4) alkylene-H)—CO—(C0-C4)alkylene-(C3-C6) cycloalkyl, (C0-C4) alkylene-N((C0-C4) alkylene-H)—CO—(C0-C4) alkylene-(C6-C10)aryl, (C0-C4) alkylene-N((C0-C4) alkylene-H)—CO—(C0-C4) alkylene-(C3-C15)heterocycloalkyl, (C0-C4)alkylene-N((C0-C4) alkylene-H)—CO—(C0-C4)alkylene-(C3-C15)heterocycloalkenyl, (C0-C4)alkylene-N((C0-C4) alkylene-H)—CO—(C0-C4)alkylene-(C5-C15)heteroaryl, (C0-C4) alkylene-(C6-C14) aryl and (C0-C4) alkylene-(C3-C15) heterocycloalkyl, (C0-C4) alkylene-(C3-C15) heterocycloalkenyl, or (C0-C4) alkylene-(C5-C15) heteroaryl, wherein the heteroaryl, heterocycloalkyl and heterocycloalkenyl can be mono- or disubstituted by oxo, and wherein the alkyl can be unsubstituted or mono-, di- or trisubstituted by F;

Z is a bond, (C1-C8) alkylene, (C2-C8) alkenylene, (C2-C8) alkylidene, or (C1-C6) alkylene-O—(C1-C6) alkylene; and R7 and R8 are independently H, halogen, (C1-C8) alkyl, (C0-C4) alkylene-O—(C0-C4) alkylene-H, SCF3, SF5, S(O)2CF3, (C0-C4) alkylene-O—(C6-C12) aryl, (C0-C4) alkylene (C6-C12) aryl, or NO2, wherein the alkyl and alkylene are unsubstituted or mono-, di- or trisubstituted by F, and the aryl is unsubstituted or mono-, di- or trisubstituted by halogen, (C1-C4) alkyl or O—(C1-C4) alkyl;

or a stereoisomer, enantiomer or tautomer thereof, or a physiologically acceptable salt thereof.

2. The compound according to claim 1, wherein:
R4 is H, (C1-C8) alkyl, or (C0-C4) alkylene-O—(C0-C4) alkylene-H, wherein the alkyl and alkylene are unsubstituted or mono, di- or trisubstituted by F;

or a stereoisomer, enantiomer or tautomer thereof, or a physiologically acceptable salt thereof.

3. The compound according to claim 1, wherein
B is C(R4); and
R4 is H;

or a stereoisomer, enantiomer or tautomer thereof, or a physiologically acceptable salt thereof.

4. The compound according to claim 1, wherein
R1 is halogen, (C1-C4) alkyl, (C0-C4) alkylene-O—(C0-C2) alkylene-H, or O—(C0-C2) alkylene-(C3-C6) cycloalkyl, wherein the alkyl and alkylene are unsubstituted or mono, di- or trisubstituted by F;

or a stereoisomer, enantiomer or tautomer thereof, or a physiologically acceptable salt thereof.

5. The compound according to claim 1, wherein
W is (C1-C3) alkylene;
Y is N(R6); and
R5 and R6 together with the nitrogen atom to which they are attached form a (C3-C7)-heterocycloalkyl, a (C4-C7)-heterocycloalkenyl or a (C5-C8)-heteroaryl, each of which can contain additionally 1 to 2 heteroatoms selected from N, O and S, and each of which is unsubstituted or mono- or disubstituted by F, CF3, (C1-C3) alkyl, (C0-C3) alkylene-O—(C0-C3) alkylene-H, SO2-(C1-C3) alkyl, CO—(C1-C3) alkyl, CO—NH2, NH—CO—(C1-C3) alkyl, phenyl, (C5-C6) heteroaryl, (C3-C7) heterocycloalkyl or (C4-C7) heterocycloalkenyl, wherein the heterocycloalkyl, heterocycloalkenyl and heteroaryl can be mono- or disubstituted by oxo;

or a stereoisomer, enantiomer or tautomer thereof, or a physiologically acceptable salt thereof.

6. The compound according to claim 1, wherein
W is (C1-C3) alkylene;
Y is N(R6),
R5 is H, (C1-C4) alkyl, (C0-C3) alkylene-(C3-C7) cycloalkyl, (C0-C3) alkylene-phenyl, (C0-C3) alkylene-(C3-C7) heterocycloalkyl, (C0-C4) alkylene-(C4-C7) heterocycloalkenyl, (C0-C3) alkylene-(C5-C6) heteroaryl, CO—(C0-C3) alkyl, or CO—O-phenyl, wherein the alkyl and alkylene can be mono-, di- or trisubstituted by F, S—(C1-C3) alkyl, SO—(C1-C3) alkyl, SO2-(C1-C3) alkyl, N((C0-C3) alkylene-H)-(C0-C3) alkylene-H, CO—O(C1-C3) alkyl or O—(C0-C3) alkylene-H, wherein the cycloalkyl, phenyl, heterocycloalkyl, heterocycloalkenyl and heteroaryl are mono-, di- or trisubstituted by F or (C0-C4)-alkylen-O(C0-C4) alkylene-H, and
R6 is H, (C1-C3) alkyl or (C0-C3) alkylene-(C3-C6) cycloalkyl, wherein the alkyl is unsubstituted or mono-, di- or trisubstituted by O—(C0-C4)-alkylene-H; or
Y is S, S(O) or S(O)2, and R5 is (C1-C3) alkyl or (C0-C3) alkylene-(C3-C6) cycloalkyl, wherein the alkyl is unsubstituted or mono-, di- or trisubstituted by F;
Z is —CH2-, —CH2-CH2-, —CH2-O—CH2-, or —CH=CH—;

or a stereoisomer, enantiomer or tautomer thereof, or a physiologically acceptable salt thereof.

7. The compound according to claim 1, wherein
V is N; and
U is O or S;

or a stereoisomer, enantiomer or tautomer thereof, or a physiologically acceptable salt thereof.

8. The compound according to claim 1, wherein X is O or O—CH2;

or a stereoisomer, enantiomer or tautomer thereof, or a physiologically acceptable salt thereof.

9. The compound according to claim 1, wherein
W is a bond or —CH2-;

or a stereoisomer, enantiomer or tautomer thereof, or a physiologically acceptable salt thereof.

10. The compound according to claim 1, wherein
R7 is at para-position;

or a stereoisomer, enantiomer or tautomer thereof, or a physiologically acceptable salt thereof.

11. The compound according to claim 1, wherein
R8 is H;

or a stereoisomer, enantiomer or tautomer thereof, or a physiologically acceptable salt thereof.

12. The compound according to claim 1, wherein
R1 is halogen, (C1-C4) alkyl, (C0-C4) alkylene-O—(C0-C2) alkylene-H, or O—(C0-C2) alkylene-(C3-C6) cycloalkyl, wherein the alkyl and alkylene are unsubstituted or mono, di- or trisubstituted by F;
W is (C1-C3) alkylene;
Y is N(R6), and
R5 and R6 together with the nitrogen atom to which they are attached form a (C3-C7)-heterocycloalkyl, a (C4-C7)-heterocycloalkenyl or a (C5-C8)-heteroaryl, each of which can contain additionally 1 to 2 heteroatoms selected from N, O and S, and each of which is unsubstituted or mono- or disubstituted by F, CF3, (C1-C3) alkyl, (C0-C3) alkylene-O—(C0-C3) alkylene-H, SO2-(C1-C3) alkyl, CO—(C1-C3) alkyl, CO—NH2, NH—CO—(C1-C3) alkyl, phenyl, (C5-C6) heteroaryl, (C3-C7) heterocycloalkyl or (C4-C7) heterocycloalkenyl, wherein the heterocycloalkyl, heterocycloalkenyl and heteroaryl can be mono- or disubstituted by oxo; or
Y is N(R6),
R5 is H, (C1-C4) alkyl, (C0-C3) alkylene-(C3-C7) cycloalkyl, (C0-C3) alkylene-phenyl, (C0-C3) alkylene-(C3-C7) heterocycloalkyl, (C0-C4) alkylene-(C4-C7) heterocycloalkenyl, (C0-C3) alkylene-(C5-C6) heteroaryl, CO—(C0-C3) alkyl, or CO—O-phenyl, wherein the alkyl and alkylene can be mono-, di- or trisubstituted by F, S—(C1-C3) alkyl, SO—(C1-C3) alkyl, SO2-(C1-C3) alkyl, N((C0-C3) alkylene-H)-(C0-C3) alkylene-H, CO-O(C1-C3) alkyl or O —(C0-C3) alkylene-H and wherein the cycloalkyl, phenyl, heterocycloalkyl, heterocycloalkenyl and heteroaryl are mono-, di- or trisubstituted by F or (C0-C4)-alkylen-O—(C0-C4) alkylene-H, and
R6 is H, (C1-C3) alkyl or (C0-C3) alkylene-(C3-C6) cycloalkyl, wherein the alkyl is unsubstituted or mono-, di- or trisubstituted by O—(C0-C4)-alkylene-H; or
Y is S, S(O), or S(O)2, and R5 is (C1-C3) alkyl or (C0-C3) alkylene-(C3-C6) cycloalkyl, wherein the alkyl is unsubstituted or mono-, di- or trisubstituted by F; and Z is —CH2-, —CH2-CH2-, —CH2-O—CH2-, —CH=CH—;

or a stereoisomer, enantiomer or tautomer thereof, or a physiologically acceptable salt thereof.

13. The compound according to claim 1, wherein
B is C(R4);
R4 is H;
R1 is F, Cl, (C1-C4) alkyl, (C0-C4) alkylene-O—(C1-C4) alkylene-H, or (C0-C2) alkylene-O—(C0-C2) alkylene-(C3-C6) cycloalkyl, wherein the alkyl and alkylene are unsubstituted or mono, bi- or trisubstituted by F;
R2 is H;
R3 is H, F or Br;
R4 is H;
X is O or O—CH2;
U is S or O, and
V is N; or
U is N, and
V is O;
W is a bond, or (C1-C4) alkylene;
Y is N(R6), and
R5 is (C1-C8) alkyl, (C0-C4) alkylene-(C3-C13) cycloalkyl, (C0-C4) alkylene-(C6-C12) aryl, (C0-C4) alkylene-(C3-C15) heterocycloalkyl CO—(C0-C4) alkyl, or CO—O—(C6-C10) aryl, wherein the alkyl and alkylene can be mono-, di- or trisubstituted by S—(C1-C4) alkyl, SO—(C1-C4) alkyl, N((C0-C4) alkylene-H)-(C0-C4) alkylene-H or O—(C0-C4) alkylene-H, and wherein the aryl and heterocycloalkyl are mono-, di- or trisubstituted by F or (C0-C4)-alkylene-O—(C0-C4) alkylene-H,
R6 is H, (C1-C8) alkyl or (C0-C4) alkylene-(C3-C6) cycloalkyl, wherein the alkyl is unsubstituted or mono-, di- or trisubstituted by O—(C0-C4)-alkylene-H, or
R5 and R6 together with the nitrogen atom to which they are attached can form a (C3-C8)-heterocycloalkyl, or a (C3-C10)-heterocycloalkenyl, each of which can contain additionally 1 to 3 heteroatoms selected from N, O and S, and each of which is unsubstituted or mono-, di- or trisubstituted by F, CF3, (C1-C4) alkyl, (C0-C4) alkylene-O—(C0-C4) alkylene-H, SO2-(C1-C4) alkyl, or CO—(C1-C4) alkyl, wherein the heterocycloalkyl can be mono- or disubstituted by oxo; or
Y is S, S(O), or S(O)2, and
R5 is (C1-C3) alkyl;
Z is a bond, (C1-C2) alkylene, (C2) alkenylene, (C1-C2) alkylene-O—(C1-C2) alkylene;
R7 is H, O—(C1-C4) alkyl, or CF3; and
R8 is H;

or a stereoisomer, enantiomer or tautomer thereof, or a physiologically acceptable salt thereof.

14. The compound according to claim 1, wherein:
R1 is halogen, (C1-C4) alkyl, OH, or O—(C1-C3) alkyl, wherein the alkyl is unsubstituted or mono, di- or trisubstituted by F;
R2 is H;
R3 is H or F;
B is C(R4) or N;
R4 is H;
X is O;
one of U and V is N, and the other is S or O;
W is (C1-C3) alkylene;

Y is N(R6), and R5 and R6 together with the nitrogen atom to which they are attached form a (C3-C7)-heterocycloalkyl, a (C4-C7)-heterocycloalkenyl or a (C5-C8)-heteroaryl, each of which can contain additionally 1 to 2 heteroatoms selected from N, O and S, and each of which is unsubstituted or mono- or disubstituted by F, CF3, (C1-C3) alkyl, (C0-C3) alkylene-O—(C0-C3) alkylene-H, SO2-(C1-C3) alkyl, CO—(C1-C3) alkyl, CO—NH2, NH—O—(C1-C3) alkyl, phenyl, (C5-C6) heteroaryl, (C3-C7) heterocycloalkyl or (C4-C7) heterocycloalkenyl, wherein the heterocycloalkyl, heterocycloalkenyl and heteroaryl can be mono- or disubstituted by oxo; or
Y is N(R6),
R5 is H, (C1-C4) alkyl, (C0-C3) alkylene-(C3-C7) cycloalkyl, (C0-C3) alkylene-phenyl, (C0-C3) alkylene-(C3-C7) heterocycloalkyl, (C0-C4) alkylene-(C4-C7) heterocycloalkenyl, (C0-C3) alkylene-(C5-C6) heteroaryl, CO—(C0-C3) alkyl, or CO—O-phenyl, wherein the alkyl and alkylene can be mono-, di- or trisubstituted by F, S—(C1-C3) alkyl, SO—(C1-C3) alkyl, SO2-(C1-C3) alkyl, N((C0-C3) alkylene-H)-(C0-C3) alkylene-H, CO—O(C1-C3) alkyl or O—(C0-C3) alkylene-H, and wherein the cycloalkyl, phenyl, heterocycloalkyl, heterocycloalkenyl and heteroaryl are mono-, di- or trisubstituted by F or (C0-C4)-alkylen-O—(C0-C4) alkylene-H, and
R6 is H, (C1-C3) alkyl or (C0-C3) alkylene-(C3-C6) cycloalkyl, wherein the alkyl is unsubstituted or mono-, di- or trisubstituted by O—(C0-C4)-alkylene-H; or
Y is S, S(O), or S(O)2, and
R5 is (C1-C3) alkyl or (C0-C3) alkylene-(C3-C6) cycloalkyl, wherein the alkyl is unsubstituted or mono-, di- or trisubstituted by F;
Z is a bond, (C1-C2) alkylene, (C2) alkenylene, (C1-C2) alkylene-O—(C1-C2) alkylene;
R7 is H, halogen, (C1-C3) alkyl, or O—(C1-C3) alkyl, wherein the alkyl is unsubstituted or mono-, di- or trisubstituted by F; and
R8 is H;

or a stereoisomer, enantiomer or tautomer thereof, or a physiologically acceptable salt thereof 15. The compound according to claim 1, wherein:
R1 is F, OH, OCH3, OCHF2, or OCH2CF3;
R2 is H;
R3 is H or F;
B is C(R4) or N;
R4 is H;
X is O;
one of U and V is N, and the other is S or O;
W is CH2, or CH2CH2CH2;
Y is N(R6), and
R5 and R6 together with the nitrogen atom to which they are bonded (Y =N(R6)) form piperidine, pyrrolidine, azetidine, azepine, morpholine, thiomorpholine, thiomorpholine-S-oxide, thiomorpholine-S-dioxide, piperazine, piperazinone, or iso-indoline, each of which is unsubstituted or mono- or disubstituted by F, CF3, (C1-C3) alkyl, O—(C1-C3) alkyl, OH, CH2OH, SO2CH3, COCH3, or phenyl; or
Y is S, S(O), or S(O)2, and
R5 is CH3;
Z is a bond;
R7 is CF3; and
R8 is H;

or a stereoisomer, enantiomer or tautomer thereof, or a physiologically acceptable salt thereof.

16. A pharmaceutical composition comprising the compound according to claim 1, or a stereoisomer, enantiomer or tautomer thereof, or a physiologically acceptable salt thereof, in combination with a pharmaceutically acceptable carrier or excipient.

17. The pharmaceutical composition according to claim 16, further comprising an additional active substance, wherein the additional active substance has a favorable effect on metabolic disturbance or a disorder that may be associated therewith.

18. The pharmaceutical composition according to claim 16, further comprising an antidiabetics.

19. The pharmaceutical composition according to claim 16, further comprising a lipid lowering agent.

20. A method for treating a disorder of fatty acid metabolism, glucose utilization disorder, a disorder in which insulin resistance is involved, diabetes mellitus or a squeal associated therewith, dyslipidemia or a squeal associated therewith, a condition which is associated with metabolic syndrome, in a patient in need thereof, comprising administering to the patient a pharmaceutically effective amount of the compound according to claim 1, or a stereoisomer, enantiomer or tautomer thereof, or a physiologically acceptable salt thereof.

21. A process for preparing a pharmaceutical composition comprising the compound according to claim 1, or a stereoisomer, enantiomer or tautomer thereof, or a physiologically acceptable salt thereof, in combination with a pharmaceutically acceptable carrier or excipient, which comprises mixing the compound according to claim 1, or the stereoisomer, enantiomer or tautomer thereof, or the physiologically acceptable salt thereof, with the pharmaceutically acceptable carrier or excipient and bringing this mixture into a form suitable for administration.

* * * * *